US011326167B2

(12) United States Patent
Simons et al.

(10) Patent No.: US 11,326,167 B2
(45) Date of Patent: May 10, 2022

(54) METHODS AND COMPOSITIONS FOR TREATING ATHEROSCLEROSIS

(71) Applicant: YALE UNIVERSITY, New Haven, CT (US)

(72) Inventors: Michael Simons, Hamden, CT (US); Pei-Yu Chen, East Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/086,809

(22) PCT Filed: Mar. 21, 2017

(86) PCT No.: PCT/US2017/023347
§ 371 (c)(1),
(2) Date: Sep. 20, 2018

(87) PCT Pub. No.: WO2017/165371
PCT Pub. Date: Sep. 28, 2017

(65) Prior Publication Data
US 2019/0100760 A1    Apr. 4, 2019

Related U.S. Application Data

(60) Provisional application No. 62/406,732, filed on Oct. 11, 2016, provisional application No. 62/311,086, filed on Mar. 21, 2016.

(51) Int. Cl.
*C12N 15/113*    (2010.01)
*A61P 9/10*    (2006.01)
(Continued)

(52) U.S. Cl.
CPC ........ *C12N 15/1138* (2013.01); *A61K 9/0019* (2013.01); *A61K 9/51* (2013.01);
(Continued)

(58) Field of Classification Search
CPC ............ C12N 15/1138; C12N 2310/14; C12N 2310/141; C12N 2310/321;
(Continued)

(56) References Cited

U.S. PATENT DOCUMENTS 9,446,175 B2 *   9/2016  Breuer .................. A61L 31/041
2012/0252867 A1  10/2012  Juo et al.
2014/0348889 A1  11/2014  Breuer et al.

FOREIGN PATENT DOCUMENTS

WO   WO-2005013915 A2 *  2/2005  ........... C12Y 111/01
WO   WO-2012138223 A2 * 10/2012  .............. A61P 21/00

OTHER PUBLICATIONS

Atheroma—From Wikipedia, the free encyclopedia (downloaded from https://en.wikipedia.org/wiki/Atheroma on Jul. 21, 2020).*
(Continued)

*Primary Examiner* — Terra C Gibbs
(74) *Attorney, Agent, or Firm* — Saul Ewing Arnstein & Lehr LLP; Kathryn Doyle; Justin Crotty

(57) ABSTRACT

In some aspects, the invention provides a method of treating atherosclerosis in a subject. The method comprises administering to the subject an agent that increases the activity or level of a let-7 miRNA or an agent that decreases activity or level of a TGFβ signaling polypeptide in an endothelial cell in the subject. In some embodiments, the subject is administered an additional agent comprising a therapeutically effective amount of rapamycin or any derivative thereof. In some embodiments, the agent is a let-7 miRNA. In some other aspects, the invention provides a pharmaceutical composition comprising a let-7 miRNA. In some embodiments, the let-7 miRNA is encapsulated in a nanoparticle formulated for selective delivery to an endothelial cell.

6 Claims, 85 Drawing Sheets

Specification includes a Sequence Listing.

(51) Int. Cl.
*C12Q 1/68* (2018.01)
*A61K 9/00* (2006.01)
*A61K 9/51* (2006.01)
*A61K 31/436* (2006.01)

(52) U.S. Cl.
CPC .............. *A61P 9/10* (2018.01); *C12N 15/113* (2013.01); *C12Q 1/68* (2013.01); *A61K 31/436* (2013.01); *C12N 2310/14* (2013.01); *C12N 2310/141* (2013.01); *C12N 2310/321* (2013.01); *C12N 2320/32* (2013.01)

(58) Field of Classification Search
CPC ........ C12N 2310/3521; C12N 2320/32; A61K 9/51; A61P 9/10
See application file for complete search history.

(56) References Cited

OTHER PUBLICATIONS

Chen et al. (Journal of Cell Science, 2011 vol. 124:4115-4124).*
Liao et al. (Journal of the American College of Cardiology, 2014 vol. 63:1685-1694).*
Partial European Search Report dated Oct. 31, 2019 for European Patent Application No. 17770956.5.
Chen, et al., "Endothelial-to-mesenchymal transition drives atherosclerosis progression", Journal of Clinical Investigation 125(12), Dec. 2015, 4514-4528.
Chen, et al., "Smooth muscle FGF/TGF(beta) cross talk regulates atherosclerosis progression", EMBO Molecular Medicine, 8(7), May 2016, 712-728.
Clarke, et al., "Gene delivery: cell-specific therapy on target", Nat Nanotechnol. 9(8), Aug. 2014, 568-569.
Dahlman, et al., "In vivo endothelial siRNA delivery using polymeric nanoparticles with low molecular weight", Nat Nanotechnol. 9(8), Aug. 2014, 648-655.
Kheirolomoom, et al., "Multifunctional Nanoparticles Facilitate Molecular Targeting and miRNA Delivery to Inhibit Atherosclerosis in ApoE(−/−) Mice", ACS Nano. 9(9), Sep. 2015, 8885-8897.
Park, et al., "Pharmacokinetics and Biodistribution of Recently-Developed siRNA Nanomedicines", Adv Drug Deliv Rev. 104, Dec. 2015, 93-109.
International Search Report and Written Opinion for PCT International Application No. PCT/US2017/023347 dated Aug. 25, 2017.
Chen, et al., "FGF regulates TGF-β signaling and endothelial-to-mesenchymal transition via control of let-7 miRNA expression," Cell Rep. 2(6), Dec. 2012, 1684-1696.
Dahlman, et al., "Designing nanoparticles for highly efficient endothelial siRNA delivery," Thesis Submitted to the Harvard-MIT Program in Health Sciences and Technology on Nov. 13, 2014, Massachusetts Institute of Technology, Apr. 2015, 1-136.
Dol-Gleizes, et al., "A new synthetic FGF receptor antagonist inhibits arteriosclerosis in a mouse vein graft model and atherosclerosis in apolipoprotein E-deficient mice," PLoS One. 8(11), Nov. 2013, e8002.
Gadioli, et al., "Oral rapamycin attenuates atherosclerosis without affecting the arterial responsiveness of resistance vessels in apolipoprotein E-deficient mice," Braz J Med Biol Res. 42(12), 2009, 1191-1195.
Ghosh, et al., "Molecular basis of cardiac endothelial-to-mesenchymal transition (EndMT): differential expression of microRNAs during EndMT," Cell Signal. 24(5), May 2012, 1031-1036.
Qin, et al., "MicroRNA let-7c inhibits Bcl-xl expression and regulates ox-LDL-induced endothelial apoptosis," BMB Rep. 45(8), Aug. 2012, 464-469.

* cited by examiner

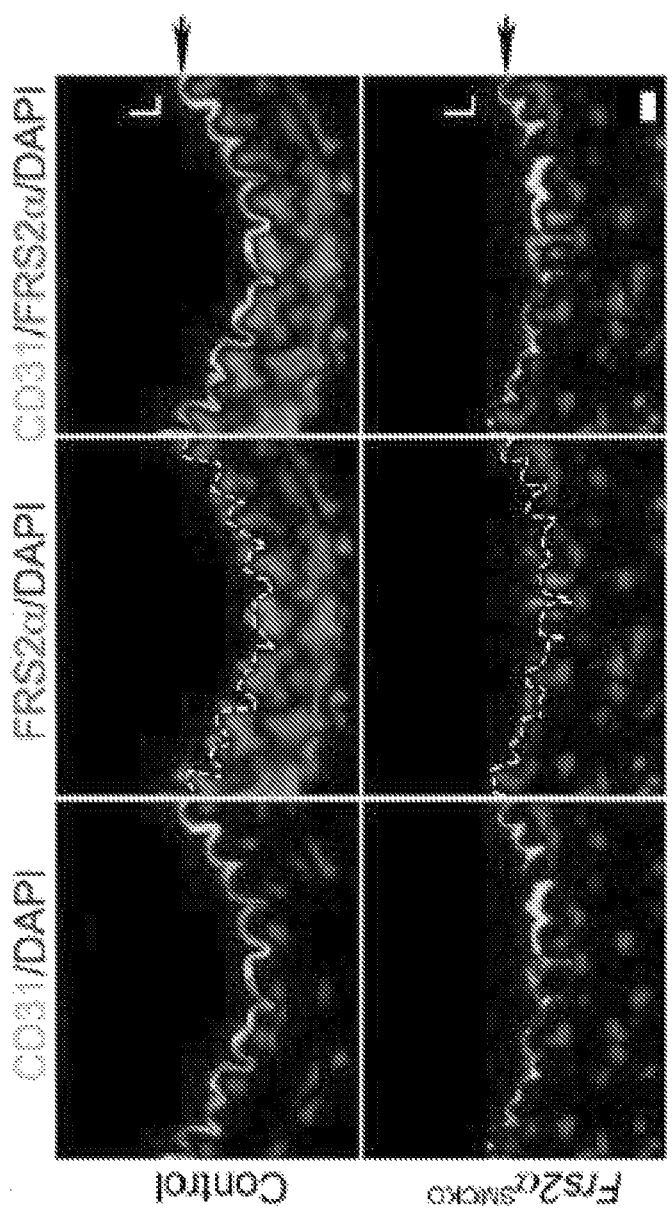
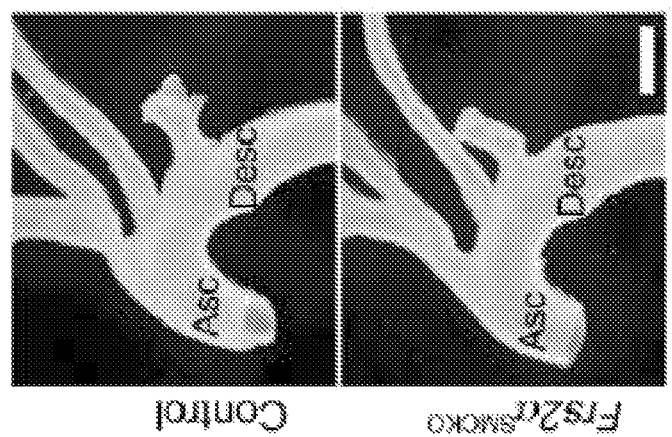
FIG. 11C
FIG. 11D

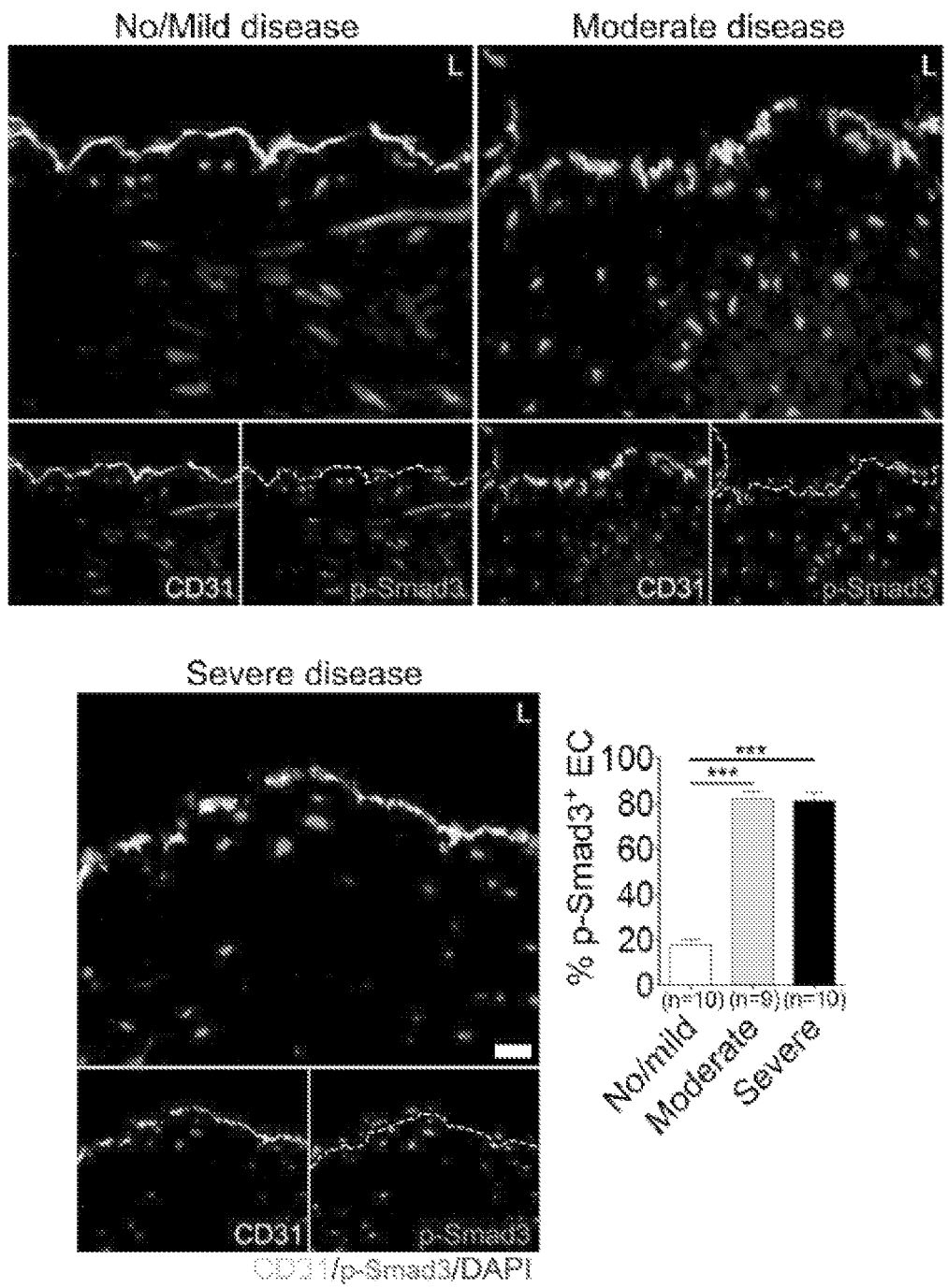

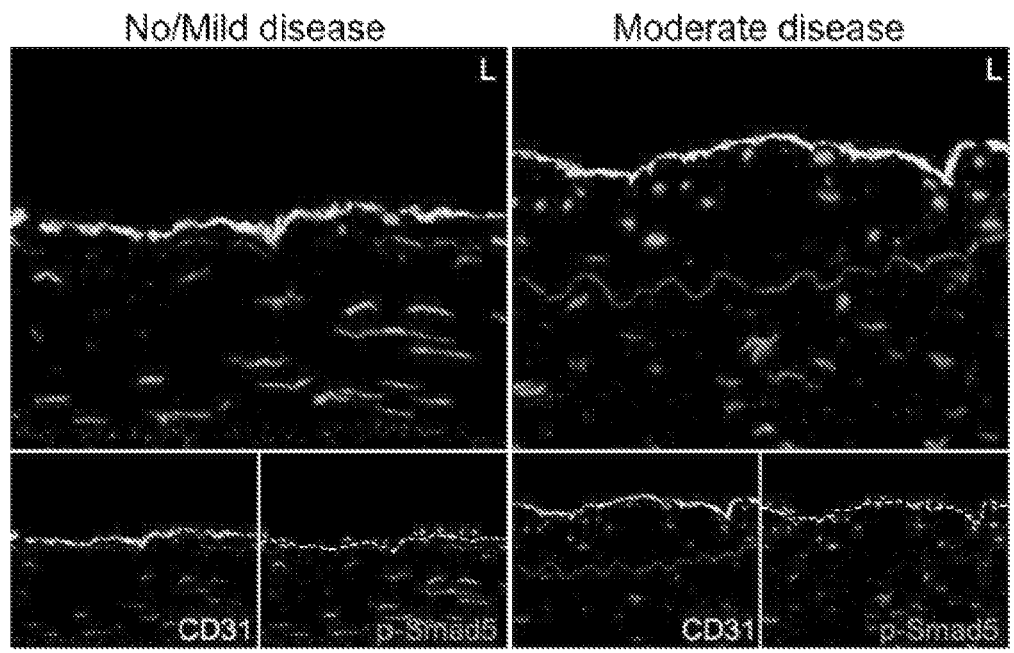
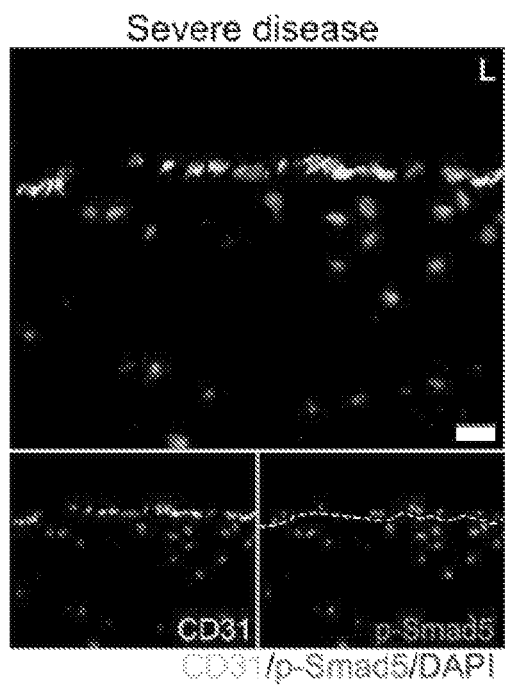
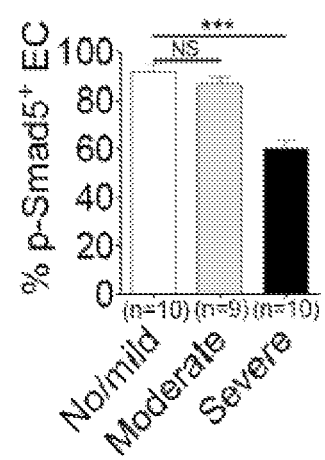
FIG. 35B
FIG. 35C

FIG. 37A
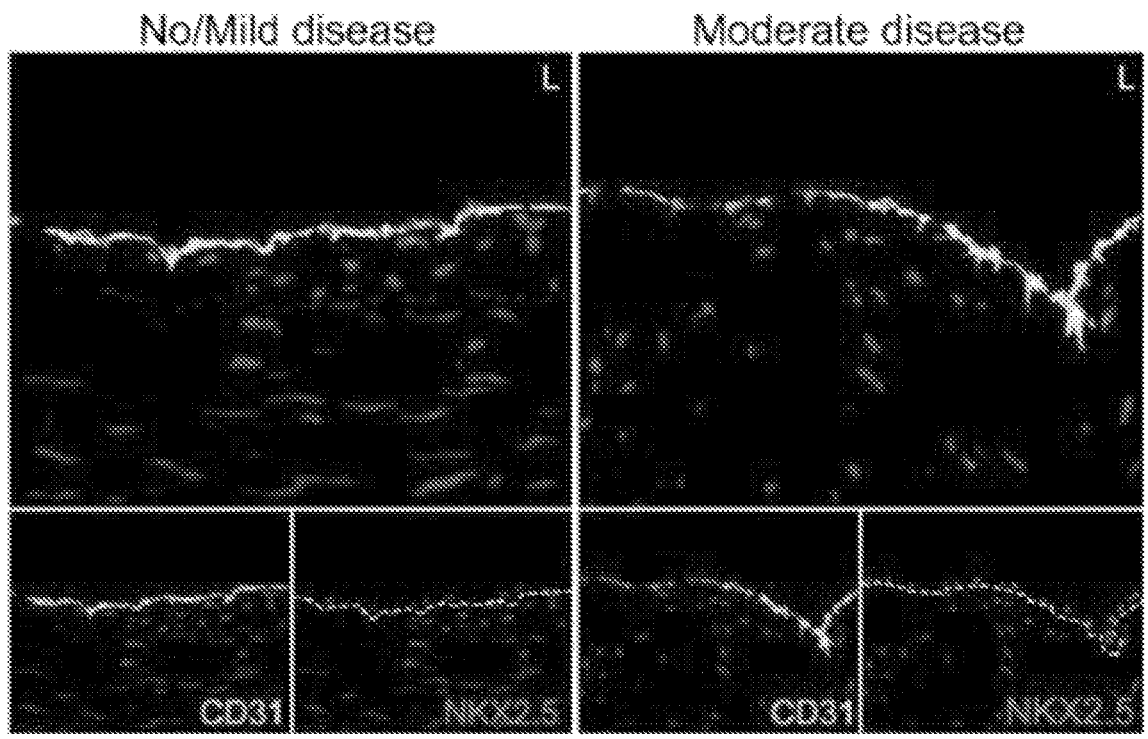
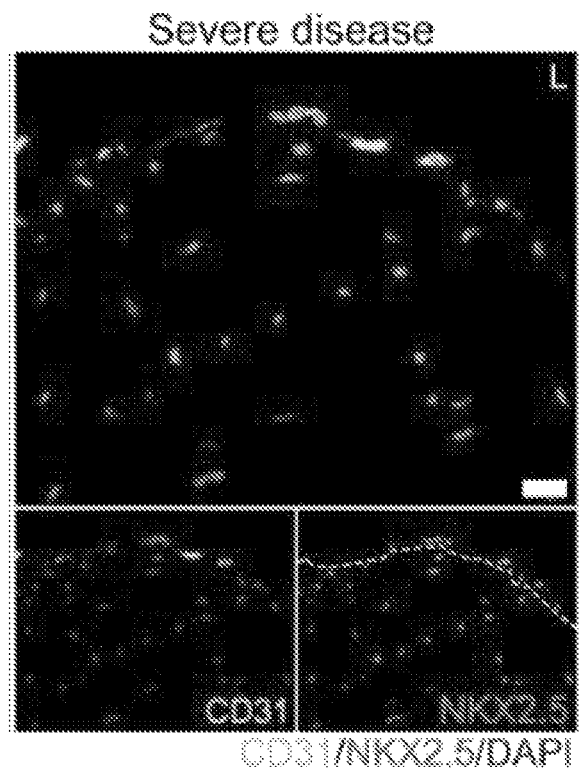
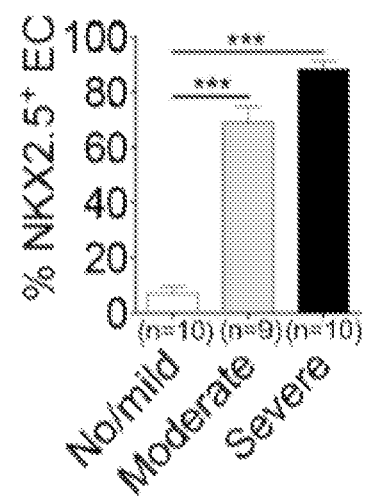
FIG. 37B

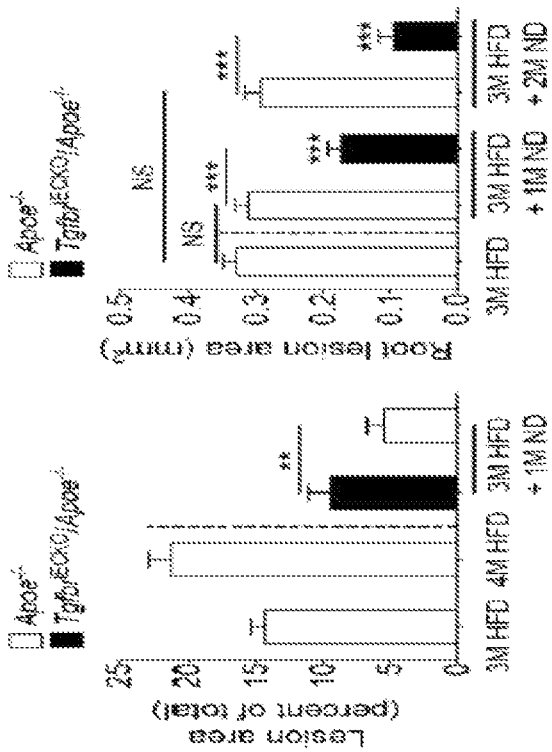
FIG. 39E
FIG. 39F
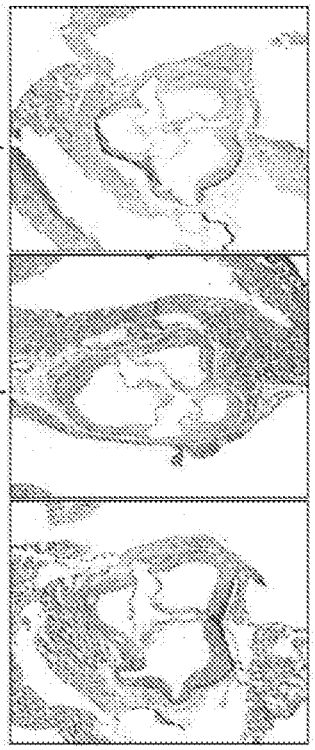
FIG. 39G
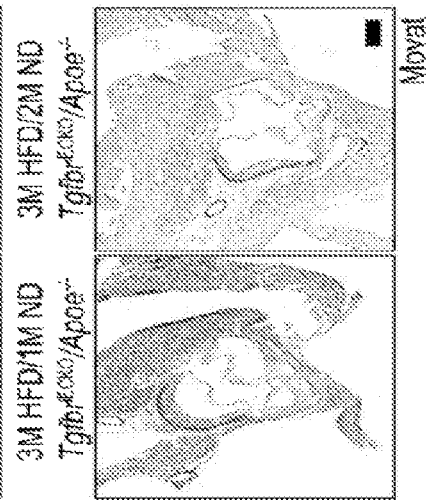
FIG. 39H

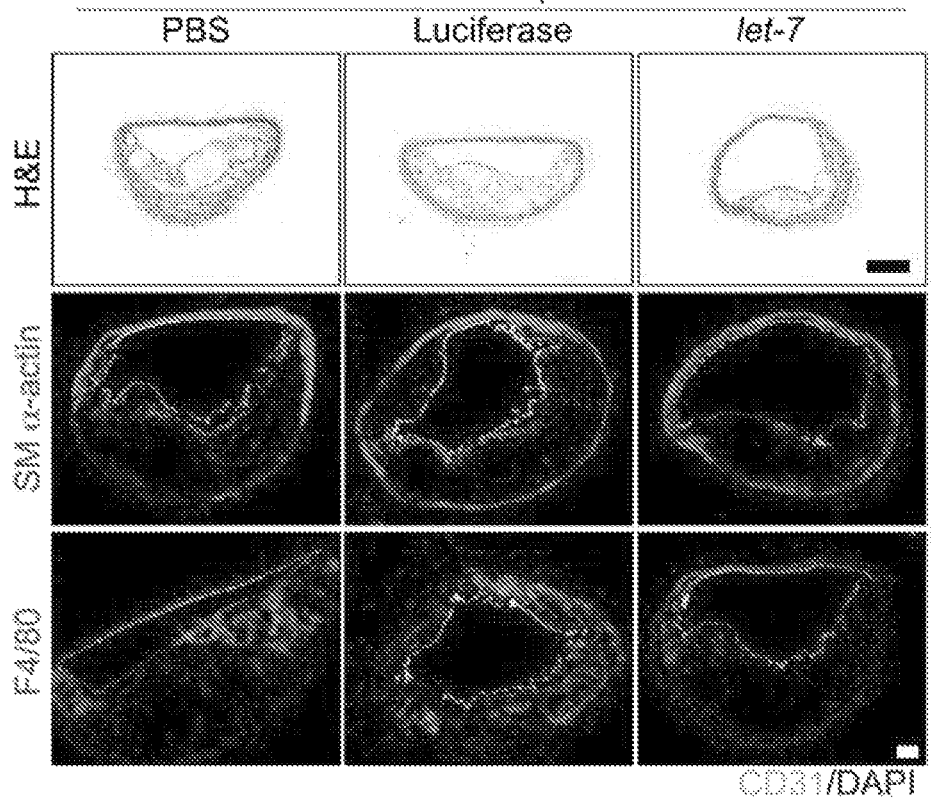
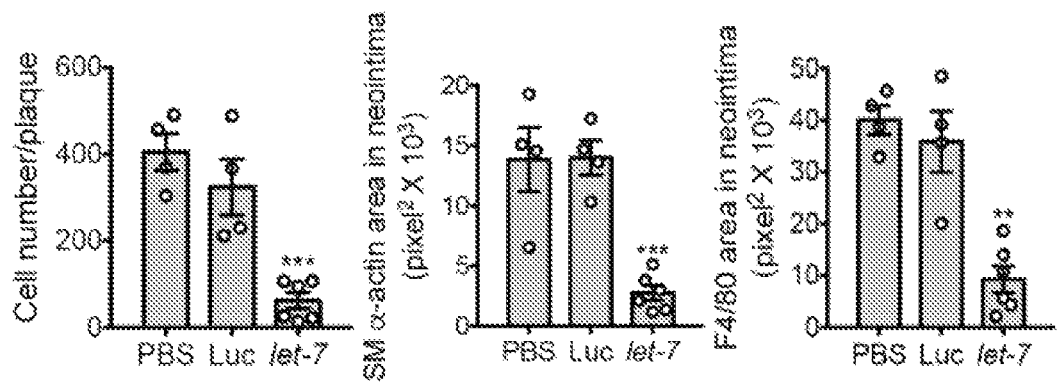

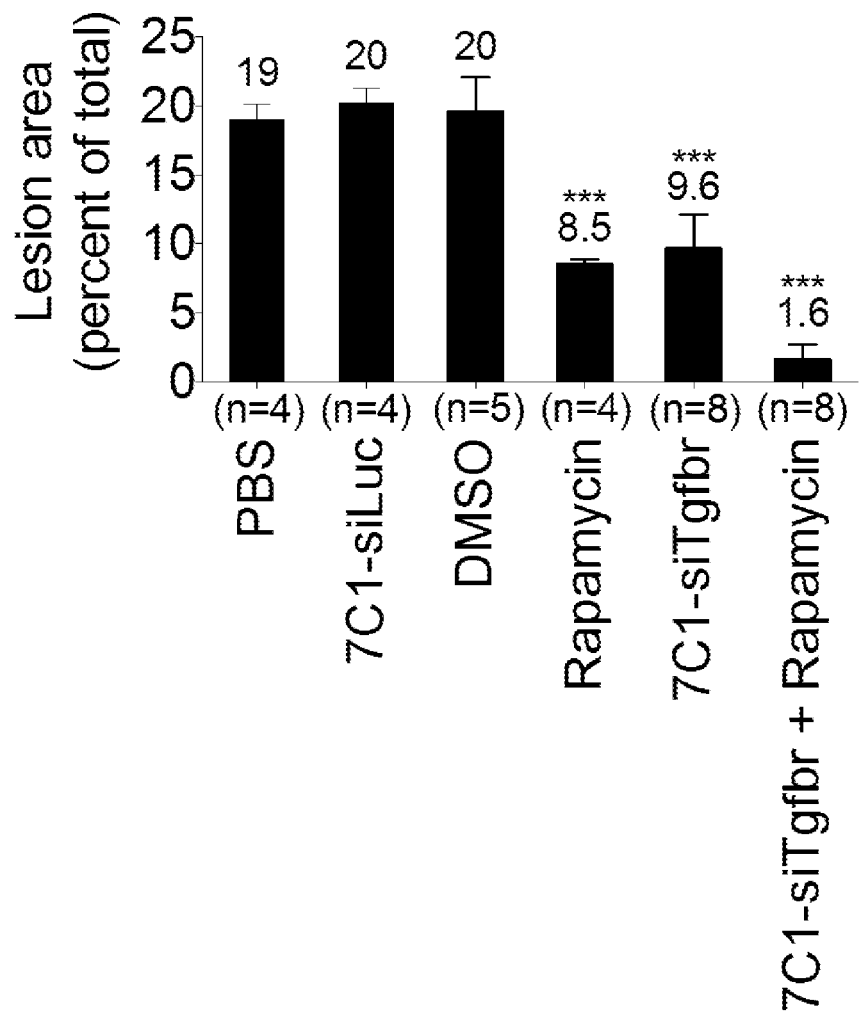

```
                            SEQUENCE LISTING

<160> NUMBER OF SEQ ID NOS: 38

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gagtgtgctg tgattggaag gcag                                              24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
ggcacgagtg tctgcagaca catg                                              24

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gtctggcagt aaaaactatc                                                   20

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
gtgaaacagc attgctgtca ctt                                               23

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
ctaggccaca gaattgaaag atct                                              24

<210> SEQ ID NO 6
<211> LENGTH: 25
<212> TYPE: DNA
<213> ORGANISM: Artificial Sequence
<220> FEATURE:
<223> OTHER INFORMATION: Primer
```

<400> SEQUENCE: 6
gtaggtggaa attctagcat catcc                                      25

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gcctagccga gggagagccg                                            20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gtgacttggg agctctgcag c                                          21

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gccgccccga ctgcatct                                              18

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
gcctgcatta ccggtcgatg caacga                                     26

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
gtggcagatg gcgcggcaac accatt                                     26

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
actcacatgt tggctctcac tgtc                                       24

<210> SEQ ID NO 13
<211> LENGTH: 24

```
<212> TYPE: DNA
<213> ORGANISM: Artificial Sequence
<220> FEATURE:
<223> OTHER INFORMATION: Primer

<400> SEQUENCE: 13
agtcatagag catgtgttag agtc                                              24

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
taaacaaggt ccggagccca                                                   20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
acttctgcaa gaggtcccct                                                   20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ctctgctgcc tcctggcttc t                                                 21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
cgaggcggat cacaagcaat a                                                 21

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
tcaatgggcg ggggtcgtt                                                    19

<210> SEQ ID NO 19
<211> LENGTH: 22
<212> TYPE: RNA
<213> ORGANISM: Artificial Sequence
<220> FEATURE:
<223> OTHER INFORMATION: Primer

<400> SEQUENCE: 19
```
ugagguagua gguugugugg uu                                                 22

<210> SEQ ID NO 20
<211> LENGTH: 22
<212> TYPE: RNA
<213> ORGANISM: Artificial Sequence
<220> FEATURE:
<223> OTHER INFORMATION: Primer

<400> SEQUENCE: 20
cuauacaacc uacugccuuc cc                                                 22

<210> SEQ ID NO 21
<211> LENGTH: 820
<212> TYPE: PRT
<213> ORGANISM: homo sapiens

<400> SEQUENCE: 21

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300
```

-continued

```
Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Tyr Cys Thr Gly Ala
370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
            485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
        515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
            565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
            645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
```

```
                    725                 730                 735
Ala Val Pro Ser Gln Arg Pro Thr Phe Lys Gln Leu Val Glu Asp Leu
                740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 22
<211> LENGTH: 3913
<212> TYPE: PRT
<213> ORGANISM: homo sapiens

<400> SEQUENCE: 22

Ala Gly Cys Gly Cys Thr Cys Thr Thr Gly Cys Gly Gly Cys Cys Ala
1               5                   10                  15

Cys Ala Gly Gly Cys Gly Cys Gly Gly Cys Gly Thr Cys Cys Thr Cys
                20                  25                  30

Gly Gly Cys Gly Gly Cys Gly Gly Cys Gly Gly Cys Ala Gly Cys
            35                  40                  45

Thr Ala Gly Cys Gly Gly Ala Gly Cys Cys Gly Gly Ala Cys
        50                  55                  60

Gly Cys Cys Gly Gly Thr Gly Cys Ala Gly Cys Cys Gly Cys Ala Gly
65                  70                  75                  80

Cys Gly Cys Gly Cys Gly Gly Ala Gly Ala Ala Cys Cys Cys Gly
                85                  90                  95

Gly Gly Thr Gly Thr Gly Cys Cys Gly Gly Ala Gly Cys Thr Gly
            100                 105                 110

Gly Gly Cys Gly Gly Cys Cys Ala Cys Gly Thr Cys Cys Gly Gly Ala
            115                 120                 125

Cys Gly Gly Gly Ala Cys Cys Gly Ala Gly Ala Cys Cys Cys Cys Thr
        130                 135                 140

Cys Gly Thr Ala Gly Cys Gly Cys Ala Thr Thr Gly Cys Gly Gly Cys
145                 150                 155                 160

Gly Ala Cys Cys Thr Cys Gly Cys Cys Thr Thr Cys Cys Cys Gly
                165                 170                 175

Gly Cys Cys Gly Cys Gly Ala Cys Gly Cys Gly Cys Cys Gly Cys
            180                 185                 190

Thr Gly Cys Thr Thr Gly Ala Ala Ala Gly Cys Cys Gly Cys Gly
        195                 200                 205

Gly Ala Ala Cys Cys Cys Ala Ala Gly Gly Ala Cys Thr Thr Thr
    210                 215                 220

Cys Thr Cys Cys Gly Gly Thr Cys Cys Gly Ala Gly Cys Thr Cys Gly
225                 230                 235                 240

Gly Gly Gly Cys Gly Cys Cys Cys Gly Cys Ala Gly Gly Gly Cys
                245                 250                 255

Gly Cys Ala Cys Gly Gly Thr Ala Cys Cys Gly Thr Gly Cys Thr
            260                 265                 270
```

```
Gly Cys Ala Gly Thr Cys Gly Gly Cys Ala Gly Cys Cys Gly
        275                 280                 285
Cys Gly Gly Cys Gly Cys Gly Gly Gly Cys Cys Thr Cys Cys
        290                 295                 300
Gly Cys Ala Gly Gly Cys Gly Ala Thr Gly Gly Ala Gly Cys
305                 310                 315                 320
Cys Gly Gly Thr Cys Thr Gly Cys Ala Ala Gly Gly Ala Gly
                325                 330                 335
Thr Gly Ala Gly Gly Cys Gly Cys Gly Cys Gly Cys Thr Gly
                340                 345                 350
Cys Gly Thr Thr Cys Thr Gly Ala Gly Gly Ala Gly Gly Gly
                355                 360                 365
Gly Gly Cys Ala Cys Cys Ala Gly Cys Thr Cys Cys Gly Cys Thr
        370                 375                 380
Cys Cys Ala Thr Thr Gly Thr Thr Cys Cys Cys Gly Cys Cys Gly
385                 390                 395                 400
Gly Gly Cys Thr Gly Gly Ala Gly Gly Cys Gly Cys Cys Gly Ala Gly
                405                 410                 415
Cys Ala Cys Cys Gly Ala Gly Cys Cys Gly Cys Cys Gly Gly
        420                 425                 430
Gly Ala Gly Thr Cys Gly Ala Gly Cys Gly Cys Cys Gly Cys Cys
                435                 440                 445
Gly Cys Gly Gly Ala Gly Cys Thr Cys Thr Thr Gly Cys Ala Cys
        450                 455                 460
Cys Cys Cys Gly Cys Cys Ala Gly Gly Ala Cys Cys Gly Ala Ala
465                 470                 475                 480
Cys Ala Gly Ala Gly Cys Cys Cys Gly Gly Gly Gly Cys Gly Gly
                485                 490                 495
Cys Gly Gly Gly Cys Cys Gly Gly Ala Gly Cys Cys Gly Gly Gly
        500                 505                 510
Ala Cys Gly Cys Gly Gly Gly Cys Ala Cys Ala Cys Gly Cys Cys Cys
        515                 520                 525
Gly Cys Thr Cys Gly Cys Ala Cys Ala Ala Gly Cys Ala Cys Gly
        530                 535                 540
Gly Cys Gly Gly Ala Cys Thr Cys Thr Cys Cys Gly Ala Gly Gly
545                 550                 555                 560
Cys Gly Gly Ala Ala Cys Cys Thr Cys Ala Cys Gly Cys Cys Gly
                565                 570                 575
Ala Gly Cys Gly Ala Gly Gly Thr Cys Ala Gly Thr Thr Thr Gly
        580                 585                 590
Ala Ala Ala Ala Gly Gly Ala Gly Ala Thr Cys Gly Ala Gly Cys
                595                 600                 605
Thr Cys Ala Cys Thr Gly Thr Gly Gly Ala Gly Thr Ala Thr Cys Cys
        610                 615                 620
Ala Thr Gly Gly Ala Gly Ala Thr Gly Thr Gly Gly Ala Gly Cys Cys
625                 630                 635                 640
Thr Thr Gly Thr Cys Ala Cys Cys Ala Ala Cys Cys Thr Cys Thr Ala
                645                 650                 655
Ala Cys Thr Gly Cys Ala Gly Ala Ala Cys Thr Gly Gly Ala Thr
                660                 665                 670
Gly Thr Gly Gly Ala Gly Cys Thr Gly Gly Ala Ala Gly Thr Gly Cys
        675                 680                 685
Cys Thr Cys Cys Thr Cys Thr Thr Cys Thr Gly Gly Gly Cys Thr Gly
```

-continued

```
            690             695             700
Thr Gly Cys Thr Gly Gly Thr Cys Ala Cys Ala Gly Cys Cys Ala Cys
705                 710                 715                 720

Ala Cys Thr Cys Thr Gly Cys Ala Cys Cys Gly Cys Thr Ala Gly Gly
                725                 730                 735

Cys Cys Gly Thr Cys Cys Cys Gly Ala Cys Cys Thr Thr Gly Cys
            740                 745                 750

Cys Thr Gly Ala Ala Cys Ala Ala Gly Cys Cys Ala Gly Cys Cys
        755                 760                 765

Cys Thr Gly Gly Gly Ala Gly Cys Cys Cys Thr Gly Thr Gly
        770                 775                 780

Gly Ala Ala Gly Thr Gly Gly Ala Gly Thr Cys Cys Thr Thr Cys Cys
785                 790                 795                 800

Thr Gly Gly Thr Cys Cys Ala Cys Cys Cys Cys Gly Gly Thr Gly Ala
                805                 810                 815

Cys Cys Thr Gly Cys Thr Gly Cys Ala Gly Cys Thr Thr Cys Gly Cys
                820                 825                 830

Thr Gly Thr Cys Gly Gly Cys Thr Gly Cys Gly Gly Ala Cys Gly
            835                 840                 845

Ala Thr Gly Thr Gly Cys Ala Gly Ala Gly Cys Ala Thr Cys Ala Ala
850                 855                 860

Cys Thr Gly Gly Cys Thr Gly Cys Gly Gly Ala Cys Gly Gly
865                 870                 875                 880

Gly Thr Gly Cys Ala Gly Cys Thr Gly Cys Gly Gly Ala Ala Ala
            885                 890                 895

Gly Cys Ala Ala Cys Cys Gly Cys Ala Cys Cys Gly Cys Ala Thr
        900                 905                 910

Cys Ala Cys Ala Gly Gly Gly Ala Gly Gly Ala Gly Gly Thr Gly
        915                 920                 925

Gly Ala Gly Gly Thr Gly Cys Ala Gly Gly Ala Cys Thr Cys Cys Gly
        930                 935                 940

Thr Gly Cys Cys Cys Gly Cys Ala Gly Ala Cys Thr Cys Cys Gly Gly
945                 950                 955                 960

Cys Cys Thr Cys Thr Ala Thr Gly Cys Thr Thr Gly Cys Gly Thr Ala
            965                 970                 975

Ala Cys Cys Ala Gly Cys Ala Gly Cys Cys Cys Thr Cys Gly Gly
            980                 985                 990

Gly Cys Ala Gly Thr Gly Ala Cys  Ala Cys Cys Ala Cys  Cys Thr Ala
            995                  1000                 1005

Cys Thr  Thr Cys Thr Cys Cys  Gly Thr Cys Ala Ala  Thr Gly Thr
   1010                 1015                 1020

Thr Thr  Cys Ala Gly Ala Thr  Gly Cys Thr Cys Thr  Cys Cys Cys
   1025                 1030                 1035

Cys Thr  Cys Cys Thr Cys Gly  Gly Ala Gly Gly Ala  Thr Gly Ala
   1040                 1045                 1050

Thr Gly  Ala Thr Gly Ala Thr  Gly Ala Thr Gly Ala  Thr Gly Ala
   1055                 1060                 1065

Cys Thr  Cys Cys Thr Cys Thr   Thr Cys Ala Gly Ala  Gly Gly Ala
   1070                 1075                 1080

Gly Ala  Ala Ala Gly Ala Ala  Ala Cys Ala Gly Ala  Thr Ala Ala
   1085                 1090                 1095

Cys Ala  Cys Cys Ala Ala Ala   Cys Cys Ala Ala Ala  Cys Cys Gly
   1100                 1105                 1110
```

Thr Ala Thr Gly Cys Cys Cys Gly Thr Ala Cys Thr Cys Cys
        1115                 1120                 1125

Ala Thr Ala Thr Thr Gly Gly Ala Cys Ala Thr Cys Cys Cys
        1130                 1135                 1140

Ala Gly Ala Ala Ala Ala Gly Ala Thr Gly Gly Ala Ala Ala
        1145                 1150                 1155

Gly Ala Ala Ala Thr Thr Gly Cys Ala Thr Gly Cys Ala Gly Thr
        1160                 1165                 1170

Gly Cys Cys Gly Gly Cys Thr Gly Cys Cys Ala Ala Gly Ala Cys
        1175                 1180                 1185

Ala Gly Thr Gly Ala Ala Gly Thr Thr Cys Ala Ala Ala Thr Gly
        1190                 1195                 1200

Cys Cys Cys Thr Thr Cys Cys Ala Gly Thr Gly Gly Gly Ala Cys
        1205                 1210                 1215

Cys Cys Cys Ala Ala Ala Cys Cys Cys Ala Cys Ala Cys Thr
        1220                 1225                 1230

Gly Cys Gly Cys Thr Gly Gly Thr Thr Gly Ala Ala Ala Ala Ala
        1235                 1240                 1245

Thr Gly Gly Cys Ala Ala Ala Gly Ala Ala Thr Thr Cys Ala Ala
        1250                 1255                 1260

Ala Cys Cys Thr Gly Ala Cys Cys Ala Cys Ala Gly Ala Ala Thr
        1265                 1270                 1275

Thr Gly Gly Ala Gly Gly Cys Thr Ala Cys Ala Ala Gly Gly Thr
        1280                 1285                 1290

Cys Cys Gly Thr Thr Ala Thr Gly Cys Cys Ala Cys Cys Thr Gly
        1295                 1300                 1305

Gly Ala Gly Cys Ala Thr Cys Ala Thr Ala Ala Thr Gly Gly Ala
        1310                 1315                 1320

Cys Thr Cys Thr Gly Thr Gly Gly Thr Gly Cys Cys Cys Thr Cys
        1325                 1330                 1335

Thr Gly Ala Cys Ala Ala Gly Gly Gly Cys Ala Ala Cys Thr Ala
        1340                 1345                 1350

Cys Ala Cys Cys Thr Gly Cys Ala Thr Thr Gly Thr Gly Gly Ala
        1355                 1360                 1365

Gly Ala Ala Thr Gly Ala Gly Thr Ala Cys Gly Gly Cys Ala Gly
        1370                 1375                 1380

Cys Ala Thr Cys Ala Ala Cys Ala Cys Ala Cys Ala Thr Ala
        1385                 1390                 1395

Cys Cys Ala Gly Cys Thr Gly Gly Ala Thr Gly Thr Cys Gly Thr
        1400                 1405                 1410

Gly Gly Ala Gly Cys Gly Gly Thr Cys Cys Cys Thr Cys Ala
        1415                 1420                 1425

Cys Cys Gly Gly Cys Cys Cys Ala Thr Cys Cys Thr Gly Cys Ala
        1430                 1435                 1440

Ala Gly Cys Ala Gly Gly Gly Thr Thr Gly Cys Cys Cys Gly Cys
        1445                 1450                 1455

Cys Ala Ala Cys Ala Ala Ala Ala Cys Ala Gly Thr Gly Gly Cys
        1460                 1465                 1470

Cys Cys Thr Gly Gly Gly Thr Ala Gly Cys Ala Ala Cys Gly Thr
        1475                 1480                 1485

Gly Gly Ala Gly Thr Thr Cys Ala Thr Gly Thr Gly Thr Ala Ala
        1490                 1495                 1500

```
Gly Gly Thr Gly Thr Ala Cys Ala Gly Thr Gly Ala Cys Cys Cys
        1505                1510                1515
Gly Cys Ala Gly Cys Cys Gly Cys Ala Cys Ala Thr Cys Cys Ala
        1520                1525                1530
Gly Thr Gly Gly Cys Thr Ala Ala Ala Gly Cys Ala Cys Ala Thr
        1535                1540                1545
Cys Gly Ala Gly Gly Thr Gly Ala Ala Thr Gly Gly Gly Ala Gly
        1550                1555                1560
Cys Ala Ala Gly Ala Thr Thr Gly Gly Cys Cys Cys Ala Gly Ala
        1565                1570                1575
Cys Ala Ala Cys Cys Thr Gly Cys Cys Thr Thr Ala Thr Gly Thr
        1580                1585                1590
Cys Cys Ala Gly Ala Thr Cys Thr Thr Gly Ala Ala Gly Ala Cys
        1595                1600                1605
Thr Gly Cys Thr Gly Gly Ala Gly Thr Thr Ala Ala Thr Ala Cys
        1610                1615                1620
Cys Ala Cys Cys Gly Ala Cys Ala Ala Ala Gly Ala Gly Ala Thr
        1625                1630                1635
Gly Gly Ala Gly Gly Thr Gly Cys Thr Thr Cys Ala Cys Thr Thr
        1640                1645                1650
Ala Ala Gly Ala Ala Ala Thr Gly Thr Cys Thr Cys Cys Thr Thr
        1655                1660                1665
Thr Gly Ala Gly Gly Ala Cys Gly Cys Ala Gly Gly Gly Gly Ala
        1670                1675                1680
Gly Thr Ala Thr Ala Cys Gly Thr Gly Cys Thr Thr Gly Gly Cys
        1685                1690                1695
Gly Gly Gly Thr Ala Ala Cys Thr Cys Thr Ala Thr Cys Gly Gly
        1700                1705                1710
Ala Cys Thr Cys Thr Cys Cys Ala Thr Cys Ala Cys Thr Cys
        1715                1720                1725
Thr Gly Cys Ala Thr Gly Gly Thr Thr Gly Ala Cys Cys Gly Thr
        1730                1735                1740
Thr Cys Thr Gly Gly Ala Ala Gly Cys Cys Thr Gly Gly Ala
        1745                1750                1755
Ala Gly Ala Gly Ala Gly Gly Cys Cys Gly Gly Cys Ala Gly Thr
        1760                1765                1770
Gly Ala Thr Gly Ala Cys Cys Thr Cys Gly Cys Cys Cys Cys Thr
        1775                1780                1785
Gly Thr Ala Cys Cys Thr Gly Gly Ala Gly Ala Thr Cys Ala Thr
        1790                1795                1800
Cys Ala Thr Cys Thr Ala Thr Thr Gly Cys Ala Cys Ala Gly Gly
        1805                1810                1815
Gly Gly Cys Cys Thr Thr Cys Cys Thr Cys Ala Thr Cys Thr Cys
        1820                1825                1830
Cys Thr Gly Cys Ala Thr Gly Gly Thr Gly Gly Gly Gly Thr Cys
        1835                1840                1845
Gly Gly Thr Cys Ala Thr Cys Gly Thr Cys Thr Ala Cys Ala Ala
        1850                1855                1860
Gly Ala Thr Gly Ala Ala Gly Ala Gly Thr Gly Gly Thr Ala Cys
        1865                1870                1875
Cys Ala Ala Gly Ala Ala Gly Ala Gly Thr Gly Ala Cys Thr Thr
        1880                1885                1890
Cys Cys Ala Cys Ala Gly Cys Cys Ala Gly Ala Thr Gly Gly Cys
```

-continued

```
    1895                1900                1905

Thr Gly  Thr Gly Cys Ala Cys  Ala Ala Gly Cys Thr  Gly Gly Cys
    1910                1915                1920

Cys Ala  Ala Gly Ala Gly Cys  Ala Thr Cys Cys Cys  Thr Cys Thr
    1925                1930                1935

Gly Cys  Gly Cys Ala Gly Ala  Cys Ala Gly Gly Thr  Gly Thr Cys
    1940                1945                1950

Thr Gly  Cys Thr Gly Ala Cys  Thr Cys Cys Ala Gly  Thr Gly Cys
    1955                1960                1965

Ala Thr  Cys Cys Ala Thr Gly  Ala Ala Cys Thr Cys  Thr Gly Gly
    1970                1975                1980

Gly Gly  Thr Thr Cys Thr Thr  Cys Thr Gly Gly Thr  Thr Cys Gly
    1985                1990                1995

Gly Cys  Cys Ala Thr Cys Ala  Cys Gly Gly Cys Thr  Cys Thr Cys
    2000                2005                2010

Cys Thr  Cys Cys Ala Gly Thr  Gly Gly Gly Ala Cys  Thr Cys Cys
    2015                2020                2025

Cys Ala  Thr Gly Cys Thr Ala  Gly Cys Ala Gly Gly  Gly Gly Thr
    2030                2035                2040

Cys Thr  Cys Thr Gly Ala Gly  Thr Ala Thr Gly Ala  Gly Cys Thr
    2045                2050                2055

Thr Cys  Cys Cys Gly Ala Ala  Gly Ala Cys Cys Cys  Thr Cys Gly
    2060                2065                2070

Cys Thr  Gly Gly Gly Ala Gly  Cys Thr Gly Cys Cys  Thr Cys Gly
    2075                2080                2085

Gly Gly  Ala Cys Ala Gly Ala  Cys Thr Gly Gly Thr  Cys Thr Thr
    2090                2095                2100

Ala Gly  Gly Cys Ala Ala Ala  Cys Cys Cys Cys Thr  Gly Gly Gly
    2105                2110                2115

Ala Gly  Ala Gly Gly Gly Cys  Thr Gly Cys Thr Thr  Thr Gly Gly
    2120                2125                2130

Gly Cys  Ala Gly Gly Thr Gly  Gly Thr Gly Thr Thr  Gly Gly Cys
    2135                2140                2145

Ala Gly  Ala Gly Gly Cys Thr  Ala Thr Cys Gly Gly  Gly Cys Thr
    2150                2155                2160

Gly Gly  Ala Cys Ala Ala Gly  Gly Ala Cys Ala Ala  Ala Cys Cys
    2165                2170                2175

Cys Ala  Ala Cys Cys Gly Thr  Gly Thr Gly Ala Cys  Cys Ala Ala
    2180                2185                2190

Ala Gly  Thr Gly Gly Cys Thr  Gly Thr Gly Ala Ala  Gly Ala Thr
    2195                2200                2205

Gly Thr  Thr Gly Ala Ala Gly  Thr Cys Gly Gly Ala  Cys Gly Cys
    2210                2215                2220

Ala Ala  Cys Ala Gly Ala Gly  Ala Ala Ala Gly Ala  Cys Thr Thr
    2225                2230                2235

Gly Thr  Cys Ala Gly Ala Cys  Cys Thr Gly Ala Thr  Cys Thr Cys
    2240                2245                2250

Ala Gly  Ala Ala Ala Thr Gly  Gly Ala Gly Ala Thr  Gly Ala Thr
    2255                2260                2265

Gly Ala  Ala Gly Ala Thr Gly  Ala Thr Cys Gly Gly  Gly Ala Ala
    2270                2275                2280

Gly Cys  Ala Thr Ala Ala Gly  Ala Ala Thr Ala Thr  Cys Ala Thr
    2285                2290                2295
```

```
Cys Ala Ala Cys Cys Thr Gly Cys Thr Gly Gly Gly Gly Cys
        2300                2305            2310

Cys Thr Gly Cys Ala Cys Gly Cys Ala Gly Gly Ala Thr Gly Gly
        2315                2320            2325

Thr Cys Cys Cys Thr Thr Gly Thr Ala Thr Gly Thr Cys Ala Thr
        2330                2335            2340

Cys Gly Thr Gly Gly Ala Gly Thr Ala Thr Gly Cys Cys Thr Cys
        2345                2350            2355

Cys Ala Ala Gly Gly Cys Ala Ala Cys Cys Thr Gly Cys Gly
        2360            2365            2370

Gly Gly Ala Gly Thr Ala Cys Cys Thr Gly Cys Ala Gly Gly Cys
        2375                2380            2385

Cys Cys Gly Gly Ala Gly Cys Cys Cys Cys Ala Gly Gly
        2390            2395            2400

Gly Cys Thr Gly Gly Ala Ala Thr Ala Cys Thr Gly Cys Thr Ala
        2405                2410            2415

Cys Ala Ala Cys Cys Cys Ala Gly Cys Cys Ala Cys Ala Ala
        2420            2425            2430

Cys Cys Cys Ala Gly Ala Gly Gly Ala Gly Cys Ala Gly Cys Thr
        2435                2440            2445

Cys Thr Cys Cys Thr Cys Cys Ala Ala Gly Gly Ala Cys Cys Thr
        2450                2455            2460

Gly Gly Thr Gly Thr Cys Cys Thr Gly Cys Gly Cys Cys Thr Ala
        2465                2470            2475

Cys Cys Ala Gly Gly Thr Gly Gly Cys Cys Cys Gly Ala Gly Gly
        2480                2485            2490

Cys Ala Thr Gly Gly Ala Gly Thr Ala Thr Cys Thr Gly Gly Cys
        2495                2500            2505

Cys Thr Cys Cys Ala Ala Gly Ala Ala Gly Thr Gly Cys Ala Thr
        2510                2515            2520

Ala Cys Ala Cys Cys Gly Ala Gly Ala Cys Cys Thr Gly Gly Cys
        2525                2530            2535

Ala Gly Cys Cys Ala Gly Gly Ala Ala Thr Gly Thr Cys Cys Thr
        2540                2545            2550

Gly Gly Thr Gly Ala Cys Ala Gly Ala Gly Gly Ala Cys Ala Ala
        2555                2560            2565

Thr Gly Thr Gly Ala Thr Gly Ala Ala Gly Ala Thr Ala Gly Cys
        2570                2575            2580

Ala Gly Ala Cys Thr Thr Thr Gly Gly Cys Cys Thr Cys Gly Cys
        2585                2590            2595

Ala Cys Gly Gly Gly Ala Cys Ala Thr Thr Cys Ala Cys Cys Ala
        2600                2605            2610

Cys Ala Thr Cys Gly Ala Cys Thr Ala Cys Thr Ala Thr Ala Ala
        2615                2620            2625

Ala Ala Ala Gly Ala Cys Ala Ala Cys Cys Ala Ala Cys Gly Gly
        2630                2635            2640

Cys Cys Gly Ala Cys Thr Gly Cys Cys Thr Gly Thr Gly Ala Ala
        2645                2650            2655

Gly Thr Gly Gly Ala Thr Gly Gly Cys Ala Cys Cys Cys Gly Ala
        2660                2665            2670

Gly Gly Cys Ala Thr Thr Ala Thr Thr Thr Gly Ala Cys Cys Gly
        2675                2680            2685
```

Gly Ala Thr Cys Thr Ala Cys Ala Cys Cys Cys Ala Cys Cys Ala
2690 2695 2700

Gly Ala Gly Thr Gly Ala Thr Gly Thr Gly Thr Gly Gly Thr Cys
2705 2710 2715

Thr Thr Thr Cys Gly Gly Gly Gly Thr Gly Cys Thr Cys Cys Thr
2720 2725 2730

Gly Thr Gly Gly Gly Ala Gly Ala Thr Cys Thr Thr Cys Ala Cys
2735 2740 2745

Thr Cys Thr Gly Gly Gly Cys Gly Gly Cys Thr Cys Cys Cys Cys
2750 2755 2760

Ala Thr Ala Cys Cys Cys Cys Gly Gly Thr Gly Thr Gly Cys Cys
2765 2770 2775

Thr Gly Thr Gly Gly Ala Gly Gly Ala Ala Cys Thr Thr Thr Thr
2780 2785 2790

Cys Ala Ala Gly Cys Thr Gly Cys Thr Gly Ala Ala Gly Gly Ala
2795 2800 2805

Gly Gly Gly Thr Cys Ala Cys Cys Gly Cys Ala Thr Gly Gly Ala
2810 2815 2820

Cys Ala Ala Gly Cys Cys Cys Ala Gly Thr Ala Ala Cys Thr Gly
2825 2830 2835

Cys Ala Cys Cys Ala Ala Cys Gly Ala Gly Cys Thr Gly Thr Ala
2840 2845 2850

Cys Ala Thr Gly Ala Thr Gly Ala Thr Gly Cys Gly Gly Gly Ala
2855 2860 2865

Cys Thr Gly Cys Thr Gly Gly Cys Ala Thr Gly Cys Ala Gly Thr
2870 2875 2880

Gly Cys Cys Cys Thr Cys Ala Cys Ala Gly Ala Gly Ala Cys Cys
2885 2890 2895

Cys Ala Cys Cys Thr Thr Cys Ala Ala Gly Cys Ala Gly Cys Thr
2900 2905 2910

Gly Gly Thr Gly Gly Ala Ala Gly Ala Cys Cys Thr Gly Gly Ala
2915 2920 2925

Cys Cys Gly Cys Ala Thr Cys Gly Thr Gly Gly Cys Cys Thr Thr
2930 2935 2940

Gly Ala Cys Cys Thr Cys Cys Ala Ala Cys Cys Ala Gly Gly Ala
2945 2950 2955

Gly Thr Ala Cys Cys Thr Gly Gly Ala Cys Cys Thr Gly Thr Cys
2960 2965 2970

Cys Ala Thr Gly Cys Cys Cys Cys Thr Gly Gly Ala Cys Cys Ala
2975 2980 2985

Gly Thr Ala Cys Thr Cys Cys Cys Cys Cys Ala Gly Cys Thr Thr
2990 2995 3000

Thr Cys Cys Cys Gly Ala Cys Ala Cys Cys Gly Gly Ala Gly
3005 3010 3015

Cys Thr Cys Thr Ala Cys Gly Thr Gly Cys Thr Cys Cys Thr Cys
3020 3025 3030

Ala Gly Gly Gly Gly Ala Gly Gly Ala Thr Thr Cys Cys Gly Thr
3035 3040 3045

Cys Thr Thr Cys Thr Cys Thr Cys Ala Thr Gly Ala Gly Cys Cys
3050 3055 3060

Gly Cys Thr Gly Cys Cys Cys Gly Ala Gly Gly Ala Gly Cys Cys
3065 3070 3075

Cys Thr Gly Cys Cys Thr Gly Cys Cys Cys Cys Gly Ala Cys Ala 3080 3085 3090

Cys Cys Cys Ala Gly Cys Cys Cys Ala Gly Cys Thr Thr Gly Cys
3095 3100 3105

Cys Ala Ala Thr Gly Gly Cys Gly Gly Ala Cys Thr Cys Ala Ala
3110 3115 3120

Ala Cys Gly Cys Cys Gly Cys Thr Gly Ala Cys Thr Gly Cys Cys
3125 3130 3135

Ala Cys Cys Cys Ala Cys Ala Cys Gly Cys Cys Cys Thr Cys Cys
3140 3145 3150

Cys Cys Ala Gly Ala Cys Thr Cys Cys Ala Cys Cys Gly Thr Cys
3155 3160 3165

Ala Gly Cys Thr Gly Thr Ala Ala Cys Cys Cys Thr Cys Ala Cys
3170 3175 3180

Cys Cys Ala Cys Ala Gly Cys Cys Cys Cys Thr Gly Cys Thr Gly
3185 3190 3195

Gly Gly Cys Cys Cys Ala Cys Cys Ala Cys Cys Thr Gly Thr Cys
3200 3205 3210

Cys Gly Thr Cys Cys Cys Thr Gly Thr Cys Cys Cys Cys Thr Thr
3215 3220 3225

Thr Cys Cys Thr Gly Cys Thr Gly Gly Cys Ala Gly Gly Ala Gly
3230 3235 3240

Cys Cys Gly Gly Cys Thr Gly Cys Cys Thr Ala Cys Cys Ala Gly
3245 3250 3255

Gly Gly Gly Cys Cys Thr Thr Cys Cys Thr Gly Thr Gly Thr Gly
3260 3265 3270

Gly Cys Cys Thr Gly Cys Cys Thr Thr Cys Ala Cys Cys Cys Cys
3275 3280 3285

Ala Cys Thr Cys Ala Gly Cys Thr Cys Ala Cys Cys Thr Cys Thr
3290 3295 3300

Cys Cys Cys Thr Cys Cys Ala Cys Cys Thr Cys Cys Thr Cys Thr
3305 3310 3315

Cys Cys Ala Cys Cys Thr Gly Cys Thr Gly Gly Thr Gly Ala Gly
3320 3325 3330

Ala Gly Gly Thr Gly Cys Ala Ala Ala Gly Ala Gly Gly Cys Ala
3335 3340 3345

Gly Ala Thr Cys Thr Thr Thr Gly Cys Thr Gly Cys Cys Ala Gly
3350 3355 3360

Cys Cys Ala Cys Thr Thr Cys Ala Thr Cys Cys Cys Cys Thr Cys
3365 3370 3375

Cys Cys Ala Gly Ala Thr Gly Thr Thr Gly Gly Ala Cys Cys Ala
3380 3385 3390

Ala Cys Ala Cys Cys Cys Cys Thr Cys Cys Cys Thr Gly Cys Cys
3395 3400 3405

Ala Cys Cys Ala Gly Gly Cys Ala Cys Thr Gly Cys Cys Thr Gly
3410 3415 3420

Gly Ala Gly Gly Gly Cys Ala Gly Gly Gly Ala Gly Thr Gly Gly
3425 3430 3435

Gly Ala Gly Cys Cys Ala Ala Thr Gly Ala Ala Cys Ala Gly Gly
3440 3445 3450

Cys Ala Thr Gly Cys Ala Ala Gly Thr Gly Ala Gly Ala Gly Cys
3455 3460 3465

Thr Thr Cys Cys Thr Gly Ala Gly Cys Thr Thr Thr Cys Thr Cys
3470 3475 3480

```
Cys Thr Gly Thr Cys Gly Gly Thr Thr Gly Gly Thr Cys Thr
    3485            3490                3495

Gly Thr Thr Thr Thr Gly Cys Cys Thr Thr Cys Ala Cys Cys Cys
    3500            3505                3510

Ala Thr Ala Ala Gly Cys Cys Cys Cys Thr Cys Gly Cys Ala Cys
    3515            3520                3525

Thr Cys Thr Gly Gly Thr Gly Gly Cys Ala Gly Thr Gly Cys
    3530            3535                3540

Cys Thr Thr Gly Thr Cys Cys Thr Cys Ala Gly Gly Cys Thr
    3545            3550                3555

Ala Cys Ala Gly Cys Ala Gly Thr Ala Gly Gly Ala Gly Gly
    3560            3565                3570

Thr Cys Ala Gly Thr Gly Cys Thr Thr Cys Gly Thr Gly Cys Cys
    3575            3580                3585

Thr Cys Gly Ala Thr Thr Gly Ala Ala Gly Gly Thr Gly Ala Cys
    3590            3595                3600

Cys Thr Cys Thr Gly Cys Cys Cys Cys Ala Gly Ala Thr Ala Gly
    3605            3610                3615

Gly Thr Gly Gly Thr Gly Cys Cys Ala Gly Thr Gly Gly Cys Thr
    3620            3625                3630

Thr Ala Thr Thr Ala Ala Thr Thr Cys Cys Gly Ala Thr Ala Cys
    3635            3640                3645

Thr Ala Gly Thr Thr Thr Gly Cys Thr Thr Thr Gly Cys Thr Gly
    3650            3655                3660

Ala Cys Cys Ala Ala Ala Thr Gly Cys Cys Thr Gly Gly Thr Ala
    3665            3670                3675

Cys Cys Ala Gly Ala Gly Gly Ala Thr Gly Gly Thr Gly Ala Gly
    3680            3685                3690

Gly Cys Gly Ala Ala Gly Gly Cys Cys Ala Gly Gly Thr Thr Gly
    3695            3700                3705

Gly Gly Gly Gly Cys Ala Gly Thr Gly Thr Thr Gly Thr Gly Gly
    3710            3715                3720

Cys Cys Cys Thr Gly Gly Gly Gly Cys Cys Cys Ala Gly Cys Cys
    3725            3730                3735

Cys Cys Ala Ala Ala Cys Thr Gly Gly Gly Gly Cys Thr Cys
    3740            3745                3750

Thr Gly Thr Ala Thr Ala Thr Ala Gly Cys Thr Ala Thr Gly Ala
    3755            3760                3765

Ala Gly Ala Ala Ala Ala Cys Ala Cys Ala Ala Ala Gly Thr Gly
    3770            3775                3780

Thr Ala Thr Ala Ala Ala Thr Cys Thr Gly Ala Gly Thr Ala Thr
    3785            3790                3795

Ala Thr Ala Thr Thr Thr Ala Cys Ala Thr Gly Thr Cys Thr Thr
    3800            3805                3810

Thr Thr Thr Ala Ala Ala Ala Gly Gly Gly Thr Cys Gly Thr Thr
    3815            3820                3825

Ala Cys Cys Ala Gly Ala Gly Ala Thr Thr Thr Ala Cys Cys Cys
    3830            3835                3840

Ala Thr Cys Gly Gly Gly Thr Ala Ala Gly Ala Thr Gly Cys Thr
    3845            3850                3855

Cys Cys Thr Gly Gly Thr Gly Gly Cys Thr Gly Gly Ala Gly
    3860            3865                3870
```

```
Gly Cys Ala Thr Cys Ala Gly Thr Thr Gly Cys Thr Ala Thr Ala
    3875              3880              3885

Thr Ala Thr Thr Ala Ala Ala Ala Ala Cys Ala Ala Ala Ala Ala
    3890              3895              3900

Ala Ala Ala Ala Ala Ala Ala Ala Ala Ala
    3905              3910

<210> SEQ ID NO 23
<211> LENGTH: 508
<212> TYPE: PRT
<213> ORGANISM: homo sapiens

<400> SEQUENCE: 23

Met Gly Ser Cys Cys Ser Cys Pro Asp Lys Asp Thr Val Pro Asp Asn
1               5                   10                  15

His Arg Asn Lys Phe Lys Val Ile Asn Val Asp Asp Gly Asn Glu
            20                  25                  30

Leu Gly Ser Gly Ile Met Glu Leu Thr Asp Thr Glu Leu Ile Leu Tyr
        35                  40                  45

Thr Arg Lys Arg Asp Ser Val Lys Trp His Tyr Leu Cys Leu Arg Arg
50                  55                  60

Tyr Gly Tyr Asp Ser Asn Leu Phe Ser Phe Glu Ser Gly Arg Arg Cys
65                  70                  75                  80

Gln Thr Gly Gln Gly Ile Phe Ala Phe Lys Cys Ala Arg Ala Glu Glu
                85                  90                  95

Leu Phe Asn Met Leu Gln Glu Ile Met Gln Asn Asn Ser Ile Asn Val
            100                 105                 110

Val Glu Glu Pro Val Val Glu Arg Asn Asn His Gln Thr Glu Leu Glu
        115                 120                 125

Val Pro Arg Thr Pro Arg Thr Pro Thr Pro Gly Phe Ala Ala Gln
    130                 135                 140

Asn Leu Pro Asn Gly Tyr Pro Arg Tyr Pro Ser Phe Gly Asp Ala Ser
145                 150                 155                 160

Ser His Pro Ser Ser Arg His Pro Ser Val Gly Ser Ala Arg Leu Pro
                165                 170                 175

Ser Val Gly Glu Glu Ser Thr His Pro Leu Leu Val Ala Glu Gln
            180                 185                 190

Val His Thr Tyr Val Asn Thr Thr Gly Val Gln Glu Glu Arg Lys Asn
        195                 200                 205

Arg Thr Ser Val His Val Pro Leu Glu Ala Arg Val Ser Asn Ala Glu
    210                 215                 220

Ser Ser Thr Pro Lys Glu Glu Pro Ser Ser Ile Glu Asp Arg Asp Pro
225                 230                 235                 240

Gln Ile Leu Leu Glu Pro Glu Gly Val Lys Phe Val Leu Gly Pro Thr
                245                 250                 255

Pro Val Gln Lys Gln Leu Met Glu Lys Glu Lys Leu Glu Gln Leu Gly
            260                 265                 270

Arg Asp Gln Val Ser Gly Ser Gly Ala Asn Asn Thr Glu Trp Asp Thr
        275                 280                 285

Gly Tyr Asp Ser Asp Glu Arg Arg Asp Ala Pro Ser Val Asn Lys Leu
    290                 295                 300

Val Tyr Glu Asn Ile Asn Gly Leu Ser Ile Pro Ser Ala Ser Gly Val
305                 310                 315                 320

Arg Arg Gly Arg Leu Thr Ser Thr Ser Thr Ser Asp Thr Gln Asn Ile
                325                 330                 335
```

```
Asn Asn Ser Ala Gln Arg Arg Thr Ala Leu Leu Asn Tyr Glu Asn Leu
                340                 345                 350

Pro Ser Leu Pro Pro Val Trp Glu Ala Arg Lys Leu Ser Arg Asp Glu
            355                 360                 365

Asp Asp Asn Leu Gly Pro Lys Thr Pro Ser Leu Asn Gly Tyr His Asn
370                 375                 380

Asn Leu Asp Pro Met His Asn Tyr Val Asn Thr Glu Asn Val Thr Val
385                 390                 395                 400

Pro Ala Ser Ala His Lys Ile Glu Tyr Ser Arg Arg Arg Asp Cys Thr
                405                 410                 415

Pro Thr Val Phe Asn Phe Asp Ile Arg Arg Pro Ser Leu Glu His Arg
            420                 425                 430

Gln Leu Asn Tyr Ile Gln Val Asp Leu Glu Gly Gly Ser Asp Ser Asp
                435                 440                 445

Asn Pro Gln Thr Pro Lys Thr Pro Thr Thr Pro Leu Pro Gln Thr Pro
450                 455                 460

Thr Arg Arg Thr Glu Leu Tyr Ala Val Ile Asp Ile Glu Arg Thr Ala
465                 470                 475                 480

Ala Met Ser Asn Leu Gln Lys Ala Leu Pro Arg Asp Asp Gly Thr Ser
                485                 490                 495

Arg Lys Thr Arg His Asn Ser Thr Asp Leu Pro Met
                500                 505

<210> SEQ ID NO 24
<211> LENGTH: 6676
<212> TYPE: DNA
<213> ORGANISM: homo sapiens

<400> SEQUENCE: 24
aaaacccttc cctcccccgc tcccccggaa gtgcttttcc aagattcggg ccggagagag      60
gccttgtagg cacagcggct gagactcgat ctgctccaag taggggctcc agcgcgggtc     120
ggagtctggg ggttcgcgcc cgccgacccg cgccctgctc cctctcagca cctgggcgga     180
cggttaaatc agcaaacaaa gaaaacatgg tattttgaaa tatgattaaa ctcctgatgc     240
tgcagcagag gctaagaata ttaatggcca gatctagtgc acacatggtc ttctgaagaa     300
gccatgggta gctgttgtag ctgtccagat aaagacactg tcccagataa ccatcggaac     360
aagtttaagg tcattaatgt ggatgatgat gggaatgagt taggttctgg cataatggaa     420
cttacagaca cagaactgat tttatacacc cgcaaacgtg actcagtaaa atggcactac     480
ctctgcctgc gacgctatgg ctatgactcg aatctctttt cttttgaaag tggtcgaagg     540
tgtcaaactg acaaggaat ctttgccttt aagtgtgccc gtgcagaaga attatttaac      600
atgttgcaag agattatgca aataatagt ataaatgtgg tggaagagcc agttgtagaa      660
agaaataatc atcagacaga attggaagtc cctagaacac tcgaacacc tacaactcca      720 ggatttgctg ctcagaactt acctaatgga tatccccgat atccctcatt tggagatgct     780
tcatcccatc cgtcaagcag acatccttct gtgggaagtg ctcgcctgcc ttcagtaggg     840
gaagaatcta cacatccttt gcttgtggct gaggaacaag tacataccta tgtcaacact     900
acaggtgtgc aagaagagcg gaaaaaccgc acaagtgtgc atgttccatt ggaggcgagg     960
gtttctaacg ctgaaagcag cacaccaaaa gaagaaccaa gtagtattga ggacagggat    1020
cctcagattt tcttgaacc tgaaggagtc aaatttgttt tagggccaac ccctgttcaa    1080
aagcagttaa tggaaaaaga gaaactggag caacttggaa gagatcaagt tagtggaagt    1140
```

```
ggagcaaata acacagaatg ggacactggc tatgacagtg atgaacgaag agatgcaccc    1200
tctgttaaca aactggtgta tgaaaatata aatgggctat ctatccctag tgcctcaggg    1260
gtcaggagag gtcgtctgac atccaccagt acctcagata cccagaatat caacaactca    1320
gctcagagaa gaactgcatt attaaactat gaaaatctac catctttgcc tcctgtttgg    1380
gaagcccgca agctaagtag ggatgaagat gacaatttag gaccaaagac cccatctcta    1440
aatggctacc ataataatct agatccaatg cataactatg taaatacaga gaatgtaaca    1500
gtgccagcaa gtgctcacaa aatagaatat tcaaggcgtc gggactgtac accaacagtc    1560
tttaactttg atatcagacg cccaagttta gaacacaggc agcttaatta catacaggtt    1620
gacttggaag gtggcagtga ctctgacaac cctcagactc caaaaacgcc tacaactccc    1680
cttccacaaa cccctaccag gcgcacagag ctgtatgccg tgatagacat cgagagaact    1740
gctgctatgt caaatttgca gaaagcactg ccacgagatg atggtacatc taggaaaact    1800
agacacaata gtactgatct gcccatgtga gcctggaaag cattgtgttg tttgcacctt    1860
tgtgaagttt ttaaaaatga agatgcaagt gcttcatttt catttctaaa cactaactcc    1920
ttttatagac tgataaaatt ttttttctgaa tatttcatgt gcatctttaa ctaaagggaa    1980
ttaatgtaga gcaggtactc cttaaagaac actaatttca ttatatacta ctcgttgtac    2040
agcagcattc ccgttttcac agtgcctatt taaaatgaga gttgaagtaa atgacatgct    2100
ggttgatttt tatcaatatt ctggacttaa cgcataccct tcatgtctaa gtcatggttg    2160
gcttttaaaa cttttttataa agcctcttga caatgtacat tgctaacagg taactatagg    2220 cttttgaaagt aatgctcgta gattcagtgt tcacagtatg tggcctccag catgtaacat    2280
gaggaatcct ttatttcatt aattaatggc ttttttgactt gagccaaaac atatgtaaag    2340
gaaacagaag taccgcacct cctcttacac cagtcagctc ctttgccttc agtgttacta    2400
gaaagcggcc tgtgtccatg agtgtgcttt gctgttggtg cactgaaagg caggaaggag    2460
acaagatttt ctatttactc atctcatgat gtcatttgaa gggcatgtcc agatatctta    2520
aaattataat aggctcaaga atcagtctca ggtcacttta cccaaaaaca tttgaaaatc    2580
tgaaccacaa tctcctgaaa gttttttctcc tatagattgt tgacaacaca ttgttttctg    2640
gaggcatttg tgccattagg tttccattta tcttcagttt ttttctttgg tgtttgggat    2700
gtcttatttt gttgccttat gtccttttca atttaaaatg tttgagtttg tatatagttt    2760
tgaaattgga ttatgtgttc attgttgttt agtttgcatt tttgtcaaat tatggttttg    2820
aaggttcatt tggaacttac tgttagtctg taacagggt gcccttgtcc agtatttatt    2880
tataagctgt ttacttttca agttgataaa aacattctcc aattctaaat ttgcttgtgt    2940
ccataggtga tctctttagc aaactgagaa aaaaggaag ctacttttaa catgcaaagt    3000
tccctcaagg tgtaccgtgt tgtctctgtg ggcactcttc cccagcactt tagcagtaat    3060 tccccccagct acacgctgca gttgtactct gcccactcta gtgttcctca gctctgctgt    3120
ccttttactt gtagctggat cttttgattat ccttcgattt ccatgaaata ttaatattgt    3180
tgccagcata gcaggtacag tggaagtctt gtagcagtga gattgtatca taatttagga    3240
tttaaaatga attaaagttt atataaactg aagagtctcc atatgtcaaa ctcttggaaa    3300
atcaaagatg ttccaatttc ctaaacacta gagaatacga gagaaggtag agtggaaaag    3360
gttaggtaac cttgcaaaat attttactat tttctctaaa tatgaggaag tttgagatta    3420
tgatctggat ctaccagata taactaaggt taatttagca tgaaaaagtt ttagtcatat    3480
```

```
tggcatccaa cctattcagt aaccgaatca taggacaatg atggattagg agaacaatag    3540
agtgggatca ttataaagaa aataaattat taaaggtgtc tttatcgttt tagtgccatt    3600
tttagtgtct ttactataaa tcaatatcag tgtattttat cattctatgt gcatagcaga    3660
attttctttt ctcccttttg ttccctgtg aacttggtgc ttattaaagt gctcactgtt    3720
ctcttaaaag agagcagtgg tataggtgtg cagttccat gatgcaggtt ccattttaa     3780 tatattgttc cacttatcct ttcttctgag taaattgcta attgtgccaa atttatgtaa    3840 tagttttgt aatgtggaat aagaattatg atggaaccat tgcacatttt tttctgaaac     3900
agccagtcaa ggcagaacat taatctccaa atgcaagggc tgatctattt attcattttg    3960
gaggttgggt actttattct ttctttccgt catccttttc attgtttccc ccggattcta    4020
attagttttt attttttta gataactcca atataatcat tacagtttat gcttaaata     4080 ctatgtgctt taaaaggaa aatgggacca atttgtctgc taagaatttg attttaggta    4140
ctataagagt attaggaaaa tatatacaac tggtgttaat ttctagatat tttctagaaa    4200
tcacttgtgt tcctatttaa taaaaggtaa tttagaatac tacttgtcct ttgcagtagt    4260
ttagtaatgg gcattaagct gtgtcctcga aggatgtacc tattactagg tgcatttttag   4320 aatgaaatat tgatattta ttagcatata attgtggcca tatatctcag attttctgag    4380
gcagatctaa ttttagataa ttctgttggt agaccatgtg atccttcttt ttggttttgg    4440
aaatataatc attgttaatg ttttccctcc aaatagaata ctgttttatc catacaaatc    4500
ataacagcat ctatcccatg ctagggttgg aaactgatat tggtattact tgtgttttt    4560 cttagtgtgt tttatttccc agtttcatct tcttctaaaa atgaaaatat ggtgccttcc    4620
ctccctccag gaagactggc aaatatttcc ttttatttac tgctgctgtg gagtgatgag    4680
atatgcactt tactctttaa gattcagcaa aaagcttttc acttctcagt atatccagaa    4740
tacatcatat ctgggactta ggaaaatttg ccaagcaatc tttgttttta tagatactaa    4800 tgttgacct ctccagcgtt caatgttata aatagaacaa gtcaagctag tgtttatctc     4860
ctccccctcc ccaaaactgt ggcacagcat ataaaatgt acctcaataa tgttctatta     4920
aaaatgggac aggggcctta tgttttcata atttcccaac aatgtgccgc catattttg     4980 cctcaaggta aaggttttaa cagatgaaaa agtacttccc aattccccg tgctattcct     5040 aacctataat gcccaaatgt tttgtgcaat gtgtagtgtg tgtgtataaa tacatatatt    5100
cttgaaatag acataccatc agagacatca ttcacaagta actgatgtat tggcatctca    5160
ttcatatttc tgatgtgtga ggtatatggt actaattacc ttttccttga tgtttgccaa    5220
atttgaataa aggcattggt acgaaattac agaatgtaaa gaaaatgttt ttggcttgaa    5280
aaattaacat attttatgac gtaccacagt atactctgcc caaaccagca ccctatctat    5340
ctttcctgtt ctttacatcc ctgttcccca tccctacttc ctcattttg gtataacaca     5400 gttcttttgt agcatcatta taattgcagt tctatggcaa ttggacagtt atagcatgga    5460
aacagactgg tataagtagt acagtagtca ccagtgtgcc acatttgcat tagtaatgca    5520
aaatatacat tttataaagg acaaactttg tgttatgttt tattttcatt acattgtata    5580
atattgtaag actattgtat gtcctaattt gcattataaa tgttttttc ctacgtaaag     5640 gcataaatat agcaactttg tataaaggta gcttattaga ttttaatttt tttctttat    5700 aaaaaattgt ccaacagtgg gactaccatt gccaaattgt atatgaaata tgaattttac    5760
ccccatggtt aatttctttt ataaacattc catatttctc taataaaaag acataagtga    5820
tactgtacta tgcatacatt gtatcttaat gctgtttcag atcagcattt taaattttgg   5880
```

```
tttgcatttt taatattggc aaaacgtaac cactgttaat taaaataaaa ccttgttgta    5940
tatgtaacaa cataatttc cctctatccc ttcccaccct ttgttctcta tttctcccta    6000
tcagtgccaa cttcatacat tttgtagcat ggcaataaaa tataactttt acactgaggc    6060
cgagtgtggc tttttggagg aagtgggat gggacgattg ccctctagtt gtcctttgca    6120
tatgactgtt ttttgccata taagccatgt catcaggcat gaaaagtttt ctcatatatg    6180
atgtaaactt gcttttaagg acaagtgtga atgtgctttt taagcttaat ttttgtcatg    6240
acaactaatt ttttttatct ttggagaagt cagagttctt tacaatcaaa cgtttattaa    6300
ctggagtact tagaataagc tagtaattga atttagttca agggctaagc aacacatttt    6360
taaatcctta tttattgtag agtattagta tactgtccta caaattatgt aaaatatggt    6420
ttaatattag atgactttgg atttgcaat gccttactgt tgtcattcta gcataaatat    6480
ccataatgag gtactcaagt tgatactgga agctgagctg atcatacact gacctgaagc    6540
attcatgaaa agctgcttta ttgaataaag tctgattgga gttcttttca tgctcacttt    6600
ccccttattg ctgaaagtag attgcaataa accccaata aaacgtttgg tcggatatct    6660
acttaaaaaa aaaaaa                                                    6676
```

<210> SEQ ID NO 25
<211> LENGTH: 390
<212> TYPE: PRT
<213> ORGANISM: homo sapiens

<400> SEQUENCE: 25

```
Met Pro Pro Ser Gly Leu Arg Leu Leu Leu Leu Leu Pro Leu Leu
 1               5                  10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220
```

```
Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
            290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
370                 375                 380

Arg Ser Cys Lys Cys Ser
385                 390
```

<210> SEQ ID NO 26
<211> LENGTH: 1746
<212> TYPE: DNA
<213> ORGANISM: homo sapiens

<400> SEQUENCE: 26

| | | | | |
|---|---|---|---|---|
| cccagacctc | gggcgcaccc | cctgcacgcc | gccttcatcc | ccggcctgtc | tcctgagccc | 60 |
| ccgcgcatcc | tagacccttt | ctcctccagg | agacggatct | ctctccgacc | tgccacagat | 120 |
| cccctattca | agaccaccca | ccttctggta | ccagatcgcg | cccatctagg | ttatttccgt | 180 |
| gggatactga | gacaccccg | gtccaagcct | ccctccacc | actgcgccct | tctccctgag | 240 |
| gacctcagct | ttccctcgag | gccctcctac | cttttgccgg | gagaccccca | gcccctgcag | 300 |
| gggcggggcc | tccccaccac | accagccctg | ttcgcgctct | cggcagtgcc | gggggggcgcc | 360 |
| gcctccccca | tgccgccctc | cgggctgcgg | ctgctgctgc | tgctgctacc | gctgctgtgg | 420 |
| ctactggtgc | tgacgcctgg | ccggccggcc | gcgggactat | ccacctgcaa | gactatcgac | 480 |
| atggagctgg | tgaagcggaa | gcgcatcgag | gccatccgcg | ccagatcct | gtccaagctg | 540 |
| cggctcgcca | gcccccgag | ccaggggag | gtgccgcccg | gccgctgcc | cgaggccgtg | 600 |
| ctcgccctgt | acaacagcac | ccgcgaccgg | gtggccgggg | agagtgcaga | accggagccc | 660 |
| gagcctgagg | ccgactacta | cgccaaggag | gtcacccgcg | tgctaatggt | ggaaacccac | 720 |
| aacgaaatct | atgacaagtt | caagcagagt | acacacagca | tatatatgtt | cttcaacaca | 780 |
| tcagagctcc | gagaagcggt | aacctgaaccc | gtgttgctct | cccgggcaga | gctgcgtctg | 840 |
| ctgaggctca | gttaaaagt | ggagcagcac | gtggagctgt | accagaaata | cagcaacaat | 900 |
| tcctggcgat | acctcagcaa | ccggctgctg | cacccagcg | actcgccaga | gtggttatct | 960 |
| tttgatgtca | ccggagttgt | gcggcagtgg | ttgagccgtg | gagggaaat | tgagggcttt | 1020 |
| cgccttagcg | cccactgctc | ctgtgacagc | agggataaca | cactgcaagt | ggacatcaac | 1080 |
| gggttcacta | ccggccgccg | aggtgacctg | gccaccattc | atggcatgaa | ccggccttc | 1140 |

-continued

```
ctgcttctca tggccacccc gctggagagg gcccagcatc tgcaaagctc ccggcaccgc    1200
cgagccctgg acaccaacta ttgcttcagc tccacggaga agaactgctg cgtgcggcag    1260
ctgtacattg acttccgcaa ggacctcggc tggaagtgga tccacgagcc caagggctac    1320
catgccaact tctgcctcgg gccctgcccc tacatttgga gcctggacac gcagtacagc    1380
aaggtcctgg ccctgtacaa ccagcataac ccgggcgcct cggcggcgcc gtgctgcgtg    1440
ccgcaggcgc tggagccgct gcccatcgtg tactacgtgg gccgcaagcc caaggtggag    1500
cagctgtcca acatgatcgt gcgctcctgc aagtgcagct gaggtcccgc cccgccccgc    1560
cccgccccgg caggcccggc cccacccgc cccgccccg ctgccttgcc catgggggct    1620
gtatttaagg acacccgtgc cccaagccca cctggggccc cattaaagat ggagagagga    1680
aaaaaaaaaa aaaaaaaaaa aaaaaaaaaa aaaaaaaaaa aaaaaaaaaa aaaaaaaaaa    1740
aaaaaa                                                                1746
```

<210> SEQ ID NO 27
<211> LENGTH: 413
<212> TYPE: PRT
<213> ORGANISM: homo sapiens

<400> SEQUENCE: 27

```
Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Ala Ile Pro Pro Thr Phe Tyr Arg Pro Tyr Phe Arg Ile
        115                 120                 125

Val Arg Phe Asp Val Ser Ala Met Glu Lys Asn Ala Ser Asn Leu Val
    130                 135                 140

Lys Ala Glu Phe Arg Val Phe Arg Leu Gln Asn Pro Lys Ala Arg Val
145                 150                 155                 160

Pro Glu Gln Arg Ile Glu Leu Tyr Gln Ile Leu Lys Ser Lys Asp Leu
                165                 170                 175

Thr Ser Pro Thr Gln Arg Tyr Ile Asp Ser Lys Val Val Lys Thr Arg
            180                 185                 190

Ala Glu Gly Glu Trp Leu Ser Phe Asp Val Thr Asp Ala Val His Glu
        195                 200                 205

Trp Leu His His Lys Asp Arg Asn Leu Gly Phe Lys Ile Ser Leu His
    210                 215                 220

Cys Pro Cys Cys Thr Phe Val Pro Ser Asn Asn Tyr Ile Ile Pro Asn
225                 230                 235                 240

Lys Ser Glu Glu Leu Glu Ala Arg Phe Ala Gly Ile Asp Gly Thr Ser
                245                 250                 255

Thr Tyr Thr Ser Gly Asp Gln Lys Thr Ile Lys Ser Thr Arg Lys Lys
```

```
                  260                 265                 270
Asn Ser Gly Lys Thr Pro His Leu Leu Met Leu Leu Pro Ser Tyr
            275                 280                 285

Arg Leu Glu Ser Gln Gln Thr Asn Arg Arg Lys Lys Arg Ala Leu Asp
            290                 295                 300

Ala Ala Tyr Cys Phe Arg Asn Val Gln Asp Asn Cys Cys Leu Arg Pro
305                 310                 315                 320

Leu Tyr Ile Asp Phe Lys Arg Asp Leu Gly Trp Lys Trp Ile His Glu
                325                 330                 335

Pro Lys Gly Tyr Asn Ala Asn Phe Cys Ala Gly Ala Cys Pro Tyr Leu
                340                 345                 350

Trp Ser Ser Asp Thr Gln His Ser Arg Val Leu Ser Leu Tyr Asn Thr
            355                 360                 365

Ile Asn Pro Glu Ala Ser Ala Ser Pro Cys Cys Val Ser Gln Asp Leu
            370                 375                 380

Glu Pro Leu Thr Ile Leu Tyr Tyr Ile Gly Lys Thr Pro Lys Ile Glu
385                 390                 395                 400

Gln Leu Ser Asn Met Ile Val Lys Ser Cys Lys Cys Ser
                405                 410
```

<210> SEQ ID NO 28
<211> LENGTH: 2570
<212> TYPE: DNA
<213> ORGANISM: homo sapiens

<400> SEQUENCE: 28

```
gcccctcccg tcagttcgcc agctgccagc cccgggacct tttcatctct tcccttttgg   60
ccggaggagc cgagttcaga tccgccactc cgcacccgag actgacacac tgaactccac  120
ttcctcctct taaatttatt tctacttaat agccactcgt ctcttttttt ccccatctca  180
ttgctccaag aattttttc ttcttactcg ccaaagtcag ggttccctct gcccgtcccg   240
tattaatatt tccacttttg gaactactgg ccttttcttt ttaaaggaat tcaagcagga  300
tacgtttttc tgttgggcat tgactagatt gtttgcaaaa gtttcgcatc aaaaacaaca  360
acaacaaaaa accaaacaac tctccttgat ctatactttg agaattgttg atttcttttt  420
tttattctga cttttaaaaa caactttttt ttccactttt ttaaaaaatg cactactgtg  480
tgctgagcgc ttttctgatc ctgcatctgg tcacggtcgc gctcagcctg tctacctgca  540
gcacactcga tatggaccag ttcatgcgca agaggatcga ggcgatccgc gggcagatcc  600
tgagcaagct gaagctcacc agtccccag aagactatcc tgagcccgag aagtccccc   660
cggaggtgat ttccatctac aacagcacca gggacttgct ccaggagaag gcgagccgga  720
gggcggccgc ctgcgagcgc gagaggagcg acgaagagta ctacgccaag gaggtttaca  780
aaatagacat gccgccttc ttccctcccg aaactgtctg cccagttgtt acaacaccct  840
ctggctcagt gggcagcttg tgctccagac agtcccaggt gctctgtggg taccttgatg  900
ccatcccgcc cactttctac agaccctact tcagaattgt tcgatttgac gtctcagcaa  960
tggagaagaa tgcttccaat ttggtgaaag cagagttcag agtctttcgt ttgcagaacc 1020
caaaagccag agtgcctgaa caacggattg agctatatca gattctcaag tccaaagatt 1080
taacatctcc aacccagcgc tacatcgaca gcaaagttgt gaaaacaaga gcagaaggcg 1140
aatggctctc cttcgatgta actgatgctg ttcatgaatg gcttcaccat aaagacagga 1200
acctgggatt taaaataagc ttacactgtc cctgctgcac ttttgtacca tctaataatt 1260
```

```
acatcatccc aaataaaagt gaagaactag aagcaagatt tgcaggtatt gatggcacct    1320
ccacatatac cagtggtgat cagaaaacta taaagtccac taggaaaaaa aacagtggga    1380
agaccccaca tctcctgcta atgttattgc cctcctacag acttgagtca caacagacca    1440
accggcggaa gaagcgtgct ttggatgcgg cctattgctt tagaaatgtg caggataatt    1500
gctgcctacg tccactttac attgatttca gagggatct  agggtggaaa tggatacacg    1560
aacccaaagg gtacaatgcc aacttctgtg ctggagcatg cccgtattta tggagttcag    1620
acactcagca cagcagggtc ctgagcttat ataataccat aaatccagaa gcatctgctt    1680
ctccttgctg cgtgtcccaa gatttagaac ctctaaccat tctctactac attggcaaaa    1740
cacccaagat tgaacagctt tctaatatga ttgtaaagtc ttgcaaatgc agctaaaatt    1800
cttggaaaag tggcaagacc aaaatgacaa tgatgatgat aatgatgatg acgacgacaa    1860
cgatgatgct tgtaacaaga aaacataaga gagccttggt tcatcagtgt taaaaaattt    1920
ttgaaaaggc ggtactagtt cagacacttt ggaagtttgt gttctgtttg ttaaaactgg    1980
catctgacac aaaaaaagtt gaaggcctta ttctacattt cacctacttt gtaagtgaga    2040
gagacaagaa gcaaattttt tttaaagaaa aaaataaaca ctggaagaat ttattagtgt    2100
taattatgtg aacaacgaca acaacaacaa caacaacaaa caggaaaatc ccattaagtg    2160
gagttgctgt acgtaccgtt cctatcccgc gcctcacttg attttctgt  attgctatgc    2220
aataggcacc cttcccattc ttactcttag agttaacagt gagttattta ttgtgtgtta    2280
ctatataatg aacgtttcat tgcccttgga aaataaaaca ggtgtataaa gtggagacca    2340
aatactttgc cagaaaactca tggatggctt aaggaacttg aactcaaacg agccagaaaa    2400
aaagaggtca tattaatggg atgaaaaccc aagtgagtta ttatatgacc gagaaagtct    2460
gcattaagat aaagaccctg aaaacacatg ttatgtatca gctgcctaag gaagcttctt    2520
gtaaggtcca aaaactaaaa agactgttaa taaaagaaac tttcagtcag                2570
```

<210> SEQ ID NO 29
<211> LENGTH: 412
<212> TYPE: PRT
<213> ORGANISM: homo sapiens

<400> SEQUENCE: 29

```
Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Lys Arg Val Glu Ala Ile Arg Gly Gln Ile Leu
            35                  40                  45

Ser Lys Leu Arg Leu Thr Ser Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
    130                 135                 140
```

```
Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
            165                 170                 175

Asp Glu His Ile Ala Lys Gln Arg Tyr Ile Gly Gly Lys Asn Leu Pro
        180                 185                 190

Thr Arg Gly Thr Ala Glu Trp Leu Ser Phe Asp Val Thr Asp Thr Val
    195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
            245                 250                 255

Asp His Gly Arg Gly Asp Leu Gly Arg Leu Lys Lys Gln Lys Asp
        260                 265                 270

His His Asn Pro His Leu Ile Leu Met Met Ile Pro Pro His Arg Leu
            275                 280                 285

Asp Asn Pro Gly Gln Gly Gly Gln Arg Lys Lys Arg Ala Leu Asp Thr
290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
            325                 330                 335

Lys Gly Tyr Tyr Ala Asn Phe Cys Ser Gly Pro Cys Pro Tyr Leu Arg
        340                 345                 350

Ser Ala Asp Thr Thr His Ser Thr Val Leu Gly Leu Tyr Asn Thr Leu
    355                 360                 365

Asn Pro Glu Ala Ser Ala Ser Pro Cys Cys Val Pro Gln Asp Leu Glu
370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
            405                 410
```

<210> SEQ ID NO 30
<211> LENGTH: 930
<212> TYPE: DNA
<213> ORGANISM: homo sapiens

<400> SEQUENCE: 30

```
atgaagatgc acttgcaaag ggctctggtg gtcctggccc tgctgaactt tgccacggtc      60
agcctctctc tgtccacttg caccaccttg gacttcggcc acatcaagaa gaagagggtg     120
gaagccatta ggggacagat cttgagcaag ctcaggctca ccagccccccc tgagccaacg    180
gtgatgaccc acgtccccta tcaggtcctg gcctttaca acagcacccg ggagctgctg      240
gaggagatgc atggggagag ggaggaaggc tgcacccagg aaaacaccga gtcggaatac     300
tatgccaaag aaatccataa attcgacatg atccaggggc tggcggagca caacgaactg    360
gctgtctgcc ctaaaggaat tacctccaag gttttccgct tcaatgtgtc ctcagtggag    420
aaaaatagaa ccaacctatt ccgagcagaa ttccgggtct gcgggtgcc aaccccagc      480
tctaagcgga atgagcagag gatcgagctc ttccagatcc ttcggccaga tgagcacatt    540
gccaaacagc gctatatcgg tggcaagaat ctgcccacac ggggcactgc cgagtggctg    600
```

```
tcctttgatg tcactgacac tgtgcgtgag tggctgttga agagagagtc caacttaggt    660
ctagaaatca gcattcactg tccatgtcac acctttcagc ccaatggaga tatcctggaa    720
aacattcacg aggtgatgga aatcaaattc aaaggcgtgg acaatgagga tgaccatggc    780
cgtggagatc tggggcgcct caagaagcag aaggatcacc acaaccctca tctaatcctc    840
atgatgattc ccccacaccg gctcgacaac ccgggccagg ggggtcagag gaagaagcgg    900
gctttggaca ccaattactg cttccggtag                                      930
```

```
<210> SEQ ID NO 31
<211> LENGTH: 426
<212> TYPE: PRT
<213> ORGANISM: homo sapiens

<400> SEQUENCE: 31
```

```
Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Leu Pro Leu Leu Val Gln Arg Thr Ile Ala Arg Thr Ile
        115                 120                 125

Val Leu Gln Glu Ser Ile Gly Lys Gly Arg Phe Gly Glu Val Trp Arg
    130                 135                 140

Gly Lys Trp Arg Gly Glu Glu Val Ala Val Lys Ile Phe Ser Ser Arg
145                 150                 155                 160

Glu Glu Arg Ser Trp Phe Arg Glu Ala Glu Ile Tyr Gln Thr Val Met
                165                 170                 175

Leu Arg His Glu Asn Ile Leu Gly Phe Ile Ala Ala Asp Asn Lys Asp
            180                 185                 190

Asn Gly Thr Trp Thr Gln Leu Trp Leu Val Ser Asp Tyr His Glu His
        195                 200                 205

Gly Ser Leu Phe Asp Tyr Leu Asn Arg Tyr Thr Val Thr Val Glu Gly
    210                 215                 220

Met Ile Lys Leu Ala Leu Ser Thr Ala Ser Gly Leu Ala His Leu His
225                 230                 235                 240

Met Glu Ile Val Gly Thr Gln Gly Lys Pro Ala Ile Ala His Arg Asp
                245                 250                 255

Leu Lys Ser Lys Asn Ile Leu Val Lys Lys Asn Gly Thr Cys Cys Ile
            260                 265                 270

Ala Asp Leu Gly Leu Ala Val Arg His Asp Ser Ala Thr Asp Thr Ile
        275                 280                 285

Asp Ile Ala Pro Asn His Arg Val Gly Thr Lys Arg Tyr Met Ala Pro
    290                 295                 300

Glu Val Leu Asp Asp Ser Ile Asn Met Lys His Phe Glu Ser Phe Lys
305                 310                 315                 320
```

Arg Ala Asp Ile Tyr Ala Met Gly Leu Val Phe Trp Glu Ile Ala Arg
            325                 330                 335

Arg Cys Ser Ile Gly Gly Ile His Glu Asp Tyr Gln Leu Pro Tyr Tyr
            340                 345                 350

Asp Leu Val Pro Ser Asp Pro Ser Val Glu Glu Met Arg Lys Val Val
            355                 360                 365

Cys Glu Gln Lys Leu Arg Pro Asn Ile Pro Asn Arg Trp Gln Ser Cys
    370                 375                 380

Glu Ala Leu Arg Val Met Ala Lys Ile Met Arg Glu Cys Trp Tyr Ala
385                 390                 395                 400

Asn Gly Ala Ala Arg Leu Thr Ala Leu Arg Ile Lys Lys Thr Leu Ser
            405                 410                 415

Gln Leu Ser Gln Gln Glu Gly Ile Lys Met
            420                 425

<210> SEQ ID NO 32
<211> LENGTH: 5766
<212> TYPE: DNA
<213> ORGANISM: homo sapiens

<400> SEQUENCE: 32

```
gcggcggcta gggaggtggg gcgaggcgag gtttgctggg gtgaggcagc ggcgcggccg      60
ggccgggccg ggccacaggc ggtggcggcg ggaccatgga ggcggcggtc gctgctccgc     120
gtccccggct gctcctcctc gtgctggcgg cggcggcggc ggcggcggcg cgctgctcc      180
cggggcgac ggcgttacag tgtttctgcc acctctgtac aaaagacaat tttacttgtg     240
tgacagatgg gctctgcttt gtctctgtca cagagaccac agacaaagtt atacacaaca    300
gcatgtgtat agctgaaatt gacttaattc ctcgagatag gccgtttgta tgtgcaccct    360
cttcaaaaac tgggtctgtg actacaacat attgctgcaa tcaggaccat gcaataaaa     420
tagaacttcc aactactggt ttaccattgc ttgttcagag aacaattgcg agaactattg    480
tgttacaaga aagcattggc aaaggtcgat ttggagaagt ttggagagga agtggcgggg   540
gagaagaagt tgctgttaag atattctcct ctagagaaga acgttcgtgg ttccgtgagg    600
cagagattta tcaaactgta atgttacgtc atgaaaacat cctgggattt atagcagcag    660
acaataaaga caatggtact tggactcagc tctggttggt gtcagattat catgagcatg    720
gatccctttt tgattactta aacagataca cagttactgt ggaaggaatg ataaaacttg    780
ctctgtccac ggcgagcggt cttgcccatc ttcacatgga gattgttggt acccaaggaa    840
agccagccat tgctcataga gatttgaaat caaagaatat cttggtaaag aagaatggaa    900
cttgctgtat tgcagactta ggactggcag taagacatga ttcagccaca gataccattg    960
atattgctcc aaaccacaga gtgggaacaa aaaggtacat ggcccctgaa gttctcgatg   1020
attccataaa tatgaaacat tttgaatcct tcaaacgtgc tgacatctat gcaatgggct   1080
tagtattctg ggaaattgct cgacgatgtt ccattggtgg aattcatgaa gattaccaac   1140
tgccttatta tgatcttgta ccttctgacc catcagttga agaaatgaga aagttgtttt   1200
gtgaacagaa gttaaggcca aatatcccaa acagatggca gagctgtgaa gccttgagag   1260
taatggctaa aattatgaga gaatgttggt atgccaatgg agcagctagg cttacagcat   1320
tgcggattaa gaaaacatta tcgcaactca gtcaacagga aggcatcaaa atgtaattct   1380
acagctttgc ctgaactctc ctttttttctt cagatctgct cctgggtttt aattgggag     1440
gtcaattgtt ctacctcact gagagggaac agaaggatat tgcttccttt tgcagcagtg    1500
```

```
taataaagtc aattaaaaac ttcccaggat ttctttggac ccaggaaaca gccatgtggg    1560
tcctttctgt gcactatgaa cgcttctttc ccaggacaga aaatgtgtag tctaccttta    1620
tttttattta acaaaacttg tttttaaaa agatgattgc tggtcttaac tttaggtaac    1680
tctgctgtgc tggagatcat ctttaagggc aaaggagttg gattgctgaa ttacaatgaa    1740
acatgtctta ttactaaaga aagtgattta ctcctggtta gtacattctc agaggattct    1800
gaaccactag agtttccttg attcagactt tgaatgtact gttctatagt ttttcaggat    1860
cttaaaacta acacttataa aactcttatc ttgagtctaa aaatgacctc atatagtagt    1920
gaggaacata attcatgcaa ttgtattttg tatactatta ttgttctttc acttattcag    1980
aacattacat gccttcaaaa tgggattgta ctataccagt aagtgccact tctgtgtctt    2040
tctaatggaa atgagtagaa ttgctgaaag tctctatgtt aaaacctata gtgtttgaat    2100
tcaaaaagct tatttatctg ggtaacccaa acttttctg ttttgttttt ggaagggttt     2160
ttgtggtatg tcatttggta ttctattctg aaaatgcctt tctcctacca aaatgtgctt    2220
aagccactaa agaaatgaag tggcattaat tagtaaatta ttagcatggt catgtttgaa    2280
tattctcaca tcaagctttt gcattttaat tgtgttgtct aagtatactt ttaaaaaatc    2340
aagtggcact ctagatgctt atagtacttt aatatttgta gcatacagac taattttct     2400 aaaagggaaa gtctgtctag ctgcttgtga aaagttatgt ggtattctgt aagccatttt    2460
tttctttatc tgttcaaaga cttatttttt aagacatgaa ttacatttaa aattagaata    2520
tggttaatat taaataatag gccttttct aggaaggcga aggtagttaa taatttgaat      2580
agataacaga tgtgcaagaa agtcacattt gttatgtatg taggagtaaa cgttcggtgg    2640
atcctctgtc tttgtaactg aggttagagc tagtgtggtt ttgaggtctc actacacttt    2700
gaggaaggca gcttttaatt cagtgtttcc ttatgtgtgc gtacattgca actgcttaca    2760
tgtaatttat gtaatgcatt cagtgcaccc ttgttacttg ggagaggtgg tagctaaaga    2820
acattctgag tataggtttt tctccattta cagatgtctt tggtcaaata ttgaaagcaa    2880
acttgtcatg gtcttcttac attaagttga aactagctta taataactgg tttttacttc    2940
caatgctatg aagtctctgc agggctttta cagttttcga agtcctttta tcactgtgat    3000
cttattctga ggggagaaaa aactatcata gctctgaggc aagacttcga ctttatagtg    3060
ctatcagttc cccgatacag ggtcagagta acccatacag tatttggtc aggaagagaa      3120 agtggccatt tacactgaat gagttgcatt ctgataatgt cttatctctt atacgtagaa    3180
taaatttgaa agactatttg atcttaaaac caaagtaatt ttagaatgag tgacatatta    3240
cataggaatt tagtgtcaat ttcatgtgtt taaaaacatc atgggaaaaa tgcttagagg    3300
ttactatttt gactacaaag ttgagttttt ttctgtagtt accataattt cattgaagca    3360
aatgaatgag tttgagaggt ttgtttttat agttgtgttg tattacttgt ttaataataa    3420
tctctaattc tgtgatcagg tacttttttt gtgggggttt tttttttgtt ttttttttt     3480 tttgttgttg tttttgggcc atttctaagc ctaccagatc tgctttatga aatccagggg    3540
accaatgcat tttatcacta aaactatttt tatataattt taagaatata ccaaaagttg    3600
tctgatttaa agttgtaata catgattct cactttcatg taaggttatc cacttttgct     3660
gaagatattt tttattgaat caaagattga gttacaatta tactttctt acctaagtgg     3720 ataaaatgta cttttgatga atcagggaat ttttttaaag ttggagttta gttctaaatt    3780
gactttacgt attactgcag ttaattcctt ttttggctag ggatggtttg ataaaccaca    3840
```

| | |
|---|---|
| attggctgat attgaaaatg aaagaaactt aaaaggtggg atggatcatg attactgtcg | 3900 |
| ataactgcag ataaatttga ttagagtaat aattttgtca tttaaaaaca cagttgttta | 3960 |
| tactgcccat cctaggatgc tcaccttcca agattcaacg tggctaaaac atcttctggt | 4020 |
| aaattgtgcg tccatattca ttttgtcagt agccaggaga aatggggatg ggggaaatac | 4080 |
| gacttagtga ggcatagaca tccctggtcc atcctttctg tctccagctg tttcttggaa | 4140 |
| cctgctctcc tgcttgctgg tccctgacgc agagaccgtt gcctccccca cagccgtttg | 4200 |
| actgaaggct gctctggaga cctagagtaa aacggctgat ggaagttgtg ggacccactt | 4260 |
| ccatttcctt cagtcattag aggtggaagg gaggggtctc caagtttgga gattgagcag | 4320 |
| atgaggcttg ggatgcccct gctttgactt cagccatgga tgaggagtgg gatggcagca | 4380 |
| aggtggctcc tgtggcagtg gagttgtgcc agaaacagtg gccagttgta tcgcctataa | 4440 |
| gacagggtaa ggtctgaaga gctgagcctg taattctgct gtaataatga tagtgctcaa | 4500 |
| gaagtgcctt gagttggtgt acagtgccat ggccatcaag aatcccagat tcaggttttt | 4560 |
| attacaaaat gtaagtggtc acttggcgat tttgtagtac atgcatgagt tacctttttt | 4620 |
| ctctatgtct gagaactgtc agattaaaac aagatggcaa agagatcgtt agagtgcaca | 4680 |
| acaaaatcac tatcccatta gacacatcat caaaagctta ttttattct tgcactggaa | 4740 |
| gaatcgtaag tcaactgttt cttgaccatg gcagtgttct ggctccaaat ggtagtgatt | 4800 |
| ccaataatg gttctgttaa cactttggca gaaaatgcca gctcagatat tttgagatac | 4860 |
| taaggattat ctttggacat gtactgcagc ttcttgtctc tgttttggat tactggaata | 4920 |
| cccatgggcc ctctcaagag tgctggactt ctaggacatt aagatgattg tcagtacatt | 4980 |
| aaacttttca atcccattat gcaatcttgt ttgtaaatgt aaacttctaa aaatatggtt | 5040 |
| aataacattc aacctgttta ttacaactta aaaggaactt cagtgaattt gttttattt | 5100 |
| tttaacaaga tttgtgaact gaatatcatg aaccatgttt tgatacccct ttttcacgtt | 5160 |
| gtgccaacgg aatagggtgt ttgatatttc ttcatatgtt aaggagatgc ttcaaaatgt | 5220 |
| caattgcttt aaacttaaat tacctctcaa gagaccaagg tacatttacc tcattgtgta | 5280 |
| tataatgttt aatatttgtc agagcattct ccaggtttgc agttttattt ctataaagta | 5340 |
| tgggtattat gttgctcagt tactcaaatg gtactgtatt gtttatattt gtaccccaaa | 5400 |
| taacatcgtc tgtactttct gttttctgta ttgtatttgt gcaggattct ttaggcttta | 5460 |
| tcagtgtaat ttctgccttt taagatatgt acagaaaatg tccatataaa tttccattga | 5520 |
| agtcgaatga tactgagaag cctgtaaaga ggagaaaaaa cataagctgt gtttccccat | 5580 |
| aagttttttt aaattgtata ttgtatttgt agtaatattc caaaagaatg taaataggaa | 5640 |
| atagaagagt gatgcttatg ttaagtccta acactacagt agaagaatgg aagcagtgca | 5700 |
| aataaattac attttcccca aaaaaaaaaa aaaaaaaaaa aaaaaaaaaa gaaaaaaaaa | 5760 |
| aaaaaa | 5766 |

<210> SEQ ID NO 33
<211> LENGTH: 567
<212> TYPE: PRT
<213> ORGANISM: homo sapiens

<400> SEQUENCE: 33

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

```
Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
 50                  55                  60

Lys Ser Cys Met Ser Asn Cys Ser Ile Thr Ser Ile Cys Glu Lys Pro
 65              70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
                115                 120                 125

Pro Gly Glu Thr Phe Phe Met Cys Ser Cys Ser Ser Asp Glu Cys Asn
        130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
        180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
        210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
        290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445
```

-continued

```
Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
                515                 520                 525

Leu Thr Ala Gln Cys Val Ala Glu Arg Phe Ser Glu Leu Glu His Leu
530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 34
<211> LENGTH: 487
<212> TYPE: DNA
<213> ORGANISM: homo sapiens

<400> SEQUENCE: 34
cctcctggct ggcgagcggg cgccacatct ggcccgcaca tctgcgctgc cggcccggcg      60
cggggtccgg agagggcgcg gcgcggaggc gcagccaggg gtccgggaag cgccgtccg     120 ctgcgctggg ggctcggtct atgacgagca gcggggtctg ccatgggtcg ggggctgctc    180 agggcctgt ggccgctgca catcgtcctg tggacgcgta tcgccagcac gatcccaccg     240
cacgttcaga agtcgggtga gtggtcccca gcccgggctc ggcggggcgc cggggggtctt   300 cctggggtcc ccgcctctcc gctgcgcttg acagtcgggc ccggcaaccc ggcccccggg    360
cggaaacgag gaaagtttcc cccgcgacac tcacgcagcc cgactcccgt agctgcaggg    420
attgtgagtt tttcttgaaa aagagaagga aagttcagtt gcaaggggcg cggggcacgt    480
ttggtcc                                                              487

<210> SEQ ID NO 35
<211> LENGTH: 23
<212> TYPE: DNA
<213> ORGANISM: Artificial Sequence
<220> FEATURE:
<223> OTHER INFORMATION: siRNA sequence for Tgfbr1 sense strand

<400> SEQUENCE: 35
ugucaaggag augcuucaau att                                             23

<210> SEQ ID NO 36
<211> LENGTH: 25
<212> TYPE: DNA
<213> ORGANISM: Artificial Sequence
<220> FEATURE:
<223> OTHER INFORMATION: siRNA sequence for Tgfbr1 antisense strand

<400> SEQUENCE: 36
uauugaagca ucuccuugac auatt                                           25

<210> SEQ ID NO 37
<211> LENGTH: 23
<212> TYPE: DNA
<213> ORGANISM: Artificial Sequence
```

```
<220> FEATURE:
<223> OTHER INFORMATION: siRNA sequence for Tgfbr2 sense strand

<400> SEQUENCE: 37
ggcucgcuga acacuaccaa att                                              23

<210> SEQ ID NO 38
<211> LENGTH: 25
<212> TYPE: DNA
<213> ORGANISM: Artificial Sequence
<220> FEATURE:
<223> OTHER INFORMATION: siRNA sequence for Tgfbr2 antisense strand

<400> SEQUENCE: 38
uuugguagug uucagcgagc cautt                                            25
```

METHODS AND COMPOSITIONS FOR TREATING ATHEROSCLEROSIS

CROSS-REFERENCE TO RELATED APPLICATIONS

This present application is a 35 U.S.C. § 371 national phase application from, and claims priority to, International Application No. PCT/US2017/023347, filed Mar. 21, 2017, and published under PCT Article 21(2) in English, which claims priority under 35 U.S.C. § 119(e) to U.S. Provisional Patent Application No. 62/311,086, filed Mar. 21, 2016 and U.S. Provisional Patent Application No. 62/406,732, filed Oct. 11, 2016, which are incorporated herein by reference in their entirety.

STATEMENT REGARDING FEDERALLY SPONSORED RESEARCH OR DEVELOPMENT

This invention was made with government support under HL053793 and HL107205 awarded by National Institutes of Health. The government has certain rights in the invention.

BACKGROUND OF THE INVENTION

Atherosclerosis is responsible for the vast majority of cardiovascular diseases. Despite decades of work, statins remain the only effective therapy, but they can only slow, not stop or reverse disease progression. There is no currently available therapy to stop the development of atherosclerosis and induce its regression.

In healthy mature blood vessels, vascular smooth muscle cells (SMCs) are quiescent, fully differentiated cells that exhibit a very low rate of proliferation. They express a number of contractile proteins necessary for maintaining vessel tone, blood pressure, and blood flow, including smooth muscle α-actin (SM α-actin), smooth muscle 22 alpha (SM22α), SM-calponin, and smooth muscle myosin heavy chain (SM-MHC) (Liu et al, 2015 Biochimica et biophysica acta 1849: 448-453; Owens et al, 2004, Physiological reviews 84: 767-801; Shi & Chen, 2014, Journal of biomedical research 28: 40-46). Following vascular injury or in association with a variety of diseases, SMCs exhibit a decrease in expression of differentiation markers and acquire a proliferative phenotype characterized by enhanced cell proliferation and migration (Kawai-Kowase & Owens, 2007, Cell physiology 292: C59-69; Owens et al, 2004, Physiological reviews 84: 767-801). This form of SMC phenotypic modulation is especially robust in atherosclerosis and vascular stenosis following angioplasty where it is thought to contribute to the growth of atherosclerotic plaques and neointima (Gomez & Owens, 2012, Cardiovascular research 95: 156-164; Marx et al, 2011, Circulation Cardiovascular interventions 4: 104-111; Tabas et al, 2015, J Cell Biol 209: 13-22). Therefore, elucidation of mechanisms that control normal SMC phenotypic switch in disease states is likely to provide key insights toward understanding the biology of atherosclerosis and development of new therapeutic targets.

Smooth muscle differentiation is promoted by a number of signaling pathways including transforming growth factor β (TGFβ), Notch3 as well as integrin- and extracellular matrix-derived differentiation signals. TGFβ signaling is particularly critical for the maintenance of normal adult vasculature (Li et al, 2014, Journal of clinical investigation 124: 755-767) and the growth factor plays a critical role in mediating balance between inflammation and fibrous plaque growth in atherosclerosis (Lutgens et al, 2002, Arterioscler Thromb Vasc Biol 22: 975-982). TGFβ exerts its effects via a complex of two serine/threonine kinase type II receptors (TGFβR2) and the type I receptor Alk5 (TGFβR1) (Carvalho et al, 2007, Journal of cell science 120: 4269-4277; Mack, 2011, Arterioscler Thromb Vasc Biol 31: 1495-1505). TGFβR1 phosphorylation by TGFβR2 results in recruitment and phosphorylation of Smad2 and Smad3 that then complex with Smad4 and translocate to the nucleus. Subsequent activation of contractile SMC-specific gene expression involves both direct binding of Smads to certain DNA binding sites as well as interactions with other SMC transcription factors such as SRF and myocardin. TGFβ also activates non-Smad-dependent signaling pathways that also play a role in the induction of SMC differentiation (Li et al, 2014, Journal of clinical investigation 124: 755-767). In agreement with these results, genetic deletions of either TGFβ1, TGFβ2, their receptors (TGFβR1, TGFβR2) or signaling molecules (Smad2, Smad3), are all associated with various vascular wall pathologies including aneurysm formation (Carvalho et al, 2007, Journal of cell science 120: 4269-4277; Crosas-Molist et al, 2015, Arterioscler Thromb Vasc Biol 35: 960-972; Doyle et al, 2012, Nature genetics 44: 1249-1254; Li et al, 2014, Journal of clinical investigation 124: 755-767; Lindsay et al, 2012, Nature genetics 44: 922-927; Tang et al, 2010, Journal of biological chemistry 285: 17556-17563).

While the central role played by TGFβ in regulation of SMC differentiation has been previously demonstrated (Hirschi et al, 1998, J Cell Biol 141: 805-814; Kawai-Kowase et al, 2004, Arterioscler Thromb Vasc Biol 24: 1384-1390; Lindner & Reidy, 1991, Proc Natl Acad Sci USA 88: 3739-3743), little is known about what regulates this pathway and what contribution SMC proliferation makes to progression of lesions seen in atherosclerosis (Tabas et al, 2015, J Cell Biol 209: 13-22). Recent studies in endothelial cells demonstrated FGF-dependent regulation of TGFβ. The loss of endothelial cell FGF signaling input in vitro or in vivo leads to a profound decrease in let-7 miRNAs levels that results in marked prolongation of TGFβR1 mRNA half-life and increased TGFβR1 protein expression. Together with a large increase in TGFβ2 levels, this leads to activation of TGFβ signaling including phosphorylation of Smad2 and Smad3 and induction of expression of various smooth muscle and mesenchymal markers thereby inducing endothelial-to-mesenchymal transition (EndMT) (Chen et al, 2012, Cell reports 2: 1684-1696; Chen et al, 2014, Science signaling 7: ra90). Importantly, EndMT, in turn, leads to acceleration of atherosclerosis progression (Chen et al, 2015, Journal of clinical investigation 125: 4529-4543). Prior studies also reported FGF antagonism of TGFβ activity in SMCs and pericytes in vitro but the mechanism of this effect and its functional consequences have not been fully established. (Kawai-Kowase et al, 2004, Arterioscler Thromb Vasc Biol 24: 1384-1390; Papetti et al, 2003, Investigative ophthalmology & visual science 44: 4994-5005).

New methods of treating atherosclerosis, particularly methods of inhibiting development or progression and methods of reversing atherosclerosis that target the molecular events that drive progression of atherosclerosis, are urgently needed.

SUMMARY OF THE INVENTION

In one aspect, the invention comprises a pharmaceutical composition comprising an effective amount of a let-7 miRNA in a nanoparticle formulated for selective delivery to an endothelial cell, in a pharmaceutically acceptable excipient. In various embodiments, the let-7 miRNA comprises a chemical modification that increases stability of the miRNA and/or reduces an immune response to the miRNA in a subject. In various embodiments, the chemical modification is a 2'-O-methyl modification. In various embodiments, the let-7 miRNA is selected from the group consisting of human let-7b miRNA and human let-7c miRNA. In various embodiments, the nanoparticle is a 7C1 nanoparticle.

In another aspect, the invention comprises a method of reducing an atherosclerotic lesion in a subject, the method comprising administering to the subject an agent that modulates the activity or level of let-7 miRNA in an endothelial cell in the subject, thereby reducing or inhibiting the atherosclerotic lesion in the subject.

In another aspect, the invention comprises a method of reducing an atherosclerotic lesion in a subject, the method comprising administering to the subject an agent that decreases in an endothelial cell in the subject the activity or level of a endothelial TGFβ signaling polypeptide selected from the group consisting of TGFβ1, TGFβ2, TGFβ3, TGFβR1, and TGFβR2, thereby reducing or inhibiting the atherosclerotic lesion in the subject.

In another aspect, the invention comprises a method of inhibiting progression of atherosclerosis in a subject, the method comprising administering to the subject an agent that increases the activity or level of let-7 miRNA in an endothelial cell in the subject, thereby inhibiting progression of atherosclerosis in the subject.

In another aspect, the invention comprises a method of inhibiting progression of atherosclerosis in a subject, the method comprising administering to the subject an agent that decreases in an endothelial cell in the subject the activity or level of a TGFβ signaling polypeptide selected from the group consisting of TGFβ1, TGFβ2, TGFβ3, TGFβR1, and TGFβR2, thereby inhibiting progression of atherosclerosis in the subject.

In another aspect, the invention comprises a method of reversing atherosclerosis in a subject, the method comprising administering to the subject an agent that increases the activity or level of let-7 miRNA in an endothelial cell in the subject, thereby reversing atherosclerosis in the subject.

In another aspect, the invention comprises a method of reversing atherosclerosis in a subject, the method comprising administering to the subject an agent that decreases in an endothelial cell in the subject the activity or level of a TGFβ signaling polypeptide selected from the polypeptide selected from the group consisting of TGFβ1, TGFβ2, TGFβ3, TGFβR1, and TGFβR2, thereby reversing atherosclerosis in the subject.

In another aspect, the invention comprises a method of treating atherosclerosis in a subject, the method comprising administering to the subject an agent that increases the activity or level of let-7 miRNA in an endothelial cell in the subject, thereby treating atherosclerosis in the subject.

In another aspect, the invention comprises a method of treating atherosclerosis in a subject, the method comprising administering to the subject an agent that decreases in an endothelial cell in the subject the activity or level of a TGFβ signaling polypeptide selected from the group consisting of TGFβR1, and TGFβR2, thereby treating atherosclerosis in the subject.

In another aspect, the invention comprises a method of inhibiting progression of atherosclerosis in a subject, the method comprising administering to the subject an agent that decreases the activity or level of FRS2α in a smooth muscle cell in the subject, thereby inhibiting progression of atherosclerosis in the subject.

In another aspect, the invention comprises a method of reversing atherosclerosis in a subject, the method comprising administering to the subject an agent that decreases the activity or level of FRS2α in a smooth muscle cell in the subject, thereby reversing atherosclerosis in the subject.

In another aspect, the invention comprises a method of treating atherosclerosis in a subject, the method comprising administering to the subject an agent that decreases the activity or level of FRS2α in a smooth muscle cell in the subject, thereby treating atherosclerosis in the subject.

In various embodiments, the agent is selectively delivered to an endothelial cell in the subject.

In various embodiments, the agent is in a nanoparticle.

In various embodiments, the nanoparticle is a 7C1 nanoparticle.

In various embodiments, the agent is selectively delivered to a smooth muscle cell in the subject.

In various embodiments, the agent is administered intravenously.

In various embodiments, the agent that increases the activity or level of let-7 miRNA is selected from the group consisting of human let-7b miRNA and human let-7c miRNA.

In various embodiments, the agent that increases the activity or level of let-7 miRNA is one of the above described compositions.

In various embodiments, the agent that decreases the activity or level of a TGFβ signaling polypeptide is an inhibitory polynucleotide that reduces expression of the TGFβ signaling polypeptide.

In various embodiments, the agent that decreases the activity or level of FRS2α is an inhibitory polynucleotide that reduces expression of a FRS2α polypeptide.

In various embodiments, the increased level of let-7 miRNA in the subject decreases expression of a TGFβ signaling polypeptide, thereby decreasing TGFβ signaling in the cell.

In various embodiments, the decrease in the activity or level of the TGFβ signaling polypeptide inhibits an endothelial-to-mesenchymal transition.

In various embodiments, the decrease in the activity or level of the FRS2α polypeptide promotes smooth muscle cell proliferation.

In various embodiments, the subject is identified as having a decreased level of let-7 miRNA or an increased level or activity of a TGFβ signaling polypeptide in a biological sample obtained from the subject relative to a reference. In various embodiments, the biological sample is an endothelial cell.

In various embodiments, the subject is identified as having an increased level of let-7 miRNA or a decreased level or activity of a TGFβ signaling polypeptide in a biological sample obtained from the subject relative to a reference.

In various embodiments, the biological sample is a smooth muscle cell.

In various embodiments, the subject is human.

In another aspect, the invention comprises a method of identifying an agent that modulates atherosclerosis, the method comprising measuring the activity or level of a TGFβ signaling polypeptide or polynucleotide, a let-7 miRNA, or a FGF signaling polypeptide or polynucleotide in a cell contacted with a candidate agent, wherein an alteration in the activity or level of the TGFβ signaling polypeptide or polynucleotide, the let-7 miRNA, or the FGF signaling polypeptide or polynucleotide relative to a reference indicates the candidate agent modulates atherosclerosis. In various embodiments, the TGFβ signaling polypeptide or polynucleotide is a TGFβ1, TGFβ2, TGFβ3, TGFβR1, or a TGFβR2 polypeptide or polynucleotide. In various embodiments, the FGF signaling polypeptide is FRS2α. In various embodiments, the cell is an endothelial cell. In various embodiments, an increase in the activity or level of let-7 miRNA or FGF signaling polypeptide or polynucleotide or a decrease in the activity or level of a TGFβ signaling polypeptide or polynucleotide indicates the candidate agent inhibits progression or reverses atherosclerosis. In various embodiments, the cell is a smooth muscle cell. In various embodiments, a decrease in the activity or level of let-7 miRNA or FGF signaling polypeptide or an increase in the activity or level of a TGFβ signaling polypeptide or polynucleotide indicates the candidate agent inhibits progression or reverses atherosclerosis.

In another aspect, the invention comprises a method of reducing, inhibiting or reversing an endothelial-to-mesenchymal transition (EndMT) in an endothelial cell in a subject in need thereof, the method comprising administering to the subject an agent that decreases in the endothelial cell of the subject the activity or level of at least one selected from the group consisting of let-7 miRNA, endothelial TGFβ signaling polypeptide and FRS2α, thereby reducing, inhibiting or reversing the EndMT in the endothelial cell in the subject in need thereof.

In various embodiments, the TGFβ signaling polypeptide is selected from the group consisting of TGFβ1, TGFβ2, TGFβ3, TGFβR1, and TGFβR2. In various embodiments, the let-7 miRNA is selected from the group consisting of human let-7b miRNA and human let-7c miRNA.

In various embodiments, the methods further comprise administering to the subject an additional agent comprising a therapeutically effective amount of rapamycin or any derivative thereof. In various embodiments, the agent that decreases the activity or level of a TGFβ signaling polypeptide and the additional agent are co-administered to the subject.

In various embodiments, the agent that decreases the activity or level of a TGFβ signaling polypeptide is a nucleic acid capable of downregulating the gene expression of at least one gene selected from the group selected from the group consisting of TGFβ1, TGFβ2, TGFβ3, TGFβR1, and TGFβR2. In various embodiments, the at least one gene is selected from the group consisting of TGFβR1, and TGFβR2. In various embodiments, the nucleic acid is selected from the group consisting of an antisense RNA, siRNA, shRNA, and a CRISPR system. In various embodiments, the nucleic acid is combined with a therapeutically effective amount of rapamycin or any derivative thereof. In various embodiments, the nucleic acid is encapsulated in a nanoparticle formulated for selective delivery to an endothelial cell, in a pharmaceutically acceptable excipient. In various embodiments, the nanoparticle is a 7C1 nanoparticle.

In another aspect, the invention comprises a method of reducing, inhibiting or reversing an endothelial-to-mesenchymal transition (EndMT) in an endothelial cell in a subject in need thereof, the method comprising administering to the subject at least one siRNA that decreases in the endothelial cell of the subject the activity or level of at least one TGFβ receptor, thereby reducing, inhibiting or reversing the EndMT in the endothelial cell in the subject in need thereof.

In various embodiments, the at least one TGFβ receptor comprises TGFβR1 or TGFβR2.

BRIEF DESCRIPTION OF THE DRAWINGS

FIGS. 1A-1B show qRT-PCR analysis of TGFβ ligands, TGFβ receptors, and TGFβ target expression in control and FRS2α knockdown HASMCs (NS: not significant compared to control, *p<0.05; p<0.01; *p<0.001 compared to control; unpaired two-tailed Student's t test). β-actin was used for sample loading normalization. Histogram of qRT-PCR results are representative of three independent experiments. FIG. 1C shows an immunoblot analysis of TGFβRs, phosphorylated Smad2 (p-Smad2), and phosphorylated Smad3 (p-Smad3) in control and FRS2α knockdown HASMCs. Blots are representative of four independent experiments.

FIG. 2A shows an immunoblot analysis of smooth muscle marker gene expression in control and FRS2α knockdown HASMCs. Blots are representative of four independent experiments. FIG. 2B shows a qRT-PCR analysis of SMC transcription factor gene expression in control and FRS2α knockdown HASMCs (*p<0.05; p<0.01; *p<0.001 compared to control; unpaired two-tailed Student's t test. N=3). R-actin was used for sample loading normalization. FIG. 2C shows results of collagen gel contraction assays used to determine the contractile ability of control or FRS2α knockdown HASMCs (*p<0.05 compared to control; unpaired two-tailed Student's t test. N=3). FIGS. 2D-2F show immunoblots of smooth muscle markers, phosphorylated Smad2 (p-Smad2), and TGFβR1 expression in control and FRS2α knockdown HASMCs treated with SB431542 (10 μm), TGFβR2 or Smad2 shRNA lentiviruses. Blots are representative of three independent experiments.

FIG. 3A shows a quantitative real-time PCR analysis of mature let-7 family in control and FRS2α knockdown HASMCs. SNORD47 was used to normalize the variability in template loading. Histogram of qRT-PCR results are three independent experiments. FIG. 3B shows immunoblots of SM-calponin, phosphorylated Smad2 (p-Smad2), and TGFβR1 expression in control and FRS2α knockdown HASMCs transduced with let-7b lentiviruses. Blots are representative of three independent experiments. FIG. 3C shows phase-contrast and immunofluorescence staining of smooth muscle markers in HASMCs. Nuclei were counterstained with DAPI. Scale bar: 12 μm. Images are representative of three independent experiments. FIG. 3D shows quantitative real-time PCR analysis of mature let-7 family in HASMCs. HASMCs were cultured in the growth medium (M231+SMGS) at day 0 then switched from growth conditions to differentiation medium (M231+SMDS) for 8 days. SNORD47 was used to normalize the variability in template loading. Histogram of qRT-PCR results are three independent experiments. FIG. 3E shows immunoblots of smooth muscle markers, phosphorylated Smad2 (p-Smad2), and TGFβR1 expression in control and FRS2α knockdown HASMCs with or without let-7b lentiviruses. Control and FRS2α knockdown HASMCs were cultured in the growth medium (M231+SMGS) at day 0 then switched from growth conditions to differentiation medium (M231+SMDS) for 6 days with or without let-7b lentiviruses. Blots are representative of three independent experiments.

FIG. 4A shows coronary arteries dissected from the human heart. Left main (LM), left anterior descending (LAD), and left circumflex (LCX) branches Scale bar: 1 cm. FIG. 4B shows Elastic-Van Gieson (EVG) staining of human coronary arteries demonstrating various degrees of atherosclerosis. FIGS. 4C-4D are representative images of immunofluorescence staining for CD31 and SM α-actin or SM-MHC in No/mild, moderate, and severe disease human left main coronary arteries. No: no-disease. Nuclei were stained with DAPI. Images are representative of ten No/mild, nine moderate and ten severe disease human left main coronary artery samples. Scale bar: 16 µm. FIGS. 4E and 4G show representative images of immunofluorescence staining for p-FGFR1 or FGFR1 in the same patient cohort. Nuclei were counter-stained with DAPI. Scale bar: 16 µm. FIGS. 4F and 4H show percentage of medial p-FGFR1$^+$ SMC and FGFR1$^+$ SMC (***p<0.001 compared to No/mild disease, NS: not significant compared to No/mild disease; one-way ANOVA with Newman-Keuls post hoc test for multiple comparison correction).

FIGS. 5A, 5C, and 5E show representative images of immunofluorescence staining for TGFβ, p-Smad2, or p-Smad3 from patients with No/mild, moderate, or severe disease. Nuclei were counter-stained with DAPI. Scale bar: 16 µm. FIGS. 5B, 5D, and 5F show percentage of medial TGFβ, p-Smad2, and p-Smad3 (***p<0.001 compared to No/mild disease; one-way ANOVA with Newman-Keuls post hoc test for multiple comparison correction).

FIG. 6A shows a dissected mouse aorta demonstrating lipid-rich plaques in brachiocephalic artery after 4 months of high fat diet compared to the normal diet in Apoe$^{-/-}$ mice. Portions of FIG. 6A labeled "b" and "d," respectively show a cross-section of brachiocephalic artery from the portions of FIG. 6A labeled "a" and "c" stained with Oil Red O. FIG. 6B shows a histological analysis of mouse normal artery or atherosclerotic plaque in brachiocephalic artery with anti-SM α-actin, anti-Notch3, and anti-SM-MHC antibodies. Nuclei were counterstained with DAPI. Scale bar: 62 µm. FIGS. 6C-6F shows analysis of brachiocephalic artery of Apoe$^{-/-}$ mice maintained for 4 months on either normal or high fat diet using anti-CD31, anti-p-FGFR1, anti-FGFR1, anti-p-Smad2, and anti-p-Smad3 antibodies. Nuclei counterstained with DAPI. Scale bar: 62 µm. (6 mice/group). L: lumen. M: Media. FIGS. 6G-6J show quantification of the number of media smooth muscle cells expressing p-FGFR1, FGFR1, p-Smad2, and p-Smad3 (***p<0.001 compared to ND, NS: not significant compared to ND; unpaired two-tailed Student's t test.). ND: Normal diet. HFD: High fat diet.

FIG. 7A shows representative photomicrographs of Oil Red O-stained atherosclerotic lesions in the aortic arch, of Apoe$^{-/-}$ or Frs2$^{SMCKO}$/Apoe$^{-/-}$ mice after 16 weeks of high fat diet. FIG. 7B (on the left) shows microphotographs of aortas (en face) from Apoe$^{-/-}$ and Frs2$^{SMCKO}$/Apoe$^{-/-}$ mice after 16 weeks of high fat diet after staining with Oil Red O. Shown on the right of FIG. 7B is lesion area quantification. All data shown as mean±SD. (*p<0.001 compared to Apoe$^{-/-}$; unpaired two-tailed Student's t test). FIGS. 7C-7D show representative cross-sections of brachiocephalic arteries Apoe$^{-/-}$ and Frs2$^{SMCKO}$/Apoe$^{-/-}$ mice stained with hematoxylin and eosin (H&E) (C) and Movat (D). (a)&(b) are high magnification view of the atherosclerotic plaque shown by black dot boxes. NC: necrotic core. FIG. 7E shows histological analysis of atherosclerotic plaque with anti-Ki67 antibody. Nuclei were counterstained with DAPI. Scale bar: 62 µM. FIG. 7F shows quantification of plaque cellularity; Apoe$^{-/-}$ mice N=9, Frs2$^{SMCKO}$/Apoe$^{-/-}$ mice N=12 (*p<0.001 compared to Apoe$^{-/-}$; unpaired two-tailed Student's t test). FIG. 7G shows quantifications of the extent of fibrous cap and necrotic areas in brachiocephalic artery of Apoe$^{-/-}$ and Frs2$^{SMCKO}$/Apoe$^{-/-}$ mice. Apoe$^{-/-}$ mice N=9, Frs2$^{SMCKO}$/Apoe$^{-/-}$ mice N=12. (*p<0.05, **p<0.01 compared to Apoe$^{-/-}$; unpaired two-tailed Student's t test). FIG. 7H shows measurement of Ki67T$^+$ cells (*p<0.05, ***p<0.001 compared to Apoe$^{-/-}$; unpaired two-tailed Student's t test).

FIG. 9A shows control and FRS2α knockdown HASMCs that were cultured in the growth medium (M231+SMGS). Cell proliferation was analyzed using real-time cell analysis (xCELLigence). Cell proliferation curves are representative of three independent experiments (***p<0.05 compared to control; unpaired two-tailed Student's t test). FIG. 9B shows control and FRS2α knockdown HASMCs were cultured in the growth medium (M231+SMGS). Immunoblots of cell cycle regulators Cyclin D1, p21, and p27 in control and FRS2α knockdown HASMCs. Blots are representative of four independent experiments. FIG. 9C shows control and FRS2α knockdown HASMCs cultured in the growth medium (M231+SMGS). Flow cytometry analysis with propidium iodide (PI) staining was used to evaluate the percentage of cellular DNA content in control and FRS2α knockdown HASMCs. Histogram of cell cycle distribution results are representative of three independent experiments.

FIG. 10A shows qRT-PCR analysis of FGFRs, FRS2α, and Klotho family gene expression in primary human aortic smooth muscle cells (HASMCs). Data are presented as mean±SD. β-actin was used for sample loading normalization. Histogram of qRT-PCR results are representative of four independent experiments. FIGS. 10B-10C show qRT-PCR analysis of TGFβ ligands, TGFβ receptors, and downstream target genes in control and FGFR1 knockdown HASMCs. (NS: not significant compared to control, *p<0.05; p<0.01; *p<0.001 compared to control; unpaired two-tailed Student's t test). β-actin was used for sample loading normalization. Histogram of qRT-PCR results are representative of three independent experiments. FIG. 10D shows qRT-PCR analysis of smooth muscle cell transcription factors and smooth muscle marker gene expression in control and FGFR1 knockdown HASMCs. (*p<0.05; p<0.01; *p<0.001 compared to control; unpaired two-tailed Student's t test. N=3). β-actin was used for sample loading normalization. FIG. 10E shows an immunoblot analysis of TGFβ signaling, TGFβ downstream targets, and smooth muscle markers in control and FGFR1 knockdown HASMCs. Blots are representative of four independent experiments.

FIGS. 11A-11H are plots and images showing Frs2α$^{SMCKO}$ mice display normal vascular morphology and vascular density. FIG. 11A shows a qRT-PCR analysis of Frs2a expression in mouse aorta (***p<0.001 compared to control). β-actin was used for sample loading normalization. All of the data represent the mean±SD. 3 control and 3 Frs2α$^{SMCKO}$ mice were analyzed. FIG. 11B shows an immunoblot analysis of FRS2α expression in mouse aorta. In each group aorta were pooled from 4 mice/group. FIG. 11C shows representative images of FRS2α immunofluorescence staining of control and Frs2α$^{SMCKO}$ aorta. Endothelial cells are visualized by CD31. Black arrows indicate endothelial cells. L: lumen. Nuclei were stained with DAPI. Images are representative of 3 mice/group. Scale bar: 10 μm. FIG. 11D shows gross appearance of aorta in 8-week-old control and Frs2α$^{SMCKO}$ mice. Asc: Ascending; Desc: Descending. FIG. 11E shows 5 μm cross-sections of control and Frs2α$^{SMCKO}$ mouse brachiocephalic artery were stained with EVG (elastic Van Gieson), anti-SM α-actin, anti-SM22α, and anti-Notch3 antibodies. Nuclei were counterstained with DAPI. L: lumen. Scale bar: 10 μm. Images are representative of 3 mice/group. FIG. 11F (left) shows a histological analysis of control and Frs2α$^{SMCKO}$ mouse brachiocephalic artery with anti-CD31 and anti-p-Smad2 antibodies. Nuclei were counterstained with DAPI. L: lumen. Scale bar: 10 μm. Right: Percentage of p-Smad2$^+$ cells in the media (NS: not significant compared to control; unpaired two-tailed Student's t test). Images are representative of 6 mice/group. FIGS. 11G-11H (left) show representative images of vascular structure in heart and skeletal muscle in control and Frs2α$^{SMCKO}$ mice. Scale bar: 62 μm for 100× and 16 μm for 400×. Right: Vascular density was quantified (NS: not significant compared to control; unpaired two-tailed Student's t test). Images are representative of 5 mice/group.

FIGS. 12A-12B show body weight, total cholesterol, triglycerides, and HDL-C analysis of Apoe$^{-/-}$ and Frs2α$^{SMCKO}$/Apoe$^{-/-}$ mice before and after 16 weeks on a high cholesterol diet. (NS: not significant compared to Apoe$^{-/-}$; unpaired two-tailed Student's t test). FIG. 12C shows representative ultrasound images and ascending aorta diameters of Apoe$^{-/-}$ and Frs2α$^{SMCKO}$/Apoe$^{-/-}$ mice. All of the data represent the mean±SD. (NS: not significant compared to Apoe$^{-/-}$; unpaired two-tailed Student's t test). 3 Apoe$^{-/-}$ and 3 Frs2α$^{SMCKO}$/Apoe$^{-/-}$ mice were analyzed. FIG. 12D shows an echocardiographic analysis in Apoe$^{-/-}$ and Frs2α$^{SMCKO}$/Apoe$^{-/-}$ mice showed no effect on cardiac output, ejection fraction, and fractional shortening. All of the data represent the mean±SD. (NS: not significant compared to Apoe$^{-/-}$; unpaired two-tailed Student's t test). 3 Apoe$^{-/-}$ and 3 Frs2α$^{SMCKO}$/Apoe$^{-/-}$ mice were analyzed.

FIG. 13A shows representative photomicrographs of Oil Red O-stained atherosclerotic lesions in the aortic arch, of Apoe$^{-/-}$ or Frs2$^{SMCKO}$/Apoe$^{-/-}$ mice after 2 months of high fat diet or normal diet. FIG. 13B (left) shows microphotographs of aortas (en face) from Apoe$^{-/-}$ and Frs2$^{SMCKO}$/Apoe$^{-/-}$ mice after 2 months of high fat diet after staining with Oil Red 0; (right) lesion area quantification. All data shown as mean±SD. (**p<0.01 compared to Apoe$^{-/-}$; unpaired two-tailed Student's t test). FIG. 13C shows quantification of SM α-actin area in the plaque from Apoe$^{-/-}$ and Frs2$^{SMCKO}$/Apoe$^{-/-}$ mice after 4 months of high fat diet. Apoe$^{-/-}$ mice N=9, Frs2$^{SMCKO}$/Apoe$^{-/-}$ mice N=12 (*p<0.05 compared to Apoe$^{-/-}$; unpaired two-tailed Student's t test). Nuclei were counterstained with DAPI. Scale bar: 62 μm. FIG. 13D shows measurement of Collagen 1 area from Apoe$^{-/-}$ and Frs2$^{SMCKO}$/Apoe$^{-/-}$ mice after 4 months of high fat diet (*p<0.05 compared to Apoe$^{-/-}$; unpaired two-tailed Student's t test). Data expressed as the ratio of collagen 1 signal to the total vessel area. Apoe$^{-/-}$ mice N=9, Frs2$^{SMCKO}$/Apoe$^{-/-}$ mice N=12. Nuclei were counterstained with DAPI. Scale bar: 62 μm.

FIG. 16A: Scheme of the Cdh5-CreER$^{T2}$ transgene, Tgfbr1, Tgfbr2 floxed alleles, and R26-mTmG reporter constructs. FIG. 16B: PCR analysis using tail genomic DNA of the indicated genotypes. FIG. 16C shows a setup of experiments investigating TGFβ signaling and atherosclerotic plaque development using the Tgfbr$^{iECKO}$/Apoe$^{-/-}$ mice, as described elsewhere herein. FIG. 16D are immunoblots showing TGFβ (upper) and BMP (bottom) signaling in Tgfbr$^{iECKO}$/Apoe$^{-/-}$ mouse endothelial cells. Heart endothelial cells were isolated from vehicles or tamoxifen treated mice and were treated with TGFβ1 (0.5 ng/ml, upper) or BMP9 (0.5 ng/ml, bottom) for the indicated times and downstream signaling was analyzed by immunoblotting. In each group, endothelial cells were isolated and pooled from 3 mice/group.

FIG. 17A: Scheme of Tamoxifen injection (1 mg/day i.p. for 5 days starting at 6 week old) and high fat diet (HFD) feeding. FIG. 17B: Body weight analysis of Apoe$^{-/-}$ and Tgfbr$^{iECKO}$/Apoe$^{-/-}$ mice before and after 4, 8, 12, 16 weeks on a high cholesterol diet. (NS: not significant compared to Apoe$^{-/-}$; unpaired two-tailed Student's t test). FIGS. 17C-17D: Serum total cholesterol and triglycerides levels from Apoe$^{-/-}$ and Tgfbr$^{iECKO}$/Apoe$^{-/-}$ mice before and after 16 weeks on a high cholesterol diet. (NS: not significant compared to Apoe$^{-/-}$; unpaired two-tailed Student's t test).

(FIG. 22A) (Left) Microphotographs of aortas (en face) from Apoe$^{-/-}$ or Tgfbr$^{iECKO}$/Apoe$^{-/-}$ mice after 0, 1, 2, 3, 4 months of high fat diet staining with Oil Red O. (Right) Lesion area quantification. % Lesion area is lesion area/total area of aorta. All data shown as mean±SD. (*$p<0.001$ compared with Apoe$^{-/-}$; unpaired two-tailed Student's t test). 3-11 mice per group. (FIG. 22B) Representative photomicrographs of Oil Red O-stained atherosclerotic lesions in the aortic arch of Apoe$^{-/-}$ or Tgfbr$^{iECKO}$/Apoe$^{-/-}$ mice after 0, 1, 2, 3, 4 months of high fat diet. 3 mice per group. Scale bar: 5 mm. (FIG. 22C) (Left) Representative examples of cross-sections from the aortic root after 4 months of high fat diet stained with Oil Red O. Scale bar: 200 µm. 11 mice/group. (Right) Quantification of aortic root lesion areas. Mean±SD. (*$p<0.001$ compared to Apoe$^{-/-}$; unpaired two-tailed Student's t test). (FIG. 22D) Representative images of brachiocephalic artery from Apoe$^{-/-}$ and Tgfbr$^{iECKO}$/Apoe$^{-/-}$ mice stained with Movat. Scale bar: 100 µm. (FIG. 22E) Measurement of lesion area (*$p<0.001$ compared to Apoe$^{-/-}$; unpaired two-tailed Student's t test). (FIG. 22F) Quantifications of the extent of necrotic areas in branchiocephalic artery of Apoe$^{-/-}$ and Tgfbr$^{iECKO}$/Apoe$^{-/-}$ mice (*$p<0.001$ compared to Apoe$^{-/-}$; unpaired two-tailed Student's t test).

FIG. 24A: Time frame of gene inactivation and 7C1 lipid nanoparticle injections. FIG. 24B: Serum triglycerides, total cholesterol, and HDL-C levels from Apoe$^{-/-}$ and Frs2$^{iECKO}$/Apoe$^{-/-}$ mice after 16 weeks on a high cholesterol diet (NS: not significant by one-way ANOVA with Newman-Keuls post-hoc test). FIG. 24C: Individual body weights in each group were measured every week. FIGS. 24D-24E: qPCR analysis of let-7b and Tgfbr1 expression in lung endothelial cells after treatment with 7C1-let-7 particles. All data shown as mean±s.d. (*$p<0.05$; $p<0.01$; *$p<0.001$ compared with Luciferase; one-way ANOVA with Newman-Keuls post hoc test for multiple comparison correction). N=4-6 mice per group.

FIG. 32A shows levels of Type 1, Type II, and Type III TGFβ receptors in a FRS2α knockdown background. FIG. 32B shows levels of TGFβ and BMP signaling components in a FRS2α knockdown background. FIG. 32C shows a time course of levels of TGFβ signaling components in a FRS2α knockdown background. FIG. 32D shows a time course of levels of BMP signaling components in a FRS2α knockdown background.

FIGS. 34A and 34C show levels of MAPK signaling components in a FRS2α knockdown. FIG. 34B shows an analysis using anti-VE cadherin and anti-active β-catenin. Nuclei were counterstained with DAPI.

FIGS. 35A-35C are images showing TGFβ signaling activity in endothelial cells from subjects having No/mild disease, moderate disease, and severe disease, using anti-CD31, anti-p-Smad3, and anti-p-Smad5 antibodies. FIG. 35A shows immunostaining for p-Smad3. FIG. 35B shows immunostaining for p-Smad5. FIG. 35C shows quantification of immunocytochemistry data from FIG. 35B. Nuclei were counterstained with DAPI.

FIGS. 37A-37B are images and a plots showing NKX2.5 expression in endothelial cells from subjects having No/mild disease, moderate disease, and severe disease. Nuclei were counterstained with DAPI. FIG. 37A shows immunostaining for NKX2.5. FIG. 37B shows quantification of immunocytochemistry data from FIG. 37A.

FIGS. 38A-38B (Left) Representative images of the Oil Red O-stained atherosclerotic lesions in the aorta from Apoe$^{-/-}$ or Frs2α$^{iECKO}$/Apoe$^{-/-}$ mice treated with PBS, Luciferase, or let-7 mimics. (Right) Lesion area quantification. All data shown as mean±s.d. (***p<0.001 compared with Luciferase treated group; one-way ANOVA with Newman-Keuls post hoc test for multiple comparison correction). FIGS. 38C-38D (Upper) Representative images of brachiocephalic artery from PBS, Luciferase, or let-7 mimics treated mice stained with Movat (scale bar: 200 µm). (Bottom) Quantifications of the lesion area and the extent of necrotic core areas in branchiocephalic artery of PBS, Luciferase, or let-7 mimics treated mice (*p<0.05; ***p<0.001 compared with Luciferase; one-way ANOVA with Newman-Keuls post hoc test for multiple comparison correction).

FIGS. 39A-39H are a series of images and histograms depicting that endothelial cell Tgfbr1/Tgfbr2 knockout facilitates regression of advanced murine atherosclerotic plaques. FIG. 39A: Diet and treatment schemes. After 2 months of high-fat-diet, the mice were treated with tamoxifen or vehicle control. Then the high-fat-diet was continued for another 2 months. FIG. 39B: (Left) Representative images of the Oil Red O-stained atherosclerotic lesions in the aorta from Apoe$^{-/-}$ or Tgfbr$^{iECKO}$/Apoe$^{-/-}$ mice. (Right) Lesion area quantification. All data shown as mean±s.d. (NS: not significant; *p<0.001; one-way ANOVA with New-man-Keuls post hoc test for multiple comparison correction). FIG. 39C: Diet and treatment schemes. Mice were fed the high-fat-diet for 3 months to induce advanced atherosclerotic lesions. Then the diet was changed to a normal diet for another month. Mice were simultaneously treated with tamoxifen or vehicle control. FIG. 39D: Representative images of the Oil Red O-stained atherosclerotic lesions in the aorta from Apoe$^{-/-}$ or Tgfbr$^{iECKO}$/Apoe$^{-/-}$ mice. FIG. 39E: Diet and treatment schemes. Mice were fed the high-fat-diet for 3 months to induce advanced atherosclerotic lesions. Then the diet was either changed to a normal diet for another 1 or 2 months. Mice were simultaneously treated with tamoxifen or vehicle control. FIG. 39F: Representative images of the cross-sections from the aortic root after 4 months of high fat diet stained with Movat (scale bar: 200 µm). FIG. 39G: Lesion area quantification shown in FIG. 39D. All data shown as mean±s.d. (p<0.01; unpaired two-tailed Student's t test). FIG. 39H: Aortic root lesion area quantification shown in FIG. 39F. All data shown as mean±s.d. (***p<0.001; one-way ANOVA with Newman-Keuls post hoc test for multiple comparison correction).

FIG. 40A: Histological analysis of atherosclerotic plaques from Apoe$^{-/-}$ and Tgfbr$^{iECKO}$/Apoe$^{-/-}$ mice stained with Hematoxylin and eosin (H&E) and anti-SM α-actin, anti-collagen 1, anti-fibronectin, and anti-VCAM1 antibodies. Nuclei were counterstained with DAPI. Scale bar: 62 µm. FIG. 40B: Measurement of plaque cell number, SM α-actin, collagen 1, fibronectin, and VCAM-1 area (*p<0.05; p<0.01; *p<0.001 compared to Apoe$^{-/-}$ one-way ANOVA with Newman-Keuls post hoc test for multiple comparison correction).

FIGS. 41A-41D: Heart endothelial cells were isolated from vehicles or tamoxifen treated mice and were treated with TNF-α (10 ng/ml), IL-10 (10 ng/ml), IL-6 (10 ng/ml), or IFN-γ (10 ng/ml) for the indicated times and downstream signaling was analyzed by immunoblotting. In each group, endothelial cells were isolated and pooled from 3 mice/group. FIG. 41E: Histological analysis of thoracic aorta from Apoe$^{-/-}$ and Tgfbr$^{iECKO}$/Apoe$^{-/-}$ mice injected with either PBS or 100 mg LPS stained for ICAM-1 and VCAM-1. Nuclei were counterstained with DAPI. Scale bar: 62 µm. FIG. 41F: Measurement of ICAM-1 and VCAM-1 area (NS: not significant; p<0.05; *p<0.001 compared to Apoe$^{-/-}$; unpaired two-tailed Student's t test).

FIGS. 42A-42D are a series of images and histograms demonstrating that 7C1-let-7 mimics treatment reduce plaque cellularity, inhibit SM α-expression, macrophage recruitment in the plaques in both Apoe$^{-/-}$ and Frs2α$^{iECKO}$/Apoe$^{-/-}$ mice. FIG. 42A and FIG. 42C: Histological analysis of atherosclerotic plaques from PBS, 7C1-Luciferase, and 7C1-let-7 mimics treated mice stained with Hematoxylin and eosin (H&E) and anti-SM α-actin, and anti-F4/80 antibodies. Nuclei were counterstained with DAPI. Scale bar: 62 µm. FIG. 42B and FIG. 42D: Measurement of plaque cell number, SM α-actin, F4/80 area (p<0.01; *p<0.001 compared to Apoe$^{-/-}$; one-way ANOVA with Newman-Keuls post hoc test for multiple comparison correction).

FIG. 43A: Histological analysis of aortic root from Apoe$^{-/-}$ and Tgfbr$^{iECKO}$/Apoe$^{-/-}$ mice stained with anti-F4/80 antibody. Nuclei were counterstained with DAPI. Scale bar: 62 µm. FIG. 43B: Measurement of F4/80 area (NS: not significant; *p<0.05; ***p<0.001; one-way ANOVA with New-man-Keuls post hoc test for multiple comparison correction).

FIG. 44A (Lung EC) and FIG. 44B (Heart EC): C57BL/6J mice were injected intravenously with PBS or 7C1-siTgfbr1/Tgfbr2 at different concentrations. Forty-eight hours later, heart and lung endothelial cells were harvested. Expression of Tgfbr1 and Tgfbr2 were analyzed by quantitative real-time PCR. β-actin was used to normalized the variability in template loading. All data shown as mean±SD. (NS: not significant; *p<0.05; p<0.01; *p<0.001 compared with PBS; unpaired two-tailed Student's/test). N=3 mice per group.

FIG. 45A: Time frame of 7C1-siTgfbr1/Tgfbr2 lipid nanoparticle and rapamycin injections. FIG. 45B: Representative photomicrographs of Oil Red O-stained atherosclerotic lesions in PBS, 7C1-siLuciferase, DMSO, Rapamycin, or 7C1-siTgfbr treated mice.

FIG. 46 is a histogram illustrating the quantification of atherosclerotic lesions from FIG. 45B. Lesion area quantification. % Lesion area is the lesion area/total area of aorta. All data shown as mean±SD. (***p<0.001; one-way ANOVA with Newman-Keuls post hoc test for multiple comparison correction).

DETAILED DESCRIPTION OF THE INVENTION

Figure 1A:
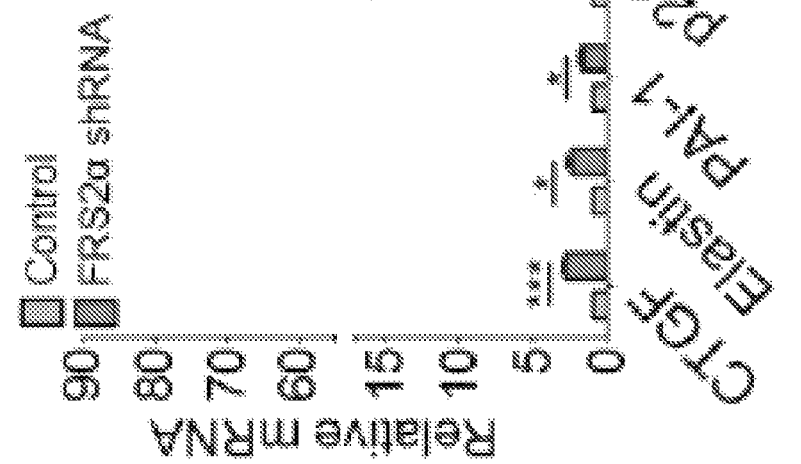
FIGS. 1A-1C are plots and an immunoblot showing that FRS2α knockdown activates TGFβ signaling in primary human aortic smooth muscle cells (HASMCs).

The invention features compositions and methods that are useful for treating atherosclerosis in a subject. The invention is based, at least in part, on the discovery of a key molecular mechanism responsible for atherosclerosis progression. The molecular mechanism is based on the relationship between fibroblast growth factor (FGF) signaling, let-7 miRNA expression, and transforming growth factor 3 (TGFβ) signaling, which contribute to growth of atherosclerotic plaque. Genetic evidence obtained herein confirm that blocking the mechanism responsible for atherosclerosis progression (e.g., activation of endothelial TGFβ signaling) not only prevents atherosclerotic plaque growth but stops its progression and facilitates it regression.

In endothelial cells (EC) and smooth muscle cells (SMC), FGF-signaling induces let-7 miRNA expression, which leads to downregulation of TGFβ signaling. Studies described herein demonstrate that overexpression of let-7 miRNA or a let-7 miRNA mimic in endothelial cells, which downregulated TGFβ signaling, reduced atherosclerotic lesions in mice. Studies herein also demonstrate that disruption of FGF signaling in smooth muscle cells, which reduced let-7 miRNA expression and led to upregulation of TGFβ signaling, reduced atherosclerotic lesions in mice.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

By "agent" is meant any small molecule chemical compound, antibody, nucleic acid molecule, or polypeptide, or fragments thereof. In some embodiments, the agent is a nucleic acid molecule.

By "alteration" is meant a change (increase or decrease) in the expression levels or activity of a gene or polypeptide as detected by standard art known methods such as those described herein. In some embodiments, an alteration in expression level includes a 10% change in expression levels, a 25% change, a 40% change, and a 50% or greater change in expression levels.

"Biological sample" as used herein means a biological material isolated from a subject, including any tissue, cell, fluid, or other material obtained or derived from the subject. In some embodiments, the subject is human. The biological sample may contain any biological material suitable for detecting the desired analytes, and may comprise cellular and/or non-cellular material obtained from the subject. In certain embodiments, the biological sample is an endothelial cell. Biological samples include tissue samples (e.g., cell samples, biopsy samples), such as tissue from the heart or aorta. Biological samples also include bodily fluids, including, but not limited to, blood, blood serum, plasma, saliva, and urine.

By "capture reagent" is meant a reagent that specifically binds a nucleic acid molecule or polypeptide to select or isolate the nucleic acid molecule or polypeptide. In some embodiments, the capture reagent is a probe or primer that specifically binds a polynucleotide encoding a TGFβ signaling polypeptide, a let-7 miRNA, or a FGF signaling polypeptide.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In some embodiments, a level of a let-7 miRNA, a TGFβ signaling polypeptide or polynucleotide, or a FGF signaling polypeptide or polynucleotide is detected.

By "disease" is meant any condition or disorder that damages or interferes with the normal function of a cell, tissue, or organ. Examples of diseases include atherosclerosis, pulmonary hypertension, and chronic inflammation induced fibrosis.

By "effective amount" is meant the amount of a required to ameliorate the symptoms of a disease relative to an untreated patient. In particular embodiments, the disease is atherosclerosis. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In some embodiments, an effective amount of an agent that modulates activity or level of a FGF signaling polypeptide, let-7 miRNA, or TGFβ signaling polypeptide is an amount of the agent that reduces the growth and/or formation of atherosclerotic lesions or reverses atherosclerosis in a subject.

As used herein, a "FGF signaling polypeptide" is meant a member or component of a fibroblast growth factor (FGF) signaling pathway. In some embodiments, the FGF signaling polypeptide is FGFR1 polypeptide or FRS2α polypeptide.

By "FGFR1 polypeptide" is meant a polypeptide or fragment thereof having at least about 85% amino acid identity to GenBank Accession No. AAH15035.1 and having a biological activity of a FGFR1 polypeptide. Biological activities of a FGFR1 polypeptide include cell surface receptor activity and tyrosine kinase activity. The sequence at GenBank Accession No. AAH15035.1 is shown below (SEQ ID No: 21):

```
  1 mwswkcllfw avlvtatlct arpsptlpeq aqpwgapvev esflvhpgdl lqlrcrlrdd 61 vqsinwlrdg vqlaesnrtr itgeevevqd svpadsglya cvtsspsgsd ttyfsvnvsd 121 alpssedddd dddssseeke tdntkpnrmp vapywtspek mekklhavpa aktvkfkcps 181 sgtpnptlrw lkngkefkpd hriggykvry atwsiimdsv vpsdkgnytc iveneygsin 241 htyqldvver sphrpilqag lpanktvalg snvefmckvy sdpqphiqwl khievngski
```

-continued

```
301 gpdnlpyvqi lktagvnttd kemevlhlrn vsfedageyt clagnsigls hhsawltvle
361 aleerpavmt splyleiiiy ctgafliscm vgsvivykmk sgtkksdfhs qmavhklaks
421 iplrrqvsad ssasmnsgvl lvrpsrlsss gtpmlagvse yelpedprwe lprdrlvlgk
481 plgegcfgqv vlaeaigldk dkpnrvtkva vkmlksdate kdlsdlisem emmkmigkhk
541 niinllgact qdgplyvive yaskgnlrey lqarrppgle ycynpshnpe eqlsskdlvs
601 cayqvargme ylaskkcihr dlaarnvlvt ednvmkiadf glardihhid yykkttngrl
661 pvkwmapeal fdriythqsd vwsfgvllwe iftlggspyp gvpveelfkl lkeghrmdkp
721 snctnelymm mrdcwhavps qrptfkqlve dldrivalts nqeyldlsmp ldqyspsfpd
781 trsstcssge dsvfsheplp eepclprhpa qlangglkrr
```

By "FGFR1 polynucleotide" is meant a polynucleotide encoding a FGFR1 polypeptide. An exemplary FGFR1 polynucleotide sequence is provided at GenBank Accession No. BC015035.1. The exemplary sequence provided at GenBank Accession No. BC015035.1 is reproduced below (SEQ ID No: 22).

```
   1 agcgctcttg cggccacagg cgcggcgtcc tcggcggcgg gcggcagcta gcgggagccg
  61 ggacgccggt gcagccgcag cgcgcggagg aacccgggtg tgccgggagc tgggcggcca
 121 cgtccggacg ggaccgagac ccctcgtagc gcattgcggc gacctcgcct tccccggccg
 181 cgagcgcgcc gctgcttgaa aagccgcgga acccaaggac ttttctccgg tccgagctcg
 241 gggcgccccg cagggcgcac ggtaccccgtg ctgcagtcgg cacgccgcg gcgccgggc
 301 ctccgcaggg cgatggagcc cggtctgcaa ggaaagtgag gcgccgccgc tgcgttctgg
 361 aggaggggg caccagctcc ggctccattt ttccccgccccg ggctggaggc gccgagcacc
 421 gagcgccgcc gggagtcgag cgccggccgc ggagctcttg cgaccccgcc aggacccgaa
 481 cagagcccgg gggcggcggg ccggagccgg ggacgcgggc acacgcccgc tcgcacaagc
 541 cacggcggac tctcccgagg cggaacctcc acgccgagcg agggtcagtt tgaaaaggag
 601 gatcgagctc actgtggagt atccatggag atgtggagcc ttgtcaccaa cctctaactg
 661 cagaactggg atgtggagct ggaagtgcct cctcttctgg gctgtgctgg tcacagccac
 721 actctgcacc gctaggccgt ccccgacctt gcctgaacaa gcccagccct ggggagcccc
 781 tgtggaagtg gagtccttcc tggtccaccc cggtgacctg ctgcagcttc gctgtcggct
 841 gcgggacgat gtgcagagca tcaactggct gcgggacggg gtgcagctgg cggaaagcaa
 901 ccgcacccgc atcacagggg aggaggtgga ggtgcaggac tccgtgcccg cagactccgg
 961 cctctatgct tgcgtaacca gcagcccctc gggcagtgac accacctact tctccgtcaa
1021 tgtttcagat gctctcccct cctcggagga tgatgatgat gatgatgact cctcttcaga
1081 ggagaaagaa acagataaca ccaaaccaaa ccgtatgccc gtagctccat attggacatc
1141 cccagaaaag atggaaaaga aattgcatgc agtgccggct gccaagacag tgaagttcaa
1201 atgcccttcc agtgggaccc caaacccac actgcgctgg ttgaaaaatg caaagaatt
1261 caaacctgac cacagaattg gaggctacaa ggtccgttat gccacctgga gcatcataat
1321 ggactctgtg gtgccctctg acaagggcaa ctacacctgc attgtggaga tgagtacgg
1381 cagcatcaac cacacatacc agctggatgt cgtggagcgg tcccctcacc ggcccatcct
1441 gcaagcaggg ttgcccgcca acaaaacagt ggccctgggt agcaacgtgg agttcatgtg
1501 taaggtgtac agtgaccgcg agccgcacat ccagtggcta aagcacatcg aggtgaatgg
1561 gagcaagatt ggcccagaca acctgccttta tgtccagatc ttgaagactg ctggagttaa
1621 taccaccgac aaagagatgg aggtgcttca cttaagaaat gtctcctttg aggacgcagg
```

-continued

```
1681 ggagtatacg tgcttggcgg gtaactctat cggactctcc catcactctg catggttgac
1741 cgttctggaa gccctggaag agaggccggc agtgatgacc tcgcccctgt acctggagat
1801 catcatctat tgcacagggg ccttcctcat ctcctgcatg gtggggtcgg tcatcgtcta
1861 caagatgaag agtggtacca agaagagtga cttccacagc cagatggctg tgcacaagct
1921 ggccaagagc atccctctgc gcagacaggt gtctgctgac tccagtgcat ccatgaactc
1981 tggggttctt ctggttcggc catcacggct ctcctccagt gggactccca tgctagcagg
2041 ggtctctgag tatgagcttc ccgaagaccc tcgctgggag ctgcctcggg acagactggt
2101 cttaggcaaa cccctgggag agggctgctt tgggcaggtg gtgttggcag aggctatcgg
2161 gctggacaag gacaaaccca accgtgtgac caaagtggct gtgaagatgt tgaagtcgga
2221 cgcaacagag aaagacttgt cagacctgat ctcagaaatg gagatgatga agatgatcgg
2281 gaagcataag aatatcatca acctgctggg ggcctgcacg caggatggtc ccttgtatgt
2341 catcgtggag tatgcctcca agggcaacct gcgggagtac ctgcaggccc ggaggccccc
2401 agggctggaa tactgctaca accccagcca caacccagag gagcagctct cctccaagga
2461 cctggtgtcc tgcgcctacc aggtggcccg aggcatggag tatctggcct ccaagaagtg
2521 catacaccga gacctggcag ccaggaatgt cctggtgaca gaggacaatg tgatgaagat
2581 agcagacttt ggcctcgcac gggacattca ccacatcgac tactataaaa agacaaccaa
2641 cggccgactg cctgtgaagt ggatggcacc cgaggcatta tttgaccgga tctacaccca
2701 ccagagtgat gtgtggtctt tcggggtgct cctgtgggag atcttcactc tgggcggctc
2761 cccatacccc ggtgtgcctg tggaggaact tttcaagctg ctgaaggagg gtcaccgcat
2821 ggacaagccc agtaactgca ccaacgagct gtacatgatg atgcgggact gctggcatgc
2881 agtgccctca cagagaccca ccttcaagca gctggtggaa gacctggacc gcatcgtggc
2941 cttgacctcc aaccaggagt acctggacct gtccatgccc ctggaccagt actcccccag
3001 cttcccgac acccggagct ctacgtgctc ctcagggag gattccgtct tctctcatga
3061 gccgctgccc gaggagccct gcctgccccg acacccagcc cagcttgcca atggcggact
3121 caaacgccgc tgactgccac ccacacgccc tccccagact ccaccgtcag ctgtaaccct
3181 cacccacagc ccctgctggg cccaccacct gtccgtccct gtcccctttc ctgctggcag
3241 gagccggctg cctaccaggg gccttcctgt gtggcctgcc ttcaccccac tcagctcacc
3301 tctccctcca cctcctctcc acctgctggt gagaggtgca agaggcaga tctttgctgc
3361 cagccacttc atcccctccc agatgttgga ccaacacccc tccctgccac caggcactgc
3421 ctggagggca gggagtggga gccaatgaac aggcatgcaa gtgagagctt cctgagcttt
3481 ctcctgtcgg tttggtctgt tttgccttca cccataagcc cctcgcactc tggtggcagg
3541 tgccttgtcc tcagggctac agcagtaggg aggtcagtgc ttcgtgcctc gattgaaggt
3601 gacctctgcc ccagataggt ggtgccagtg gcttattaat tccgatacta gtttgctttg
3661 ctgaccaaat gcctggtacc agaggatggt gaggcgaagg ccaggttggg ggcagtgttg
3721 tggccctggg gcccagcccc aaactggggg ctctgtatat agctatgaag aaaacacaaa
3781 gtgtataaat ctgagtatat atttacatgt cttttaaaa gggtcgttac cagagattta
3841 cccatcgggt aagatgctcc tggtggctgg gaggcatcag ttgctatata ttaaaaacaa
3901 aaaaaaaaaa aaa
```

By "FRS2α polypeptide" is meant a polypeptide or fragment thereof having at least about 85% amino acid identity to NCBI Accession No. NP_001265286.1 and having a biological activity of a FRS2α polypeptide. Biological activities of a FRS2α polypeptide include transmembrane receptor protein tyrosine kinase adaptor activity and binding to a FGFR1 polypeptide. The sequence at NCBI Accession No. NP_001265286.1 is shown below (SEQ ID No: 23):

```
  1 mgsccscpdk dtvpdnhrnk fkvinvdddg nelgsgimel
    tdtelilytr krdsvkwhyl 61 clrrygydsn lfsfesgrrc qtgqgifafk caraeelfnm lqe-
    imqnnsi nvveepvver 121 nnhqtelevp rtprtpttpg faaqnlpngy prypsfgdas
    shpssrhpsv gsarlpsvge 181 esthpllvae eqvhtyvntt gvqeerknrt svhvplearv
    snaesstpke epssiedrdp 241 qillepegvk fvlgptpvqk qlmekekleq lgrdqvsgsg
    anntewdtgy dsderrdaps 301 vnklvyenin glsipsasgv rrgrltstst sdtqninnsa qrr-
    tallnye nlpslppvwe 361 arklsrdedd nlgpktpsln gyhnnldpmh nyvntenvtv pasahk-
    ieys rrrdctptvf 421 nfdirrpsle hrqlnyiqvd leggsdsdnp qtpktpttpl pqtp-
    trrtel yavidierta 481 amsnlqkalp rddgtsrktr hnstdlpm
```

By "FRS2α polynucleotide" is meant a polynucleotide encoding a FRS2α polypeptide. An exemplary FRS2α polynucleotide sequence is provided at NCBI Accession No. NM_001278357.1. The exemplary sequence provided at NCBI Accession No. NM_001278357.1 is reproduced below (SEQ ID No: 24).

```
   1 aaaaccctt ccctccccgc tcccccggaa gtgcttttcc aagattcggg ccggagagag
  61 gccttgtagg cacagcggct gagactcgat ctgctccaag tagggctcc agcgcgggtc
 121 ggagtctggg ggttcgcgcc cgccgacccg cgccctgctc cctctcagca cctgggcgga
 181 cggttaaatc agcaaacaaa gaaaacatgg tattttgaaa tatgattaaa ctcctgatgc
 241 tgcagcagag gctaagaata ttaatggcca gatctagtgc acacatggtc ttctgaagaa
 301 gccatgggta gctgttgtag ctgtccagat aaagacactg tcccagataa ccatcggaac
 361 aagtttaagg tcattaatgt ggatgatgat gggaatgagt taggttctgg cataatggaa
 421 cttacagaca cagaactgat tttatacacc cgcaaacgtg actcagtaaa atggcactac
 481 ctctgcctgc gacgctatgg ctatgactcg aatctctttt cttttgaaag tggtcgaagg
 541 tgtcaaactg gacaaggaat ctttgccttt aagtgtgccc gtgcagaaga attatttaac
 601 atgttgcaag agattatgca aaataatagt ataaatgtgg tggaagagcc agttgtagaa
 661 agaaataatc atcagacaga attggaagtc cctagaacac ctcgaacacc tacaactcca
 721 ggatttgctg ctcagaactt acctaatgga tatccccgat atccctcatt tggagatgct
 781 tcatcccatc cgtcaagcag acatccttct gtgggaagtg ctcgcctgcc ttcagtaggg
 841 gaagaatcta cacatccttt gcttgtggct gaggaacaag tatataccta tgtcaacact
 901 acaggtgtgc aagaagagcg gaaaaaccgc acaagtgtgc atgttccatt ggaggcgagg
 961 gtttctaacg ctgaaagcag cacaccaaaa gaagaaccaa gtagtattga ggacagggat
1021 cctcagattc ttcttgaacc tgaaggagtc aaatttgttt tagggccaac ccctgttcaa
1081 aagcagttaa tggaaaaaga gaaactggag caacttggaa gagatcaagt tagtggaagt
1141 ggagcaaata acacagaatg ggacactggc tatgacagtg atgaacgaag agatgcaccc
1201 tctgttaaca aactggtgta tgaaatata atgggctat ctatcccctag tgcctcaggg
1261 gtcaggagag gtcgtctgac atccaccagt acctcagata cccagaatat caacaactca
1321 gctcagagaa gaactgcatt attaaactat gaaaatctac catctttgcc tcctgtttgg
1381 gaagcccgca agctaagtag ggatgaagat gacaatttag gaccaaagac cccatctcta
1441 aatggctacc ataataatct agatccaatg cataactatg taaatacaga gaatgtaaca
1501 gtgccagcaa gtgctcacaa aatagaatat tcaaggcgtc gggactgtac accaacagtc
1561 tttaactttg atatcagacg cccaagttta gaacacaggc agcttaatta catacaggtt
1621 gacttggaag gtggcagtga ctctgacaac cctcagactc caaaaacgcc tacaactccc
```

-continued

```
1681 cttccacaaa cccctaccag gcgcacagag ctgtatgccg tgatagacat cgagagaact
1741 gctgctatgt caaatttgca gaaagcactg ccacgagatg atggtacatc taggaaaact
1801 agacacaata gtactgatct gcccatgtga gcctggaaag cattgtgttg tttgcacctt
1861 tgtgaagttt ttaaaaatga agatgcaagt gcttcatttt catttctaaa cactaactcc
1921 ttttatagac tgataaaatt ttttttctgaa tatttcatgt gcatctttaa ctaaagggaa
1981 ttaatgtaga gcaggtactc cttaaagaac actaatttca ttatatacta ctcgttgtac
2041 agcagcattc ccgttttcac agtgcctatt taaaatgaga gttgaagtaa atgacatgct
2101 ggttgatttt tatcaatatt ctggacttaa cgcatacctt tcatgtctaa gtcatggttg
2161 gcttttaaaa cttttttataa agcctcttga caatgtacat tgctaacagg taactatagg
2221 ctttgaaagt aatgctcgta gattcagtgt tcacagtatg tggcctccag catgtaacat
2281 gaggaatcct ttatttcatt aattaatggc ttttttgactt gagccaaaac atatgtaaag
2341 gaaacagaag taccgcacct cctcttacac cagtcagctc ctttgccttc agtgttacta
2401 gaaagcggcc tgtgtccatg agtgtgcttt gctgttggtg cactgaaagg caggaaggag
2461 acaagatttt ctatttactc atctcatgat gtcatttgaa gggcatgtcc agatatctta
2521 aaattataat aggctcaaga atcagtctca ggtcactttta cccaaaaaca tttgaaaatc
2581 tgaaccacaa tctcctgaaa gttttttctcc tatagattgt tgacaacaca ttgttttctg
2641 gaggcatttg tgccattagg tttccattta tcttcagttt ttttctttgg tgtttgggat
2701 gtcttatttt gttgccttat gtccttttca atttaaaatg tttgagtttg tatatagttt
2761 tgaaattgga ttatgtgttc attgttgttt agtttgcatt tttgtcaaat tatggttttg
2821 aaggttcatt tggaacttac tgttagtctg taacagggtt gcccttgtcc agtatttatt
2881 tataagctgt ttacttttca agttgataaa aacattctcc aattctaaat ttgcttgtgt
2941 ccataggtga tctctttagc aaactgagaa aaaaggaag ctacttttaa catgcaaagt
3001 tccctcaagg tgtaccgtgt tgtctctgtg ggcactcttc cccagcactt tagcagtaat
3061 tcccccagct acacgctgca gttgtactct gcccactcta gtgttcctca gctctgctgt
3121 ccttttactt gtagctggat cttttgattat ccttcgattt ccatgaaata ttaatattgt
3181 tgccagcata gcaggtacag tggaagtctt gtagcagtga gattgtatca taatttagga
3241 ttttaaaatga attaaagttt atataaactg aagagtctcc atatgtcaaa ctcttggaaa
3301 atcaaagatg ttccaatttc ctaaacacta gagaatacga gagaaggtag agtggaaaag
3361 gttaggtaac cttgcaaaat attttactat tttctctaaa tatgaggaag tttgagatta
3421 tgatctggat ctaccagata taactaaggt taatttagca tgaaaaagtt ttagtcatat
3481 tggcatccaa cctattcagt aaccgaatca taggacaatg atggattagg agaacaatag
3541 agtgggatca ttataaagaa aataaattat taaaggtgtc tttatcgttt tagtgccatt
3601 tttagtgtct ttactataaa tcaatatcag tgtatttat cattctatgt gcatagcaga
3661 attttctttt ctcccttttg ttccctgtg aacttggtgc ttattaaagt gctcactgtt
3721 ctcttaaaag agagcagtgg tataggtgtg cagtttccat gatgcaggtt ccatttttaa
3781 tatattgttc cacttatcct ttcttctgag taaattgcta attgtgccaa atttatgtaa
3841 tagtttttgt aatgtggaat aagaattatg atggaaccat tgcacatttt tttctgaaac
3901 agccagtcaa ggcagaacat taatctccaa atgcaagggc tgatctattt attcattttg
3961 gaggttgggt actttattct ttctttccgt catccttttc attgttttccc ccggattcta
4021 attagttttt attttttta gataactcca atataatcat tacagtttat gctttaaata
4081 ctatgtgctt taaaaaggaa aatgggacca atttgtctgc taagaatttg attttaggta
```

-continued

```
4141 ctataagagt attaggaaaa tatatacaac tggtgttaat ttctagatat tttctagaaa
4201 tcacttgtgt tcctatttaa taaaaggtaa tttagaatac tacttgtcct ttgcagtagt
4261 ttagtaatgg gcattaagct gtgtcctcga aggatgtacc tattactagg tgcattttag
4321 aatgaaatat tgatatttta ttagcatata attgtggcca tatatctcag attttctgag
4381 gcagatctaa ttttagataa ttctgttggt agaccatgtg atccttcttt ttggttttgg
4441 aaatataatc attgttaatg ttttccctcc aaatagaata ctgttttatc catacaaatc
4501 ataacagcat ctatcccatg ctagggttgg aaactgatat tggtattact tgtgtttttt
4561 cttagtgtgt tttatttccc agtttcatct tcttctaaaa atgaaaatat ggtgccttcc
4621 ctccctccag gaagactggc aaatatttcc ttttatttac tgctgctgtg gagtgatgag
4681 atatgcactt tactctttaa gattcagcaa aaagcttttc acttctcagt atatccagaa
4741 tacatcatat ctgggactta ggaaaatttg ccaagcaatc tttgttttta tagatactaa
4801 tgttgaccct ctccagcgtt caatgttata aatagaacaa gtcaagctag tgtttatctc
4861 ctcccccctcc ccaaaactgt ggcacagcat ataaaaatgt acctcaataa tgttctatta
4921 aaaatgggac aggggcctta tgttttcata atttcccaac aatgtgccgc catattttg
4981 cctcaaggta aaggttttaa cagatgaaaa agtacttccc aattccccg tgctattcct
5041 aacctataat gcccaaatgt tttgtgcaat gtgtagtgtg tgtgtataaa tacatatatt
5101 cttgaaatag acataccatc agagacatca ttcacaagta actgatgtat tggcatctca
5161 ttcatatttc tgatgtgtga ggtatatggt actaattacc ttttccttga tgtttgccaa
5221 atttgaataa aggcattggt acgaaattac agaatgtaaa gaaaatgttt ttggcttgaa
5281 aaattaacat attttatgac gtaccacagt atactctgcc caaaccagca ccctatctat
5341 ctttcctgtt ctttacatcc ctgttcccca tccctacttc ctcattttg gtataacaca
5401 gttcttttgt agcatcatta taattgcagt tctatggcaa ttggacagtt atagcatgga
5461 aacagactgg tataagtagt acagtagtca ccagtgtgcc acatttgcat tagtaatgca
5521 aaatatacat tttataaagg acaaactttg tgttatgttt tattttcatt acattgtata
5581 atattgtaag actattgtat gtcctaattt gcattataaa tgtttttttc ctacgtaaag
5641 gcataaatat agcaactttg tataaaggta gcttattaga ttttaatttt tttcttttat
5701 aaaaaattgt ccaacagtgg gactaccatt gccaaattgt atatgaaata tgaattttac
5761 ccccatggtt aatttctttt ataaacattc catatttctc taataaaaag acataagtga
5821 tactgtacta tgcatacatt gtatcttaat gctgtttcag atcagcattt taaattttgg
5881 tttgcatttt taatattggc aaaacgtaac cactgttaat taaaataaaa ccttgttgta
5941 tatgtaacaa cataattttc cctctatccc ttcccaccct tgttctctca tttctcccta
6001 tcagtgccaa cttcatacat tttgtagcat ggcaataaaa tataacttt acactgaggc
6061 cgagtgtggc ttttggagg aagtggggat gggacgattg ccctctagtt gtcctttgca
6121 tatgactgtt ttttgccata taagccatgt catcaggcat gaaaagtttt ctcatatatg
6181 atgtaaactt gcttttaagg acaagtgtga atgtgctttt taagcttaat ttttgtcatg
6241 acaactaatt tttttatct ttggagaagt cagagttctt tacaatcaaa cgtttattaa
6301 ctggagtact tagaataagc tagtaattga atttagttca agggctaagc aacacatttt
6361 taaatcctta tttattgtag agtattagta tactgtccta caaattatgt aaaatatggt
6421 ttaatattag atgactttgg attttgcaat gccttactgt tgtcattcta gcataaaatat
6481 ccataatgag gtactcaagt tgatactgga agctgagctg atcatacact gacctgaagc
```

```
-continued
6541 attcatgaaa agctgcttta ttgaataaag tctgattgga gttcttttca tgctcactttt 6601 ccccttattg ctgaaagtag attgcaataa aacccaata aaacgtttgg tcggatatct 6661 acttaaaaaa aaaaaa
```

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "expression" as used herein is defined as the transcription and/or translation 40 of a particular nucleotide sequence driven by its promoter.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any polypeptide or polynucleotide having an alteration in expression level, sequence, or activity that is associated with a disease or disorder or risk of disease or disorder. In some embodiments, a decrease in activity or level of a FGF signaling polypeptide or let-7 miRNA in an endothelial cell is associated with development and/or progression of atherosclerosis. In some embodiments, an increase in level or activity of a TGFβ signaling polypeptide (e.g., TGFβ1, TGFβ2, TGFβ3, TGFβR1, TGFβR2) in an endothelial cell is associated with development and/or progression of atherosclerosis. In some other embodiments, an increase in activity or level of a FGF signaling polypeptide or let-7 miRNA in a smooth muscle cell is associated with development and/or progression of atherosclerosis. In still other embodiments, a decrease in level or activity of a TGFβ signaling polypeptide (e.g., TGFβ1, TGFβ2, TGFβ3, TGFβR1, TGFβR2) is associated with development and/or progression of atherosclerosis.

As used herein, "microRNA" or "miRNA" describes small non-coding RNA molecules, generally about 15 to about 50 nucleotides in length, preferably 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from 20 primary transcripts (pri-miRNA) through sequential cleavage by RNAse III enzymes. miRBase is a comprehensive microRNA database located at www.mirbase.org, incorporated by reference herein in its entirety for all purposes.

By "let-7 miRNA" is meant a miRNA member of the let-7 miRNA family. Sequences of members of the let-7 miRNA family can be found in, for example, www.mirbase.org.

Exemplary members of the let-7 miRNA family include hsa-let-7b or human let-7b (miRBase Accession No. MI0000063), hsa-let-7a-1 (miRBase Accession No. MI0000060), hsa-let-7a-2 (miRBase Accession No. MI0000061), hsa-let-7a-3 (miRBase Accession No. MI0000062), hsa-let-7b, hsa-let-7c (miRBase Accession No. MI0000064), hsa-let-7d (miRBase Accession No. MI0000065), hsa-let-7e (miRBase Accession No. MI0000066), hsa-let-7f-1 (miRBase Accession No. MI0000067), hsa-let-7f-2 (miRBase Accession No. MI0000068), hsa-let-7g (miRBase Accession No. MI0000433), and hsa-let-7i (miRBase Accession No. MI00000434). The sequence of human let-7b provided at miRBase Accession No. MI0000063 is reproduced below.

```
human let-7b (5 prime):
                                        (SEQ ID No: 19)
UGAGGUAGUAGGUUGUGUGGUU human let-7b (3 prime):
                                        (SEQ ID No: 20)
CUAUACAACCUACUGCCUUCCC
```

The let-7 miRNA family has been shown to play important roles in animal development, cell differentiation, and metabolism. In some embodiments, an activity of let-7 miRNA is repression of expression of a TGFβ signaling polypeptide. In some embodiments, an activity of let-7 miRNA is repression of TGFβ signaling.

In some embodiments, the let-7 miRNA is used as a therapeutic. Use of let-7 miRNA as a therapeutic has been demonstrated previously. For example, let-7 miRNA was used as anti-cancer therapy (Trang et al., Mol Ther. 2011 June; 19(6): 1116-1122).

In some embodiments, the let-7 miRNA is chemically modified. In particular embodiments, uracil ("U") or cytosine ("C") is chemically modified. In some embodiments, the miRNA is modified to impart properties to the miRNA to make it useful as a therapeutic, such as attenuated immunostimulation and increased serum stability. Such modifications to the miRNA include, without limitation, incorporation of a 2'-O-methyl (2'-O-Me), phosphorothioate (PS), and deoxy thymidine (dT) residues. In particular embodiments, the modified miRNA retains silencing activity in vivo. In particular embodiments, the modification is a 2'-O-methyl nucleotide modification. In some embodiments, the modification decreases the likelihood of triggering an innate immune response.

In some embodiments, the let-7 miRNA contains a "light" modification. By a miRNA containing a "light modification" is meant that the miRNA contains a 2'-O-methyl modification on all U and C nucleotide bases followed by adenosine ("A") on the antisense strand. In some other embodiments, the let-7 miRNA contains a "heavy" modification. By a miRNA containing a "heavy modification" is meant that the miRNA contains a 2'-O-methyl modification on all U and C nucleotide bases on the sense strand.

In still other embodiments, the let-7 miRNA is "mi-let-7b$_L$". mi-let-7b$_L$ is also referred to herein as "let-7 light." The sequence of mi-let-7b$_L$ is provided below:

```
mi-let-7b_L (5 prime):
                                        (SEQ ID No: 19)
UGAGGuAGuAGGUUGUGUGGUU
```

```
mi-let-7b_L (3 prime):
                                        (SEQ ID NO: 20)
CuAuAcAACCuACUGCCUUCCC
```

In some other embodiments, the let-7 miRNA is "mi-let-7b$_H$". mi-let-7b$_H$ is also referred to herein as "let-7 heavy." The sequence of mi-let-7b$_H$ miRNA is provided below:

```
mi-let-7b_H (5 prime):
                                        (SEQ ID No: 19)
UGAGGuAGuAGGUUGUGUGGUU mi-let-7b_H (3 prime):
                                        (SEQ ID NO: 20)
cuAuAcAAccuAcuGccuuccc
```

In the foregoing sequences, lower case indicates a nucleotide base containing a 2'-O-methyl modification.

As used herein, "obtaining" as in "obtaining an agent" includes synthesizing, purchasing, or otherwise acquiring the agent.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

As used herein, "polynucleotide" includes cDNA, RNA, DNA/RNA hybrid, antisense RNA, siRNA, miRNA, snoRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, the term "promoter" or "regulatory sequence" means a nucleic acid sequence which is required for expression of a gene product operably linked to the promoter or regulator sequence. In some instances, this sequence may be the core promoter sequence and in other instances, this sequence may also include an enhancer sequence and other regulatory elements which are required for expression of the gene product. The promoter or regulatory sequence may, for example, be one which expresses the gene product in an inducible manner.

By "reduces" is meant a negative alteration of at least 10%, 25%, 50%, 75%, or 100%.

By "reference" is meant a standard or control condition. In some embodiments, the reference is an activity or level of a TGFβ signaling polypeptide or polynucleotide or a FGF signaling polypeptide or polynucleotide in a healthy, normal subject or in a subject that does not have atherosclerosis. In some embodiments, the reference is an activity or level of a let-7 miRNA in a healthy, normal subject or in a subject that does not have atherosclerosis. In some embodiments, the TGFβ signaling polypeptide or polynucleotide is a TGFβ1, TGFβ2, TGFβ3, TGFβR1, or TGFβR2 polypeptide or polynucleotide. In some embodiments, the FGF signaling polypeptide is FRS2α. In some other embodiments, the let-7 miNA is at least one selected from the group consisting of human let-7b miRNA and human let-7c miRNA.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, or at least about 25 amino acids. The length of the reference polypeptide sequence can be about 35 amino acids, about 50 amino acids, or about 100 amino acids. For nucleic acids, the length of the reference nucleic acid sequence will generally be at least about 50 nucleotides, at least about 60 nucleotides, or at least about 75 nucleotides. The length of the reference nucleic acid sequence can be about 100 nucleotides, about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant an agent that recognizes and binds a polypeptide or polynucleotide of the invention, but which does not substantially recognize and bind other molecules in a sample, for example, a biological sample, which naturally includes a polynucleotide of the invention. In some embodiments, the agent is a nucleic acid molecule.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence is at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, a "TGFβ signaling polypeptide" refers to a member or component of a transformation growth factor β (TGFβ) signaling pathway. Exemplary TGFβ signaling polypeptides include polypeptides TGFβ1, TGFβ2, TGFβ3, TGFβR1, TGFβR2, SMAD1, SMAD2, SMAD3, SMAD4, SMAD5, and SMAD9.

As used herein, a "TGFβ signaling polynucleotide" is a polynucleotide encoding a TGFβ signaling polypeptide.

By "TGFβ1 polypeptide" is meant a polypeptide or fragment thereof having at least about 85% amino acid identity to GenBank Accession No. AAH22242.1 and having a biological activity of a TGFβ1 polypeptide. Biological activities of a TGFβ1 polypeptide include binding to a type II transforming growth factor β (TGFβ) receptor and homodimerization. The sequence at GenBank Accession No. AAH22242.1 is shown below (SEQ ID NO: 25):

```
  1 mppsglrlll lllpllwllv ltpgrpaagl stcktidmel vkrkrieair gqilsklrla
 61 sppsqgevpp gplpeavlal ynstrdrvag esaepepepe adyyakevtr vlmvethnei
121 ydkfkqsths iymffntsel reavpepvll sraelrllrl klkveqhvel yqkysnnswr
181 ylsnrllaps dspewlsfdv tgvvrqwlsr ggeiegfrls ahcscdsrdn tlqvdingft
241 tgrrgdlati hgmnrpflll matpleraqh lqssrhrral dtnycfsste knccvrqlyi
301 dfrkdlgwkw ihepkgyhan fclgpcpyiw sldtqyskvl alynqhnpga saapccvpqa
361 leplpivyyv grkpkveqls nmivrsckcs
```

By "TGFβ1 polynucleotide" is meant a polynucleotide encoding a TGFβ1 polypeptide. An exemplary TGFβ1 polynucleotide sequence is provided at GenBank Accession No. BC022242.1. The exemplary sequence provided at GenBank Accession No. BC022242.1 is reproduced below (SEQ ID NO: 26).

```
   1 cccagacctc gggcgcaccc cctgcacgcc gccttcatcc ccggcctgtc tcctgagccc
  61 ccgcgcatcc tagacccttt ctcctccagg agacggatct ctctccgacc tgccacagat
 121 cccctattca agaccaccca ccttctggta ccagatcgcg cccatctagg ttatttccgt
 181 gggatactga dacaccccg gtccaagcct cccctccacc actgcgccct tctccctgag
 241 gacctcagct ttccctcgag gccctcctac cttttgccgg gagaccccca gcccctgcag
 301 gggcggggcc tccccaccac accagccctg ttcgcgctct cggcagtgcc gggggcgcc
 361 gcctccccca tgccgccctc cgggctgcgg ctgctgctgc tgctgctacc gctgctgtgg
 421 ctactggtgc tgacgcctgg ccggccggcc gcgggactat ccacctgcaa gactatcgac
 481 atggagctgg tgaagcggaa gcgcatcgag gccatccgcg gccagatcct gtccaagctg
 541 cggctcgcca gccccccgag ccaggggag gtgccgcccg gcccgctgcc cgaggccgtg
 601 ctcgccctgt acaacagcac ccgcgaccgg gtggccgggg agagtgcaga accggagccc
 661 gagcctgagg ccgactacta cgccaaggag gtcacccgcg tgctaatggt ggaaacccac
 721 aacgaaatct atgacaagtt caagcagagt acacacagca tatatatgtt cttcaacaca
 781 tcagagctcc gagaagcggt acctgaaccc gtgttgctct cccgggcaga gctgcgtctg
 841 ctgaggctca agttaaaagt ggagcagcac gtggagctgt accagaaata cagcaacaat
 901 tcctggcgat acctcagcaa ccggctgctg cacccagcg actcgccaga gtggttatct
 961 tttgatgtca ccggagttgt gcggcagtgg ttgagccgtg aggggaaat tgagggcttt
1021 cgccttagcg cccactgctc ctgtgacagc agggataaca cactgcaagt ggacatcaac
1081 gggttcacta ccggccgccg aggtgacctg gccaccattc atggcatgaa ccggcctttc
1141 ctgcttctca tggccacccc gctggagagg gcccagcatc tgcaaagctc ccggcaccgc
1201 cgagccctgg acaccaacta ttgcttcagc tccacggaga agaactgctg cgtgcggcag
1261 ctgtacattg acttccgcaa ggacctcggc tggaagtgga tccacgagcc aagggctac
1321 catgccaact tctgcctcgg gccctgcccc tacatttgga gcctggacac gcagtacagc
1381 aaggtcctgg ccctgtacaa ccagcataac ccgggcgcct cggcggcgcc gtgctgcgtg
1441 ccgcaggcgc tggagccgct gcccatcgtg tactacgtgg gccgcaagcc caaggtggag
1501 cagctgtcca acatgatcgt gcgctcctgc aagtgcagct gaggtcccgc ccgccccgc
1561 cccgccccgg caggcccggc ccacccccgc cccgccccg ctgccttgcc catgggggct
1621 gtatttaagg acacccgtgc cccaagccca cctggggccc cattaaagat ggagagagga
1681 aaaaaaaaaa aaaaaaaaaa aaaaaaaaaa aaaaaaaaaa aaaaaaaaaa aaaaaaaaaa
1741 aaaaaa
```

By "TGFβ2 polypeptide" is meant a polypeptide or fragment thereof having at least about 85% amino acid identity to GenBank Accession No. AAA50405.1 and having a biological activity of a TGFβ2 polypeptide. Biological activities of a TGFβ2 polypeptide include binding to a type II transforming growth factor β (TGFβ) receptor and homodimerization. The sequence at GenBank Accession No. AAA50405.1 is shown below (SEQ ID NO: 27):

```
  1 mhycvlsafl ilhlvtvals lstcstldmd qfmrkrieai rgqilsklkl tsppedypep
 61 eevppevisi ynstrdllqe kasrraaace rersdeeyya kevykidmpp ffpseaippt
121 fyrpyfrivr fdvsamekna snlvkaefrv frlqnpkarv peqrielyqi lkskdltspt
181 qryidskvvk traegewlsf dvtdavhewl hhkdrnlgfk islhcpcctf vpsnnyiipn
241 kseelearfa gidgtstyts gdqktikstr kknsgktphl llmllpsyrl esqqtnrrkk
301 raldaaycfr nvqdncclrp lyidfkrdlg wkwihepkgy nanfcagacp ylwssdtqhs
361 rvlslyntin peasaspccv sqdlepltil yyigktpkie qlsnmivksc kcs
```

By "TGFβ2 polynucleotide" is meant a polynucleotide encoding a TGFβ2 polypeptide. An exemplary TGFβ2 polynucleotide sequence is provided at GenBank Accession No. M19154.1. The exemplary sequence provided at GenBank Accession No. M19154.1 is reproduced below (SEQ ID NO: 28).

```
   1 gcccctcccg tcagttcgcc agctgccagc cccgggacct tttcatctct tccctttttgg
  61 ccggaggagc cgagttcaga tccgccactc cgcacccgag actgacacac tgaactccac
 121 ttcctcctct taaatttatt tctacttaat agccactcgt ctctttttt ccccatctca
 181 ttgctccaag aattttttc ttcttactcg ccaaagtcag ggttccctct gcccgtcccg
 241 tattaatatt tccacttttg gaactactgg ccttttcttt ttaaaggaat tcaagcagga
 301 tacgttttc tgttgggcat tgactagatt gtttgcaaaa gtttcgcatc aaaaacaaca
 361 acaacaaaaa accaaacaac tctccttgat ctatactttg agaattgttg atttctttt
 421 tttattctga cttttaaaaa caactttttt ttccactttt ttaaaaaatg cactactgtg
 481 tgctgagcgc ttttctgatc ctgcatctgg tcacggtcgc gctcagcctg tctacctgca
 541 gcacactcga tatggaccag ttcatgcgca agaggatcga ggcgatccgc gggcagatcc
 601 tgagcaagct gaagctcacc agtccccag aagactatcc tgagcccgag gaagtccccc
 661 cggaggtgat ttccatctac aacagcacca gggacttgct ccaggagaag gcgagccgga
 721 gggcggccgc ctgcgagcgc gagaggagcg acgaagagta ctacgccaag gaggtttaca
 781 aaatagacat gccgcccttc ttcccctccg aaactgtctg cccagttgtt acaacaccct
 841 ctggctcagt gggcagcttg tgctccagac agtcccaggt gctctgtggg taccttgatg
 901 ccatcccgcc cactttctac agaccctact tcagaattgt tcgatttgac gtctcagcaa
 961 tggagaagaa tgcttccaat ttggtgaaag cagagttcag agtctttcgt ttgcagaacc
1021 caaaagccag agtgcctgaa caacggattg agctatatca gattctcaag tccaaagatt
1081 taacatctcc aacccagcgc tacatcgaca gcaaagttgt gaaaacaaga gcagaaggcg
1141 aatggctctc cttcgatgta actgatgctg ttcatgaatg gcttcaccat aaagacagga
1201 acctgggatt taaaataagc ttacactgtc cctgctgcac ttttgtacca tctaataatt
1261 acatcatccc aaataaaagt gaagaactag aagcaagatt tgcaggtatt gatggcacct
1321 ccacatatac cagtggtgat cagaaaacta taaagtccac taggaaaaaa aacagtggga
```

-continued

```
1381 agaccccaca tctcctgcta atgttattgc cctcctacag acttgagtca caacagacca 1441 accggcggaa gaagcgtgct ttggatgcgg cctattgctt tagaaatgtg caggataatt 1501 gctgcctacg tccactttac attgatttca agagggatct agggtggaaa tggatacacg 1561 aacccaaagg gtacaatgcc aacttctgtg ctggagcatg cccgtattta tggagttcag 1621 acactcagca cagcagggtc ctgagcttat ataataccat aaatccagaa gcatctgctt 1681 ctccttgctg cgtgtcccaa gatttagaac ctctaaccat tctctactac attggcaaaa 1741 cacccaagat tgaacagctt tctaatatga ttgtaaagtc ttgcaaatgc agctaaaatt 1801 cttggaaaag tggcaagacc aaaatgacaa tgatgatgat aatgatgatg acgacgacaa 1861 cgatgatgct tgtaacaaga aaacataaga gagccttggt tcatcagtgt taaaaaattt 1921 ttgaaaaggc ggtactagtt cagacacttt ggaagtttgt gttctgtttg ttaaaactgg 1981 catctgacac aaaaaaagtt gaaggcctta ttctacattt cacctacttt gtaagtgaga 2041 gagacaagaa gcaaattttt tttaaagaaa aaaataaaca ctggaagaat ttattagtgt 2101 taattatgtg aacaacgaca acaacaacaa caacaacaaa caggaaaatc ccattaagtg 2161 gagttgctgt acgtaccgtt cctatcccgc gcctcacttg atttttctgt attgctatgc 2221 aataggcacc cttcccattc ttactcttag agttaacagt gagttattta ttgtgtgtta 2281 ctatataatg aacgtttcat tgcccttgga aaataaaaca ggtgtataaa gtggagacca 2341 aatactttgc cagaaactca tggatggctt aaggaacttg aactcaaacg agccagaaaa 2401 aaagaggtca tattaatggg atgaaaaccc aagtgagtta ttatatgacc gagaaagtct 2461 gcattaagat aaagaccctg aaaacacatg ttatgtatca gctgcctaag gaagcttctt 2521 gtaaggtcca aaaactaaaa agactgttaa taaaagaaac tttcagtcag
```

By "TGFβ3 polypeptide" is meant a polypeptide or fragment thereof having at least about 85% amino acid identity to GenBank Accession No. EAW81249.1 and having a biological activity of a TGFβ3 polypeptide. Biological activities of a TGFβ3 polypeptide include binding to a type II transforming growth factor β (TGFβ) receptor and homodimerization. The sequence at GenBank Accession No. EAW81249.1 is shown below (SEQ ID NO: 29):

```
  1 mkmhlqralv vlallnfatv slslstcttl dfghikkkrv eairgqilsk lrltsppept 61 vmthvpyqvl alynstrell eemhgereeg ctqentesey yakeihkfdm iqglaehnel 121 avcpkgitsk vfrfnvssve knrtnlfrae frvlrvpnps skrneqriel fqilrpdehi 181 akqryiggkn lptrgtaewl sfdvtdtvre wllrresnlg leisihcpch tfqpngdile 241 nihevmeikf kgvdneddhg rgdlgrlkkq kdhhnphlil mmipphrldn pgqggqrkkr 301 aldtnycfrn leenccvrpl yidfrqdlgw kwvhepkgyy anfcsgpcpy lrsadtthst 361 vlglyntlnp easaspccvp qdlepltily yvgrtpkveq lsnmvvksck cs
```

By "TGFβ3 polynucleotide" is meant a polynucleotide encoding a TGFβ3 polypeptide. An exemplary TGFβ3 polynucleotide sequence is provided at NCBI Accession No. NG_011715.1. The exemplary sequence provided at NCBI Accession No. BT007287.1 is reproduced below (SEQ ID NO: 30).

```
  1 atgaagatgc acttgcaaag ggctctggtg gtcctggccc tgctgaactt tgccacggtc 61 agcctctctc tgtccacttg caccaccttg gacttcggcc acatcaagaa gaagagggtg
```

```
121 gaagccatta ggggacagat cttgagcaag ctcaggctca ccagccccc tgagccaacg 181 gtgatgaccc acgtcccta tcaggtcctg gccctttaca acagcacccg ggagctgctg 241 gaggagatgc atggggagag ggaggaaggc tgcacccagg aaaacaccga gtcggaatac 301 tatgccaaag aaatccataa attcgacatg atccaggggc tggcggagca caacgaactg 361 gctgtctgcc ctaaaggaat tacctccaag gttttccgct tcaatgtgtc ctcagtggag 421 aaaaatagaa ccaacctatt ccgagcagaa ttccgggtct tgcgggtgcc caaccccagc 481 tctaagcgga atgagcagag gatcgagctc ttccagatcc ttcggccaga tgagcacatt 541 gccaaacagc gctatatcgg tggcaagaat ctgcccacac ggggcactgc cgagtggctg 601 tcctttgatg tcactgacac tgtgcgtgag tggctgttga aagagagtc caacttaggt 661 ctagaaatca gcattcactg tccatgtcac acctttcagc ccaatggaga tatcctggaa 721 aacattcacg aggtgatgga aatcaaattc aaaggcgtgg acaatgagga tgaccatggc 781 cgtggagatc tggggcgcct caagaagcag aaggatcacc acaaccctca tctaatcctc 841 atgatgattc ccccacaccg gctcgacaac ccgggccagg ggggtcagag gaagaagcgg 901 gctttggaca ccaattactg cttccggtag
```

By "TGFβR1 polypeptide" is meant a polypeptide or fragment thereof having at least about 85% amino acid identity to GenBank Accession No. AAH71181.1 and having a biological activity of a TGFβR1 polypeptide. Biological activities of a TGFβR1 polypeptide include binding to ligands TGFβ1, TGFβ2, and TGFβ3 polypeptides, and transduction of a signal from TGFβ1, TGFβ2, or TGFβ3 polypeptide binding from the cell surface to the cytoplasm. The sequence at GenBank Accession No. AAH71181.1 is shown below (SEQ ID NO: 31):

```
  1 meaavaaprp rllllvlaaa aaaaaallpg atalqcfchl ctkdnftcvt dglcfvsvte 61 ttdkvihnsm ciaeidlipr drpfvcapss ktgsvtttyc cnqdhcnkie lpttglpllv 121 qrtiartivl qesigkgrfg evwrgkwrge evavkifssr eerswfreae iyqtvmlrhe 181 nilgfiaadn kdngtwtqlw lvsdyhehgs lfdylnrytv tvegmiklal stasglahlh 241 meivgtqgkp aiahrdlksk nilvkkngtc ciadlglavr hdsatdtidi apnhrvgtkr 301 ymapevldds inmkhfesfk radiyamglv fweiarrcsi ggihedyqlp yydlvpsdps 361 veemrkvvce qklrpnipnr wqscealrvm akimrecwya ngaarltalr ikktlsqlsq 421 qegikm
```

By "TGFβR1 polynucleotide" is meant a polynucleotide encoding a TGFβR1 polypeptide. An exemplary TGFβR1 polynucleotide sequence is provided at GenBank Accession No. BC071181.1. The exemplary sequence provided at GenBank Accession No. BC071181.1 is reproduced below (SEQ ID NO: 32).

```
  1 gcggcggcta gggaggtggg gcgaggcgag gtttgctggg gtgaggcagc ggcgcggccg 61 ggccgggccg ggccacaggc ggtggcggcg ggaccatgga ggcggcggtc gctgctccgc 121 gtccccggct gctcctcctc gtgctggcgg cggcggcggc ggcggcggcg gcgctgctcc 181 cgggggcgac ggcgttacag tgtttctgcc acctctgtac aaaagacaat tttacttgtg 241 tgacagatgg gctctgcttt gtctctgtca cagagaccac agacaaagtt atacacaaca 301 gcatgtgtat agctgaaatt gacttaattc ctcgagatag gccgtttgta tgtgcaccct
```

-continued

```
 361 cttcaaaaac tgggtctgtg actacaacat attgctgcaa tcaggaccat tgcaataaaa
 421 tagaacttcc aactactggt ttaccattgc ttgttcagag aacaattgcg agaactattg
 481 tgttacaaga aagcattggc aaaggtcgat ttggagaagt ttggagagga aagtggcggg
 541 gagaagaagt tgctgttaag atattctcct ctagagaaga acgttcgtgg ttccgtgagg
 601 cagagattta tcaaactgta atgttacgtc atgaaaacat cctgggattt atagcagcag
 661 acaataaaga caatggtact tggactcagc tctggttggt gtcagattat catgagcatg
 721 gatccctttt tgattactta aacagataca cagttactgt ggaaggaatg ataaaacttg
 781 ctctgtccac ggcgagcggt cttgcccatc ttcacatgga gattgttggt acccaaggaa
 841 agccagccat tgctcataga gatttgaaat caaagaatat cttggtaaag aagaatggaa
 901 cttgctgtat tgcagactta ggactggcag taagacatga ttcagccaca gataccattg
 961 atattgctcc aaaccacaga gtgggaacaa aaaggtacat ggcccctgaa gttctcgatg
1021 attccataaa tatgaaacat tttgaatcct tcaaacgtgc tgacatctat gcaatgggct
1081 tagtattctg ggaaattgct cgacgatgtt ccattggtgg aattcatgaa gattaccaac
1141 tgccttatta tgatcttgta ccttctgacc catcagttga agaaatgaga aaagttgttt
1201 gtgaacagaa gttaaggcca aatatcccaa acagatggca gagctgtgaa gccttgagag
1261 taatggctaa aattatgaga gaatgttggt atgccaatgg agcagctagg cttacagcat
1321 tgcggattaa gaaaacatta tcgcaactca gtcaacagga aggcatcaaa atgtaattct
1381 acagctttgc ctgaactctc ctttttttctt cagatctgct cctgggtttt aatttgggag
1441 gtcaattgtt ctacctcact gagagggaac agaaggatat tgcttccttt tgcagcagtg
1501 taataaagtc aattaaaaac ttcccaggat ttctttggac ccaggaaaca gccatgtggg
1561 tcctttctgt gcactatgaa cgcttctttc ccaggacaga aaatgtgtag tctaccttta
1621 tttttttatta acaaaacttg tttttttaaaa agatgattgc tggtcttaac tttaggtaac
1681 tctgctgtgc tggagatcat ctttaagggc aaaggagttg gattgctgaa ttacaatgaa
1741 acatgtctta ttactaaaga aagtgattta ctcctggtta gtacattctc agaggattct
1801 gaaccactag agtttccttg attcagactt tgaatgtact gttctatagt ttttcaggat
1861 cttaaaacta acacttataa aactcttatc ttgagtctaa aaatgacctc atatagtagt
1921 gaggaacata attcatgcaa ttgtattttg tatactatta ttgttctttc acttattcag
1981 aacattacat gccttcaaaa tgggattgta ctataccagt aagtgccact tctgtgtctt
2041 tctaatggaa atgagtagaa ttgctgaaag tctctatgtt aaaacctata gtgtttgaat
2101 tcaaaaagct tatttatctg ggtaacccaa acttttttctg ttttgttttt ggaagggttt
2161 ttgtggtatg tcatttggta ttctattctg aaaatgcctt tctcctacca aaatgtgctt
2221 aagccactaa agaaatgaag tggcattaat tagtaaatta ttagcatggt catgtttgaa
2281 tattctcaca tcaagctttt gcattttaat tgtgttgtct aagtatactt ttaaaaaatc
2341 aagtggcact ctagatgctt atagtacttt aatatttgta gcatacagac taattttttct
2401 aaaagggaaa gtctgtctag ctgcttgtga aaagttatgt ggtattctgt aagccatttt
2461 tttctttatc tgttcaaaga cttattttttt aagacatgaa ttacatttaa aattagaata
2521 tggttaatat taaataatag gccttttttct aggaaggcga aggtagttaa taatttgaat
2581 agataacaga tgtgcaagaa agtcacattt gttatgtatg taggagtaaa cgttcggtgg
2641 atcctctgtc tttgtaactg aggttagagc tagtgtggtt ttgaggtctc actacacttt
2701 gaggaaggca gcttttaatt cagtgtttcc ttatgtgtgc gtacattgca actgcttaca
2761 tgtaatttat gtaatgcatt cagtgcaccc ttgttacttg ggagaggtgg tagctaaaga
```

-continued

```
2821 acattctgag tataggtttt tctccattta cagatgtctt tggtcaaata ttgaaagcaa
2881 acttgtcatg gtcttcttac attaagttga aactagctta taataactgg tttttacttc
2941 caatgctatg aagtctctgc agggctttta cagttttcga agtcctttta tcactgtgat
3001 cttattctga ggggagaaaa aactatcata gctctgaggc aagacttcga ctttatagtg
3061 ctatcagttc cccgatacag ggtcagagta acccatacag tattttggtc aggaagagaa
3121 agtggccatt tacactgaat gagttgcatt ctgataatgt cttatctctt atacgtagaa
3181 taaatttgaa agactatttg atcttaaaac caaagtaatt ttagaatgag tgacatatta
3241 cataggaatt tagtgtcaat ttcatgtgtt taaaaacatc atgggaaaaa tgcttagagg
3301 ttactatttt gactacaaag ttgagttttt ttctgtagtt accataattt cattgaagca
3361 aatgaatgag tttgagaggt ttgtttttat agttgtgttg tattacttgt ttaataataa
3421 tctctaattc tgtgatcagg tactttttt gtggggtttt ttttttttgtt tttttttttt
3481 tttgttgttg tttttgggcc atttctaagc ctaccagatc tgctttatga aatccagggg
3541 accaatgcat tttatcacta aaactatttt tatataattt taagaatata ccaaaagttg
3601 tctgatttaa agttgtaata catgattcct cactttcatg taaggttatc cacttttgct
3661 gaagatattt tttattgaat caaagattga gttacaatta tacttttctt acctaagtgg
3721 ataaaatgta cttttgatga atcagggaat tttttttaaag ttggagtttta gttctaaatt
3781 gactttacgt attactgcag ttaattcctt ttttggctag ggatggtttg ataaaccaca
3841 attggctgat attgaaaatg aaagaaactt aaaaggtggg atggatcatg attactgtcg
3901 ataactgcag ataaatttga ttagagtaat aattttgtca tttaaaaaca cagttgttta
3961 tactgcccat cctaggatgc tcaccttcca agattcaacg tggctaaaac atcttctggt
4021 aaattgtgcg tccatattca ttttgtcagt agccaggaga aatggggatg ggggaaatac
4081 gacttagtga ggcatagaca tccctggtcc atcctttctg tctccagctg tttcttggaa
4141 cctgctctcc tgcttgctgg tccctgacgc agagaccgtt gcctccccca cagccgtttg
4201 actgaaggct gctctggaga cctagagtaa aacggctgat ggaagttgtg ggacccactt
4261 ccatttcctt cagtcattag aggtggaagg gaggggtctc caagtttgga gattgagcag
4321 atgaggcttg ggatgcccct gctttgactt cagccatgga tgaggagtgg gatggcagca
4381 aggtggctcc tgtggcagtg gagttgtgcc agaaacagtg gccagttgta tcgcctataa
4441 gacagggtaa ggtctgaaga gctgagcctg taattctgct gtaataatga tagtgctcaa
4501 gaagtgcctt gagttggtgt acagtgccat ggccatcaag aatcccagat ttcaggtttt
4561 attacaaaat gtaagtggtc acttggcgat tttgtagtac atgcatgagt taccttttt
4621 ctctatgtct gagaactgtc agattaaaac aagatggcaa agagatcgtt agagtgcaca
4681 acaaaatcac tatcccatta gacacatcat caaaagctta tttttattct tgcactggaa
4741 gaatcgtaag tcaactgttt cttgaccatg gcagtgttct ggctccaaat ggtagtgatt
4801 ccaaataatg gttctgttaa cactttggca gaaaatgcca gctcagatat tttgagatac
4861 taaggattat ctttggacat gtactgcagc ttcttgtctc tgttttggat tactggaata
4921 cccatgggcc ctctcaagag tgctggactt ctaggacatt aagatgattg tcagtacatt
4981 aaacttttca atcccattat gcaatcttgt tgtaaatgt aaacttctaa aaatatggtt
5041 aataacattc aacctgttta ttacaactta aaaggaactt cagtgaattt gtttttattt
5101 tttaacaaga tttgtgaact gaatatcatg aaccatgttt tgatacccct ttttcacgtt
5161 gtgccaacgg aatagggtgt ttgatatttc ttcatatgtt aaggagatgc ttcaaaatgt
```

```
5221 caattgcttt aaacttaaat tacctctcaa gagaccaagg tacatttacc tcattgtgta 5281 tataatgttt aatatttgtc agagcattct ccaggtttgc agttttattt ctataaagta 5341 tgggtattat gttgctcagt tactcaaatg gtactgtatt gtttatattt gtacccccaaa 5401 taacatcgtc tgtactttct gttttctgta ttgtatttgt gcaggattct ttaggcttta 5461 tcagtgtaat ttctgccttt taagatatgt acagaaaatg tccatataaa tttccattga 5521 agtcgaatga tactgagaag cctgtaaaga ggagaaaaaa cataagctgt gtttccccat 5581 aagttttttt aaattgtata ttgtatttgt agtaatattc caaaagaatg taaataggaa 5641 atagaagagt gatgcttatg ttaagtccta acactacagt agaagaatgg aagcagtgca 5701 aataaattac atttttccca aaaaaaaaaa aaaaaaaaaa aaaaaaaaaa gaaaaaaaaa 5761 aaaaaa
```

By "TGFβR2 polypeptide" is meant a polypeptide or fragment thereof having at least about 85% amino acid identity to GenBank Accession No. ABG65632.1 and having a biological activity of a TGFβR2 polypeptide. Biological activities of a TGFβR2 polypeptide include binding to TGFβR1 polypeptide to form a heterodimeric complex, and serine/threonine kinase activity. The sequence at GenBank Accession No. ABG65632.1 is shown below (SEQ ID NO: 33):

```
  1 mgrgllrglw plhivlwtri astipphvqk svnndmivtd nngavkfpql ckfcdvrfst 61 cdnqkscmsn csitsicekp qevcvavwrk ndenitletv chdpklpyhd filedaaspk 121 cimkekkkpg etffmcscss decndniifs eeyntsnpdl llvifqvtgi sllpplgvai 181 sviiifycyr vnrqqklsst wetgktrklm efsehcaiil eddrsdisst canninhnte 241 llpieldtlv gkgrfaevyk aklkqntseq fetvavkifp yeeyaswkte kdifsdinlk 301 henilqflta eerktelgkq ywlitafhak gnlqeyltrh viswedlrkl gsslargiah 361 lhsdhtpcgr pkmpivhrdl kssnilvknd ltcclcdfgl slrldptlsv ddlansgqvg 421 tarymapevl esrmnlenve sfkqtdvysm alvlwemtsr cnavgevkdy eppfgskvre 481 hpcvesmkdn vlrdrgrpei psfwlnhqgi qmvcetltec wdhdpearlt aqcvaerfse 541 lehldrlsgr scseekiped gslnttk
```

By "TGFβR2 polynucleotide" is meant a polynucleotide encoding a TGFβR2 polypeptide. An exemplary TGFβR2 polynucleotide sequence is provided at GenBank Accession No. DQ377553.1. The exemplary sequence provided at GenBank Accession No. DQ377553.1 is reproduced below (SEQ ID NO: 34).

```
CCTCCTGGCTGGCGAGCGGGCGCCACATCTGGCCCGCACATCTGCGCTGC

CGGCCCGGCGCGGGGTCCGGAGAGGGCGCGGCGCGGAGGCGCAGCCAGGG

GTCCGGGAAGGCGCCGTCCGCTGCGCTGGGGGCTCGGTCTATGACGAGCA

GCGGGGTCTGCCATGGGTCGGGGGCTGCTCAGGGGCCGTGTGGCCGCTGCA

CATCGTCCTGTGGACGCGTATCGCCAGCACGATCCCACCGCACGTTCAGA

AGTCGGGTGAGTGGTCCCCAGCCCGGGCTCGGCGGGCGCCGGGGGTCTT

CCTGGGGTCCCCGCCTCTCCGCTGCGCTTGACAGTCGGGCCCGGCAACCC

GGCCCCCGGGCGGAAACGAGGAAAGTTTCCCCCGCGACACTCACGCAGCC
```
```
-continued
CGACTCCCGTAGCTGCAGGGATTGTGAGTTTTTCTTGAAAAAGAGAAGGA

AAGTTCAGTTGCAAGGGGCGCGGGGCACGTTTGGTCC
```

As used herein, the term "rapamycin" refers to a compound (a macrocyclic triene antibiotic also known as Sirolimus) produced by the bacterium *Streptomyces hygroscopicus*. It inhibits the activation of T cells and B cells by reducing the production of interleukin-2 (IL-2). Rapamycin has immunosuppressant functions in humans and is especially useful in medicine for preventing organ transplant rejection such as the rejection of kidney transplants. It is also used to treat lymphangioleiomyomatosis, a lung progressive and systemic disease. Rapamycin has also been shown to inhibit proliferation of vascular smooth muscle cells migration (Poon M. et al., J Clin Invest. 1996; 98(10):2277-83). Rapamycin derivatives used according to the methods of present invention include, but are not limited to, 40-O-alkyl-rapamycin derivatives, e.g. 40-O-hydroxyalkyl-rapamycin derivatives, for example 40-O-(2-hydroxy)-ethyl-rapamycin (everolimus), rapamycin derivatives which are substituted in 40 position by heterocyclyl, e.g. 40-epi-(tetrazolyi)-rapamycin (also known as ABT578), 32-deoxo-rapamycin derivatives and 32-hydroxy-rapamycin derivatives, such as 32-deoxorapamycin, 16-O-substituted rapamycin derivatives such as 16-pent-2-ynyloxy-32-deoxorapamycin, 16-pent-2-ynyloxy-32(S or R)-dihydro-rapamycin, or 16-pent-2-ynyloxy-32(S or R)-dihydro-40-O-(2-hydroxyethyl)-rapamycin, rapamycin derivatives which are acylated at the oxygen in position 40, e.g. 40-[3-hydroxy-2-(hydroxy-methyl)-2- methylpropanoate]-rapamycin (also known as CCI779 or temsirolimus), rapamycin derivatives as disclosed in WO9802441 or WO0114387 (also sometimes designated as rapalogs), e.g. including AP23573, such as 40-O-dimethylphosphinyl-rapamycin, compounds disclosed under the name biolimus (biolimus A9), including 40-O-(2-ethoxy) ethyl-rapamycin, and compounds disclosed under the name TAFA-93, AP23464, AP23675 or AP23841; or rapamycin derivatives as e.g. disclosed in WO2004101583, WO9205179, WO9402136, WO9402385 and WO9613273.

By "subject" is meant a mammal, including, but not limited to, a human or non-human mammal, such as a bovine, equine, canine, ovine, murine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION

Molecular Events that Drive Progression of Atherosclerosis

Atherosclerosis is responsible for the vast majority of cardiovascular diseases. Despite decades of work, statins remain the only effective therapy but they can only slow but not stop or reverse disease progression. The relentless nature of atherosclerosis implies the existence of a process that drives its progression, even if the agents responsible for its initiation have been removed. Hyperlipidemia, local disturbances in fluid shear stress, smoking, hypertension etc., induce an initial vascular inflammatory response in the vessel wall characterized by the presence of macrophages, leukocytes, and production of the fibronectin-rich matrix. The disease becomes progressive as the initial bout of inflammation induces an endothelial fate change that leads to the development of endothelial-to-mesenchymal transition (EndMT). The EndMT is a process that involves phenotypic change and migration of epithelial cells into the sub-epithelial mesenchyme in the lamina propria (LP) that function as extracellular-matrix producing fibroblasts/myofibroblasts. EndMT is a vital process during embryogenesis, but can also be induced as a result of persistent damage and tissue inflammation. Active EndMT can lead to severe and even complete organ fibrosis or development of a pre-malignant stroma when associated with angiogenesis.

EndMT not only drives the accumulation of "mesenchymal type" (smooth muscle, fibroblasts) cells in the plaque, but induces further inflammatory activation of luminal endothelial cells, extracellular matrix remodeling, and increased permeability. These events promote further entry and retention of both leukocytes and lipoproteins, which promote further inflammation and further EndMT, thereby creating a self-sustaining feed-forward loop. Once set in motion, this process continues even if initiating factors are no longer present. Described herein are methods to arrest atherosclerosis and induce regression of the established disease by inhibiting EndMT using a therapeutic strategy applicable to large numbers of patients.

EndMT occurs in various inflammatory conditions. EndMT plays an equally important role in transplant arteriosclerosis, a relentless disease that is the primary reason for long-term failure of various organ drugs, such as for the heart or kidneys. There are no known therapies for this condition. EndMT is also important in pulmonary hypertension and various conditions associated with chronic inflammation induced fibrosis such as scleroderma, Systemic Lupus Erythematosus (SLE), transplant arteriopathy, cystitic fibrosis and other fibrosis and the like to name a few. Accordingly, without being bound by theory, the same treatment that is effective in reducing atherosclerosis is expected to be effective in treatment of the foregoing diseases.

In addition to EndMT, another major driver of long-term plaque growth is the loss of media smooth muscle cell (SMC) differentiation leading to uncontrolled proliferation. Described herein is the discovery of a molecular pathway controlling this process and a demonstration, using mouse genetics, that upregulating it reduced plaque size by ~50%. Without intending to be bound by theory, combining the endothelial approach outlined above with SMC-targeted therapy has the high likelihood of completely blocking atherosclerosis development and progression.

The conversion of vascular smooth muscle cells (SMCs) from contractile to proliferative phenotype is thought to play an important role in atherosclerosis. However, the contribution of this process to plaque growth has never been fully defined. The study described herein reveals that activation of SMC TGFβ signaling, achieved by suppression of SMC FGF signaling input, induces their conversion to a contractile phenotype and dramatically reduces atherosclerotic plaque size. The FGF-TGFβ signaling cross-talk was observed in vitro and in vivo. In vitro, inhibition of FGF signaling increased TGFβ activity thereby promoting smooth muscle differentiation and decreasing proliferation. In vivo, smooth muscle-specific knockout of an FGF receptor adaptor Frs2a led to a profound inhibition of atherosclerotic plaque growth when these animals were crossed on Apoe$^{-/-}$ background and subjected to a high fat diet. In particular, there was a significant reduction in plaque cellularity, increase in fibrous cap area and decrease in necrotic core size. In agreement with these findings, examination of human coronary arteries with various degrees of atherosclerosis revealed a strong correlation between the activation of FGF signaling, loss of TGFβ activity, and increased disease severity. These results identify SMC FGF/TGFβ signaling cross-talk as an important regulator of SMC phenotype switch and document a major contribution of medial SMC proliferation to atherosclerotic plaque growth.

Therapeutic Strategy for Inhibiting or Reversing Atherosclerosis

Figure 8:
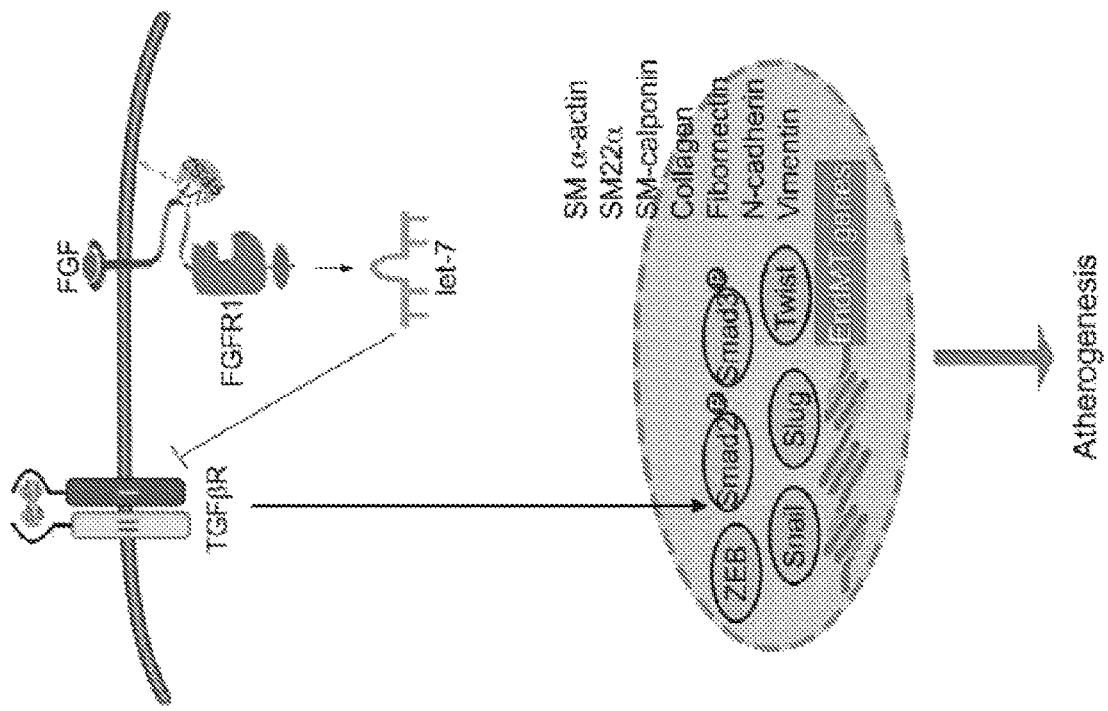
FIG. 8 is a schematic showing a scheme of FGF-dependent regulation of TGFβ signaling in smooth muscle cells and endothelial cells. In both smooth muscle cells and endothelial cells, suppression of FGF signaling leads to reduction of let-7 miRNAs expression that, in turn, results in increased TGFβR1 expression and activation of TGFβ-dependent transcriptional program. In SMC (left panel), activation of TGFβ signaling promotes SMC conversion from proliferative to contractile phenotype thereby reducing the number of SMCs in the plaque and reducing plaque growth. In contrast, in endothelial cells (EC) activation of TGFβ signaling promotes endothelial-to-mesenchymal transition thus increasing the number of plaque SMCs and promoting plaque growth.
Figure 8:
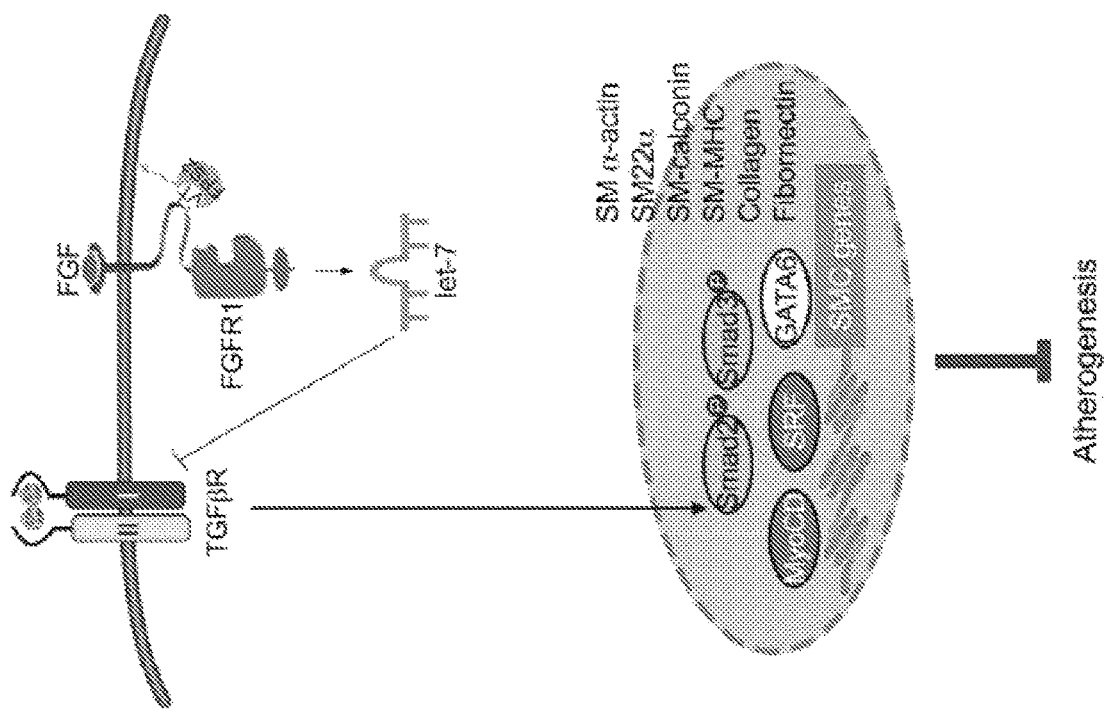

Described herein are studies demonstrating the key role of FGF signaling, let-7 miRNA expression, and TGFβ signaling in the progression of atherosclerosis by induction of endothelial-to-mesenchymal transition (EndMT) in endothelial cells and by promotion of a proliferative phenotype in smooth muscle cells. In endothelial cells, overexpression of let-7 miRNA and consequently decreased TGFβ signaling reduced atherosclerotic lesions. In smooth muscle cells, disruption of FGF signaling by deletion of FRS2α, which reduced let-7 miRNA expression and increased TGFβ signaling, was found to reduce atherosclerotic lesions. This is summarized in schematic form in FIG. 8.

Provided herein are methods to arrest atherosclerosis and induce regression of the established disease by inhibiting EndMT or smooth muscle cell proliferation using a therapeutic strategy applicable to large numbers of patients. Currently, there is no available therapy to stop the development of atherosclerosis and induce its regression. Described herein is a key mechanism responsible for atherosclerosis progression and studies demonstrating that modulating this pathway fundamentally changes the natural history or course of the disease. The mechanism involves a link between FGF signaling, let-7 miRNA, and TGFβ signaling. Targeting this mechanism would dramatically alter the management of atherosclerosis and would represent a major practical breakthrough.

The therapeutic approach described herein, based on insights derived from cell signaling studies and confirmed by rigorous in vivo mouse genetics studies and human data, is fundamentally new. Instead of trying to limit the disease complications, the focus of current approaches, the present invention includes a therapeutic approach that alters the biology of the cell type that initiates and sustains atherosclerosis in order to arrest and reverse the process. The highly targeted nature of the approach, the genetic proof of principle that this strategy works, and the ability to specifically target endothelium in a manner suitable to widespread clinical applications, renders the invention highly useful for treatment of atherosclerosis.

Endothelial-to-Mesenchymal Transition

The endothelial-to-mesenchymal transition (EndMT) is induced by activation of endothelial TGFβ signaling that occurs secondary to the loss of a protective FGF input. In healthy vessels, FGF suppresses TGFβ signaling by inducing the let-7 family of miRNAs that reduce expression of key TGFβ pathway proteins (TGFβ2, TGFβR1, Smad2). The importance of the FGF-let-7-TGFβ link is supported by human and mouse data. In human coronary arteries, a strong correlation between the reduction in FGFR1 expression, increase in p-Smad2/3 signaling, and the extent of atherosclerosis (r=0.84, p<0.01) was observed (Chen et al, 2015, Journal of clinical investigation 125: 4529-4543). Described herein is a demonstration that in mice, blocking TGFβ signaling by endothelial-specific deletion of TGFβR1 and TGFβR2, dramatically reduces atherosclerosis.

Thus, in some embodiments, the TGFβ signaling is blocked by delivering let-7 miRNA into a cell. In a particular embodiment, the cell is an endothelial cell. In a particular embodiment, a systemic treatment strategy using a modified let-7 miRNA delivered to endothelial cells in targeted nanoparticles is employed. In some embodiments, the modified let-7 miRNA is mi-let-7b$_L$ or mi-let-7b$_H$. Studies in mice demonstrate that this approach is as effective in reducing atherosclerosis as a TGFβR1/2 knockout.

In some embodiments, the therapy is cell-type specific. Systemic inhibition of TGFβ signaling has an adverse effect on atherosclerosis by promoting inflammation and smooth muscle cell proliferation.

In some embodiments, TGFβR1/2 targeted siRNAs are delivered to endothelial cells. In some embodiments, TGFβR1/2 targeted siRNAs therapy is as effective as let-7-based therapy for reducing atherosclerosis.

Described herein is genetic proof of the proposed therapeutic strategy, evidence of its clinical relevance, and the development of an effective systemic therapeutic approach suitable for large numbers of patients. Further provided herein is evidence that there are specific FGF-dependent metabolic controls that can be used to block EndMT.

In some embodiments, the invention provides a method of reducing, inhibiting or reversing an EndMT in an endothelial cell in a subject in need thereof. The method comprises administering to the subject an agent that decreases in the endothelial cell of the subject the activity or level of at least one selected from the group consisting of let-7 miRNA, endothelial TGFβ signaling polypeptide and FRS2α, thereby reducing, inhibiting or reversing the EndMT in the endothelial cell in the subject in need thereof.

Without intending to be bound by theory, it is believed that a combination of these strategies, aimed at interrupting the EndMT/inflammation cycle, provides a definitive therapeutic approach to atherosclerosis.

Smooth Muscle Cell Proliferative-to-Contractile Phenotype Switching

In the studies described herein, it was hypothesized that suppression of FGF signaling in SMC would induce a contractile phenotype and that this enforced maintenance of contractile SMC phenotype would diminish any contributions of media smooth muscle cells proliferation to atherosclerotic plaque growth. To investigate this hypothesis, a mouse line with an SMC-specific deletion of a key FGF signaling regulator Frs2a was generated. The shutdown of FGF-induced MAPK signaling in SMCs induced by Frs2a knockout resulted in increased expression of TGFβ ligands and receptors and activation of TGFβ signaling. In vitro this led to a growth arrest of proliferating SMCs and induction of their differentiation while in vivo there was a profound reduction in the size of atherosclerotic lesions. Analysis of clinical specimens confirmed the inverse relationship between the extent of medial FGF and TGFβ signaling and the severity of atherosclerosis. Overall, the results herein demonstrate that FGF regulates SMC phenotypic modulation by controlling SMC TGFβ signaling and directly elucidate the contribution of SMC proliferation to the growth of atherosclerotic plaque.

Accordingly, in some embodiments, the TGFβ signaling is activated by delivering to a cell an inhibitory polynucleotide that reduces SMC expression of FRS2α polypeptide or reduces SMC expression of a let-7 miRNA. In some embodiments, the TGFβ signaling is activated by delivering to an SMC an agent that increases the activity or level of a TGFβ signaling polypeptide. In a particular embodiment, the cell is an smooth muscle cell.

Methods of Treatment

In some aspects, the present invention provides a method of treating atherosclerosis and/or disorders or symptoms thereof which comprise administering a therapeutically effective amount of a pharmaceutical composition comprising an agent that modulates the activity or level of a TGFβ signaling polypeptide, a let-7 miRNA, or a FGF signaling polypeptide in a cell, to a subject (e.g., a mammal such as a human).

In particular embodiments, the agent that modulates the activity or level of a let-7 miRNA increases the activity or level of a let-7 miRNA in a cell. In some embodiments, the cell is an endothelial cell. In certain embodiments, the agent that increases the activity or level of a let-7 miRNA in a cell is a let-7 miRNA mimic. In some other embodiments, the agent is a polynucleotide encoding a let-7b miRNA. In some embodiments, the let-7 miRNA is let-7b and let-7c miRNA.

In some embodiments, the agent that modulates the activity or level of a let-7 miRNA decreases the activity or level of a let-7 miRNA in a cell. In certain embodiments, the cell is a smooth muscle cell. In some embodiments, the agent that decreases the activity or level of a let-7 miRNA in a cell is an inhibitory polynucleotide that reduces expression of let-7 miRNA. In still other embodiments, the agent that decreases the activity or level of a let-7 miRNA in a cell is a let-7 miRNA sponge or antagomir-let-7b/c. Such miRNA sponges are described in, for example, Ebert et al. RNA. 2010 November; 16(11): 2043-2050. In some embodiments, the let-7 miRNA is let-7b miRNA.

In some embodiments, the agent that modulates the activity or level of a TGFβ signaling polypeptide increases the activity or level of a TGFβ signaling polypeptide in a cell (in particular, a smooth muscle cell). In some other embodiments, the agent that modulates the activity or level of a TGFβ signaling polypeptide decreases the activity or level of a TGFβ signaling polypeptide in a cell (in particular, an endothelial cell). In some embodiments, the TGFβ signaling polypeptide is TGFβ1, TGFβ2, TGFβ3, TGFβR1, or TGFβR2. In some embodiments, the agent is siRNA and may be targeted to a TGFβ receptor.

In some embodiments, the agent that decreases the activity or level of a TGFβ signaling polypeptide is an inhibitory polynucleotide that reduces expression of a TGFβ signaling polypeptide. In some other embodiments, the agent that increases the activity or level of a TGFβ signaling polypeptide is a polynucleotide encoding a TGFβ signaling polypeptide.

In certain embodiments, the agent that modulates the activity or level of a FGF signaling polypeptide decreases the activity or level of a FGF signaling polypeptide in a cell (in particular, a smooth muscle cell). In some embodiments, the agent that modulates the activity or level of a FGF signaling polypeptide increases the activity or level of a FGF signaling polypeptide in a cell (in particular, an endothelial cell). In some embodiments, the FGF signaling polypeptide is FRS2α.

In certain embodiments, the agent that decreases the activity or level of a FGF signaling polypeptide in a cell is an inhibitory polynucleotide that reduces expression of a FGF signaling polypeptide. In some other embodiments, the agent that increases the activity or level of a FGF signaling polypeptide in a cell is a polynucleotide encoding a FGF signaling polypeptide.

In some embodiments, the subject is pre-selected by assessing the activity or level of a TGFβ signaling polypeptide or polynucleotide, a let-7 miRNA, or a FGF signaling polypeptide or polynucleotide in a sample from the subject when compared to reference levels.

The subject is pre-selected when an alteration in the activity or level of activity or level of a TGFβ signaling polypeptide or polynucleotide, a let-7 miRNA, or a FGF signaling polypeptide or polynucleotide in a sample from the subject is detected. In some embodiments, the subject is pre-selected when a decrease in the activity or level of let-7 miRNA or a TGFβ signaling polypeptide is observed relative to reference levels in an endothelial cell sample obtained from the subject. In other embodiments, the subject is pre-selected when a decrease in the activity or level of a FGF signaling polypeptide or polynucleotide, or an increase in the activity or level of let-7 miRNA or a TGFβ signaling polypeptide or polynucleotide is observed relative to reference levels in a smooth muscle cell sample obtained from the subject.

In other embodiments, the subject is pre-identified as having or being at risk for atherosclerosis, in certain embodiments patients suffering from coronary artery disease (CAD), peripheral vascular disease (PVD), or stroke. In other embodiments, the patient may have one or more known atherosclerotic plaques or may have experienced one or more recent ischemic events, in certain embodiments, transient ischemic attack (TIA), unstable angina (UA), or myocardial infarction (MI). In other embodiments, the subject has elevated cholesterol and/or a history of PVD, CAD or other cardiovascular disease. Thus, in one embodiment, there is provided a method of treating a subject suffering from or susceptible to atherosclerosis or disorder or symptom thereof. The method includes the step of administering to the mammal a therapeutic amount of an agent (e.g., an agent that modulates the activity or level of a TGFβ signaling polypeptide, a let-7 miRNA, or a FGF signaling polypeptide) that is sufficient to treat the disease or disorder or symptom thereof, under conditions such that the disease or disorder is treated.

In some aspects of the invention, the subject is administered an additional agent comprising a therapeutically effective amount of rapamycin or any derivative thereof. In some embodiments, the therapeutically effective amount of rapamycin or any derivative thereof is used to reduce SMC proliferation and increase its differentiation alone or in combination with EC-specific therapies. In some embodiments, the agent that decreases the activity or level of a TGFβ signaling polypeptide and the additional agent are co-administered to the subject.

In other aspects of the invention, the agent that decreases the activity or level of a TGFβ signaling polypeptide is a nucleic acid capable of downregulating the gene expression of at least one gene selected from the group consisting of TGFβ1, TGFβ2, TGFβ3, TGFβR1, and TGFβR2. In some embodiments, the at least one gene is selected from the group consisting of TGFβR1, and TGFβR2.

In some instance, downregulation of the TGFβ or TGFβ receptor (TGFβR) gene expression is desired. This downregulation may result from a full or partial knock down of the gene of interest. Briefly, a gene knock down refers to a genetic technique in which one of an organism's genes is silenced, made inoperative or partially inoperative. Gene expression may be downregulated, knocked-down, decreased, and/or inhibited by various well-established molecular techniques known in the art such as, but not limited to, RNA interference (RNAi), small inhibitor RNA (siRNA), small hairpin RNA (shRNA) and Clustered Regularly Interspaced Short Palindromic Repeats (CRISPRs)).

In some embodiments, the nucleic acid is selected from the group consisting of an antisense RNA, siRNA, shRNA, and a CRISPR system. In other embodiments, the nucleic acid is combined with a therapeutically effective amount of rapamycin or any derivative thereof. In yet other embodiments, the nucleic acid is encapsulated in a nanoparticle formulated for selective delivery to an endothelial cell, in a pharmaceutically acceptable excipient. In further embodiments, the nanoparticle is a 7C1 nanoparticle.

The methods disclosed herein include administering to the subject (including a subject identified as in need of such treatment) an effective amount of an agent described herein, or a composition described herein to produce such effect. Identifying a subject in need of such treatment can be made by a health care professional and may be subjective (e.g. opinion) or objective (e.g. measurable by a test or diagnostic method, such as using the methods described herein).

The therapeutic methods of the invention, which may also include prophylactic treatment, in general comprise administering a therapeutically effective amount of one or more of the agents herein (such as an agent that modulates the activity or level of a TGFβ signaling polypeptide, a let-7 miRNA, or a FGF signaling polypeptide) to a subject (e.g., animal, human) in need thereof, including a mammal, particularly a human. Such treatment is suitable for subjects, particularly humans, suffering from, having, susceptible to, or at risk for a atherosclerosis, disorder, or symptom thereof. In one embodiment, the invention provides a method of monitoring progression of treatment. The method comprises determining a level or activity of diagnostic marker (e.g., a TGFβ signaling polypeptide or polynucleotide, a let-7 miRNA, or a FGF signaling polypeptide or polynucleotide) in a subject suffering from or susceptible to a atherosclerosis, in which the subject has been administered a therapeutic or effective amount of a therapeutic agent sufficient to treat the atherosclerosis or symptoms thereof. The activity or level of a TGFβ signaling polypeptide or polynucleotide, a let-7 miRNA, or a FGF signaling polypeptide or polynucleotide determined in the method can be compared to a known activity or level of a TGFβ signaling polypeptide or polynucleotide, a let-7 miRNA, or a FGF signaling polypeptide or polynucleotide in either healthy normal controls, or in other afflicted patients, to establish the subject's disease status. In some embodiments, an activity or level of a TGFβ signaling polypeptide or polynucleotide, a let-7 miRNA, or a FGF signaling polypeptide or polynucleotide in an endothelial cell or smooth muscle cell sample obtained from the subject is determined. In some embodiments, a second activity or level of a TGFβ signaling polypeptide or polynucleotide, a let-7 miRNA, or a FGF signaling polypeptide or polynucleotide in the subject is determined at a time point later than the determination of the first level, and the two levels are compared to monitor the course of disease or the efficacy of the therapy. In certain embodiments, a pretreatment activity or level of a TGFβ signaling polypeptide or polynucleotide, a let-7 miRNA, or a FGF signaling polypeptide or polynucleotide is determined prior to commencing. This pre-treatment level can then be compared to the level of a TGFβ signaling polynucleotide or polypeptide or let-7 miRNA in the subject after the treatment commences, to determine the progress or efficacy of the treatment.

Pharmaceutical Compositions

The present invention features compositions useful for treating atherosclerosis in a pre-selected subject. The compositions include an agent that modulates the activity or level of a TGFβ signaling polypeptide, a let-7 miRNA, or a FGF signaling polypeptide in a cell.

In particular embodiments, the agent that modulates the activity or level of a let-7 miRNA increases the activity or level of a let-7 miRNA in a cell, in particular, an endothelial cell. In certain embodiments, the agent that increases the activity or level of a let-7 miRNA in a cell is a let-7 miRNA mimic. In some other embodiments, the agent is a polynucleotide encoding a let-7b miRNA. In certain embodiments, the agent that modulates the activity or level of a let-7 miRNA decreases the activity or level of a let-7 miRNA in a cell, in particular, a smooth muscle cell. In some embodiments, the agent that decreases the activity or level of a let-7 miRNA in a cell is an inhibitory polynucleotide that reduces expression of let-7 miRNA. In some embodiments, the let-7 miRNA is let-7b miRNA.

In some embodiments, the agent that modulates the activity or level of a TGFβ signaling polypeptide increases the activity or level of a TGFβ signaling polypeptide in a cell (in particular, a smooth muscle cell). In some other embodiments, the agent that modulates the activity or level of a TGFβ signaling polypeptide decreases the activity or level of a TGFβ signaling polypeptide in a cell (in particular, an endothelial cell). In some embodiments, the TGFβ signaling polypeptide is TGFβ1, TGFβ2, TGFβ3, TGFβR1, or TGFβR2.

In some embodiments, the agent that decreases the activity or level of a TGFβ signaling polypeptide is an inhibitory polynucleotide that reduces expression of a TGFβ signaling polypeptide. In some other embodiments, the agent that increases the activity or level of a TGFβ signaling polypeptide is a polynucleotide encoding a TGFβ signaling polypeptide.

In certain embodiments, the agent that modulates the activity or level of a FGF signaling polypeptide decreases the activity or level of a FGF signaling polypeptide in a cell (in particular, a smooth muscle cell). In some embodiments, the agent that modulates the activity or level of a FGF signaling polypeptide increases the activity or level of a FGF signaling polypeptide in a cell (in particular, an endothelial cell). In some embodiments, the FGF signaling polypeptide is FRS2α.

In certain embodiments, the agent that decreases the activity or level of a FGF signaling polypeptide in a cell is an inhibitory polynucleotide that reduces expression of a FGF signaling polypeptide. In some other embodiments, the agent that increases the activity or level of a FGF signaling polypeptide in a cell is a polynucleotide encoding an FGF signaling polypeptide The composition may be administered systemically, for example, formulated in a pharmaceutically-acceptable buffer such as physiological saline. Routes of administration include, for example, subcutaneous, intravenous, intraperitoneally, intramuscular, or intradermal injections that provide continuous, sustained levels of the agent in the patient.

The amount of the therapeutic agent to be administered varies depending upon the manner of administration, the age and body weight of the patient, and with the clinical symptoms of atherosclerosis. Generally, amounts will be in the range of those used for other agents used in the treatment of atherosclerosis, although in certain instances lower amounts will be needed because of the increased specificity of the agent. A composition is administered at a dosage that decreases effects or symptoms of atherosclerosis as determined by a method known to one skilled in the art.

The therapeutic agent may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with an organ, such as the heart; (v) formulations that allow for convenient dosing, such that doses are administered, for example, once every one or two weeks; and (vi) formulations that target atherosclerosis using carriers or chemical derivatives to deliver the therapeutic agent to a particular cell type (e.g., endothelial cells or smooth muscle cells). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The pharmaceutical composition of this invention could be coated or comprised in a drug-eluting stent (DES) ((Nikam et al., 2014 Med Devices 7:165-78)) that releases at a given site (such as an artery) and pace (i.e. slow release) the composition of this invention.

The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates atherosclerosis, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

In some embodiments, the composition of this invention is delivered locally from, but not limited to, the strut of a stent, a stent graft, a stent cover or a stent sheath. In some embodiments, the composition of this invention comprises a rapamycin or a derivative thereof (e.g. as described in U.S. Pat. No. 6,273,913 B1, incorporated herein by reference).

In some embodiments, the composition comprising the active therapeutic is formulated for intravenous delivery. As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Polynucleotide Therapy

In some embodiments, the invention includes a method for treating, slowing the progression of, or reversing atherosclerosis, where a therapeutic polynucleotide activity or level of a TGFβ signaling polypeptide, a let-7 miRNA, or a FGF signaling polypeptide is administered to the subject. In certain embodiments, the polynucleotide is a let-7 miRNA mimic; a polynucleotide encoding let-7 miRNA, a TGFβ signaling polypeptide, or FGF signaling polypeptide; or an inhibitory polynucleotide that reduces expression of a FGF signaling polypeptide, a let-7 miRNA, or a TGFβ signaling polypeptide. Inhibitory polynucleotides include, but are not limited to siRNAs that target a polynucleotide encoding a TGFβ signaling polypeptide, a let-7 miRNA, or a FGF signaling polypeptide.

In particular embodiments, the polynucleotide therapy comprises a let-7 miRNA, a polynucleotide encoding a let-7 miRNA, or an inhibitory polynucleotide that reduces expression of a TGFβ signaling polypeptide. As described elsewhere herein, let-7 miRNA inhibits expression of TGFβ signaling polypeptide(s) in endothelial cells, thereby suppressing TGFβ signaling that drives growth or formation of atherosclerotic lesions.

Such therapeutic polynucleotides can be delivered to cells of a subject having atherosclerosis. The nucleic acid molecules are delivered to the cells of a subject in a form by which they are taken up by the cells so that therapeutically effective levels of the inhibitory nucleic acid molecules are contained within the cells.

Introduction of nucleic acids into cells may be accomplished using any number of methods available in the art. For example, transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996;

Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, an inhibitory nucleic acid or miRNA (or a precursor to the miRNA) as described can be cloned into a retroviral vector where expression can be driven from its endogenous promoter, from the retroviral long terminal repeat, or from a promoter specific for a target cell type of interest. In some embodiments, the target cell type of interest is an endothelial cell. Other viral vectors that can be used to introduce nucleic acids into cells include, but are not limited to, vaccinia virus, bovine papilloma virus, or herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337: 1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). In some embodiments, a viral vector is used to administer a polynucleotide encoding inhibitory nucleic acid molecules that inhibit expression of TGFβ signaling polypeptide.

Non-viral approaches can also be employed for the introduction of the therapeutic to a cell of a patient requiring treatment of atherosclerosis. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). In some embodiments, the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of polynucleotide encoding inhibitory nucleic acid molecules into the affected tissues of a patient can also be accomplished by transferring a polynucleotide encoding the inhibitory nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

In some embodiments, the therapeutic polynucleotide is selectively targeted to an endothelial cell. In some other embodiments, the therapeutic polynucleotide is expressed in an endothelial cell using a lentiviral vector. In still other embodiments, the therapeutic polynucleotide is administered intravenously. In some embodiments, the therapeutic polynucleotide contains one or more chemical modifications that reduce immunostimulation, enhance serum stability, increase specificity, and/or improve activity, while still retaining silencing activity. Such chemical modifications are described in, for example, Foster et al., RNA. 2012 March; 18(3): 557-568. In some embodiments, the therapeutic polynucleotide contains one or more chemical modifications to prevent degradation, as described in Chen et al., Cell Reports 2012; 2(6)1684-1696.

In a particular embodiment, the therapeutic polynucleotide is selectively delivered to endothelial cells using nanoparticles formulated for selective targeting to endothelial cells, such as a 7C1 nanoparticle. Selective targeting or expression of polynucleotides to an endothelial cell is described in, for example, Dahlman et al., Nat Nanotechnol. 2014 August; 9(8): 648-655.

In some other embodiments, the therapeutic polynucleotide is selectively targeted to a smooth muscle cell. The therapeutic polynucleotide can be selectively delivered to a smooth muscle cell using tissue factor-targeted nanoparticles that can penetrate and bind stretch-activated vascular smooth muscles as described in Lanza et al., Circulation. 2002 Nov. 26; 106(22):2842-7.

Screening Assays

The treatment strategy described herein using agents that target TGFβ-let-7-FGF signaling in cells (e.g., agents that modulate the activity or level of a TGFβ signaling polypeptide, a let-7 miRNA, or a FGF signaling polypeptide in a cell) can be augmented with a comprehensive new target discovery program that leads to the development of a second generation of therapies targeting the same critical disease-inducing pathway. Accordingly, the present invention further features methods of identifying modulators of a disease, particularly atherosclerosis, comprising identifying candidate agents that interact with and/or alter the level or activity of a TGFβ signaling polypeptide or polynucleotide, a let-7 miRNA, or a FGF signaling polypeptide or polynucleotide in a cell. As described elsewhere herein, the FGF-let-7-TGFβ signaling events drive endothelial-to-mesenchymal transition (EndMT) or smooth muscle cell (SMC) proliferation that contributes to growth of atherosclerotic plaque. Without being bound by theory, it is believed that agents that block or interfere with these molecular events in endothelial cells (e.g., agents that decrease TGFβ signaling) can inhibit development or progression of or reverse atherosclerosis in a subject.

Thus, in some aspects, the invention provides a method of identifying a modulator of atherosclerosis. The method comprises (a) contacting a cell or administering an organism with a candidate agent, and (b) measuring an activity or level of a TGFβ signaling polypeptide or polynucleotide, a let-7 miRNA, or a FGF signaling polypeptide or polynucleotide. An alteration in the level of FGF signaling polynucleotide or polypeptide, a TGFβ polynucleotide or polypeptide, or let-7 miRNA compared with the reference levels, is an indication that the candidate agent is a modulator of atherosclerosis. In particular, a decrease in the activity or level of a TGFβ polynucleotide or polypeptide, or an increase the activity or level of or let-7 miRNA or a FGF signaling polypeptide or polynucleotide in an endothelial cell, would indicate that the candidate agent is an inhibitor of atherosclerosis (e.g., the candidate agent inhibits progression of or reverses atherosclerosis). In some other embodiments, an increase in the activity or level of a TGFβ polynucleotide or polypeptide, or a decrease the activity or level of or let-7 miRNA or a FGF signaling polypeptide or polynucleotide in a smooth muscle cell would indicate that the candidate agent is an inhibitor of atherosclerosis.

Methods of measuring or detecting activity and/or levels of the polypeptide or polynucleotide are known to one skilled in the art. Polynucleotide levels may be measured by standard methods, such as quantitative PCR, Northern Blot, microarray, mass spectrometry, and in situ hybridization. Standard methods may be used to measure polypeptide levels, the methods including without limitation, immunoassay, ELISA, western blotting using an antibody that binds the polypeptide, and radioimmunoassay.

Kits

The invention provides kits for treating a atherosclerosis in a subject. A kit of the invention provides a therapeutic composition comprising an agent that modulates the activity or level of a TGFβ signaling polypeptide, a let-7 miRNA, or a FGF signaling polypeptide. In particular embodiments, the let-7 miRNA is a human let-7b miRNA chemically modified to increase its stability and reduce an immune response in vivo. In some embodiments, the therapeutic composition further comprises a nanoparticle. In particular embodiments, the nanoparticle is formulated for selective targeting to an endothelial cell. In some embodiments, the nanoparticle is 7C1. In some other embodiments, the nanoparticle is formulated for selective targeting to a smooth muscle cell.

In one embodiment, the kit further includes a diagnostic composition comprising a capture reagent for measuring relative expression level or activity a TGFβ signaling polypeptide, let-7 miRNA, or FGF signaling polypeptide (e.g., a primer or hybridization probe specifically binding to a polynucleotide encoding a TGFβ signaling polypeptide, let-7 miRNA, or FGF signaling polypeptide).

In some embodiments, the kit comprises a sterile container which contains a therapeutic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the kit further comprises instructions for using the diagnostic agents and/or administering the therapeutic agents of the invention. In particular embodiments, the instructions include at least one of the following: description of the therapeutic agent; dosage schedule and administration for reducing atherosclerosis symptoms; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

In General

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Results of experiments described herein were obtained using the following materials and methods.

Materials and Methods

Chemicals

The TGFβR1 kinase inhibitor SB431542 (Sigma S4317) was reconstituted in DMSO (Sigma D2650) and used at a final concentration of 10 μM in cell culture.

Antibodies

The following antibodies were used for immunoblotting (IB), immunofluorescence (IF) or immunohistochemistry (IHC): Calponin (Sigma C2687; IB, IF), CD31 (Santa Cruz sc-1506; IHC for mouse paraffin samples), CD31 (BD 561814; IHC for mouse fixed OCT samples), CD31 (Dako M0823; IHC for human frozen samples), collagen I (Rockland 600-401-103S; IB), collagen I (Novus Biologicals NB600-408; IHC), Cyclin D1 (Santa Cruz sc-20044; IB), FGFR1 (Epitomics 2144-1; IB), FGFR1 (phospho Y654) (abcam ab59194; IHC), FGFR1 (abcam ab10646; IHC), FRS2α (abcam ab10425; IHC), FRS2α (Santa Cruz sc-8318; IB), GAPDH (glyceraldehyde phosphate dehydrogenase) (Cell Signaling #2118; IB), HSP90 (Sigma 4300541; IB), Ki-67 (Cell Signaling #9027; IHC), myosin (smooth) (Sigma M7786; IB), Notch3 (ab23426, Abcam; IHC), p21 (Cell Signaling #2947; IB), p27 (Cell Signaling #3688; IB), SM22a (abcam ab14106; IB, IF), phospho-Smad2 (Ser465/467) (Cell Signaling #3108; IB), phospho-Smad2 (Ser465/467) (Cell Signaling #3101; IHC for human paraffin samples) (Millipore AB3849; IHC for mouse paraffin samples), phospho-Smad3 (Ser465/467) (R&D AB3226; IB), phospho-Smad3 (Ser465/467) (abcam ab51451; IHC), Smad2/3 (BD 610843; IB), smooth muscle α-actin (Sigma A2547; IB, IHC), smooth muscle α-actin-Cy3 (Sigma C6198; IF), smooth muscle α-actin-APC (allophycocyanin) (R&D IC1420A; IHC), smooth muscle myosin heavy chain 11 (SM-MHC 11) (abcam ab683; IHC), TGFβ (abcam ab66043; IHC), TGFβR1 (Santa Cruz sc-398; IB), TGFβR2 (Santa Cruz sc-400; IB), and β-tubulin (Sigma T7816; IB), F4/80 (abcam ab6640; IHC 1:100), ICAM-1 (BioLegend 116102; IHC for mouse tissue 1:100), smooth muscle α-actin-APC (allophycocyanin) (R&D IC1420A; IHC 1:10), VCAM-1 (abeam ab19569; IHC for mouse tissue 1:1000), and VE-cadherin (Santa Cruz sc-6458; IB 1:100).

Cell Culture and Reagents

Human 293T T17 cells (human embryonic kidney cells, ATCC CRL-11268) were maintained in Dulbecco's modified Eagle's medium (Gibco 11965-092) with 10% fetal bovine serum (Life Technologies 16000-044) and penicillin-streptomycin (15140-122, Gibco), and were grown at 37° C., 5% $CO_2$. Human aortic smooth muscle cells (#C-007-5C), media (#M231-500), and supplements (SMGS: S-007-25; SMDS: S-008-5) were purchased from Life Technologies. The cells were grown at 37° C., 5% $CO_2$ in Medium 231 supplemented with smooth muscle growth supplement (SMGS containing 4.9% FBS, 2 ng/ml FGF2, 0.5 ng/ml EGF, 5 ng/ml heparin, 2 μg/ml IGF-1, and 0.2 μg/ml BSA). For SMC differentiation, HASMC were incubated with Medium 231 containing smooth muscle differentiation supplement (SMDS containing 1% FBS and 30 μg/ml heparin) for different time points. Primary human aortic smooth muscle cells between passages 6 and 10 were used in all experiments. Mouse bEnd.3 cells (ATCC CRL-2299) were maintained in Dulbecco's modified Eagle's medium (ATCC 30-2002) with 10% fetal bovine serum (Life Technologies 16000-044) and penicillin-streptomycin (Gibco 15140-122), and were grown at 37° C., 5% $CO_2$. Primary mouse endothelial cells were isolated from the hearts and lungs using rat anti-mouse CD31 antibody (BD #553370) and Dynabeads (Invitrogen 110.35). Briefly, minced hearts and lungs were digested with Type I collagenase (2 mg/ml; Sigma C0130) at 37° C. for 45 min with agitation. The cells were then filtered through a 70 μm disposable cell strainer (BD Falcon 352350), and centrifuged at 1300 rpm for 10 min at 4° C., and then resuspended in 2 ml of EC medium [DMEM (LONZA 12-709F), 20% FBS (Sigma 26140-079), 10 units/ml Penicillin/10 μg/ml Strep (Gibco 15140-122), 1× non-essential amino acid (Gibco 11140-050), 2 mM L-glutamine (Gibco 25030-081), 1.2 μg/ml Amphotericin B (Fisher Scientific BP2645-50), 60 μg/ml Gentamycin sulfate (Gibco 15750-060)]. The cells were then incubated with anti-mouse CD31 Dynabeads on a rotator at room temperature for 15 min. After several washes, the cells were plated on gelatin-coated 10 cm dishes or they were centrifuged at 1300 rpm for 10 min at 4° C. and storage in −80° C. freezer. Feed the cells with EC medium containing 100 mg/ml heparin (Sigma H-3933), 100 mg/ml ECGS (Alfa Aesar J64516). Primary mouse endothelial cells between passages 3 and 4 were used in all experiments.

Growth Factors and Chemicals.

Recombinant human BMP9 (553104, BioLegend), recombinant mouse IFN-γ (315-05, Peprotech), recombinant human IL-10 (200-01B, Peprotech), recombinant human IL-6 (AF-200-06, Peprotech), recombinant human TGFβ1 (580702, BioLegend), and recombinant human TNF-α (300-01A, Peprotech) were reconstituted in 0.1% BSA/PBS.

Generation of Lentiviruses

Mouse Tgfbr1 and Tgfbr2 shRNA lentiviral constructs were purchased from Sigma. Human FGFR1, human Smad2 and human TGFβR2 shRNA lentiviral constructs were purchased from Sigma and human FRS2α shRNA lentiviral construct was purchased from Open Biosystems. For the production of shRNA lentivirus, 3.7 μg of A8.2, 0.2 μg of VSVG, and 2.1 μg of pLKO.1 carrying the control, FGFR1, FRS2α, Smad2, or TGFβR2 shRNA were co-transfected into 293T cells using X-tremeGENE 9 DNA Transfection Reagent (Roche 06365787001). Forty-eight hours later the medium was harvested, cleared by 0.45 μm filter (PALL Life Sciences PN4184), mixed with polybrene (5 μg/ml) (Sigma H9268), and applied to cells. After 6 hr. incubation, the virus-containing medium was replaced by the fresh medium. For production of let-7 miRNA lentivirus, 10 μg of pMIRNA1 carrying the let-7b (PMIRHlet7bPA-1) miRNA expression cassette (System Biosciences), 5 μg of pMDLg/PRRE, 2.5 μg of RSV-REV, and 3 μg of pMD.2G were co-transfected into 293T cells using X-tremeGENE 9 DNA transfection reagent (Roche 06365787001). Forty-eight hr. later, the medium was harvested, cleared by 0.45 m filter (PALL Life Sciences PN4184), mixed with 5 μg/ml polybrene (Sigma H9268), and applied to cells. After 6 hr incubation, the virus-containing medium was replaced by fresh medium.

RNA Isolation and qRT-PCR

Cells were suspended in TRIzol Reagent (Invitrogen #15596018), and total RNA (#74134, QIAGEN) and miRNA-enriched fraction (#74204, QIAGEN) were isolated according to the manufacturer's instructions. Reverse transcriptions were performed by using iScript cDNA synthesis kit (170-8891, Bio-Rad) for mRNA or RT2 miRNA First Strand Kit (331401, QIAGEN) for miRNA. qRT-PCR was performed using Bio-Rad CFX94 (Bio-Rad) by mixing equal amount of cDNAs, iQ SYBR Green Supermix (Bio-Rad 170-8882) and gene specific primers (QIAGEN), β-actin [PPM02945B], Tgfbr1 [PPM03072C], Tgfbr2 [PPM03599B], mmu-let-7b [MPM00484A], and SNORD66 [MPM01662A]. All reactions were done in a 20-25 μl reaction volume in duplicate. Individual mRNA or miRNA expression was normalized in relation to expression of endogenous β-actin or small nuclear SNORD47/SNORD66, respectively. PCR amplification consisted of 10 min of an initial denaturation step at 95° C., followed by 46 cycles of PCR at 95° C. for 15 s, 60° C. for 30 s (for mRNA cDNA) and 10 min of an initial denaturation step at 95° C., followed by 46 cycles of PCR at 95° C. for 15 s, 55° C. for 30 s, 70° C. for 30 s (for miRNA cDNA).

Western Blot Analysis

Cells were lysed with HNTG lysis buffer (20 mM HEPES, pH 7.4/150 mM NaCl/10% glycerol/1% Triton-X 100/1.5 mM $MgCl_2$/1.0 mM EGTA) containing complete mini EDTA-free protease inhibitors (Roche #11836170001) and phosphatase inhibitors (Roche #04906837001). 20 μg of total protein from each sample was resolved on Criterion TGX Precast Gels (Bio-Rad #567-1084) with Tris/Glycin/SDS Running Buffer (Bio-Rad #161-0772), transferred to nitrocellulose membranes (Bio-Rad #162-0094) and then probed with various antibodies. Chemiluminescence measurements were performed using SuperSignal West Pico Chemiluminescent Substrate (Thermo Fisher Scientific Prod #34080).

Immunofluorescence Staining

Cultured primary human aortic smooth muscle cells were grown on 10 μg/ml fibronectin (Sigma F2006) coated glass-bottomed dishes (MatTek CORPORATION P35G-1.5-20-C). Cells were first fixed with 2% paraformaldehyde (Polysciences, Inc, 18814) in PBS for 20 minutes at 37° C. then permeabilized with 0.1% triton X-100 in PBS containing 2% PFA at room temperature for 5 minutes, and blocked with 3% bovine serum albumin (Jackson ImmunoResearch Laboratories, Inc. 001-000-162) at room temperature for 60 minutes. Cells were washed with PBS and incubated with SM α-actin-Cy3 (1:1000 in 1% BSA), SM22a (1:1000 in 1% BSA), and SM-calponin (1:500 in 1% BSA) antibodies at 4° C. overnight, washed three times with PBS and incubated with diluted Alexa Fluor-conjugated secondary antibody (1:500) (life technologies) for 1 hour at room temperature. The dishes were then washed three times with PBS and mounted using Prolong Gold antifade reagent with DAPI (life technologies P36935).

Cell Contraction Assay

Cell contraction assay was evaluated using a Cell Contraction Assay Kit according to the manufacturer's instructions (CELL BIOLABS-CBA-201). Briefly, HASMCs were harvested and suspended at $5 \times 10^5$ cells/ml, and the collagen lattice was prepared by mixing two parts of cell suspension and eight parts of cold collagen gel solution. Subsequently, 500 μl of the cell-collagen mixture was cast into each well of a 24-well plate and allowed to polymerize at 37° C. for 1 hr. After collagen polymerization, cells were incubated in SMC growth medium (Medium 231 plus SMGS) for 24 hr. during which stress developed. Upon release of the collagen lattice from the culture dish, the embedded cells become free to contract the deformable lattice thus reducing its surface area. This was quantified twenty-four hr. after detachment of the gel from the dish using ImageJ and expressed as the percentage of the area of the entire well.

xCELLigence® Real-Time Cell Analysis (RTCA)

Cell proliferation experiments were carried out using the xCELLigence® RTCA DP instrument (Roche Diagnostics GmbH) in a humidified incubator at 37° C. and 5% C02. Cell proliferation experiments were performed using modified 16-well plates (E-plate, Roche Diagnostics GmbH). Initially, 100 μL of cell-free growth medium was added to the wells. After leaving the devices at room temperature for 30 min, the background impedance for each well was measured. 100 μL of the cell suspension was then seeded into the wells (1000 cells/well). Plates were locked in the RTCA DP device in the incubator and the impedance value of each well was automatically monitored by the xCELLigence system and expressed as a CellIndex value (CI). CI was monitored every 15 min for 600 times. Two replicates of each cell concentration were used in each test. All data have been recorded by the supplied RTCA software (vs. 1.2.1).

Cell Cycle Analysis

Cell cycle analysis was performed using propidium iodide (PI) staining and flow cytometry. Cells were trypsinized, washed twice in PBS and fixed in 70% ethanol at −20° C. overnight. After washing twice in PBS, the cells were treated with 100 μg/ml RNase A (Sigma R5125) at 37° C. for 30 min and stained in 50 μg/ml PI solution (Sigma P4170). Then the cells were transferred to flow cytometry tubes with filters (BD #352235) for cell cycle analysis. 10,000 events were collected for each sample. The data were collected and analyzed with FlowJo software (Tree Star).

Patient Population

Human coronary arteries were obtained from the explanted hearts of transplant recipients or cadaver organ donors. Research protocols were approved by the Institutional Review Boards of Yale University and the New England Organ Bank. A waiver for consent was approved for surgical patients and written informed consent was obtained from a member of the family for deceased organ donors. Table 1 summarizes clinical characteristics of this patient group.

Specimen Collection

Investigators were on call with the surgical team and collected the heart at the time of explant. To minimize ex vivo artifacts, a ~5-20 mm segment of the left main coronary artery was removed within the operating room (FIG. 4A) and immediately processed as frozen sections in Optimal Cutting Temperature medium and, when of sufficient length, an additional segment was also fixed in formalin for later embedding, sectioning, and staining.

Generation of Mice

Cdh5-CreER$^{T2}$ mice were obtained from R. Adams (Max Planck Institute), Tgfbr2$^{fl/fl}$ mice were obtained from Harold L. Moses (Vanderbilt University), and Tgfbr2$^{fl/fl}$ mice were obtained from Martin M. Matzuk (Baylor College). To generate Cdh5-CreER$^{T2}$; Tgfbr2$^{fl/fl}$-Tgfbr2$^{fl/fl}$ mice, Cdh5-CreER$^{T2}$; Tgfbr2$^{fl/fl}$ mice were mated with Tgfbr2$^{fl/fl}$ mice. To generate Cdh5-CreER$^{T2}$; Tgfbr1$^{fl/fl}$-Tgfbr2$^{fl/fl}$-mT/mG mice, Cdh5-CreER$^{T2}$; Tgfbr2$^{fl/fl}$-Tgfbr2$^{fl/fl}$-mT/mG mice were mated with mT/mG mice (B6.129(Cg)-Gt(ROSA) 26Sor$^{tm4(ACTB-tdTomto,-EGFP)Luo/J}$, Stock No: 007676, The Jackson Laboratory). To generate Cdh5-CreER$^{T2}$; Tgfbr1$^{fl/fl}$-Tgfbr2$^{fl/fl}$-Apoe$^{-/-}$mT/mG mice, Cdh5-CreER$^{T2}$; Tgfbr1$^{fl/fl}$-Tgfbr2$^{fl/fl}$-mT/mG mice were mated with Apoe$^{-/-}$ mice (B6.129P2-Apoetm1Unc/J, Stock No: 002052). C57BL/6J (Stock No: 000664) and Apoe$^{-/-}$ mice (B6.129P2-Apoetm1Unc/J, Stock No: 002052) were purchased from The Jackson Laboratory. This strain had been back-crossed more than ten times to C57BL/6 background. All animal procedures were performed under protocols approved by Yale University Institutional Animal Care and Use Committee.

Frs2α$^{flox/flox}$ mice were previously described (Lin et al, 2007, Genesis 45: 554-559). Frs2α$^{flox/flox}$ mice were bred with mice expressing Cre recombinase under the SM22a promoter. SM22α$^{flox/flox}$ offspring were crossed to C57BL6 Apoe$^{-/-}$ mice (JAX SN:002052). Genotyping was performed by mouse tail DNA PCR analysis. Mouse tail DNA was isolated using the DNeasy Blood & Tissue kit (QIAGEN #69506). PCR genotyping analysis was done using the following primers: Frs2$^{flox/flox}$ (5'-GAGTGTGCTGTGAT-TGGAAGGCAG-3'(SEQ ID NO: 1) and 5'-GGCACGAGTGTCTGCAGACACATG-3' (SEQ ID NO: 2)), SM22α-Cre (5'-GCG GTC TGG CAG TAA AAA CTA TC-3' (SEQ ID NO: 3), 5'-GTG AAA CAG CAT TGC TGT CAC TT-3' (SEQ ID NO: 4), 5'-CTA GGC CAC AGA ATT GAA AGA TCT-3' (SEQ ID NO: 5), and 5'-GTA GGT GGA AAT TCT AGC ATC ATC C-3' (SEQ ID NO: 6)), Apoe (5'-GCCTAGCCGAGGGAGAGCCG-3' (SEQ ID NO: 7), 5'-GTGACTTGGGAGCTCTGCAGC-3' (SEQ ID NO: 8), and 5'-GCCGCCCCGACTGCATCT-3' (SEQ ID NO: 9)), Cdh5-CreER$^{T2}$ (5'-GCC TGC ATT ACC GGT CGA TGC AAC GA-3' (SEQ ID NO: 10), and 5'-GTG GCA GAT GGC GCG GCA ACA CCA TT-3' (SEQ ID NO: 11)), Tgfbr1$^{fl/fl}$ (5'-ACT CAC ATG TTG GCT CTC ACT GTC-3' (SEQ ID NO: 12), and 5'-AGT CAT AGA GCA TGT GTT AGA GTC-3' (SEQ ID NO: 13), Tgfbr2$^{fl/fl}$ (5'-TAA ACA AGG TCC GGA GCC CA-3' (SEQ ID NO: 14), and 5'-ACT TCT GCA AGA GGT CCC CT-3' (SEQ ID NO: 15)), and mT/mG (5'-CTC TGC TGC CTC CTG GCT TCT-3' (SEQ ID NO: 16), 5'-CGA GGC GGA TCA CAA GCA ATA-3' (SEQ ID NO: 17), and 5'-TCA ATG GGC GGG GGT CGT T-3' (SEQ ID NO: 18)).

All animal procedures were performed under protocols approved by Yale University Institutional Animal Care and Use Committee.

Echocardiographic Studies

Experiments were performed at the Yale Translational Research Imaging Center Core Facility. Cardiac function was analyzed by echocardiography using a Vevo 770® console (VisualSonics). Mice body temperature was maintained with a heading pad. Mice were anesthetized with 2% isoflurane, maintained under anesthesia with 1% isoflurane, and examined. The mouse was placed chest up on an examination board interfaced with the Vevo 770® console. Warmed Aquasonic gel was applied over the thorax and a 30-MHz probe was positioned over the chest in a patasternal position. Long and short axis B-mode and M-mode images were recorded. All measurements were obtained from three to six consecutive cardiac cycles, and the averaged values were used for analysis. Upon completion of the procedure, the gel was wiped off and the animal was returned to its cage housed in a warm chamber.

Serum Lipid Analysis

Serum was obtained through centrifugation of the blood for 2 min at 10,000 rpm at 4° C. and stored at −80° C. until each assay was performed. Total cholesterol and triglycerides were performed in the Yale Mouse Metabolic Phenotyping Center.

Histology and Morphometric Analysis

The animals were euthanized and perfusion-fixed with 4% paraformaldehyde (Polysciences, Inc. Cat #18814) via the left ventricle for 5 min. For human vessel studies, sections of left main coronary arteries were stained with Elastic Van Gieson (EVG). Digital EVG-stained photographs of one section from each block were projected at final magnifications of ×100. ImageJ software (NIH) was used for morphometric analyses. As described in FIG. 4B, measurements were made of the intima and media thickness. The ratio of intima (I) to media (M) thickness was used to grade the severity of atherosclerosis. The results for these parameters from each specimen were average of four different areas to obtain mean values. Left main coronary arteries of I/M ratio less than 0.2 were considered as no disease or mild disease; those of I/M ratio between 0.2-1 were considered as moderate disease; those of I/M ratio greater than 1 or have calcification as severe disease.

Histological Analysis of Atherosclerotic Lesions $Apoe^{-/-}$ and $Frs2^{SMCKO}/Apoe^{-/-}$ male mice were fed a Western diet (40% kcal % Fat, 1.25% Cholesterol, 0% Cholic Acid) for 8 or 16 weeks (Research Diets, product #D12108) starting at the age of 8 weeks. After 8 or 16 weeks of being fed a high-fat diet, mice were anesthetized and euthanized. Mouse heart were perfused with 10 ml of Dulbecco's Phosphate Buffered Saline (DPBS) (Life Technologies Cat #14190-144) and 10 ml of 4% paraformaldehyde (Polysciences, Inc. Cat #18814) via the left ventricle. The lesions located in the aorta, aortic roots and abdominal aorta were analyzed using Oil Red 0 staining. To measure lesions in the aorta, the whole aorta, including the ascending arch, thoracic and abdominal segments, was dissected, gently cleaned of adventitial tissue and stained with Oil Red 0 (Sigma 00625) as previously described (Huang et al, 2013, Arterioscler Thromb Vasc Biol 33: 795-804). The surface lesion area was quantified with ImageJ software (NIH). To measure lesions in the aortic root, the heart and proximal aorta were excised, and the apex and lower half of the ventricles were removed.

Immunohistochemical Staining

Blocks were sectioned at 5 μm intervals using a Microm cryostat (for frozen blocks) or a Paraffin Microtome (for paraffin blocks). For frozen tissue sections, slides were fixed in acetone for 10 min at −20° C. For paraffin sections, slides were dewaxed in xylene, boiled for 20 min in citrate buffer (10 mM, pH 6.0) for antigen retrieval, and rehydrated. After washing three times with phosphate-buffered saline, tissue sections were incubated with primary antibodies diluted in blocking solution (10% BSA and horse serum in PBS) overnight at 4° C. in a humidified chamber. For p-Smad2, p-Smad3 staining, slides were denatured with 1.5 M HCl for 20 min prior to antibody labeling.

Sections were washed three times with tris-buffered saline, incubated with appropriate Alexa Fluor 488-, Alexa Fluor 594-, or Alexa Fluor 647-conjugated secondary antibodies diluted 1:1000 in blocking solution for 1 hr at room temperature, washed again three times, and mounted on slides with ProLong Gold mounting reagent with DAPI (Life Technologies P36935). All immunofluorescence micrographs were acquired using a Zeiss microscope. Images were captured using Velocity software and quantifications performed using ImageJ software (NIH).

Statistical Analysis

Graphs and statistical analysis were prepared using GraphPad Prism software. Data are expressed as mean±SD. The level of statistical significance was determined by one-way ANOVA with Newman-Keuls test for multiple comparisons or 2-tailed Student's t test using the GraphPad Prism software. A P value less than 0.05 was considered significant (*$P<0.05$, $P<0.01$, *$P<0.001$). All results were confirmed by at least 3 independent experiments. Error bars represent mean±SD.

Study Approval

All experiments involving animals were reviewed and approved by the Animal Welfare Committee of Yale University. The ethics committee of Yale University approved the procedures related to human subjects. All patients who participated in the study provided written informed consent.

Synthesis of let-7b Mimics

Chemically-modified miRNA mimics were synthesized at Alnylam Pharmaceuticals (Cambridge, Mass.). The sequences for the mature strands of let-7b after processing by DICER, mmu-let-7b-5p (mmu-let-7b, MIMAT0000522), and mmu-let-7b-3p (mmus-let-7b*, MIMAT0004621), were obtained from the miRbase (http://www.miRbase.org). 2-O-methyl-nucleotide modifications (indicated in lower case) were introduced to both strands to decrease the likelihood of triggering an innate immune response. Double stranded miRNA mimics were obtained after annealing equimolar amounts of the chemically-modified 5p and 3p strands: mi-let-7b$_L$, for lightly modified (5p 5'-UGAGGuAGuAG-GUUGUGUGGUU-3' (SEQ ID NO: 19), 3p 5'-CuAuA-cAACCuACUGCCUUCCC-3' (SEQ ID NO: 20); and mi-let-7b$_H$, for heavily modified, (5p 5'-UGAGGuAGuAG-GUUGUGUGGUU-3' (SEQ ID NO: 19), 3p 5'-cuAuA-cAAccuAcuGccuuccc-3' (SEQ ID NO: 20). LNPs formulated with siRNA targeting luciferase, siLuc, were used as control. The siLuc, which was also incorporated 2-O-methyl-nucleotide modifications, is commonly used as a control for in vivo siRNA and miRNA studies (Dahlman et al., 2014, Nat Nanotechnol 9, 648-655; Sager et al., 2016, Science translational medicine 8, 342ra380) let-7 mimics have been validated previously in vivo (Chen et al., 2012, Cell reports 2: 1684-1696).

Synthesis of siTgfbr1 and siTgfbr2.

Chemically-modified siRNA against mouse Tgfbr1 and Tgfbr2 were synthesized at Alnylam Pharmaceuticals (Cambridge, Mass.). The siRNA sequence for Tgfbr1 sense strand (UGUCAAGGAGAUGCUUCAAuAdTsdT) (SEQ ID NO: 35) and antisense (UAUUGAAGCAUCUCCUUGA-CAUAdTsdT) (SEQ ID NO: 36); for Tgfbr2 is sense (GG-CUCGCUGAACACUACCAAAdTsdT) (SEQ ID NO: 37) antisense (UUUGGUAGUGUUCAGCGAGCCAUdTsdT) (SEQ ID NO: 38).

miRNA Formulation in Lipid Nanoparticles (LNPs).

siRNA targeting Tgfbr1, Tgfbr2, and siLuc were encapsulated in LNPs formulated with the lipid 7C1, using the same protocol and composition as previously described (Dahlman, 2014, Nat Nanotechnol 9, 648-655). More specifically, 7C1 was synthesized and purified as previously described (Dahlman, 2014, Nat Nanotechnol 9, 648-655). It was then combined with $C_{14}PEG_{2000}$ in a glass syringe (Hamilton Company), and diluted with 100% ethanol. let-7 mimics or siLuc were diluted in 10 mM citrate buffer, and loaded into a separate syringe. The two syringes were connected to a microfluidic mixing device (Chen et al, 2012 J Am Chem Soc. 2012 134(16):6948-51), before the 7C1 and RNA solutions were mixed together at a flow rate of 600 and 1800 µL/min, respectively. The resulting nanoparticles were dialyzed into 1×PBS, before being sterile filtered using a 0.22 µm filter.

Animal Treatment.

Cre-Lox recombination was induced by tamoxifen (Sigma T5648) at 1 mg/day i.p. for 5 days versus vehicle (corn oil, Sigma C8267) alone. For PBS, siluciferase, let-7 mimics and siTgfbr1/Tgfbr2 delivery in mouse atherosclerosis model, 8 to 10 week old mice were placed on a Western diet (40% kcal % Fat, 1.25% Cholesterol, 0% Cholic Acid) for 16 weeks (Research Diets, product #D12108) and injected intravenously every 10 days during this period of the following: sterile PBS (100 µl/mouse), luciferase-control (2 mg/kg), siTgfbr1/Tgfbr2 (2 mg/kg) or let-7b mimics. For LPS administration, mice were given *Escherichia coli* LPS (Sigma L2630) prepared in 0.1 ml of sterile saline and administered i.p. by single injection at a dose of 100 µg/kg. Animals were studied 3 h after the injections. For Rapamycin (Millipore 553210) treatment, 8 to 10 week old Apoe[1] mice were placed on a Western diet (40% kcal % Fat, 1.25% Cholesterol, 0% Cholic Acid) for 16 weeks (Research Diets, product #D12108) and injected at 2 mg/kg/d i.p. every day (q.d.). 4% DMSO injected mice was used as controls. Control groups received 0.1 ml of saline i.p.

The results of experiments are now described.

Example 1: FRS2α Regulates TGFβ Activity and SMC Differentiation

Figure 1B:
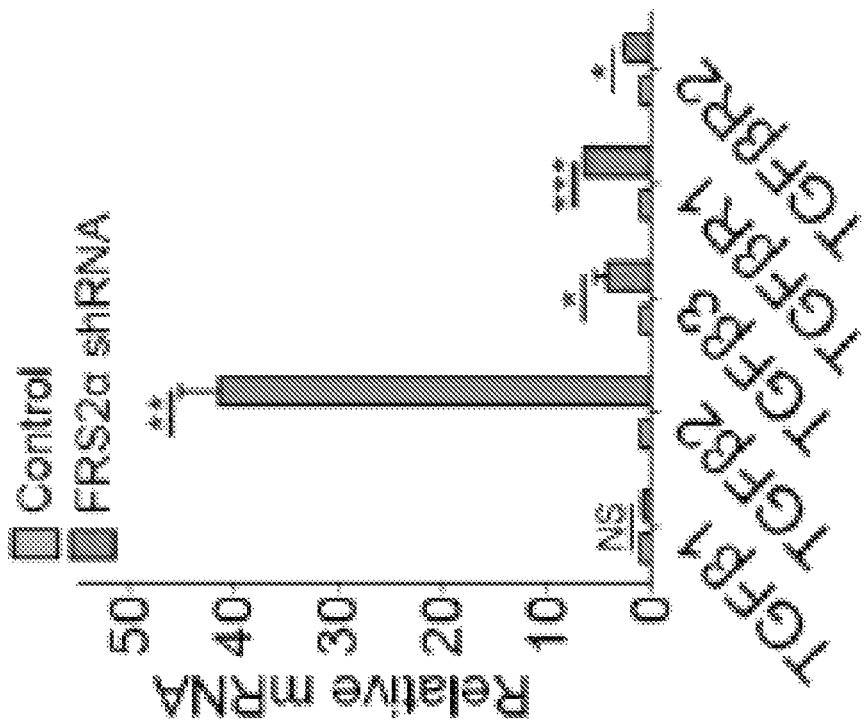
Figure 1C:
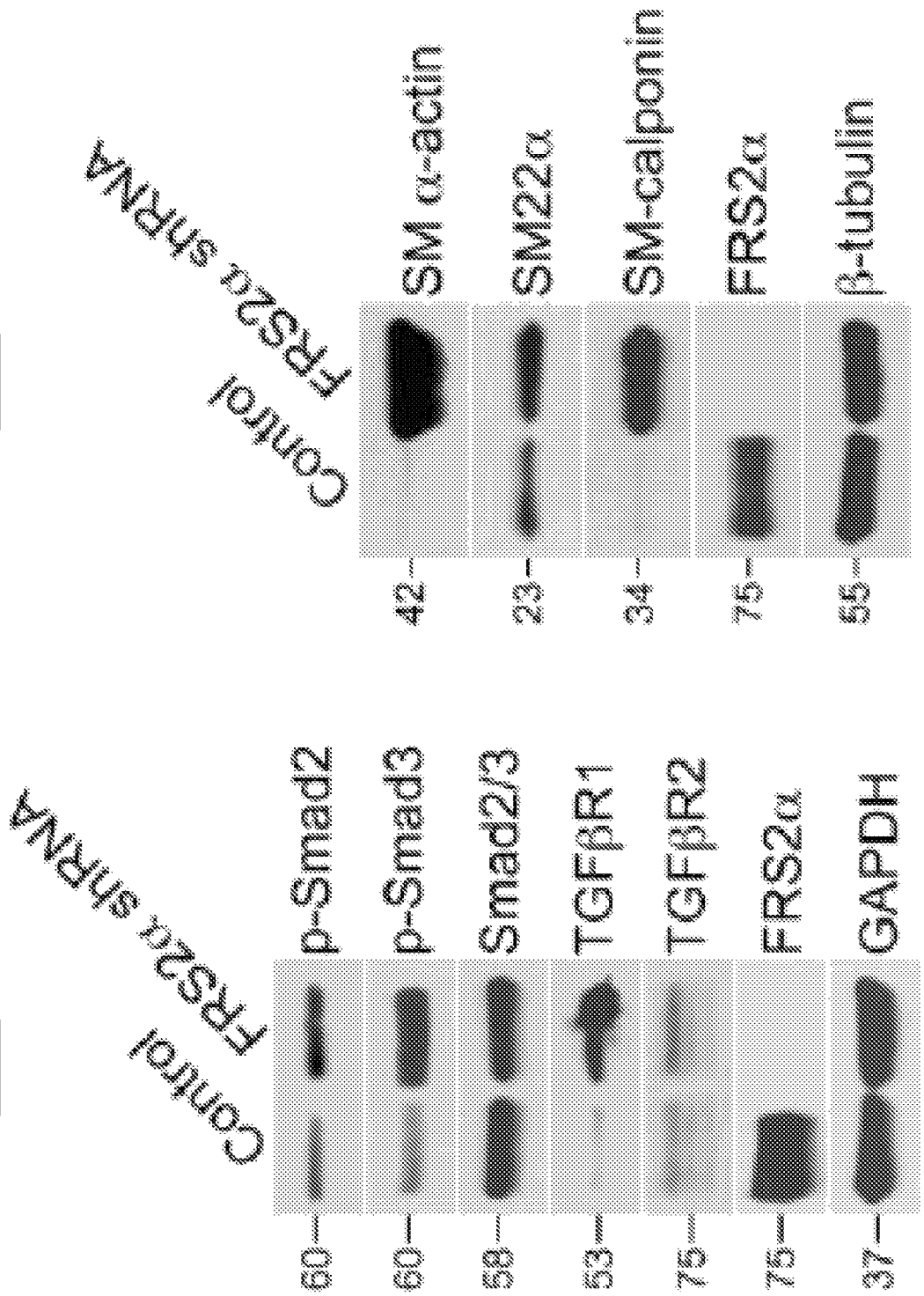

Inhibition of FGF signaling in SMCs using FRS2α knockdown and its effect on the expression of TGFβ pathway signaling molecules were examined. In cultured human aortic smooth muscle cells (HASMCs), knockdown of FRS2α led to a significant increase in expression of TGFβ2, TGFβ3, TGFβR1, and TGFβR2 (FIG. 1A). TGFβ1 was unchanged. In addition, there was an increase in the expression of a number of TGFβ-dependent genes including connective tissue growth factor (CTGF), elastin, plasminogen activator inhibitor-1 (PAI-1), p21, p27, and collagen (FIG. 1B) suggesting activation of TGFβ signaling. This was confirmed by Western blotting that demonstrated increase phosphorylation of Smad2 and Smad3 following FRS2α knockdown (FIG. 1C).

Figure 2A:
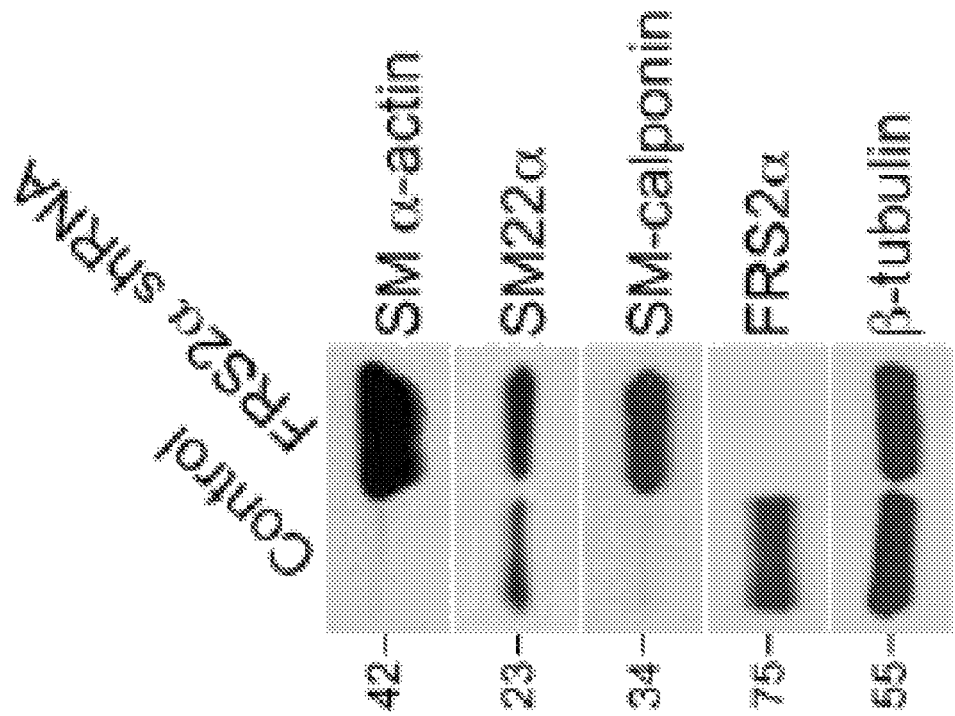
FIGS. 2A-2F are images and plots showing that FRS2α knockdown increases smooth muscle marker gene expression via the TGFβ pathway in primary human aortic smooth muscle cells (HASMCs).
Figure 2B:
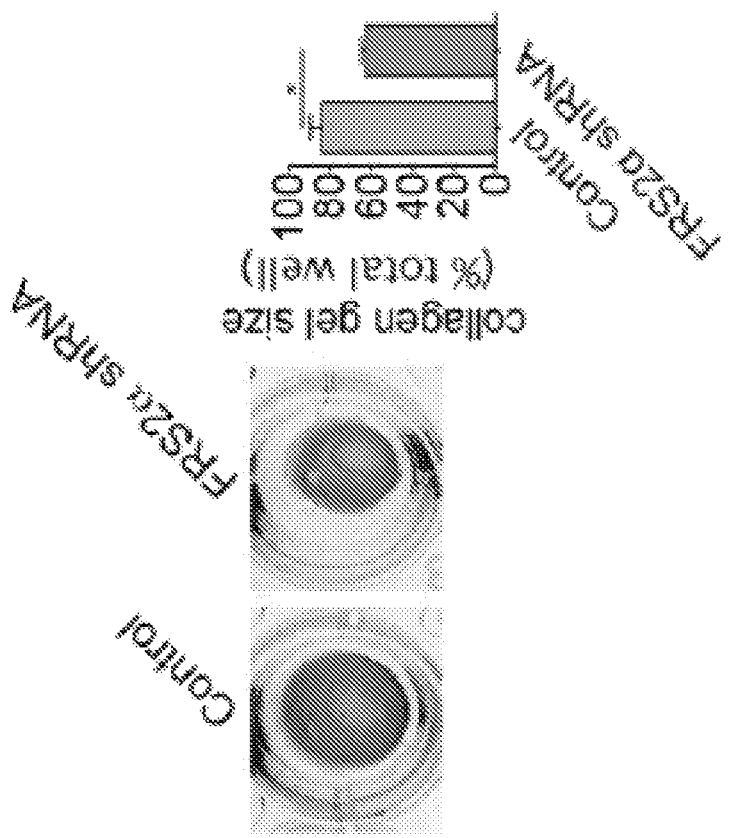
Figure 2C:
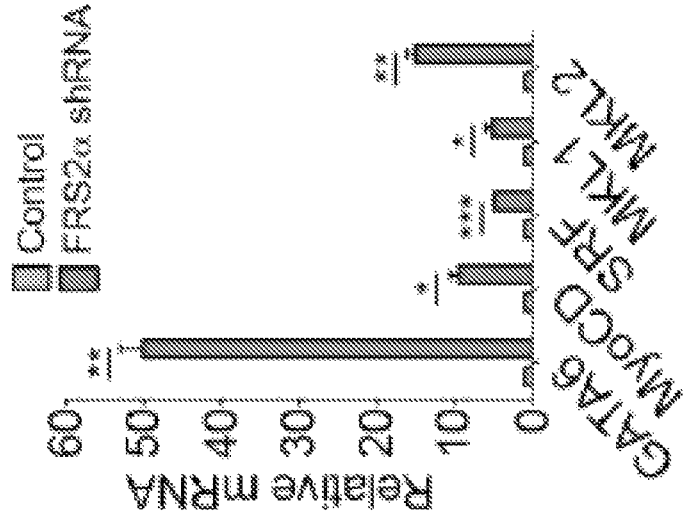

Cultured SMCs in serum-supplemented medium lose differentiation marker expression and acquire a synthetic (proliferative) phenotype. Since activation of TGFβ signaling has been linked with the induction of SMC differentiation, differentiation marker expression was next examined in cultured HASMC following FRS2α knockdown. There was a pronounced increase in expression of SM α-actin, SM22α and SM-calponin (FIG. 2A) as well as various transcription factors (GATA6, MyoCD, SRF) and transcription co-activators (MKL1, MKL2) responsible for the induction of contractile phenotype (FIG. 2B). The contractile machinery was functional as observed by increased contraction of collagen gels following FRS2α knockdown (FIG. 2C).

Figure 9A:
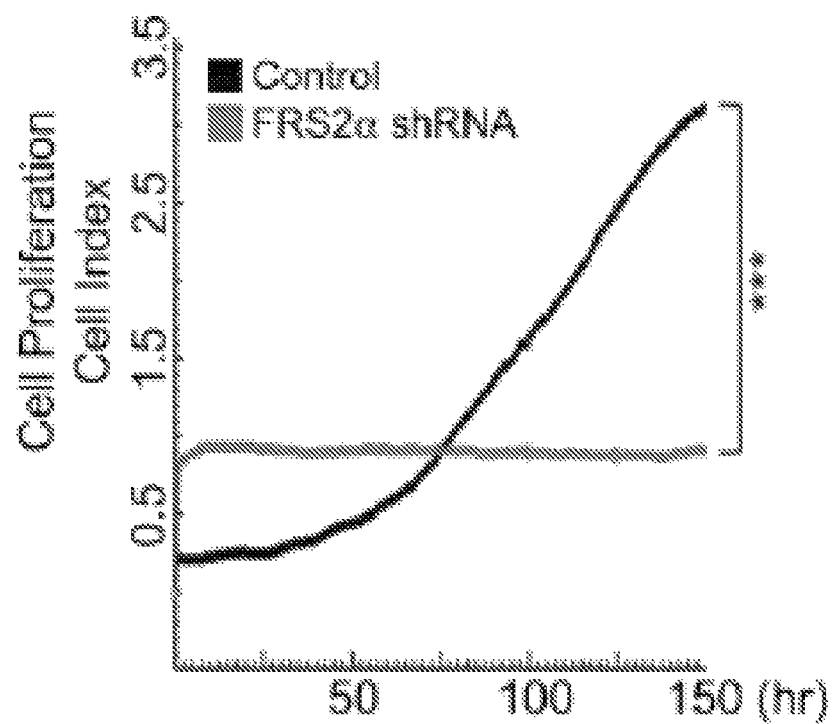
FIGS. 9A-9C are plots and images showing that FRS2α knockdown inhibits proliferation of human aortic smooth muscle cells (HASMCs).
Figure 9B:
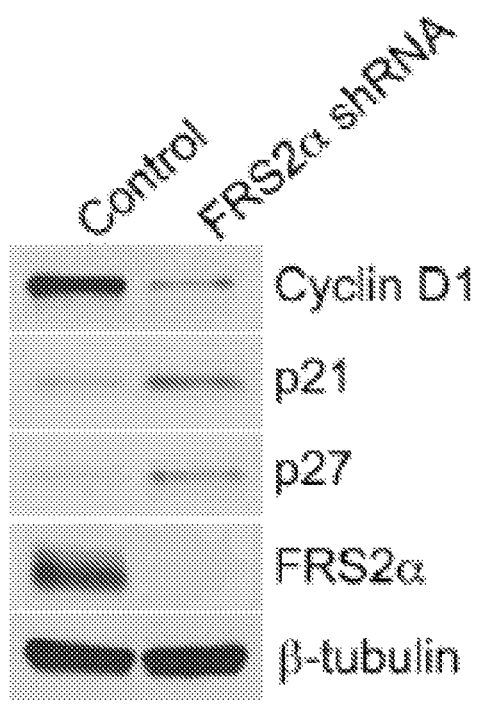
Figure 9C:
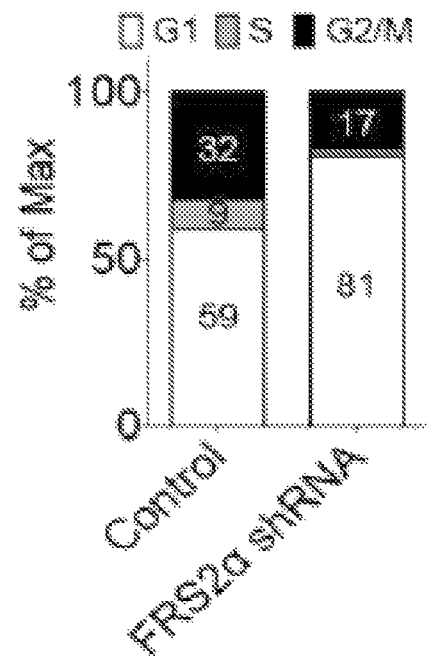

To assess the effect of FGF signaling shutdown on SMC proliferation, real time cell analysis was used to track HASMC growth in the presence and absence of FRS2α knockdown. The absence of FRS2α expression resulted in nearly complete inhibition of serum-induced HASMC proliferation (FIG. 9A). Western blot analysis demonstrated a decrease in the proliferative marker Cyclin D1 whereas expression of cell cycle inhibitor proteins p21 and p27 was upregulated (FIG. 9B). In agreement with these findings, FACS analysis showed a G1/S arrest following FRS2α knockdown (FIG. 9C).

Figure 2E:
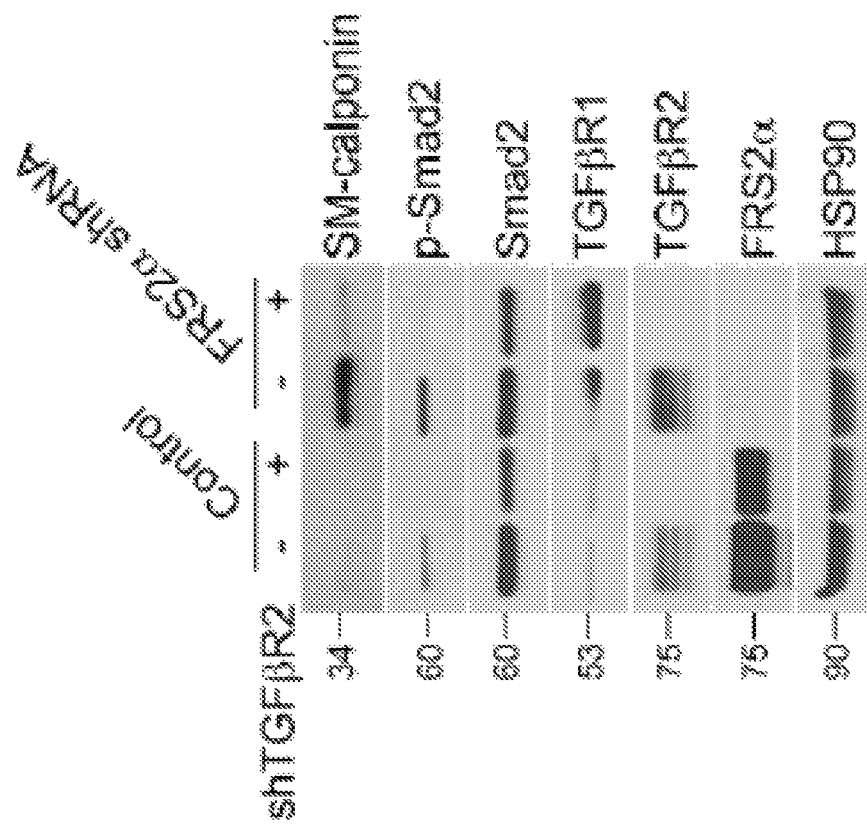
Figure 2D:
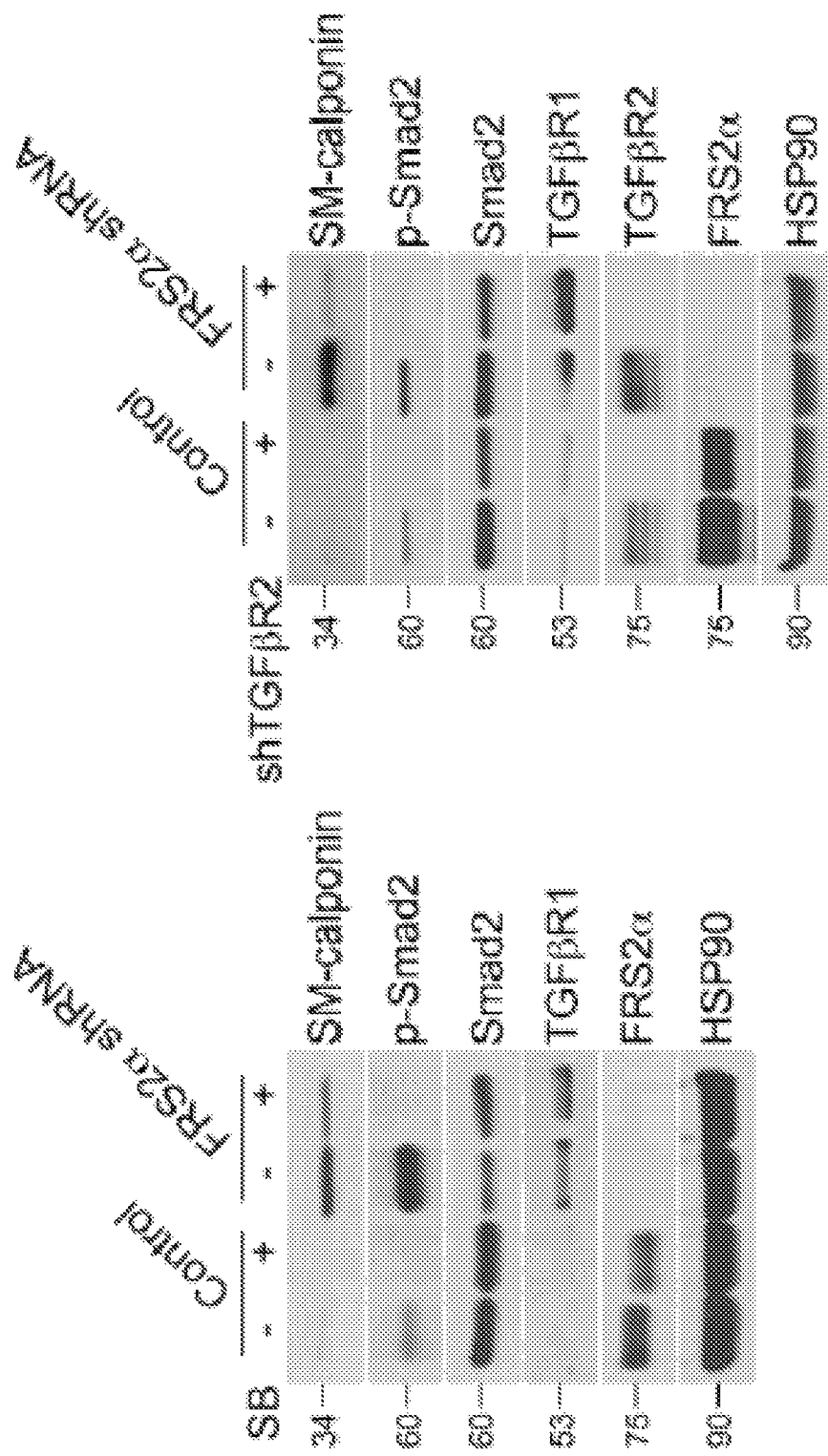
Figure 2F:
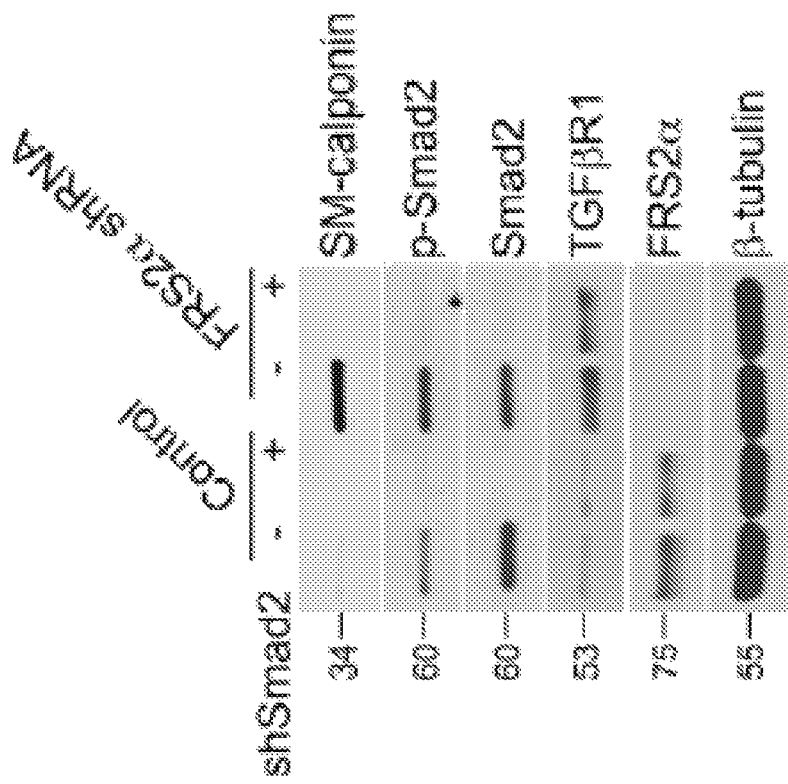

To test if TGFβ activity is required for FRS2α knockdown-induced SMC differentiation, HASMCs were exposed to FRS2α or control shRNA lentiviruses in the presence or absence of the TGFβR1 kinase inhibitor, SB431542. The inhibitor treatment effectively attenuated FRS2α knockdown-induced increase in p-Smad2 and SM-calponin levels (FIG. 2D) demonstrating that TGFβ activity is essential for FRS2α knockdown-induced contractile smooth muscle gene expression. This was further confirmed by shRNA-mediated knockdown of TGFβR2 or Smad2 with both knockdowns preventing increase in SM-calponin expression (FIGS. 2E-2F).

Figure 10A:
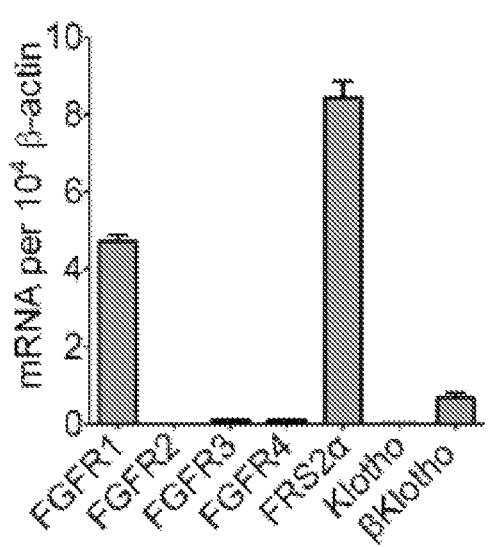
FIGS. 10A-10E are plots and images showing FGFR1 knockdown activates TGFβ signaling and induces smooth muscle marker gene expression in primary human aortic smooth muscle cells (HASMCs).
Figure 10B:
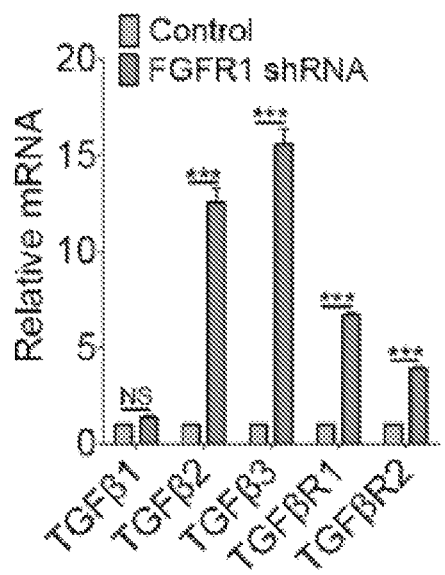
Figure 10C:
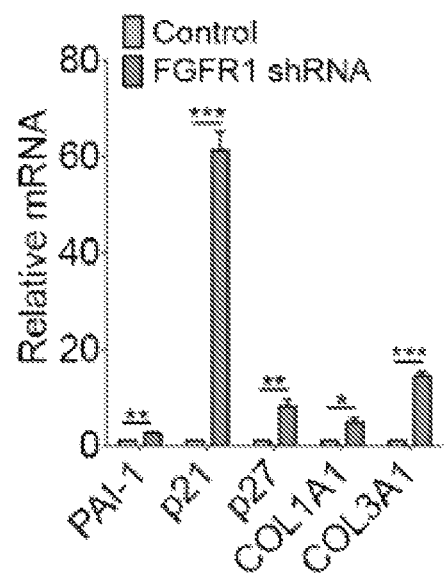
Figure 10D:
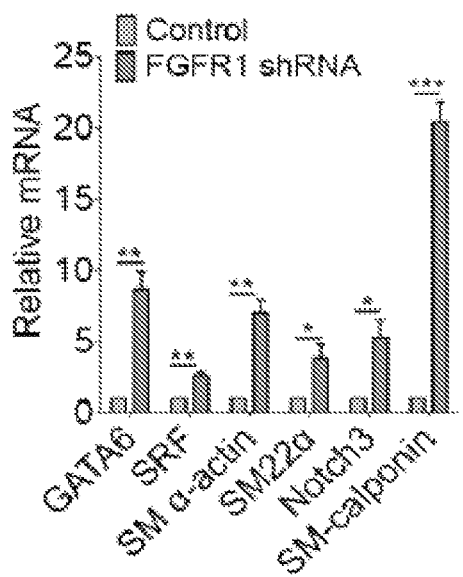
Figure 10E:
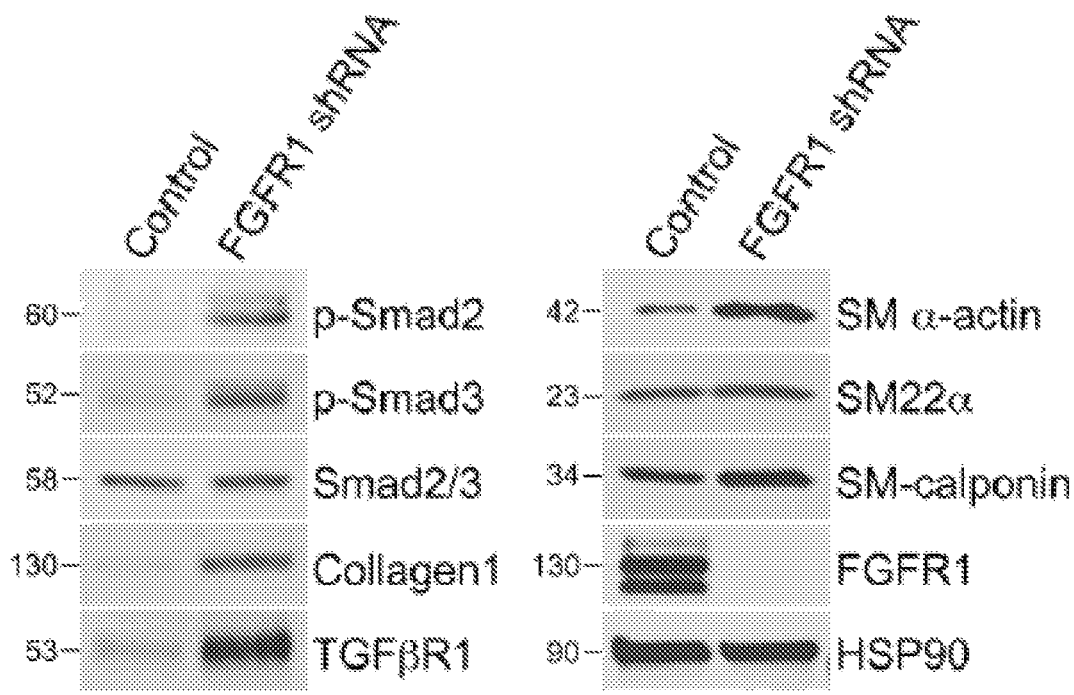

Example 2: FGFR1 and Let-7 Mediate FGF-Driven Suppression of TGFβ Signaling in SMCs FRS2α is involved in signaling of all four FGF receptors. The following experiments were conducted to establish the principal FGFR responsible for suppression of TGFβ signaling in SMC. qPCR analysis demonstrated that FGFR1 was the main FGFR expressed in cultured HASMCs (FIG. 10A). In agreement with that finding, shRNA-mediated FGFR1 knockdown markedly increased TGFβ2, TGFβ3, TGFβR1 and TGFβR2 expression (FIG. 10B) in a manner similar to that of the FRS2α knockdown. This also led to activation of TGFβ signaling as demonstrated by increased expression of a number of TGFβ-dependent genes and transcription factors (FIGS. 10C-10D). Western blotting confirmed activation of TGFβ signaling as demonstrated by increased Smad2 and Smad3 phosphorylation and increased contractile SMC gene expression (FIG. 10E).

Figure 3B:
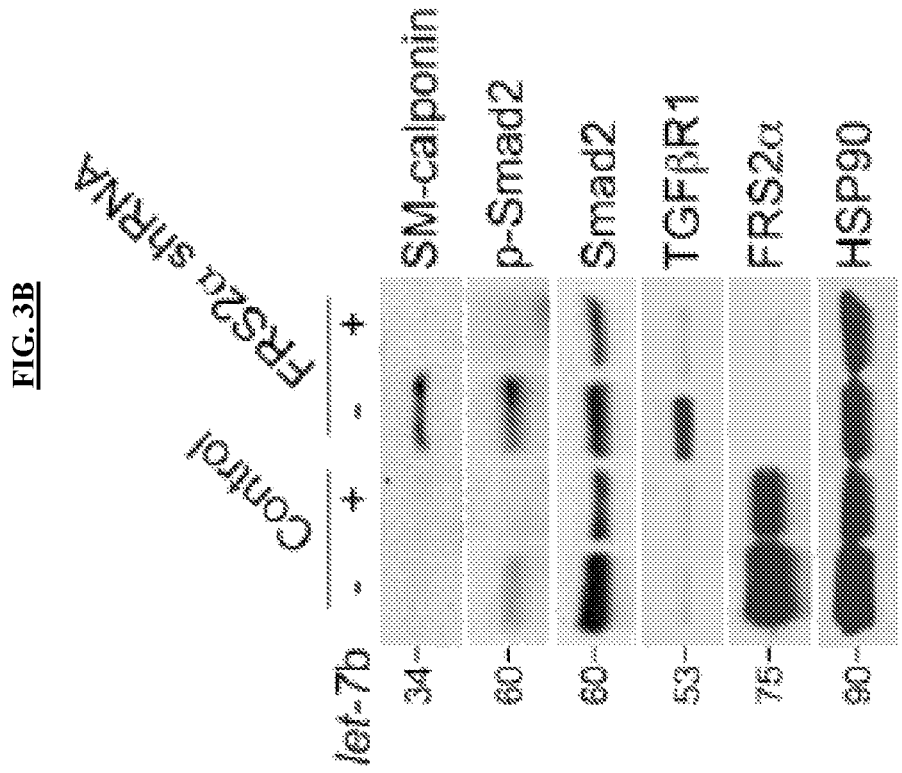
FIGS. 3A-3E are plots and images showing FRS2α knockdown increases smooth muscle marker gene expression via the let-7-TGFβ pathway in primary human aortic smooth muscle cells (HASMCs).
Figure 3A:
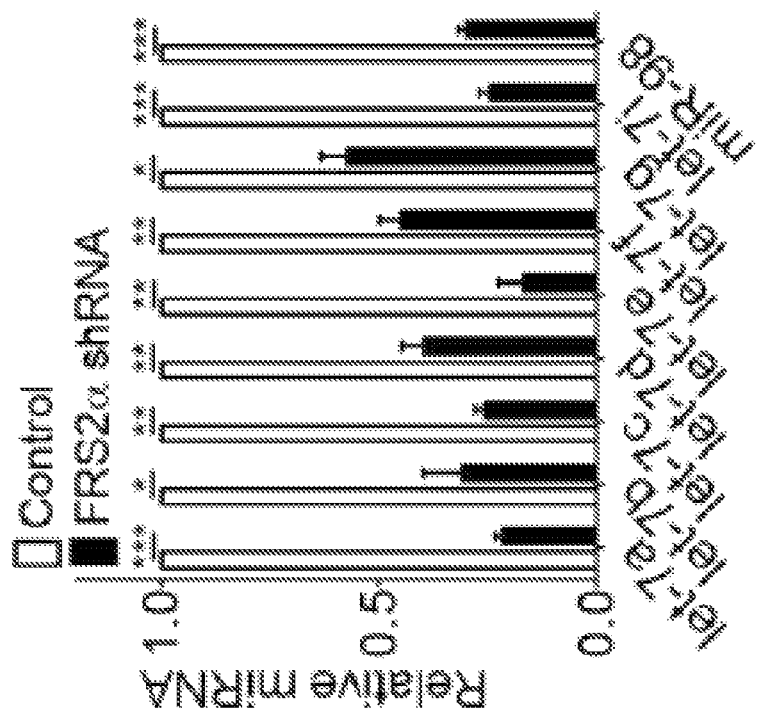

It was previously showed that suppression of FGF signaling in endothelial cells decreases expression of let-7 miRNA family members (Chen et al, 2012, Cell reports 2: 1684-1696; Chen et al, 2014, Science signaling 7: ra90). To assess if the same mechanism is operational in SMCs, let-7 levels were examined after shRNA-mediated FRS2α knockdown in HASMCs. As in endothelial cells, this led to a substantial decrease in let-7 miRNAs expression in FRS2α knockdown HASMCs (FIG. 3A). Transduction of let-7b into HASMCs following FRS2α knockdown prevented activation of TGFβ signaling as demonstrated by decreased TGFβR1, p-Smad2 and SM-calponin levels (FIG. 3B).

Figure 3C:
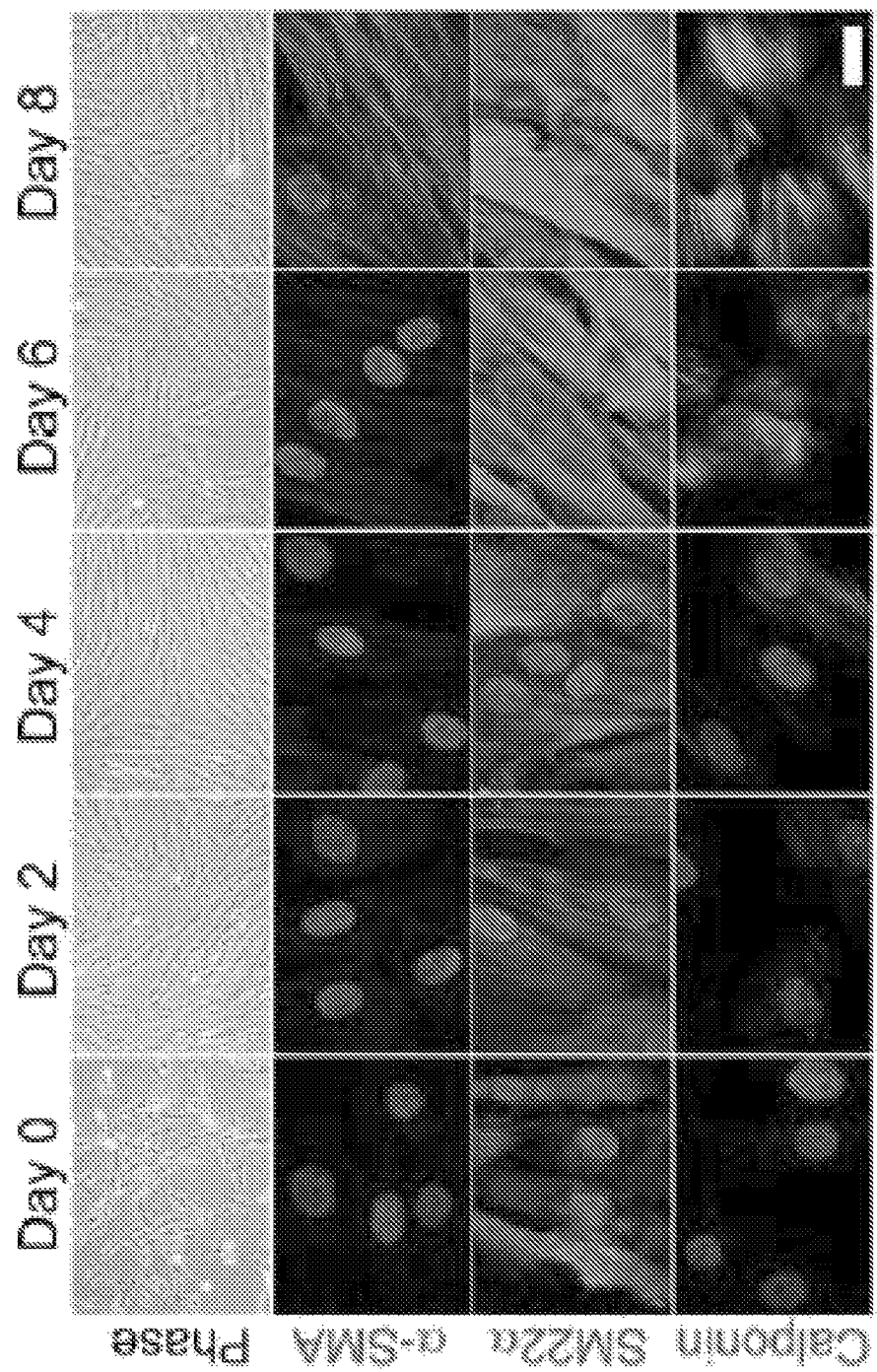
Figure 3D:
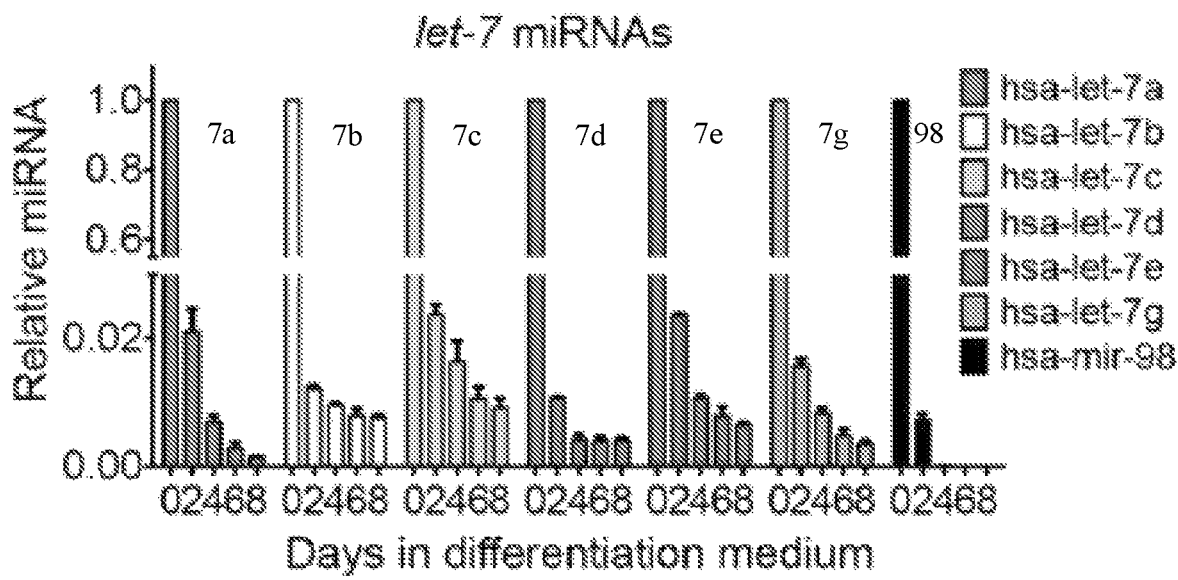

Growth arrest of cultured SMCs has been shown to induce their conversion from proliferative to contractile phenotype (Clowes et al, 1988, J Cell Biol 107: 1939-1945). Indeed, shifting HASMC cultured in 4.9% FBS to 1% FBS medium led to a gradual increase in expression of contractile SMC proteins (FIG. 3C). Analysis of let-7 family members' expression during HASMC differentiation demonstrated a profound decrease that preceded changes in contractile proteins expression suggesting let-7-dependent control of this process (FIG. 3D).

Figure 3E:
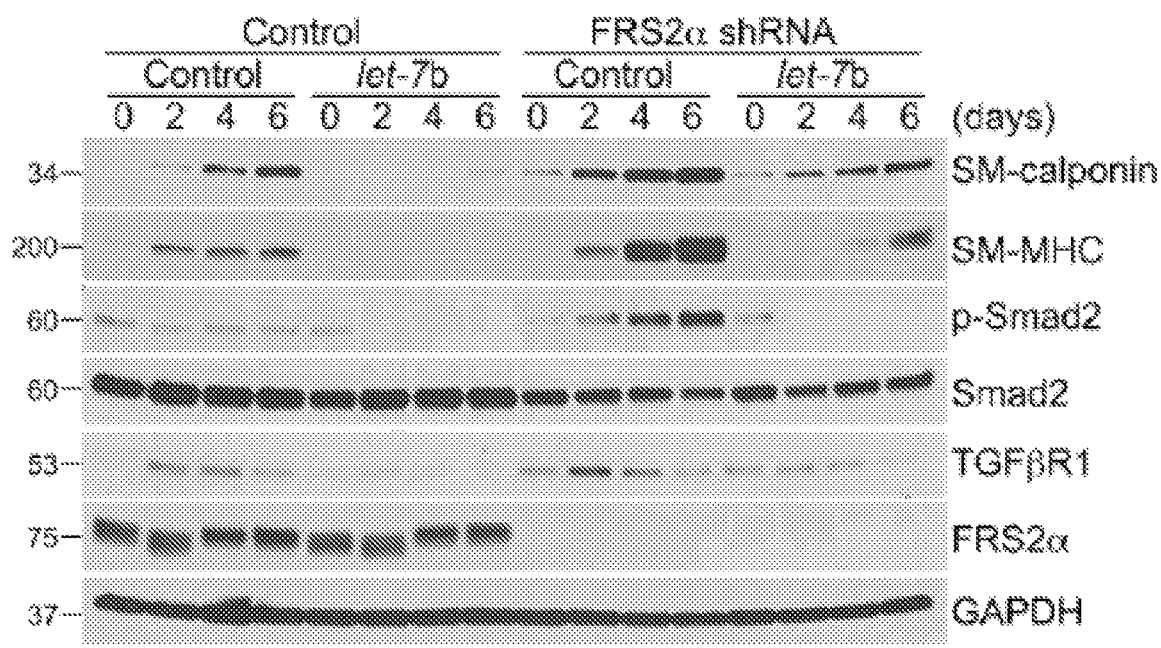

To test this further, HASMCs shifted to the growth arrest medium were exposed to FRS2α or control shRNA lentiviruses in the presence or absence of the let-7b lentivirus. In agreement with the data presented above, HASMC FRS2α knockdown accelerated reversion to the contractile phenotype (FIG. 3E). The phenotype conversion, however, was effectively blocked by let-7 overexpression as demonstrated by decreased TGFβR1, SM-calponin, and SM-MHC expression and reduced Smad2 phosphorylation (FIG. 3E).

Figure 4A:
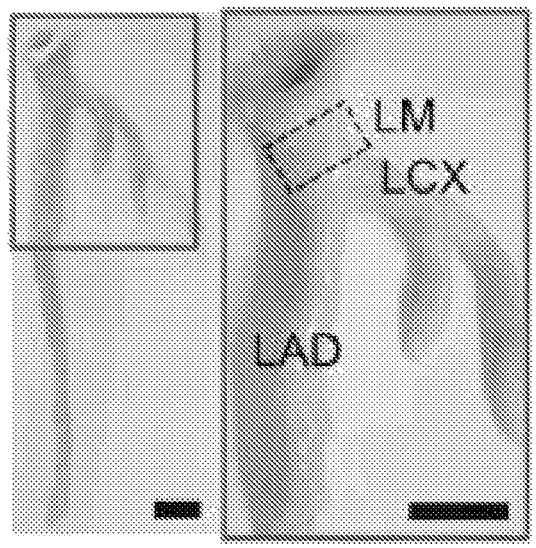
FIGS. 4A-4H are plots and images showing FGFR1 signaling activity in smooth muscle cells in human left main coronary arteries with various degrees of atherosclerosis.
Figure 4B:
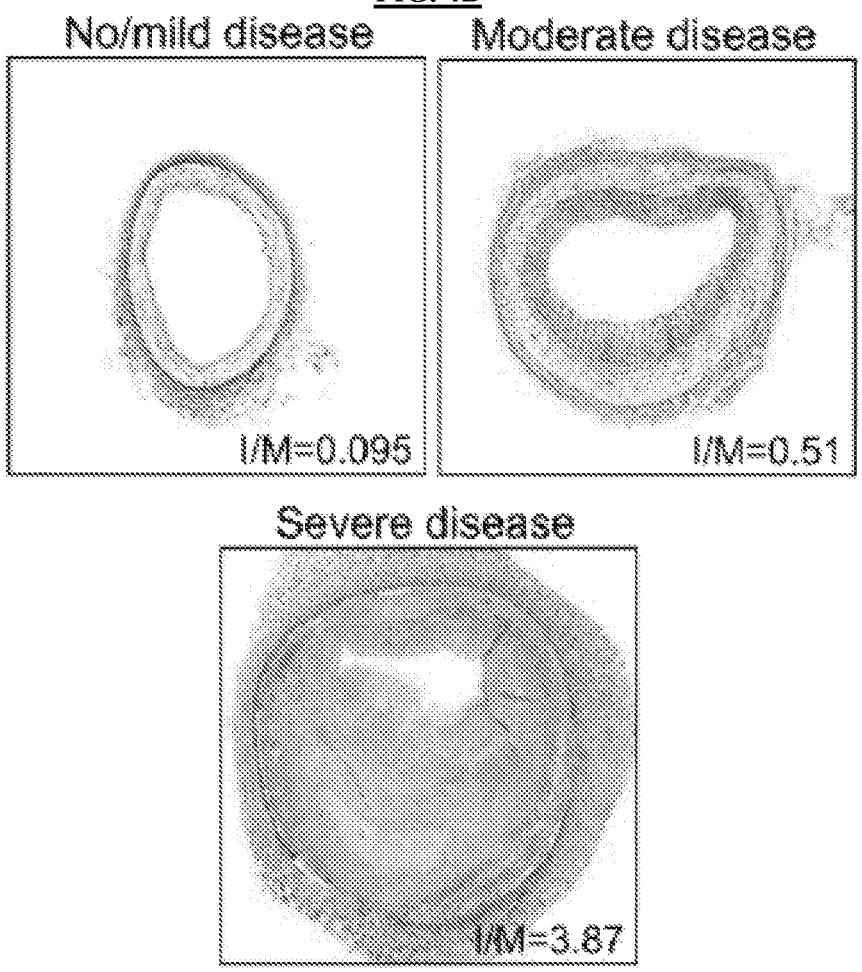
Figure 4C:
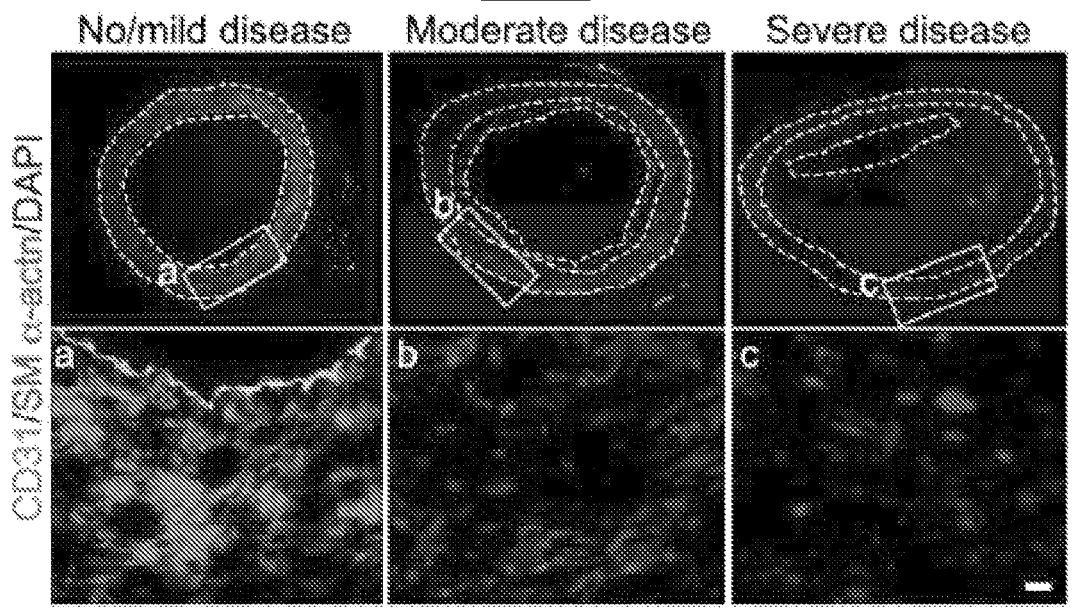
Figure 4D:
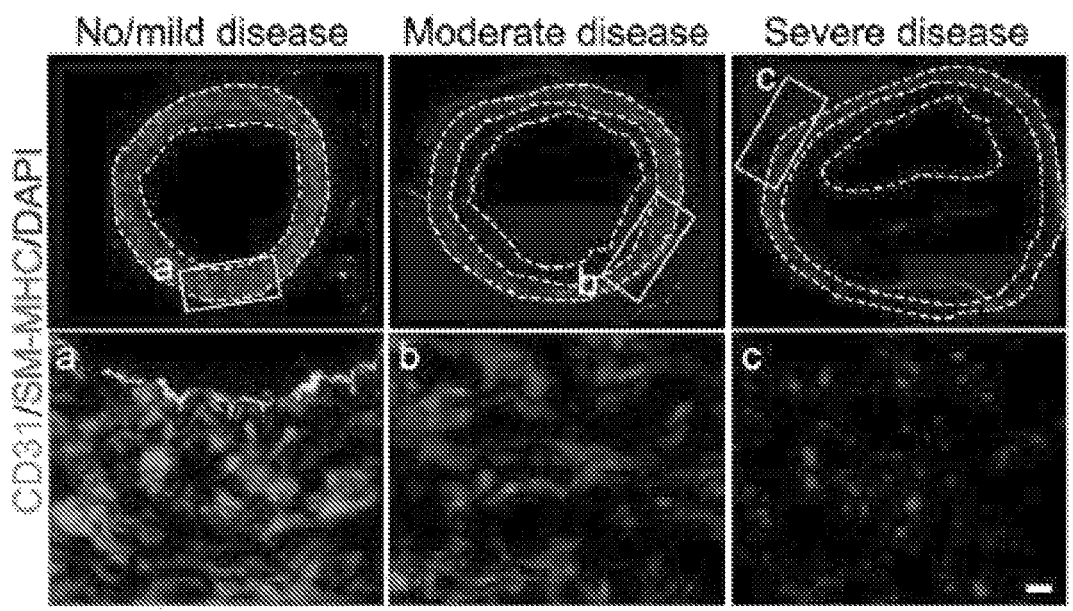
Figure 4E:
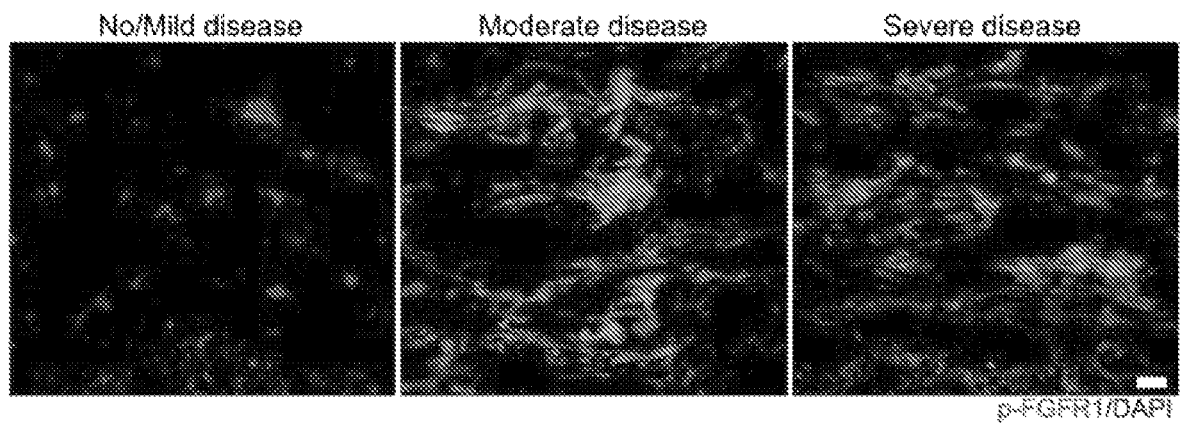
Figure 4F:
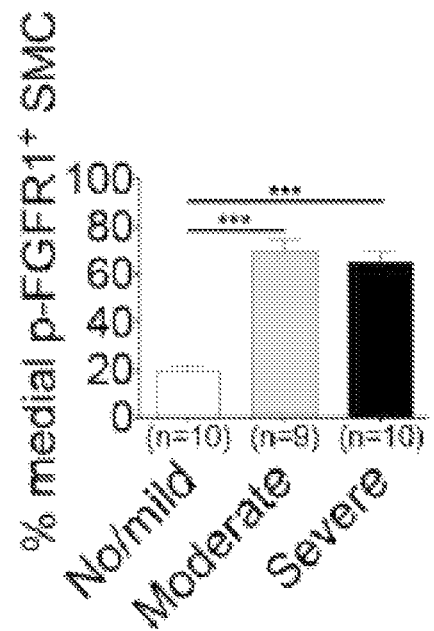
Figure 4G:
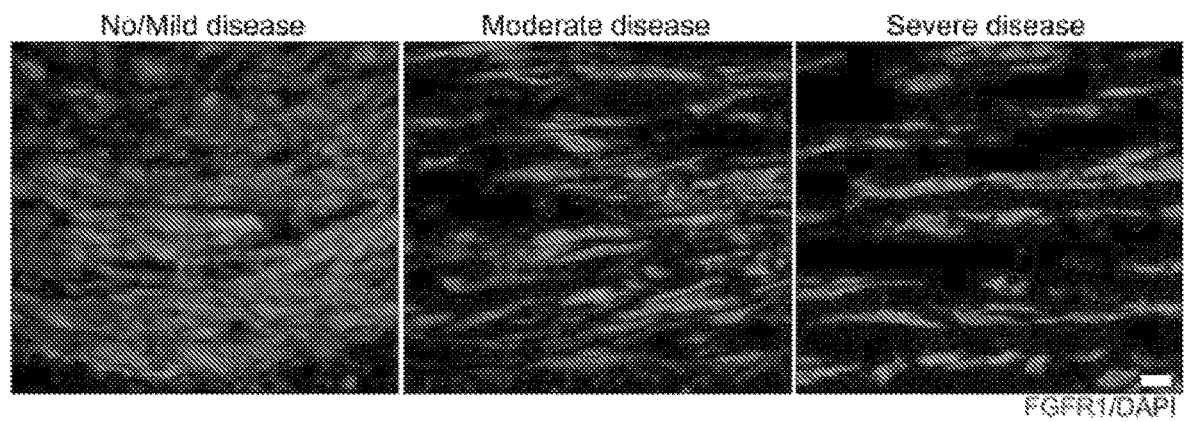
Figure 4H:
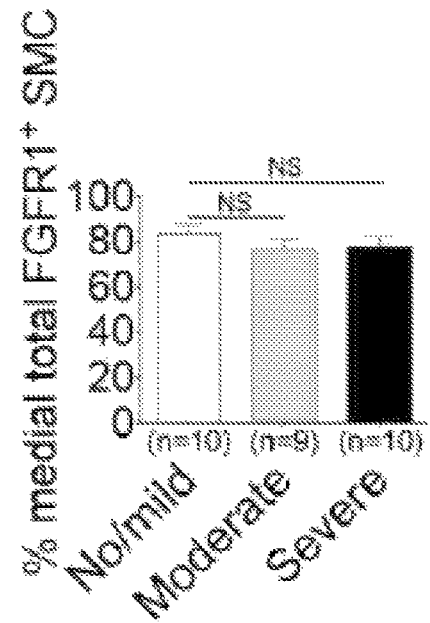

Example 3: Activation of FGF and Loss of TGFβ Signaling in Human and Mouse Atherosclerotic Lesions To examine the role played by FGF regulation of TGFβ signaling activity in SMCs in disease settings, the correlation between medial FGF and TGFβ signaling and the severity of atherosclerosis in samples of left main coronary arteries from forty-three patients was first evaluated (FIGS. 4A-4B). Table 1 summarizes clinical characteristics of this patient group. Immunostaining of serial left main coronary artery sections for SM α-actin and SM-MHC revealed decreased expression of these contractile SMC markers in the media of arteries from patients with moderate and severe coronary atherosclerosis compared to patients with No/mild disease (FIGS. 4C-4D), consistent with previous findings (Aikawa et al, 1995, Annals of the New York Academy of Sciences 748: 578-585; Aikawa et al, 1993, Circulation research 73: 1000-1012; Glukhova et al, 1988, Proc Natl Acad Sci USA 85: 9542-9546). At the same time, there was an increase in immunoreactivity for the phosphorylated form of FGFR1 in patients with moderate and severe CAD (coronary artery disease), implying an increase in FGF signaling (FIGS. 4E-4F). Yet there was no change in the medial FGFR1 expression levels (FIGS. 4G-4H).

Figure 5A:
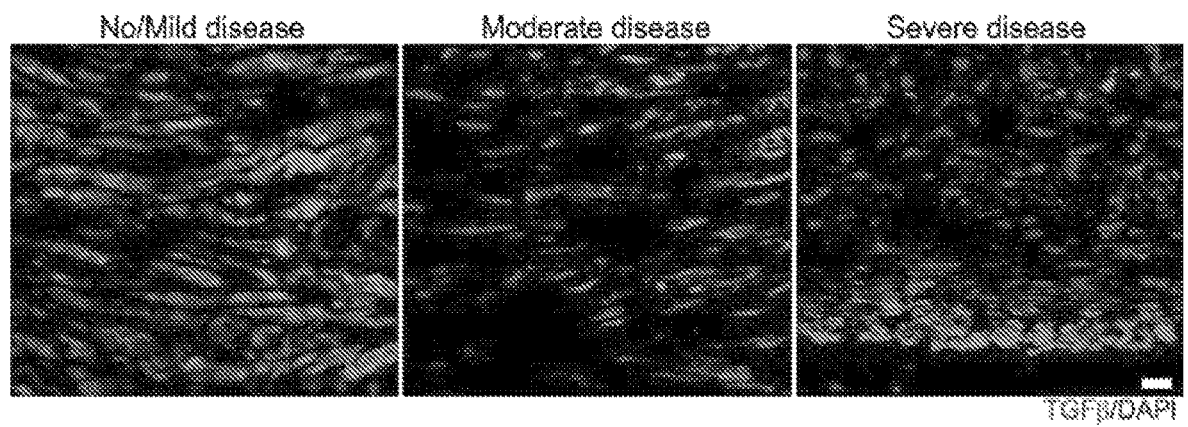
FIGS. 5A-5F are plots and images showing TGFβ signaling activity in smooth muscle cells in human left main coronary arteries with various degrees of atherosclerosis.
Figure 5B:
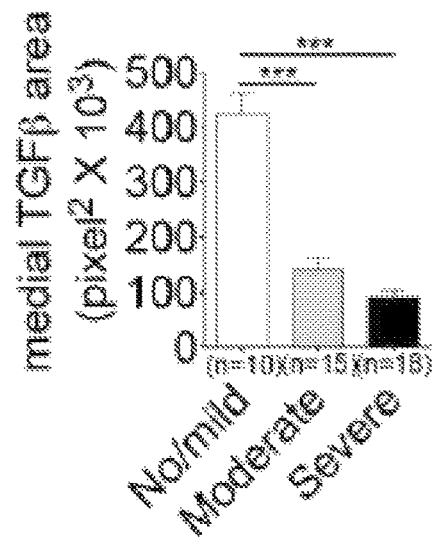
Figure 5C:
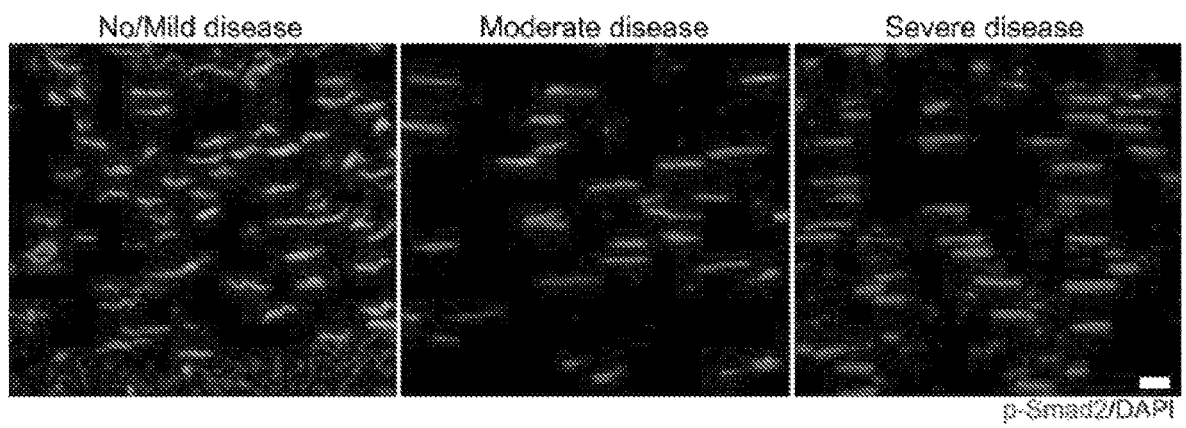
Figure 5D:
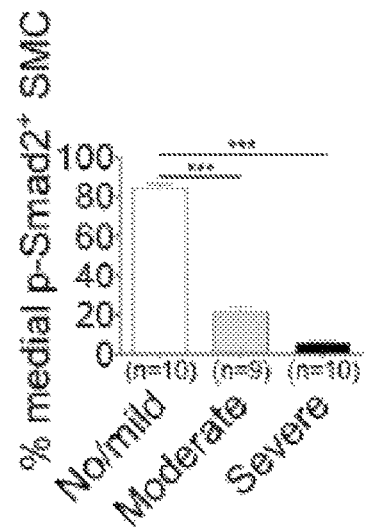
Figure 5E:
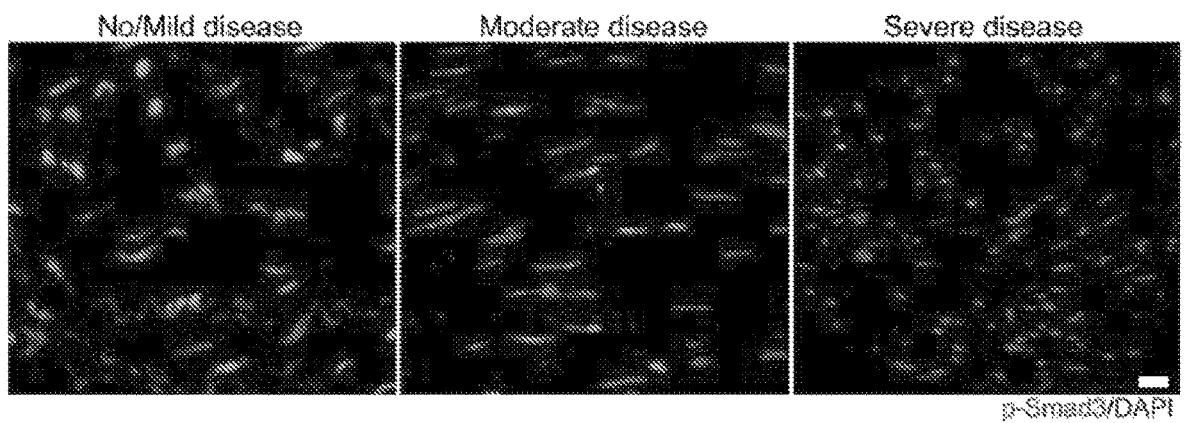
Figure 5F:
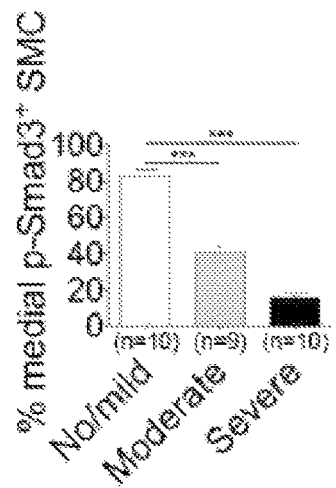

This activation of FGF signaling and the loss of smooth muscle contractile markers in advanced atherosclerotic lesions was accompanied by a decrease in TGFβ immunoreactivity in the media and the loss of p-Smad2 and p-Smad3 expression (FIGS. 5A-5F). Quantification of immunocytochemistry data from the left main coronary arteries of the entire patient cohort showed that while 84% of SMCs in patients with No/mild CAD demonstrated expression of p-Smad2 in the media of their coronary arteries, this was reduced to 21% in patients with moderate CAD and 6% in patients with severe CAD (FIG. 5D). Similarly, 83% of SMCs in patients with No/mild CAD demonstrated expression of p-Smad3 in the media of their coronary arteries, this was reduced to 41% in patients with moderate CAD and 16% in patients with severe CAD (FIG. 5F).

Figure 6A:
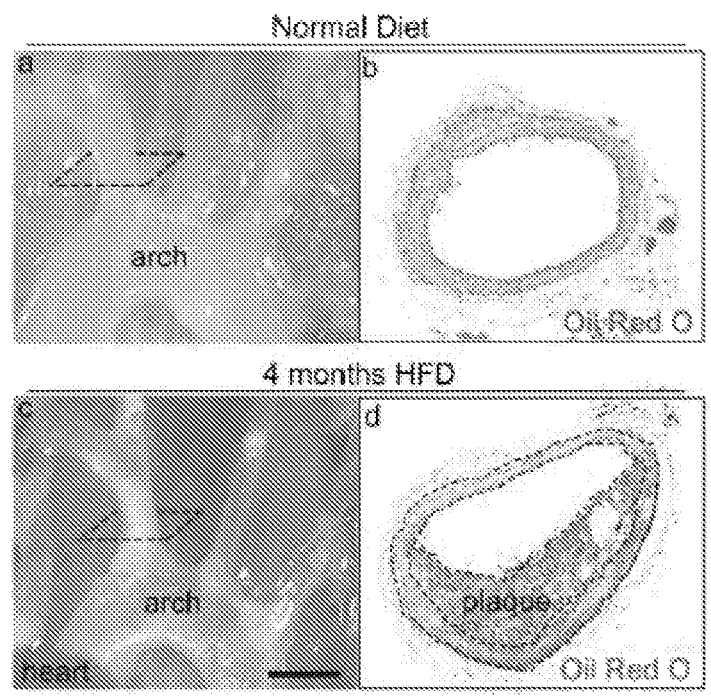
FIGS. 6A-6J are plots and images showing FGFR1 and TGFβ signaling activity in smooth muscle cells in a mouse atherosclerosis model.
Figure 6B:
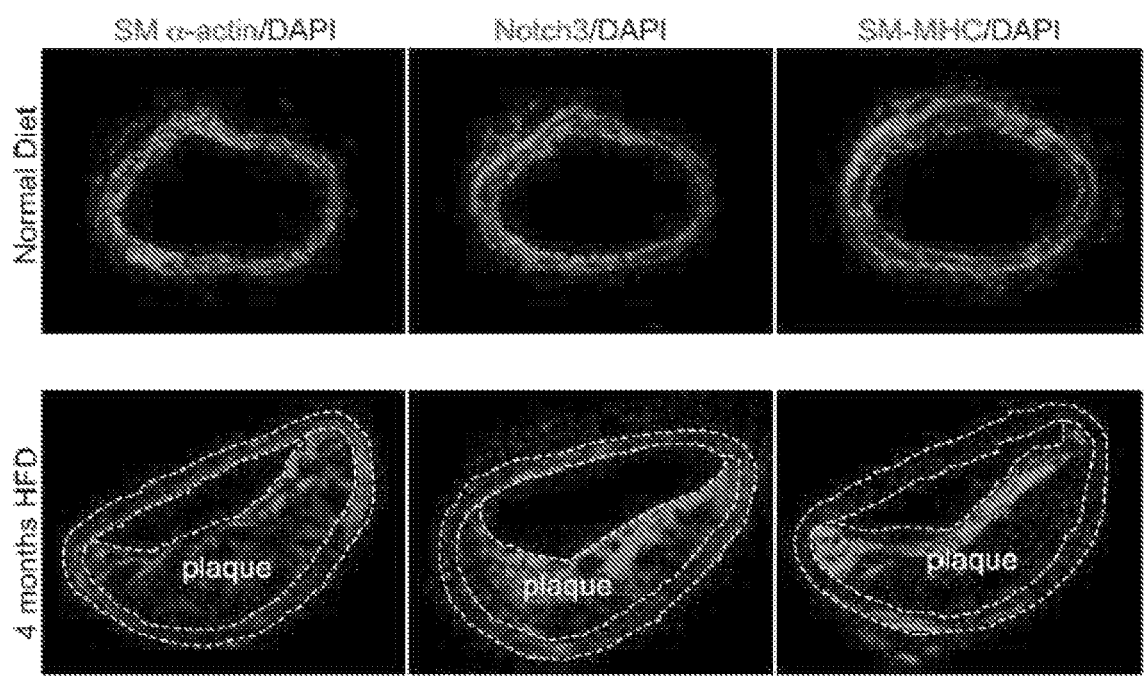
Figure 6C:
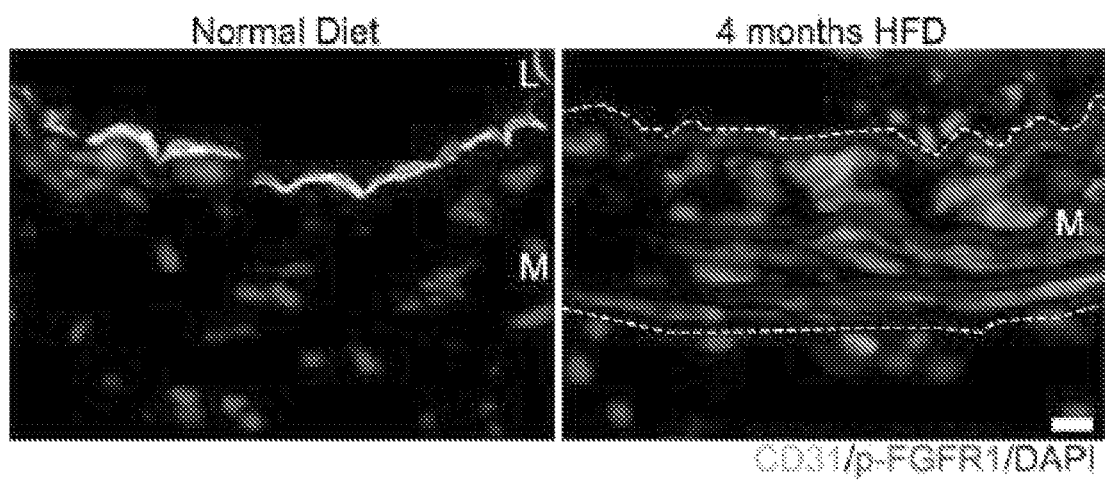
Figure 6D:
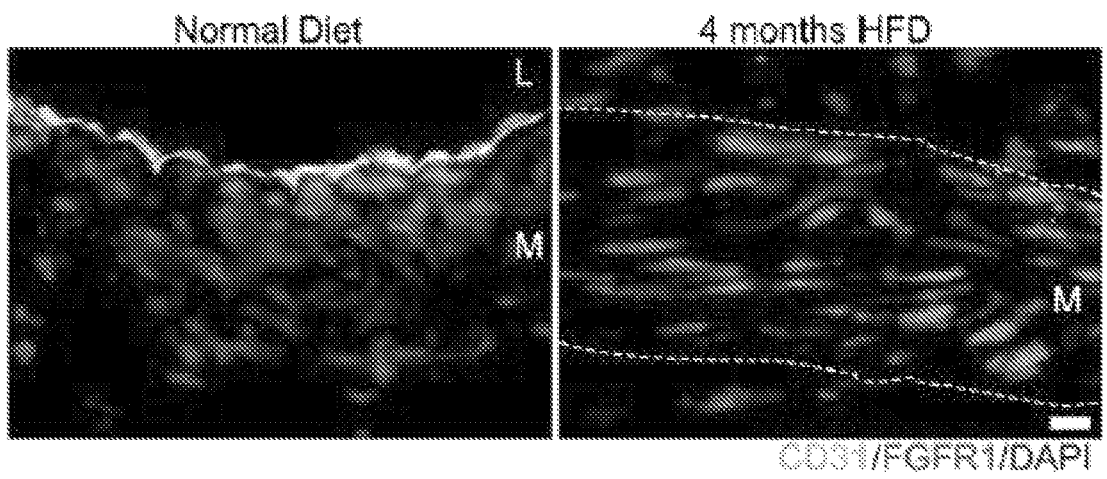
Figure 6E:
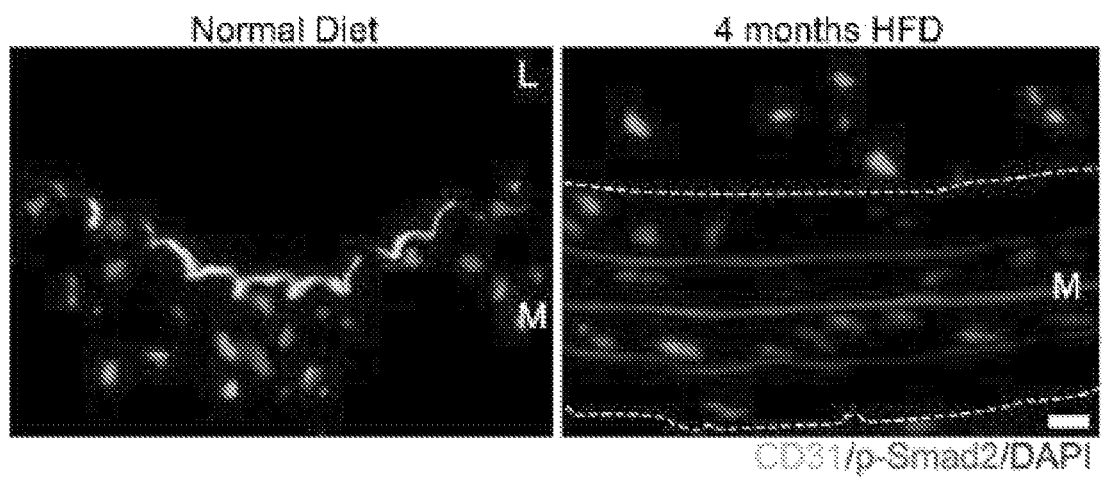
Figure 6F:
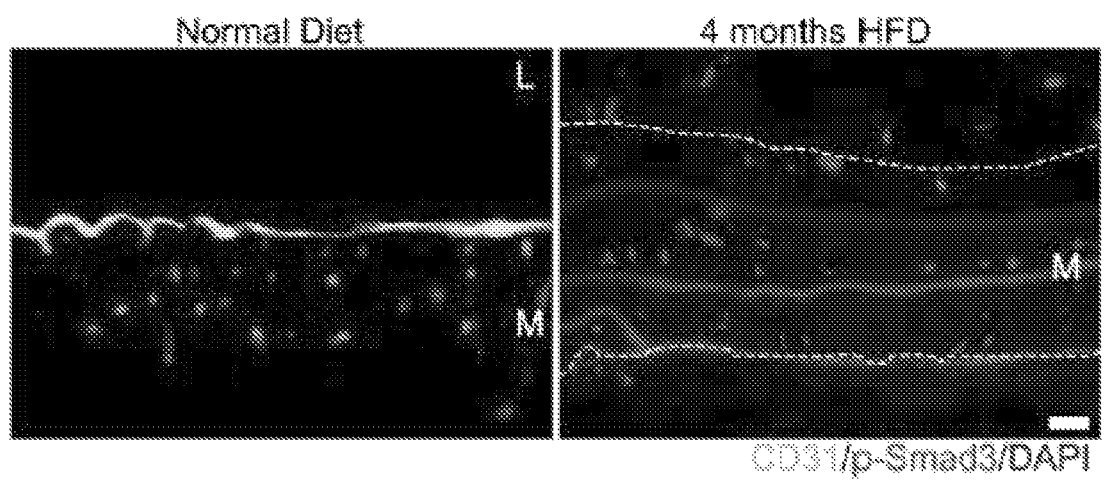
Figure 6G:
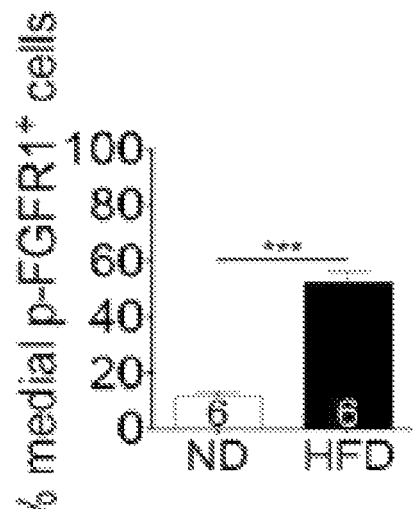
Figure 6H:
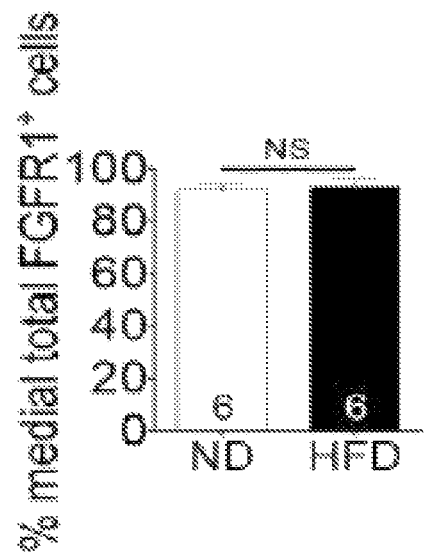
Figure 6I:
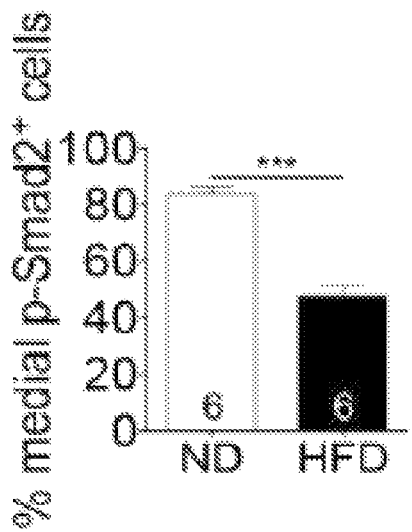
Figure 6J:
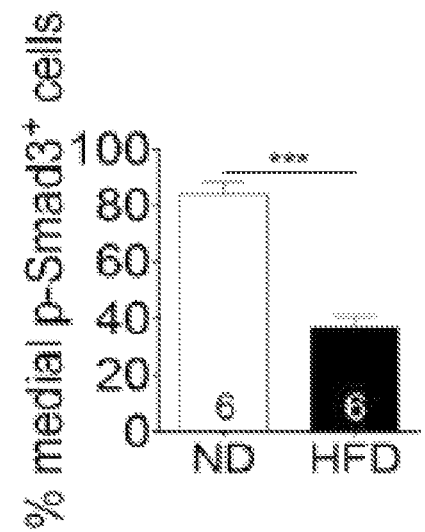

These findings were confirmed in an Apoe$^{-/-}$ mouse model of atherosclerosis. After 16 weeks of high fat diet (HFD), medial SMCs in brachiocephalic artery atherosclerotic plaque had decreased expression of contractile SMC proteins compared to medial SMC of mice on a normal chow diet (FIGS. 6A-6B). This correlated with increased p-FGFR1 expression (FIGS. 6C and 6G) while total FGFR1 levels were unchanged (FIGS. 6D and 6H) and decreased p-Smad2, p-Smad3 activity (FIGS. 6E, 6F, 6I, and 6J).

Figure 11A:
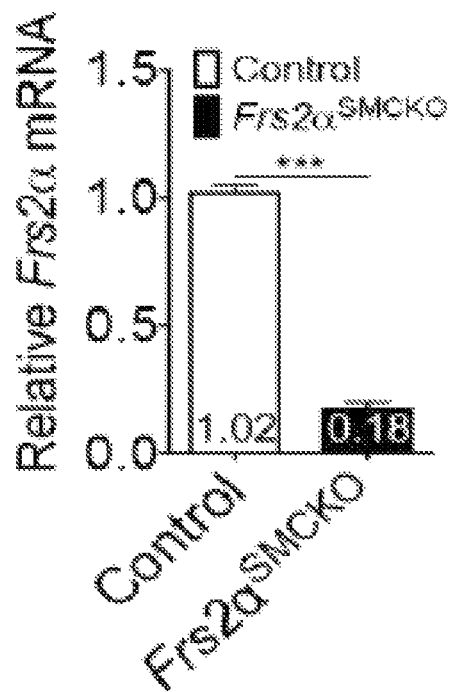
Figure 11B:
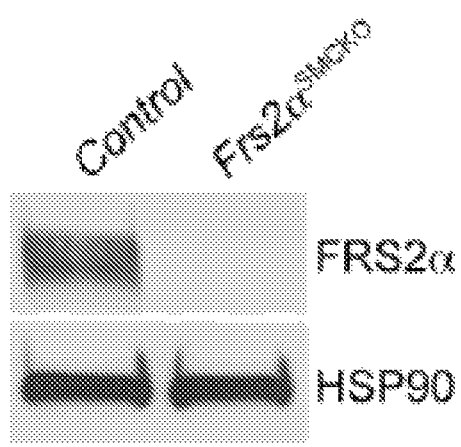
Figure 11E:
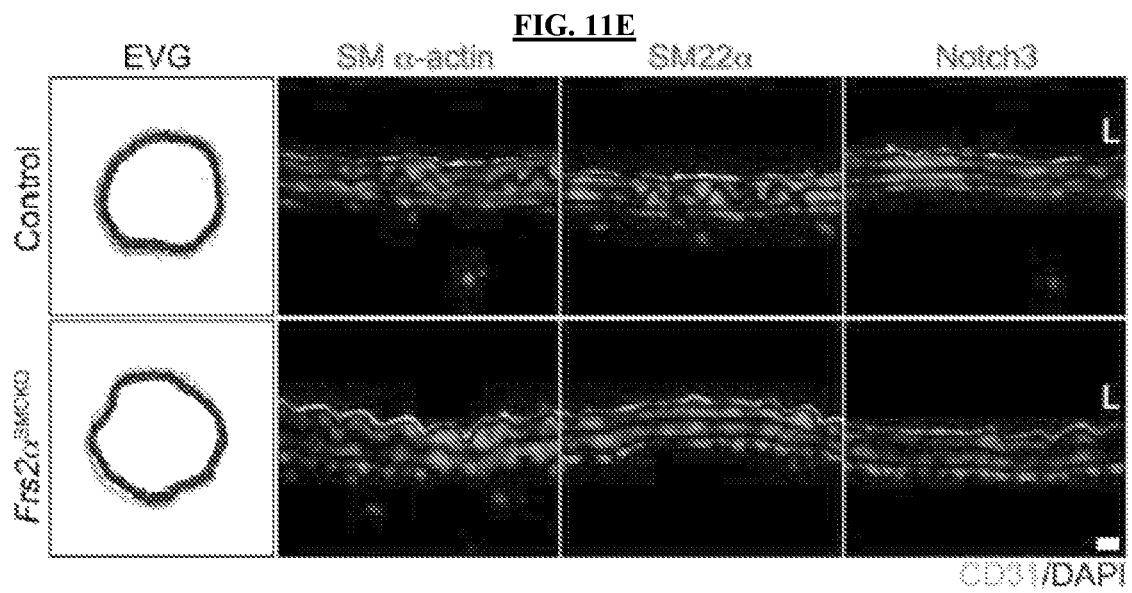
Figure 11F:
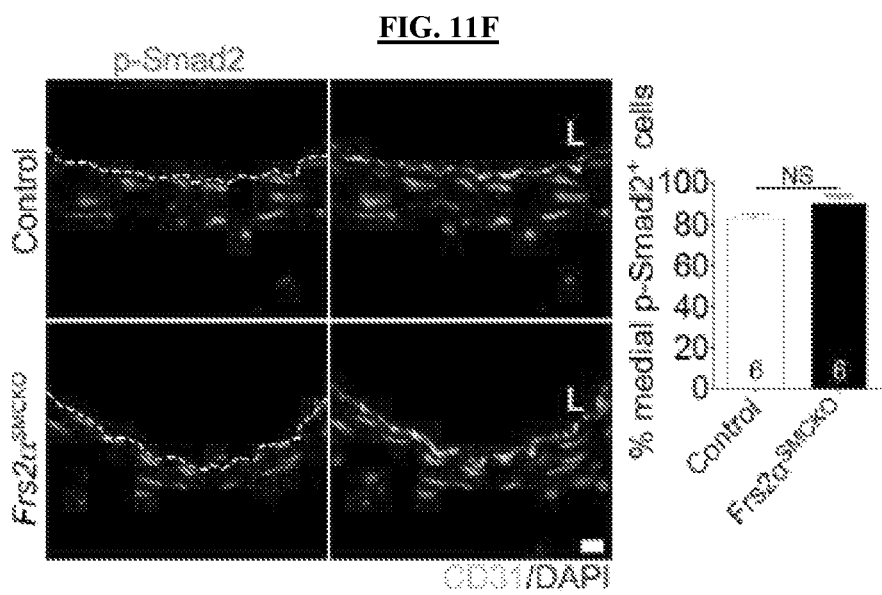
Figure 11G:
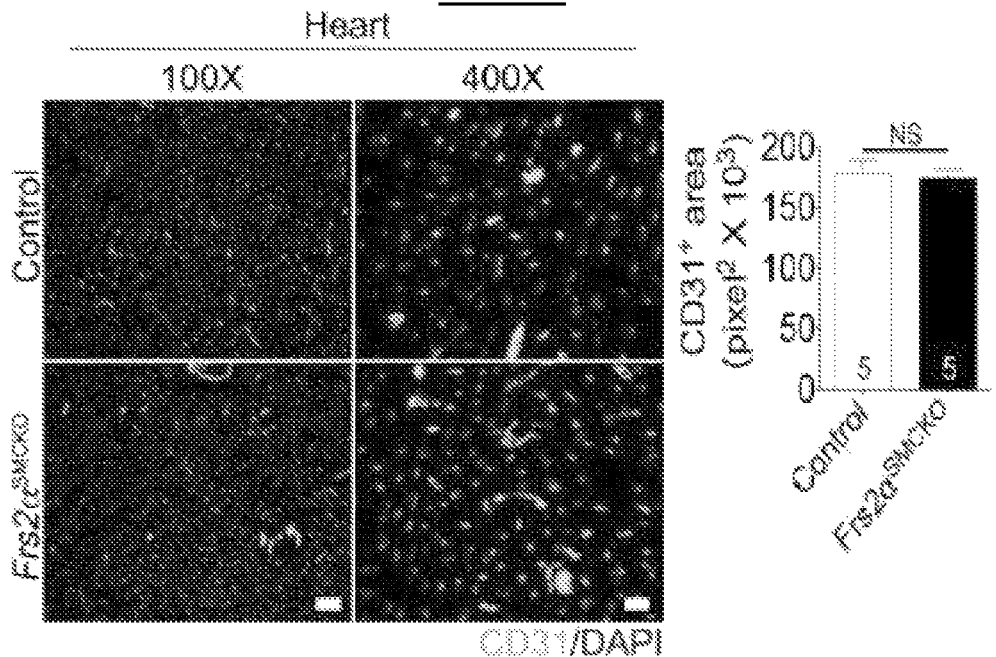
Figure 11H:
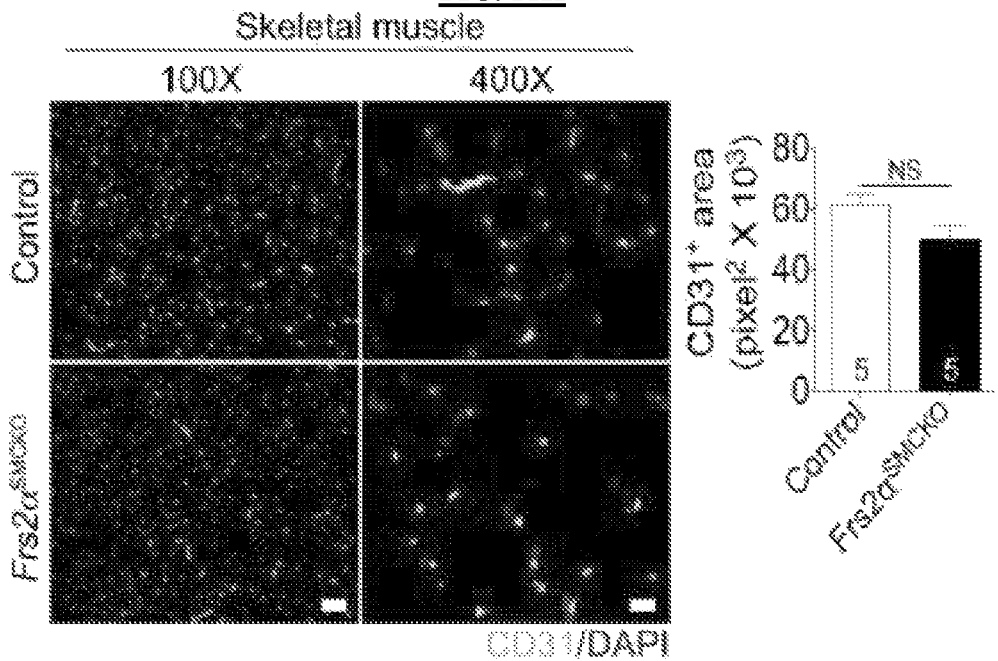
Figure 12A:
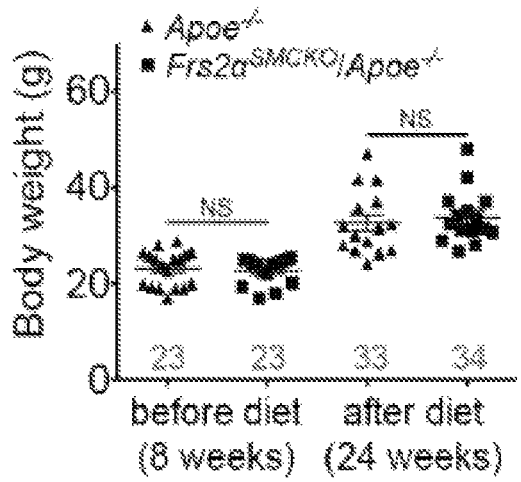
FIGS. 12A-12D are plots and images showing Frs2α$^{SMCKO}$ mice have normal body weight, lipid profiles, and heart function.
Figure 12B:
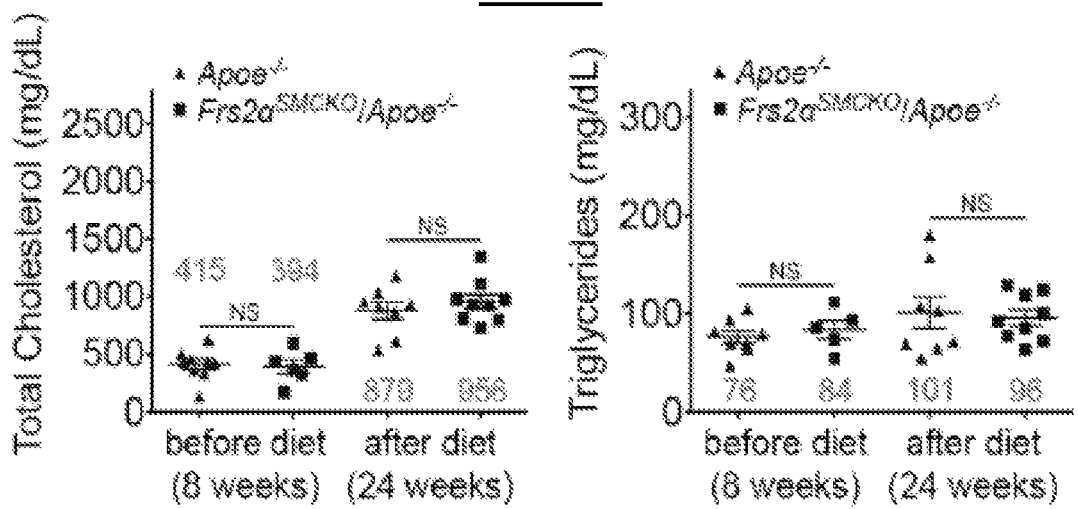
Figure 12B:
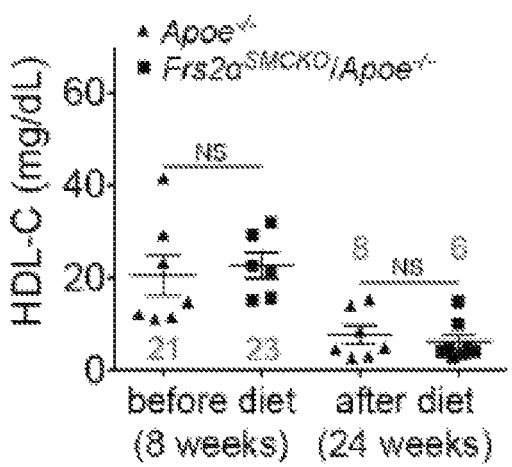
Figure 12C:
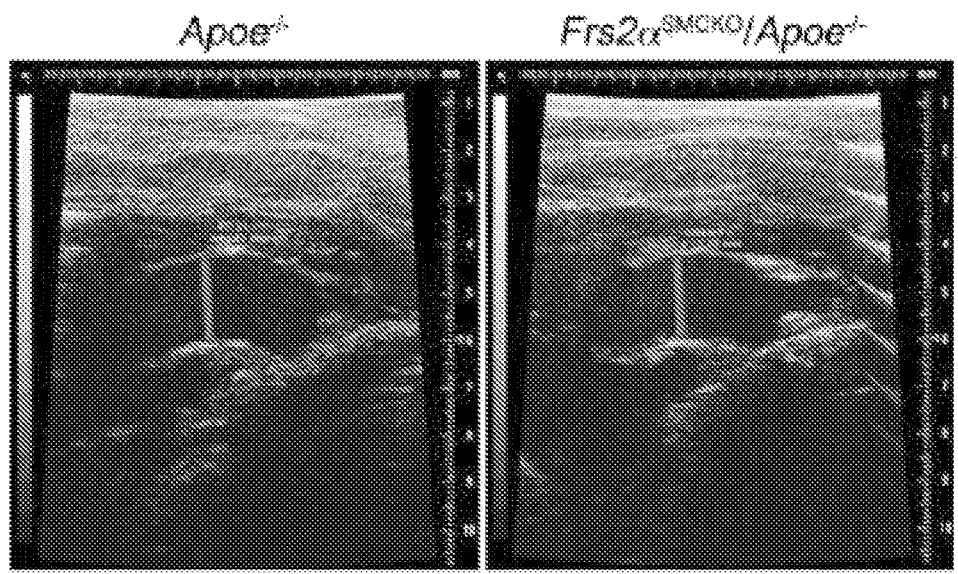
Figure 12D:
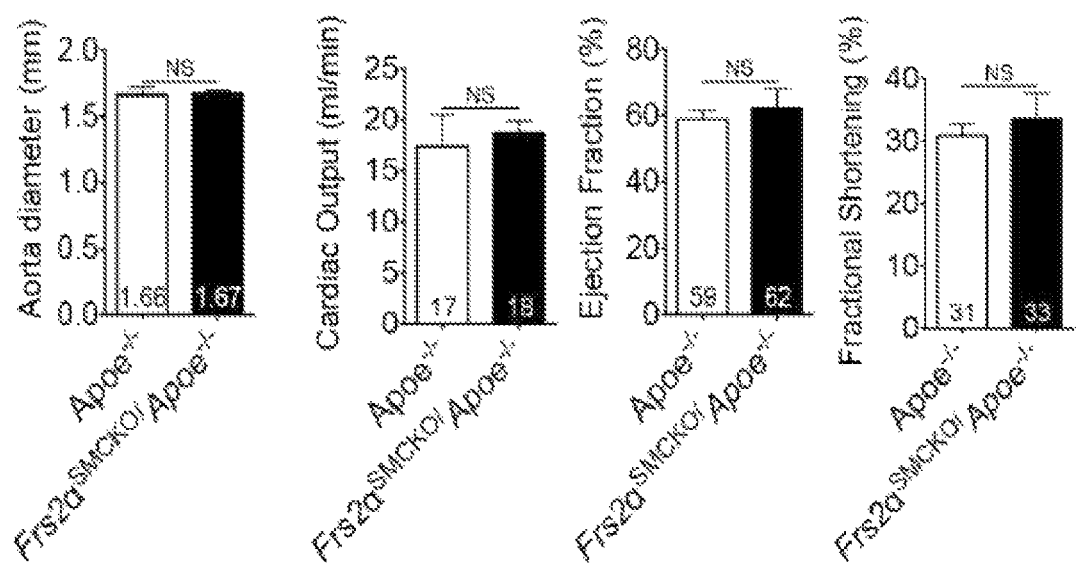

Example 4: Smooth Muscle-Specific Frs2a Deletion Reduces Atherosclerotic Lesion Growth To further study the link between the loss of SMC FGF signaling and their phenotype modulation in vivo, mice with an SMC-specific Frs2a deletion (Frs2α$^{SMCKO}$) using the SM22αCre line were generated (Holtwick et al, 2002, Proc Natl Acad Sci USA 99: 7142-7147). Frs2α$^{SMCKO}$ mice were viable and born at the expected Mendelian frequency. Assessment of FRS2α expression levels in vascular tissue revealed a robust deletion of FRS2α in the aorta (FIGS. 11A-11C). There were no differences in the gross appearance of ascending or descending aorta between control and Frs2α$^{SMCKO}$ mice (FIG. 11D) nor was there any difference in arterial wall thickness (elastic Van Gieson staining), smooth muscle contractile marker gene expression (SM α-actin, SM22α, Notch3), phosphorylated Smad2 (p-Smad2), and vascular density in the heart and skeletal muscle (FIGS. 11E-11H). Thus, the deletion of FRS2α per se did not alter the baseline structure of the normal vasculature.

To study the role of FGF signaling in the modulation of SMC phenotype during atherogenesis, Frs2α$^{SMCKO}$ mice were crossed onto the atherosclerosis-prone Apoe$^{-/-}$ background (Frs2α$^{SMCKO}$ Apoe$^{-/-}$). Male Frs2α$^{SMCKO}$ Apoe$^{-/-}$ and Apoe$^{-/-}$ littermates were placed on cholesterol-rich Western diet for eight or sixteen weeks at which point whole-mount Oil Red O staining was used to visualize the extent of aortic atherosclerotic plaques. There were no differences between these two groups with regard to body weight, total cholesterol, triglyceride, HDL-C levels, aorta diameter, or heart function (FIG. 12).

Figure 7A:
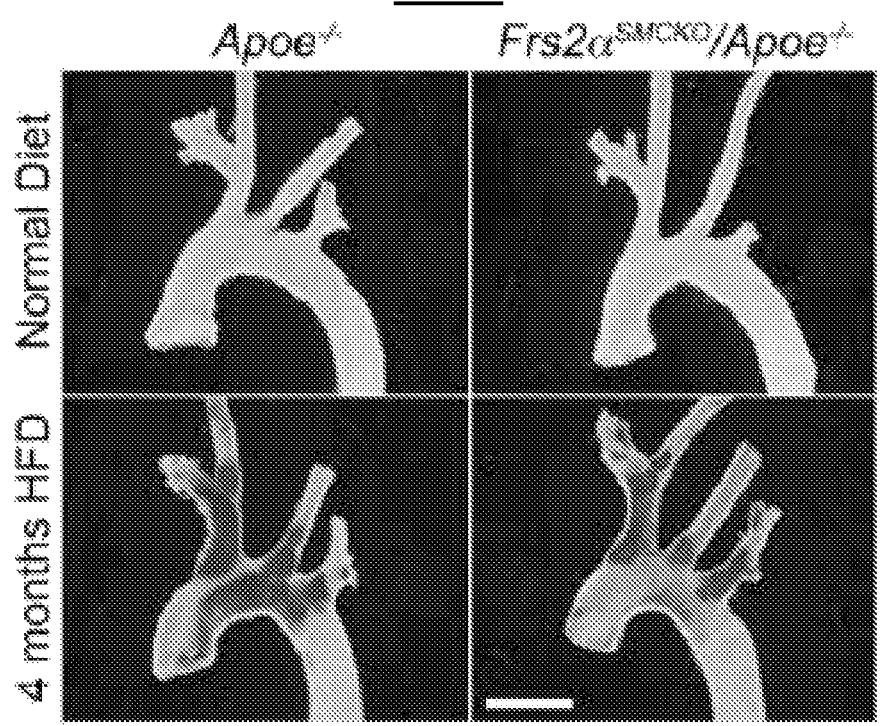
FIGS. 7A-7H are plots and images showing smooth muscle cell FRS2α knockout inhibits atherosclerosis plaque development after 16 weeks of high fat diet.
Figure 7B:
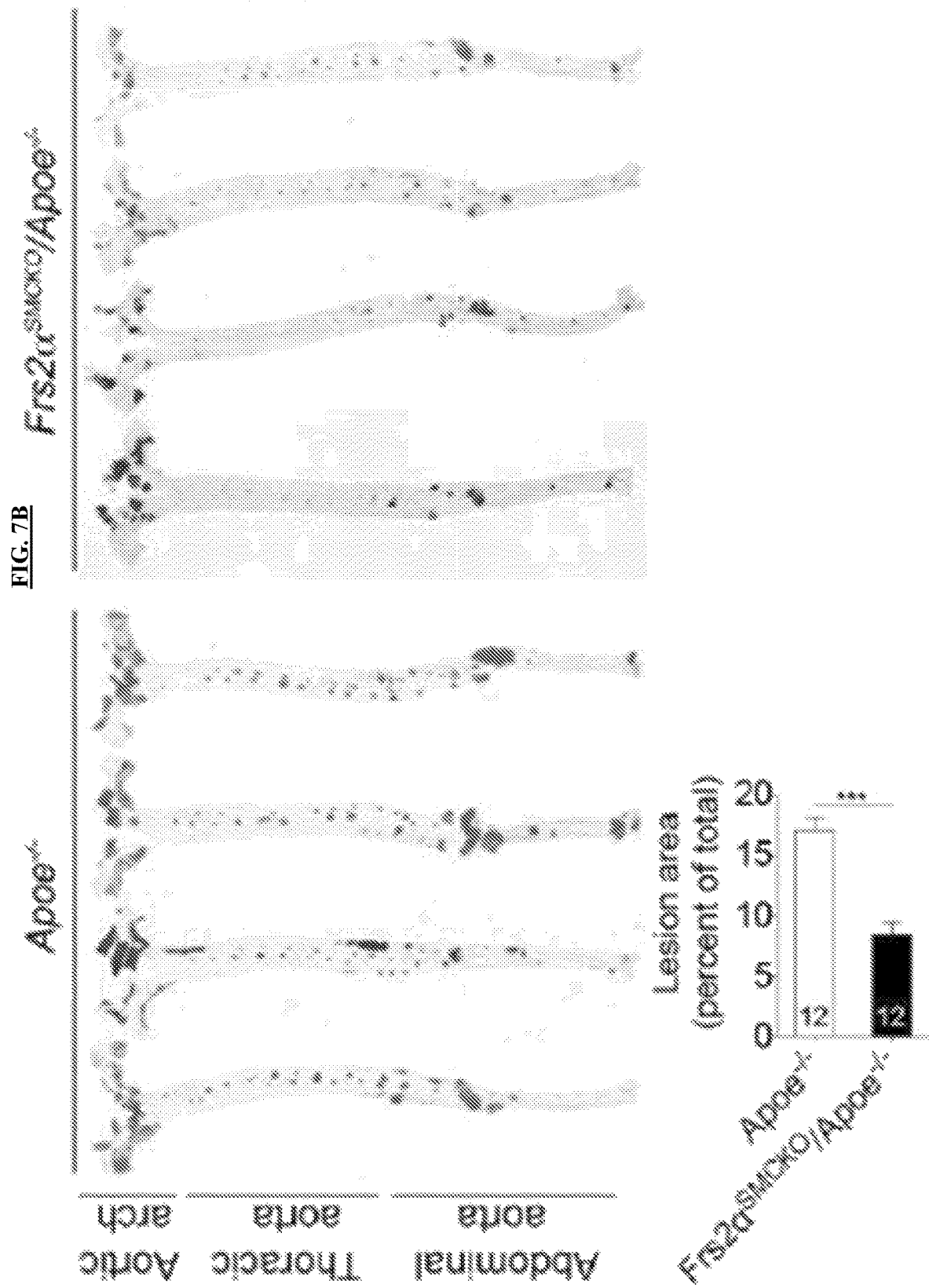
Figure 7C:
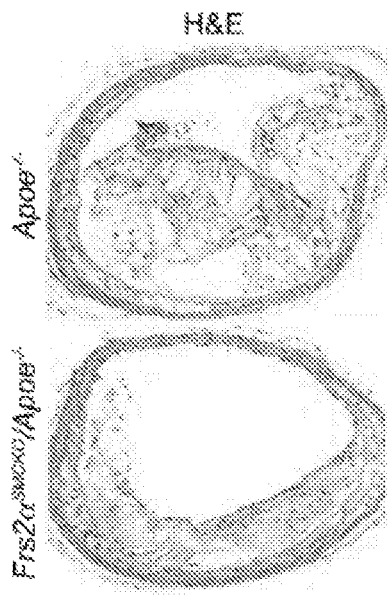
Figure 7D:
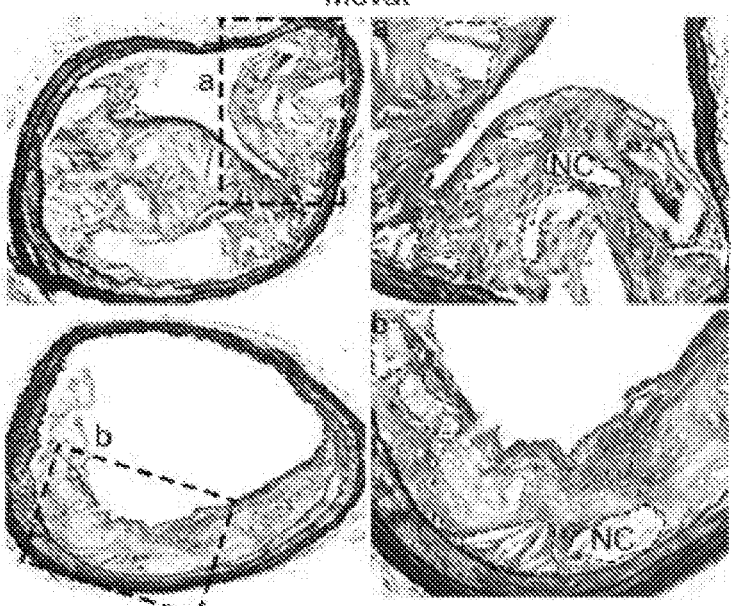
Figure 7E:
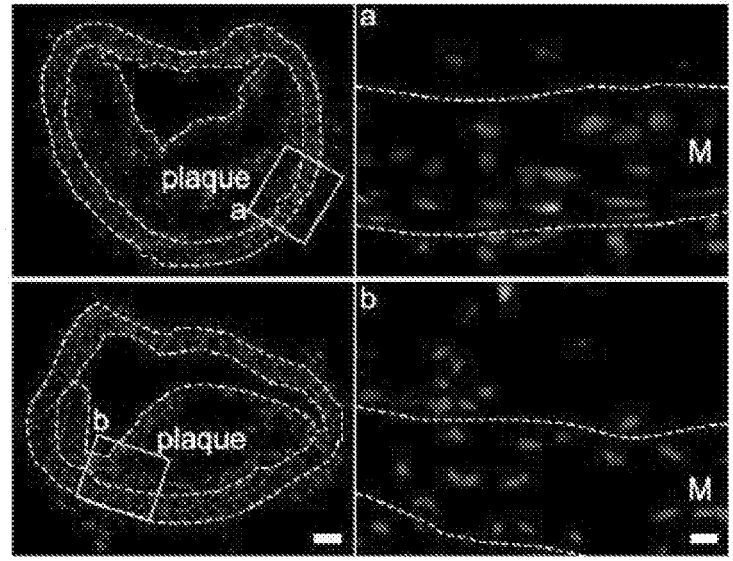
Figure 7F:
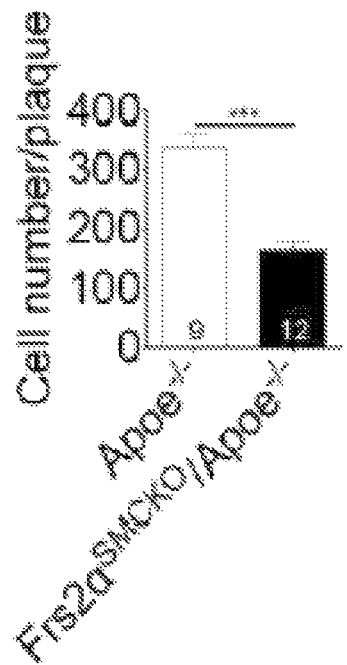
Figure 7G:
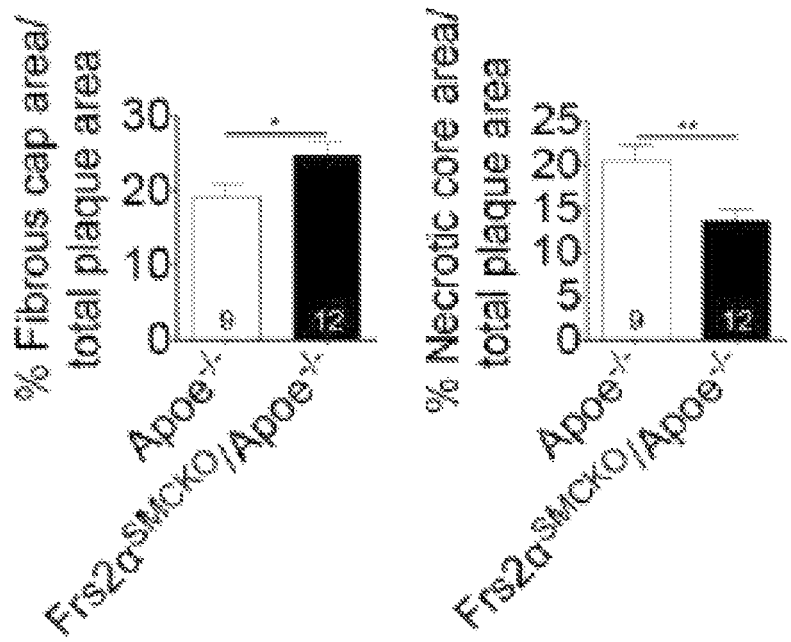
Figure 7H:
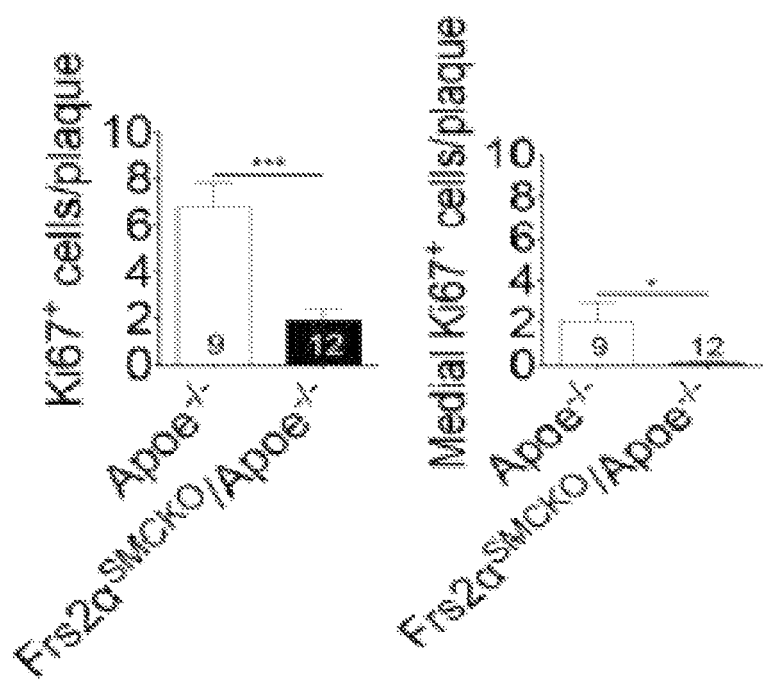
Figure 13A:
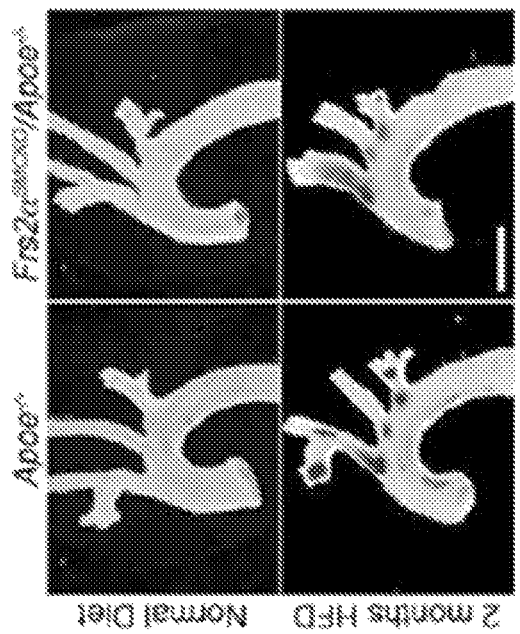
FIGS. 13A-13D are plots and images showing that smooth muscle cell FRS2α knockout inhibits atherosclerosis plaque development.
Figure 13B:
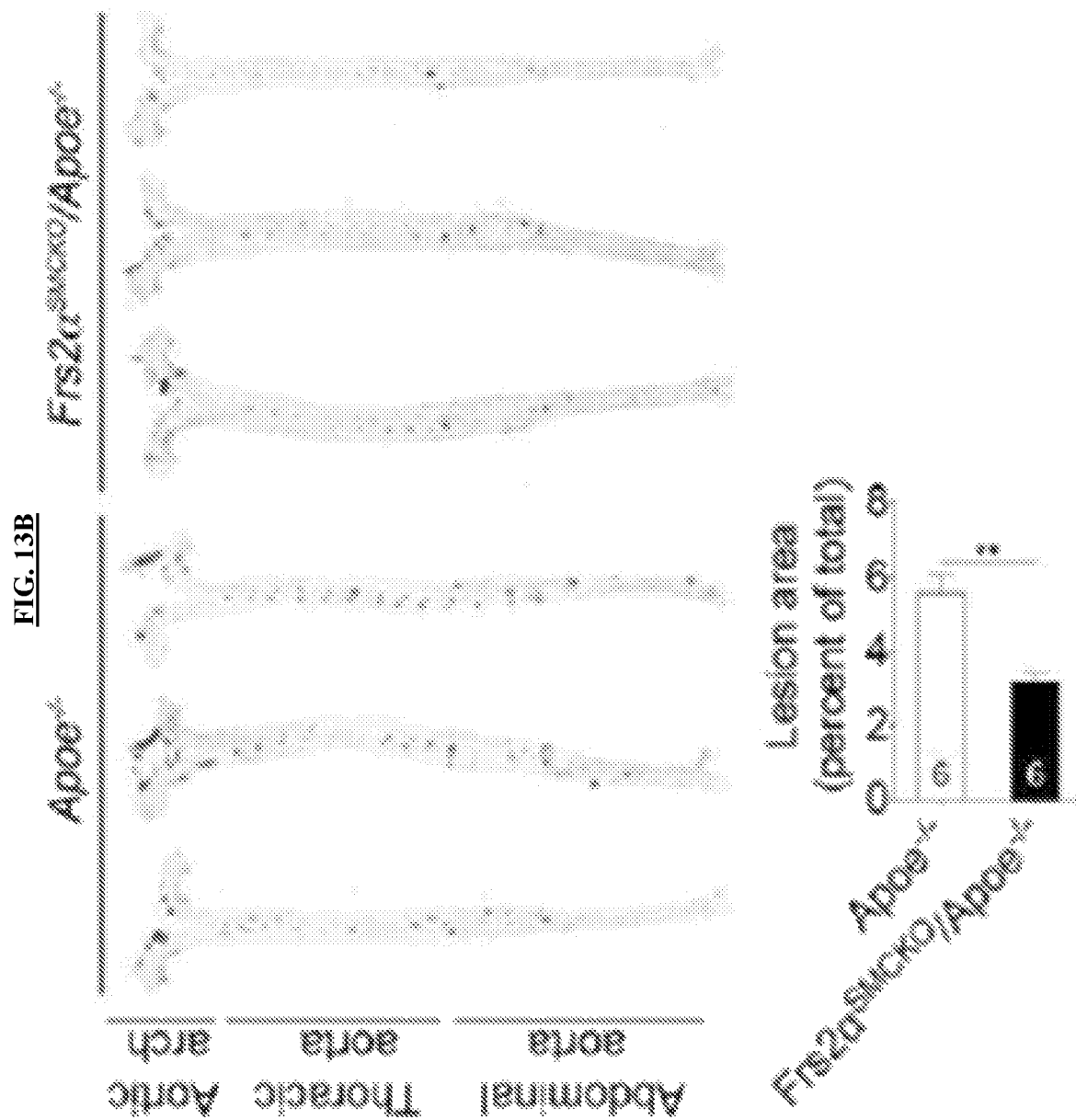
Figure 13D:
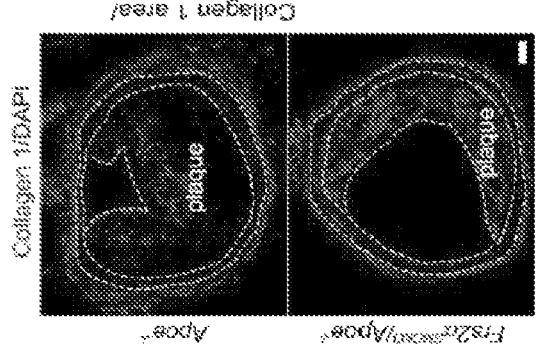
Figure 13C:
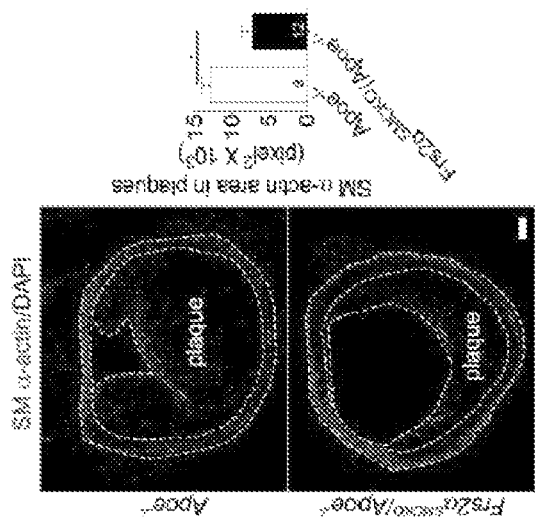

Aortas from Frs2α$^{SMCKO}$ Apoe$^{-/-}$ and Apoe$^{-/-}$ mice were examined after eight (FIGS. 13A-13B) or sixteen (FIGS. 7A-7B) weeks of high fat diet. In both cases, Frs2α$^{SMCKO}$ Apoe$^{-/-}$ animals demonstrated much lower extent of the total aorta atherosclerotic plaque burden. Notably, the progression of atherosclerosis was markedly reduced in Frs2α$^{SMCKO}$/Apoe$^{-/-}$ mice compared to Apoe$^{-/-}$ controls: by eight weeks there was a 43% decrease in the total aorta plaque size (5.57% in Apoe$^{-/-}$ vs. 3.16% in Frs2α$^{SMCKO}$/Apoe$^{-/-}$) (FIG. 13B) and by sixteen weeks 54% decrease (17.24% in Apoe$^{-/-}$ vs. 7.86% in Frs2α$^{SMCKO}$/Apoe$^{-/-}$) (FIG. 7B). Histochemical analysis of plaques showed a ~50% reduction in plaque cellularity (335 cells/plaque in Apoe$^{-/-}$ vs. 164 cells/plaque in Frs2α$^{SMCKO}$ Apoe$^{-/-}$) (FIGS. 7C and 7F). Furthermore, Movat staining demonstrated that fibrous caps were thicker and necrotic core were smaller in Frs2α$^{SMCKO}$ Apoe$^{-/-}$ compared to Apoe$^{-/-}$ mice (FIGS. 7D and 7G). Finally, Ki67 staining demonstrated reduced proliferation rate in plaque as well as media cells (FIGS. 7E and 7H). All of these findings are consistent with a more stable plaque phenotype. Consistent with these changes in plaque cellularity and fibrous cap size, there was a decrease in the plaque SM α-actin area (12.82 in Apoe$^{-/-}$ vs. 7.28 in Frs2α$^{SMCKO}$ Apoe$^{-/-}$) and increased collagen deposition (0.83 in Apoe$^{-/-}$ vs. 1.56 in Frs2α$^{SMCKO}$/Apoe$^{-/-}$) (FIGS. 13C-13D).

Example 5: Suppression of Endothelial Cell TGFβ Signaling in an Atheroslecrosis Mouse Model Reduced Formation of Artherosclerotic Lesion It was previously shown that FGF regulated TGFβ signaling via let-7 miRNA (Chen et al., 2012, Cell Reports 2: 1684-1696). Further, it was demonstrated that endothelial to mesenchymal transition drives atherosclerosis (Chen et al., 2015, Journal of clinical investigation 125: 4529-4543). In this study, blocking endothelial cell TGFβ signaling was examined to determine whether or not this would reduce atherosclerotic lesions.

Figure 14A:
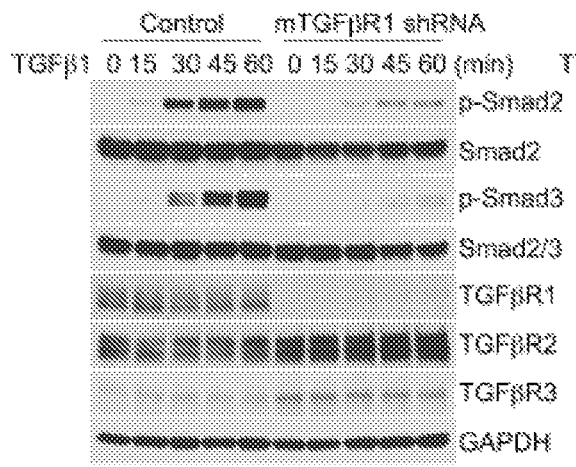
FIGS. 14A-14C are immunoblots showing TGFβ signaling in TGFβR1, TGFβR2, and TGFβR1/2 knockdown backgrounds. Each of FIGS. 14A-14C shows levels of TGFβR1, TGFβR2, and TGFβR3, and levels of p-Smad2 (phosphorylated Smad2), Smad-2, p-Smad3 (phosphorylated Smad3), and Smad 2/3 in a TGFβR1, TGFβR2, and TGFβR1/2 knockdown background, respectively.
Figure 14B:
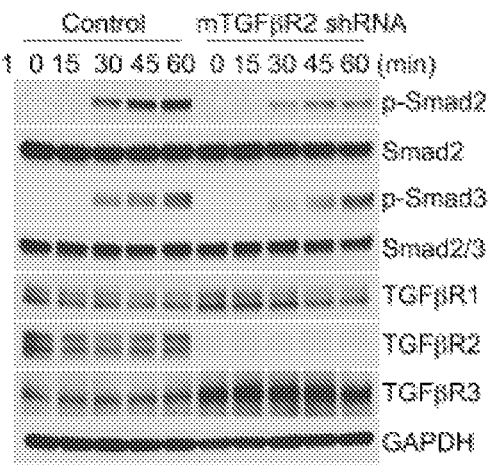
Figure 14C:
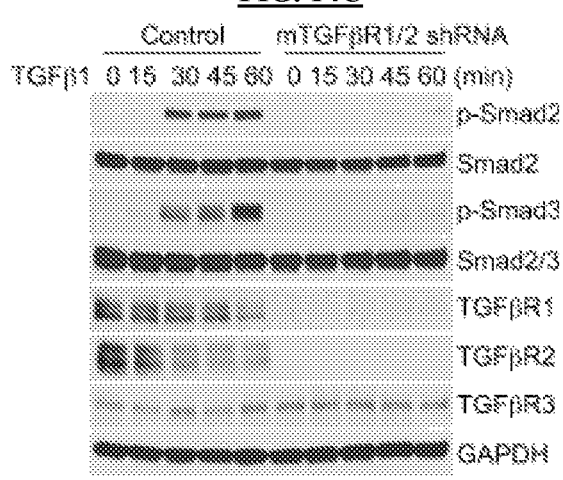
Figure 15A:
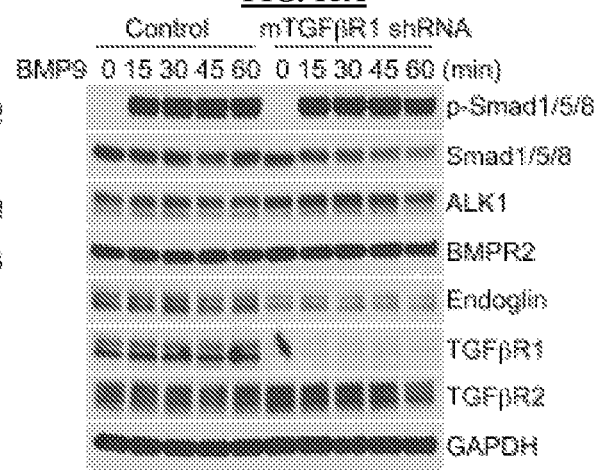
FIGS. 15A-15C are immunoblots showing BMP signaling in TGFβR1, TGFβR2, and TGFβR1/2 knockdown backgrounds. Each of FIGS. 15A-15C shows levels of p-Smad1/5/8 (phosphorylated Smad1/5/8), Smad-5, activin receptor-like kinase 1 (ALK1), bone morphogenetic protein receptor (BMPR2), endoglin, TGFβR1, and TGFβR2 in a TGFβR1, TGFβR2, and TGFβR1/2 knockdown background, respectively.
Figure 15B:
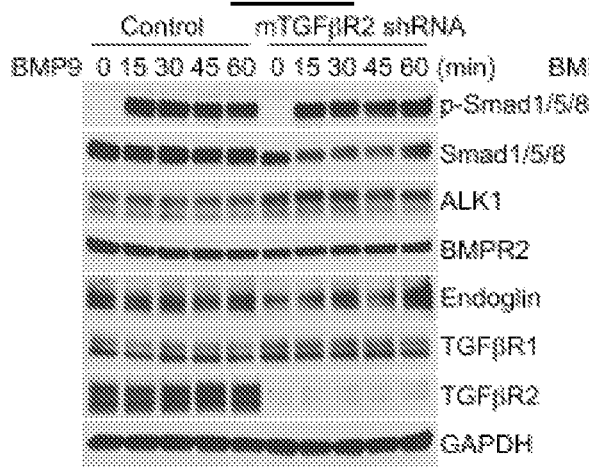
Figure 15C:
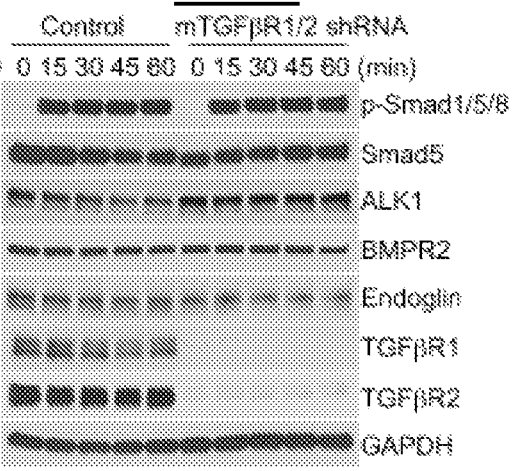
Figure 16B:
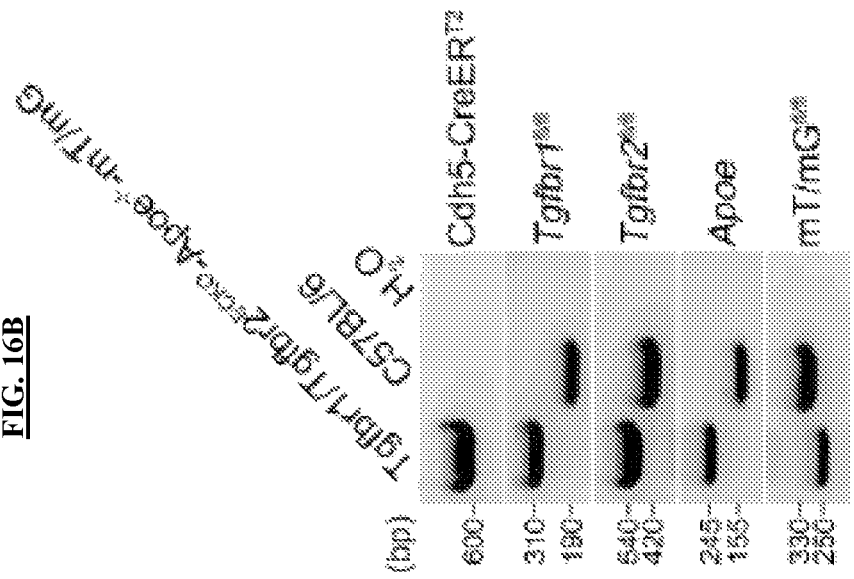
FIGS. 16A-16D are schematics and blots depicting the generation and characterization of Apoe$^{-/-}$ mice with endothelial-specific Tg/br1 and Tgfbr2 ablation.
Figure 16A:
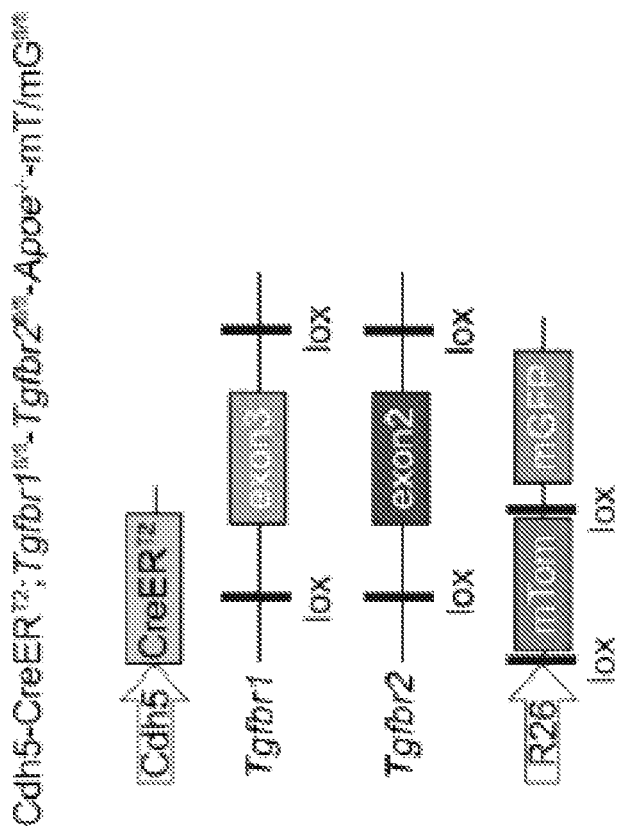
Figure 16C:
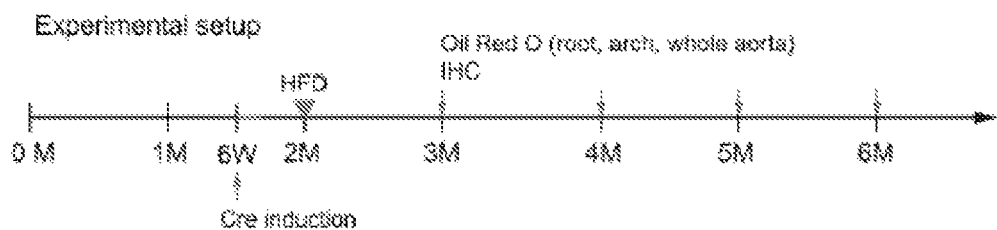
Figure 16D:
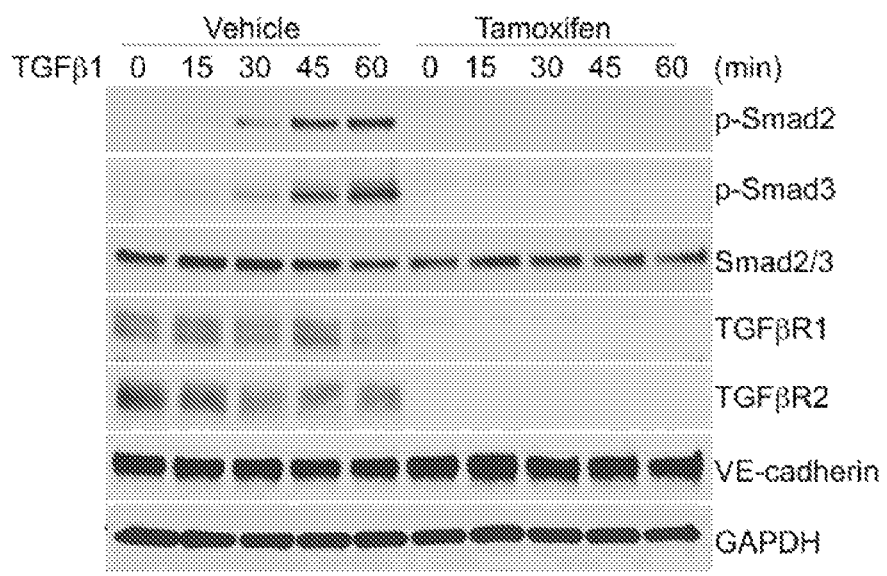
Figure 16D:
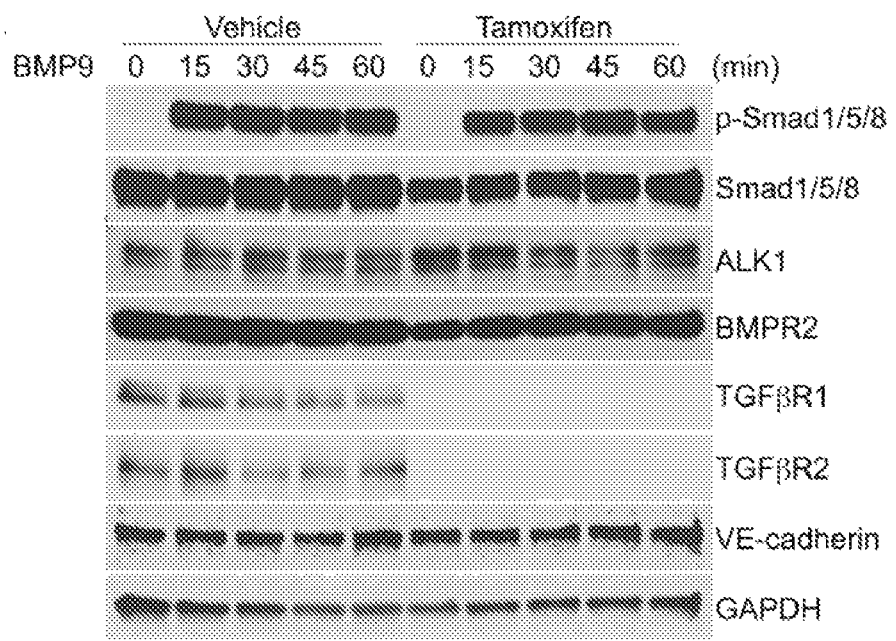

Knockdown of TGFβR1 and/or TGFβR2 suppressed TGFβ signaling activity, but not BMP signaling (FIGS. 14A-14C; FIGS. 15A-15C). Thus, to block TGFβ signaling in endothelial cells, mice with an inducible endothelial specific knockout of TGFβ receptors 1 and 2 (TGFβR1 and TGFβR2) were generated and crossed on the Apoe$^{-/-}$ background to induce atherosclerosis susceptibility. A mTmG strain was also generated to fate-map endothelial cells (FIGS. 16A-16B). Both TGFβ receptors were deleted as a knockdown of either TGFβR1 or TGFβR2 did not fully abolish TGFβ-driven Smad2 and Smad3 phosphorylation (FIG. 14A-14C). The resultant mutant mice (Cdh5CreER$^{T2}$; Tgfbr1$^{fl/fl}$; Tgfbr2$^{fl/fl}$; Apoe$^{-/-}$; mT/mG$^{fl/fl}$), hereby referred to as Tgfrbr$^{iECKO}$/Apoe$^{-/-}$, with littermate controls (absent Cdh5CreER$^{T2}$, mice without Tgfbr1 or Tgfbr2 loci and non-induced mice) were used for subsequent experiments. Testing of primary endothelial cells (tagged with eGFP) isolated from the Tgfrbr1$^{iECKO}$/Apoe$^{-/-}$ mice showed that activation of the Cdh5CreER$^{T2}$ gene at six weeks of age led to a complete deletion of both targeted Tgfbr genes (FIGS. 16C-16D). This fully blocked TGFβ signaling while preserving BMP signaling (FIG. 16D).

Figure 17A:
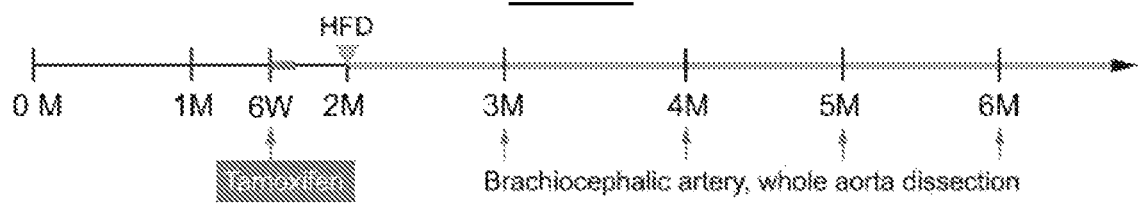
FIGS. 17A-17D are series of graphs demonstrating that endothelial cell Tgfbr1/Tgfbr2 knockout have no effect on body weight and serum lipid profile.
Figure 17B:
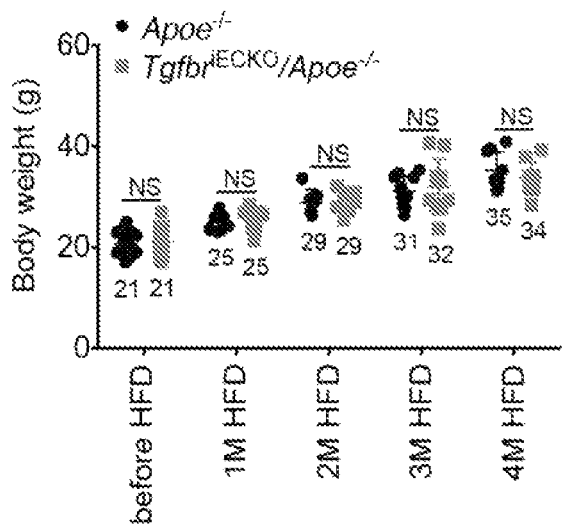
Figure 17C:
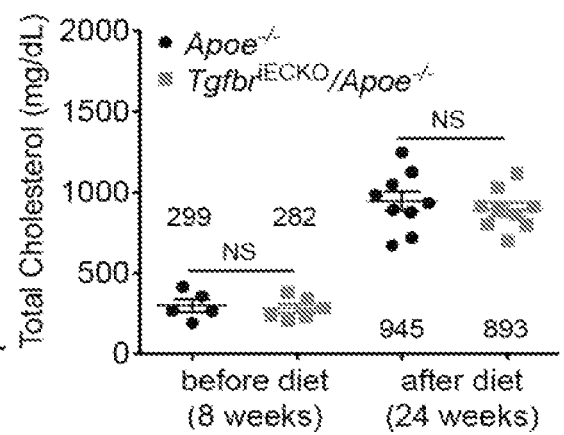
Figure 17D:
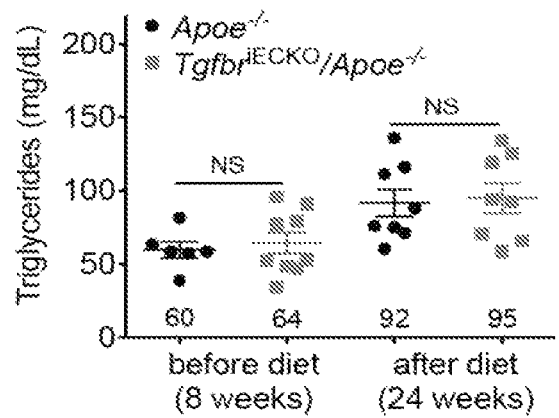
Figure 18:
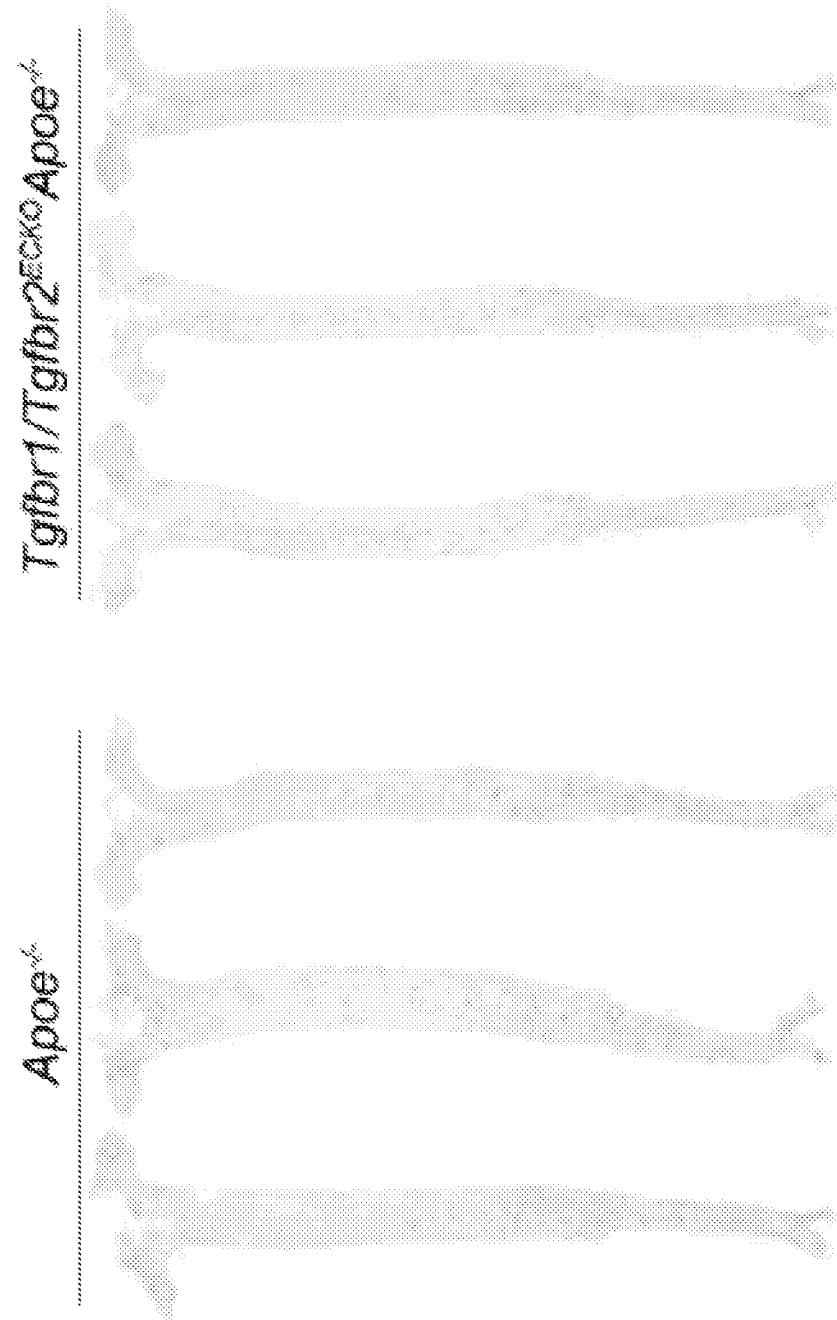
FIG. 18 is an image showing no plaque development in mice fed with a normal diet at 8 weeks old.
Figure 19:
FIG. 19 is an image showing 61% plaque reduction in Tgfbr$^{iECKO}$/Apoe$^{-/-}$ mice after 1 month on a high fat diet (HFD).
Figure 20:
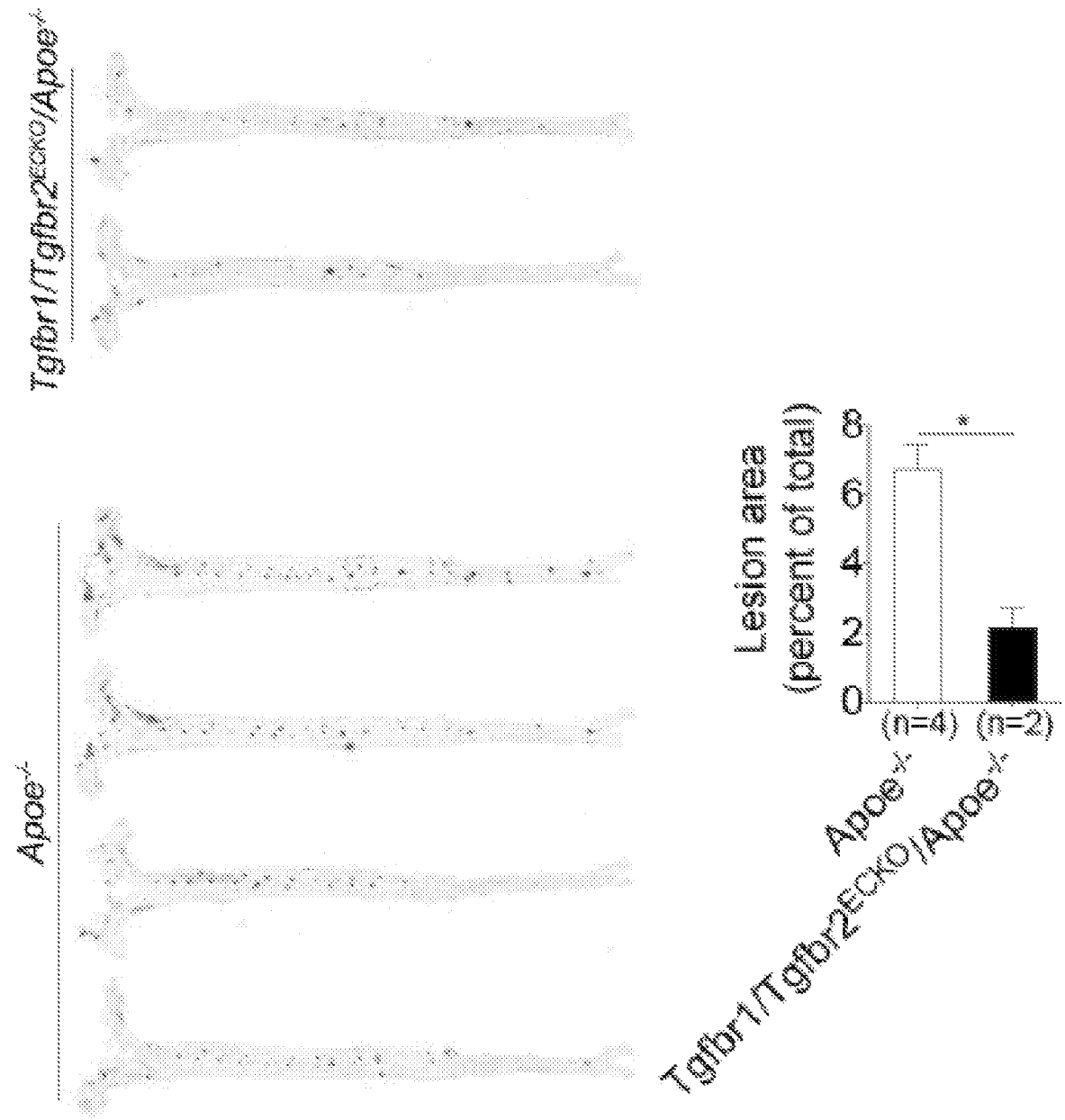
FIG. 20 is set of images and a plot showing 72% plaque reduction in Tgfbr$^{iECKO}$/Apoe$^{-/-}$ mice after 2 months on a high fat diet (HFD).
Figure 21:
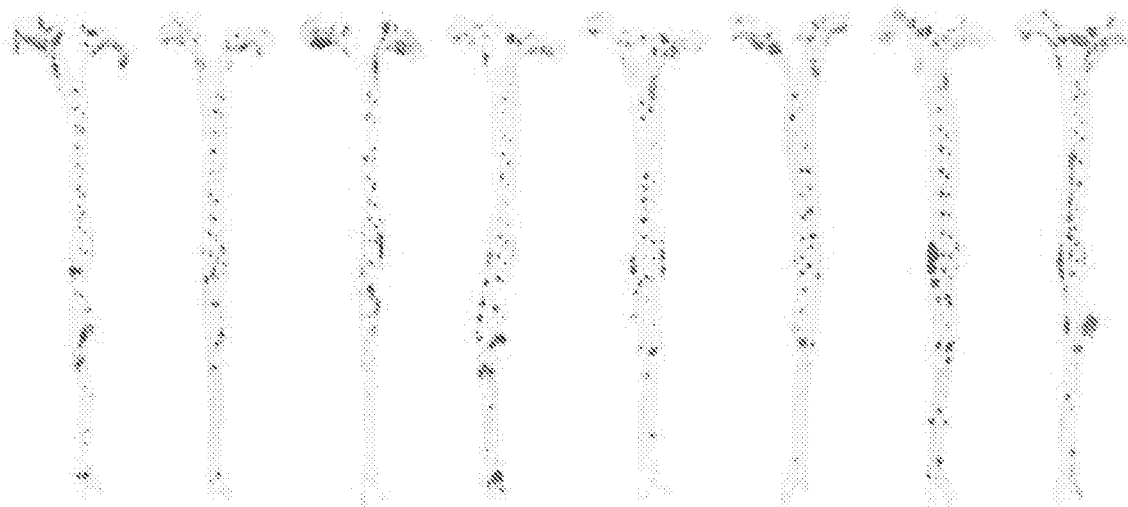
FIG. 21 is a set of images and a plot showing 52% plaque reduction in Tgfbr$^{iECKO}$/Apoe$^{-/-}$ mice after 3 months on a high fat diet (HFD).
Figure 21:
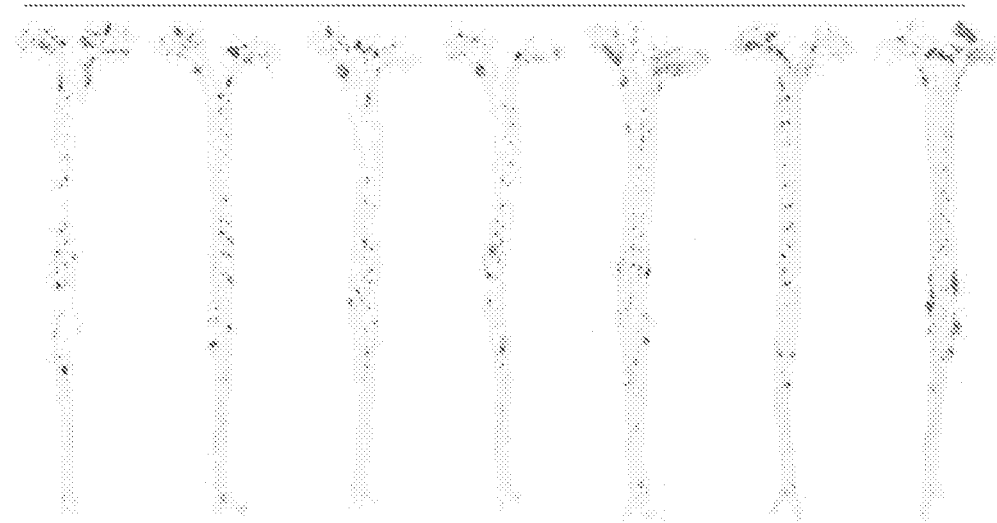
Figure 21:
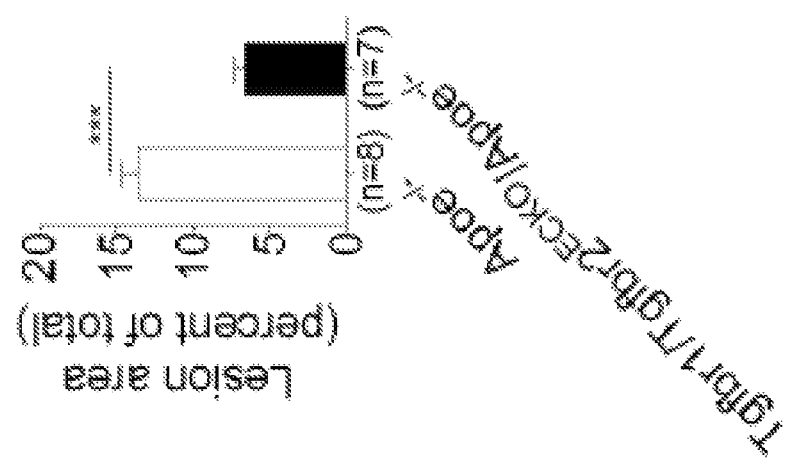
Figure 22A:
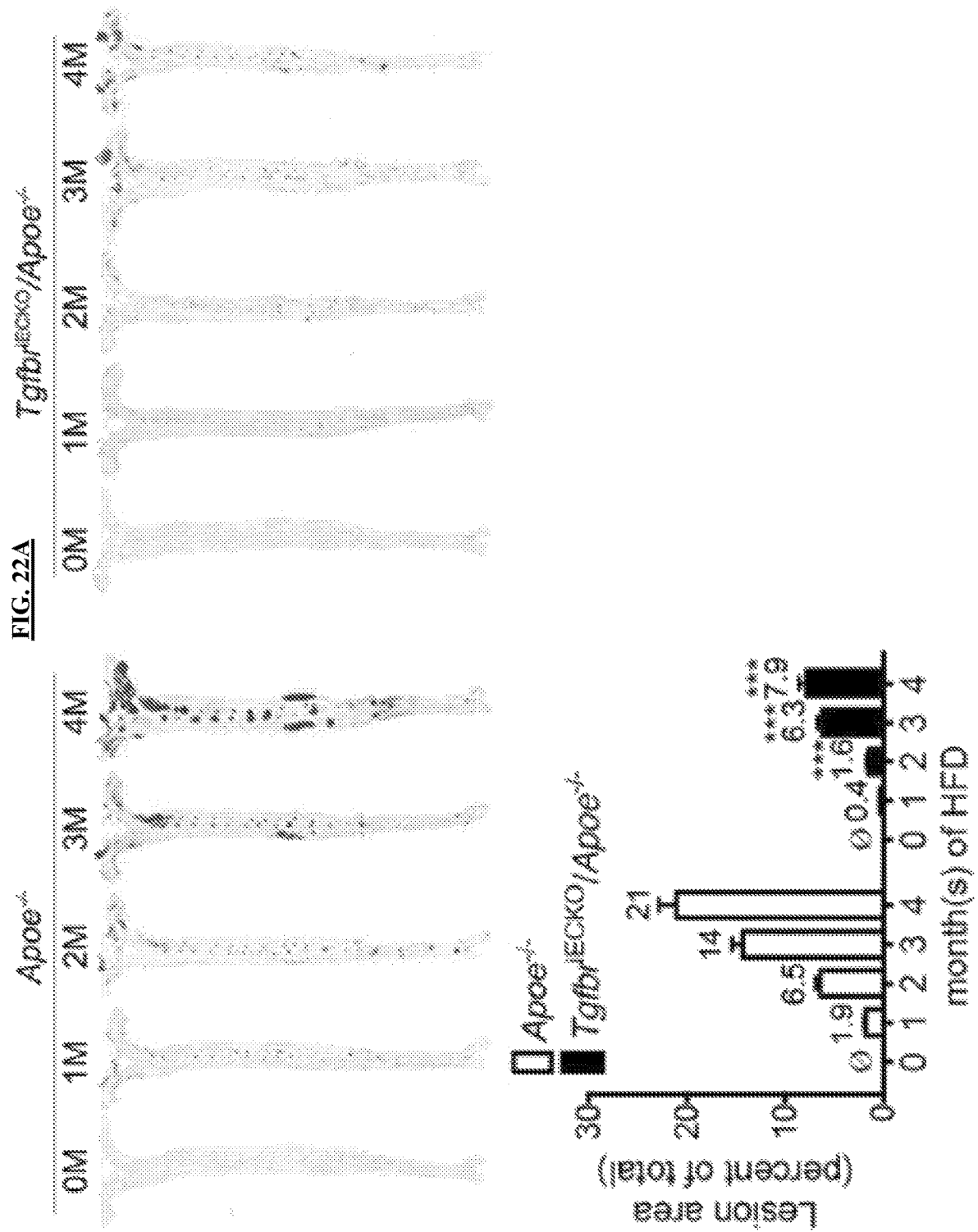
FIGS. 22A-22F are a set of images demonstrating that endothelial cell Tgfbr1/Tgfbr2 knockout inhibits atherosclerosis plaque development.
Figure 22B:
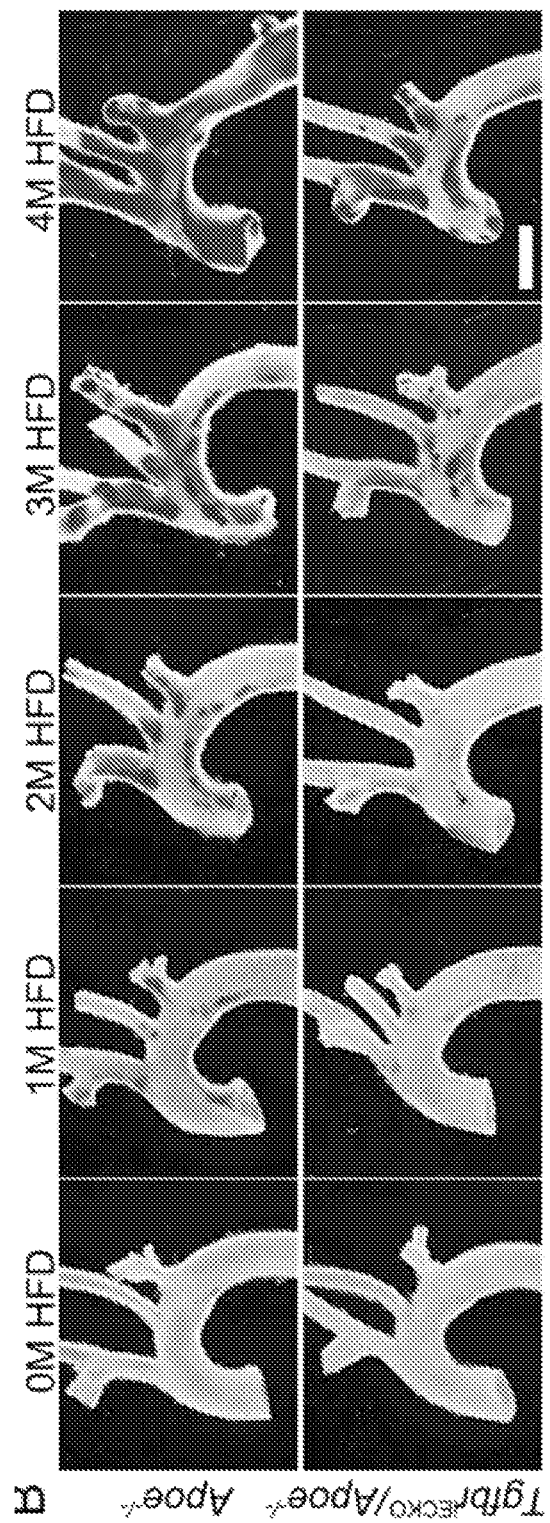
Figure 22D:
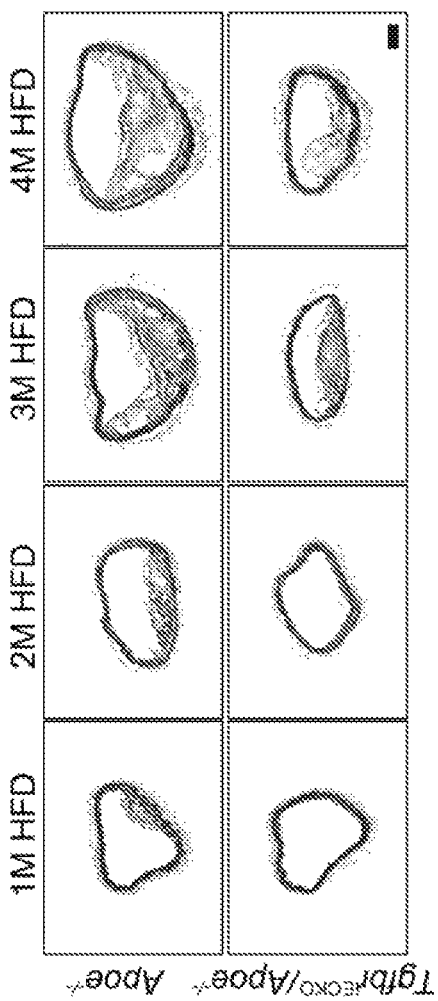
Figure 22C:
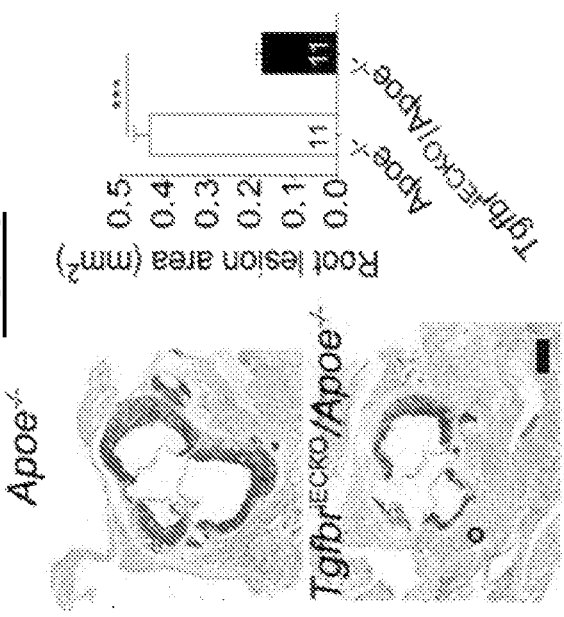
Figure 22F:
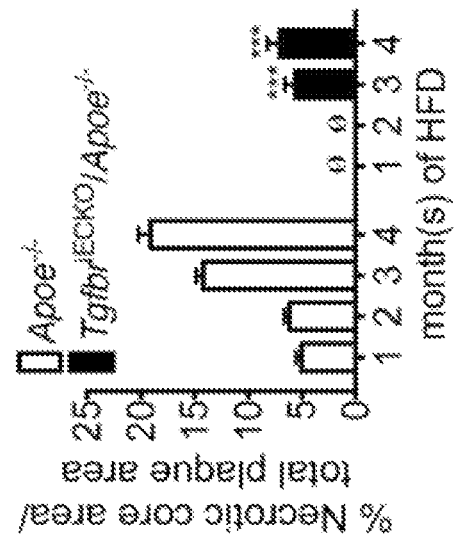
Figure 22E:
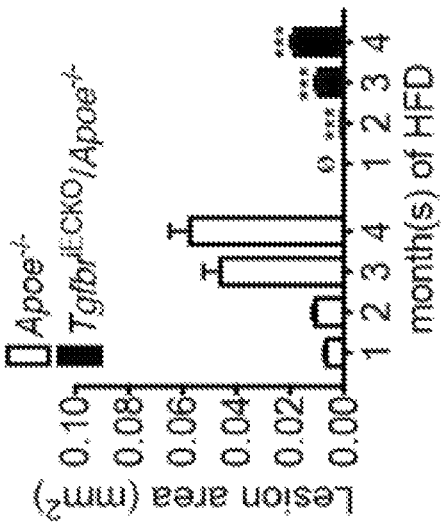
Figure 23:
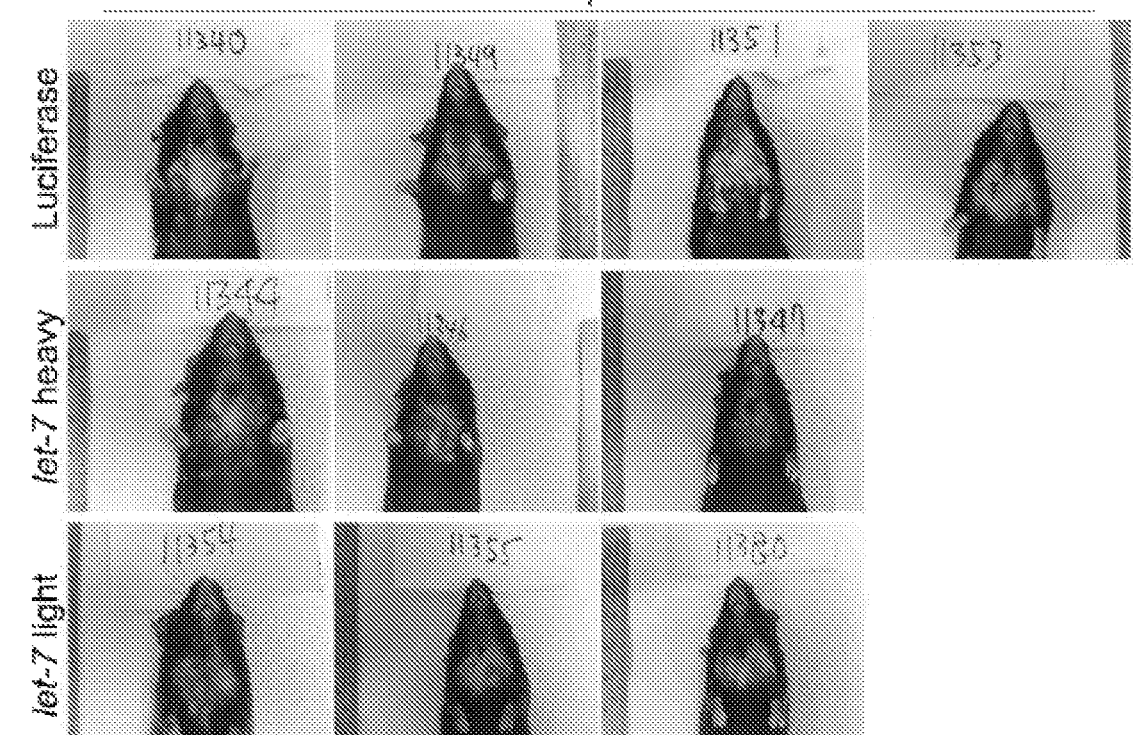
FIG. 23 is a set of images showing Apoe$^{-/-}$ and Frs2α$^{iECKO}$/Apoe$^{-/-}$ mice injected with let-7 miRNA (let-7 heavy (mi-let-7b$_H$); let-7 light (mi-let-7b$_L$)) or a luciferase control.
Figure 23:
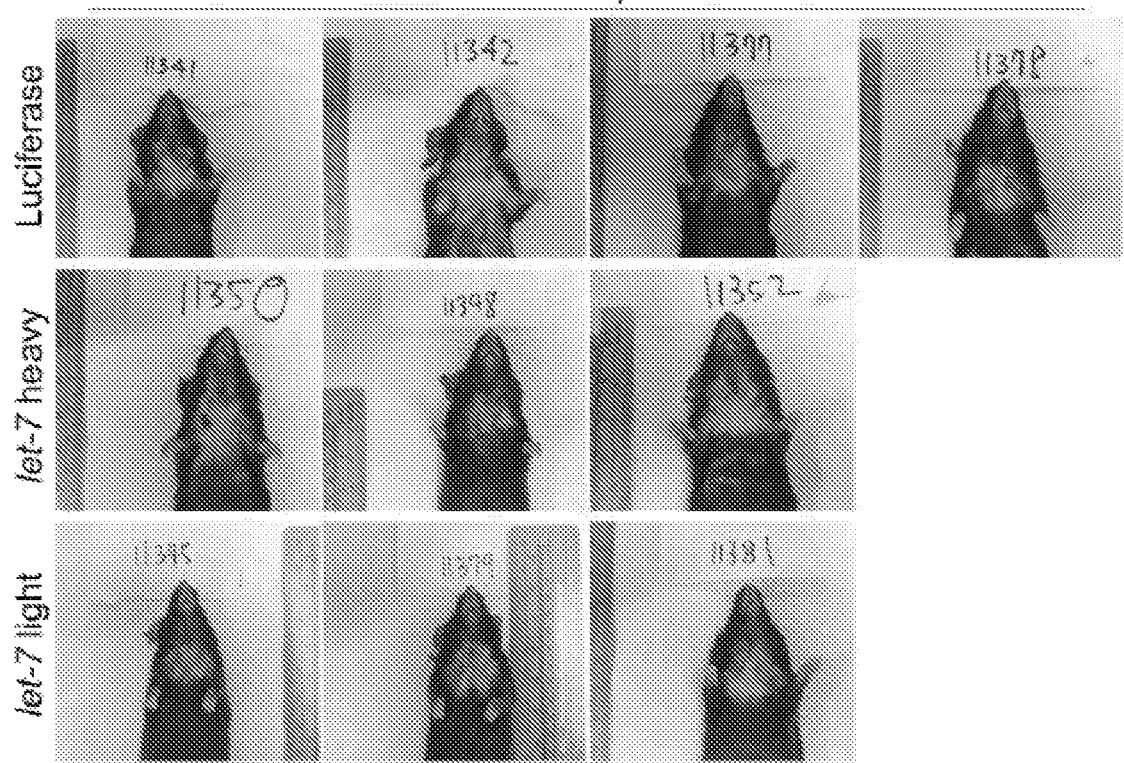

Tgfrbr$^{iECKO}$/Apoe$^{-/-}$ and littermate control mice were placed on a high fat diet (HFD) 2 weeks after induction of Tgfbr1/2 excision (FIG. 17A). The dietary intervention resulted in an increase in body weight, total serum cholesterol and triglycerides that was similar in both groups (FIGS. 17B-17D). No plaque development was observed in mice fed with a normal diet at 8 weeks old (FIG. 18). Serial analysis of whole aortas and aortic arches using Oil-Red-O staining demonstrated a significantly delayed onset and reduced extent of lipid deposition in Tgfrbr$^{iECKO}$/Apoe$^{-/-}$ mice (FIG. 19, FIG. 20, FIG. 21 and FIGS. 22A-22B). Quantitative assessment showed a 55%-79% reduction in the total aorta area of Oil-Red-O staining in aortas of Tgfrbr$^{iECKO}$/Apoe$^{-/-}$ mice over this time course (FIGS. 22A-22B). Examination of Oil-Red-O-stained aortic root cross-sections showed a 60% reduction in the plaque area after 4 months of HFD (FIG. 22C).

To study the effect of TGFβ receptors deletion on the composition and size of atherosclerotic plaques, brachiocephalic arteries from both groups of mice, sacrificed at monthly intervals, were serially sectioned. Histological examination demonstrated a marked reduction in the size of the plaque, a reduction in its necrotic core area, as well as a decrease in plaque cellularity (FIGS. 22D-22F, and FIGS. 40A-40B). The differences were most pronounced early in the time course: after 1 month of HFD, half of the Apoe$^{-/-}$ mice exhibited pathological intimal thickening and half had evidence of intimal xanthomas while all Tgfrbr$^{iECKO}$/Apoe$^{-/-}$ mice appeared normal. Fibrous cap atheromas were evident after 2 months of HFD in Apoe$^{-/-}$ mice, but they did not appear in Tgfrbr$^{iECKO}$/Apoe$^{-/-}$ mice until a month later. Even after 4 months of HFD, fibrous cap atheromas were present in only a half of Tgfrbr$^{iECKO}$/Apoe$^{-/-}$ mice (FIG. 22D) (Lutgens et al, 2010, The Journal of experimental medicine 207, 391-404; Virmani et al, 2000, Arterioscler Thromb Vasc Biol 20, 1262-1275).

Staining with an anti-αSMA Ab demonstrated a decrease in the number of neointimal αSMA$^+$ cells (FIGS. 40A-40B) and reduced neointimal expression of collagen, findings consistent with decreased EndMT. In addition, there was a reduction in fibronectin deposition and a decrease in endothelial VCAM-1 expression (FIGS. 40A-40B), indicating a reduction in "inflammatory" state of the endothelium. To further test the effect of inhibition of endothelial TGFβ signaling on its response to inflammatory mediators, primary endothelial cells from Tgfrbr$^{iECKO}$/Apoe$^{-/-}$ and Apoe$^{-/-}$ mice were treated with different inflammatory mediators (FIGS. 41A-41D).

Figure 41B:
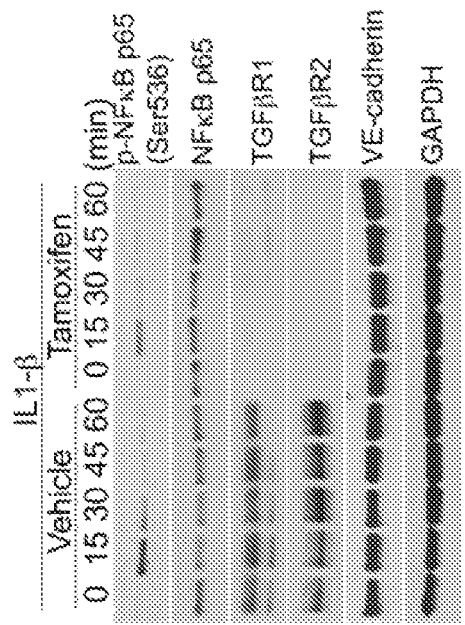
FIGS. 41A-41F are a series of images and histograms showing that endothelial Tgfbr1/Tgfbr2 knockout represses EC activation.
Figure 41D:
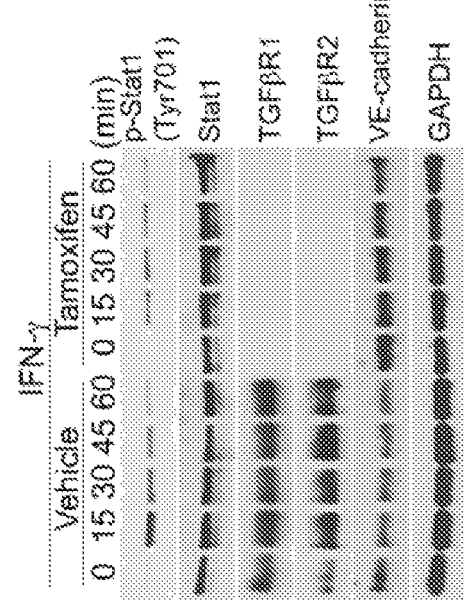
Figure 41A:
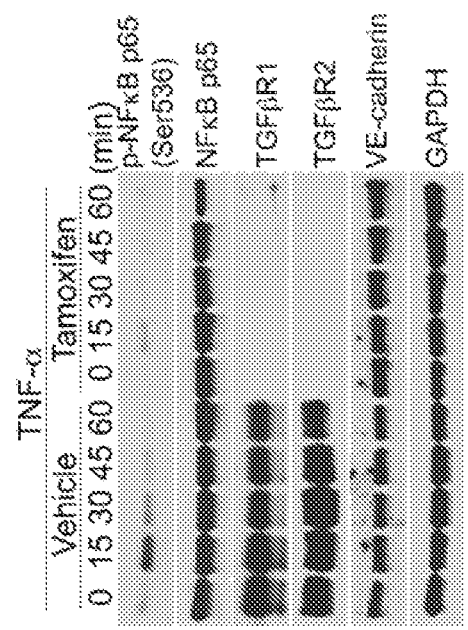
Figure 41C:
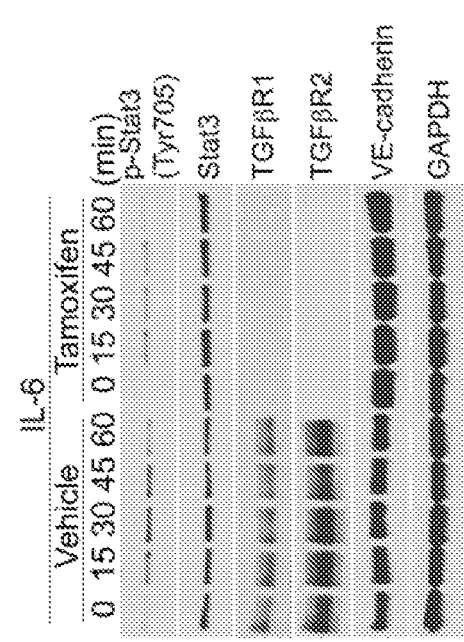
Figure 41E:
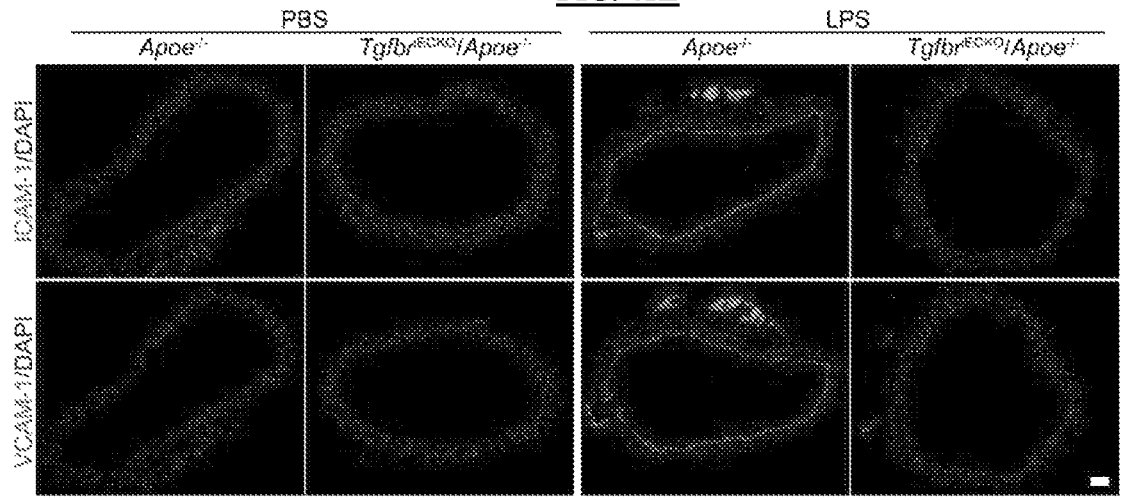
Figure 41F:
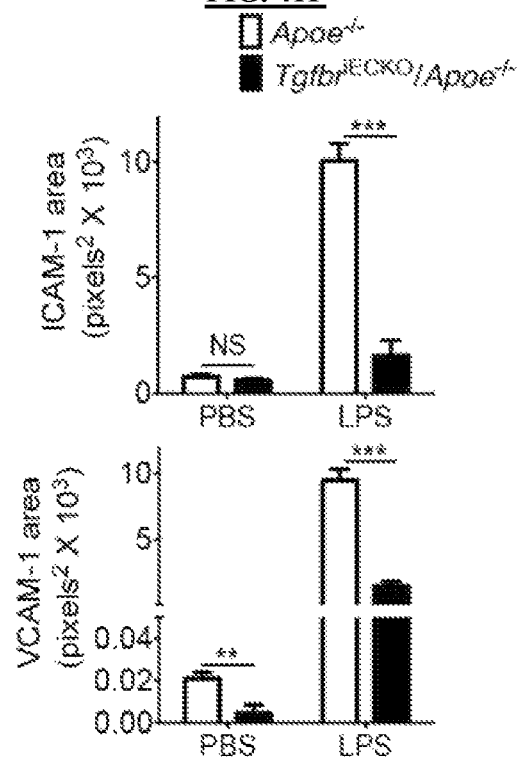
Figure 42A:
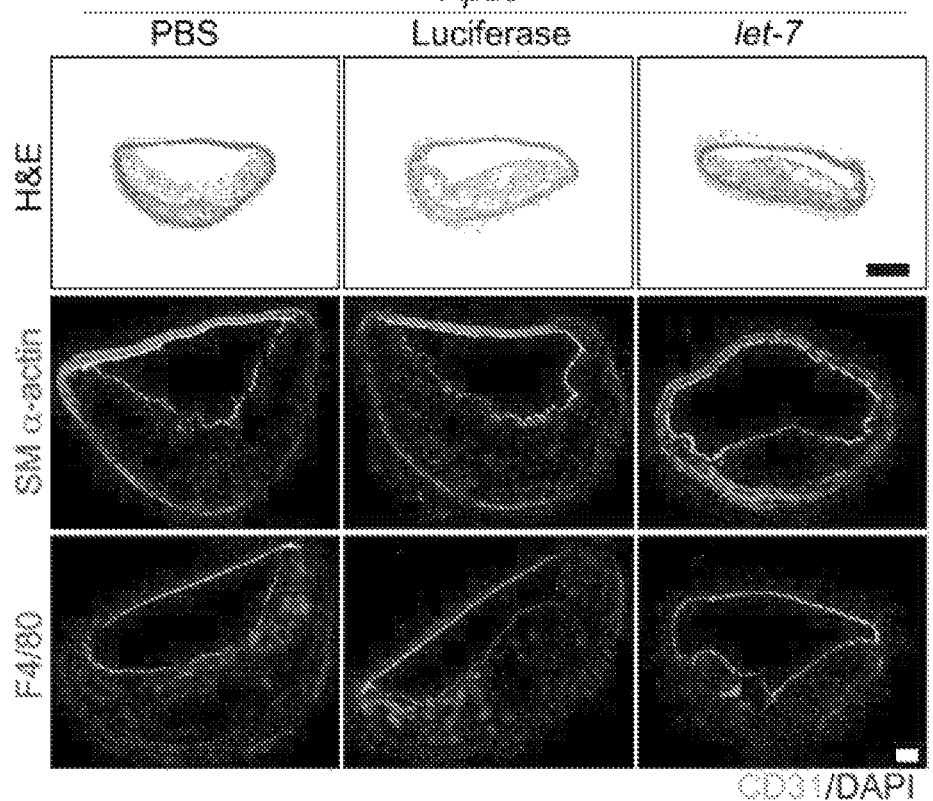
Figure 42B:
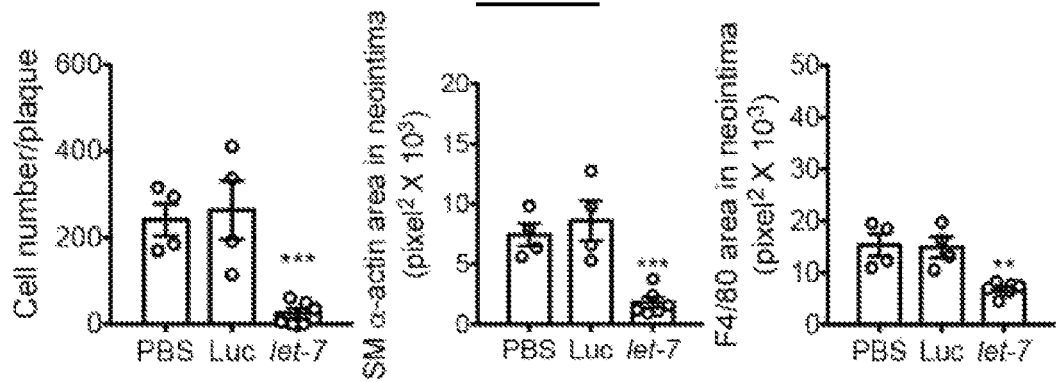

The knockout of TGFβ receptors led to a significant decrease in NFκB phosphorylation in response to TNF-α and IL1-β (FIG. 41A-41-B), Stat3 phosphorylation in response to IL-6 (FIG. 41C), and Stat1 phosphorylation in response to IFN-7 (FIG. 41D). The decreased responsiveness of Tgfrbr$^{iECKO}$/Apoe$^{-/-}$ mice to inflammatory stimuli was confirmed in vivo: staining of the thoracic aortic endothelium demonstrated a profound reduction in ICAM-1 and VCAM-1 expression after LPS injection compared to littermate controls (FIGS. 41E-41F).

In sum, this study established that endothelial TGFβ receptor knockout mice developed smaller atherosclerotic lesions than wild-type Apoe mice. The results of this study provide the first genetic evidence of pro-atherogenic endothelial cell TGFβ signaling in atherosclerosis.

Figure 26:
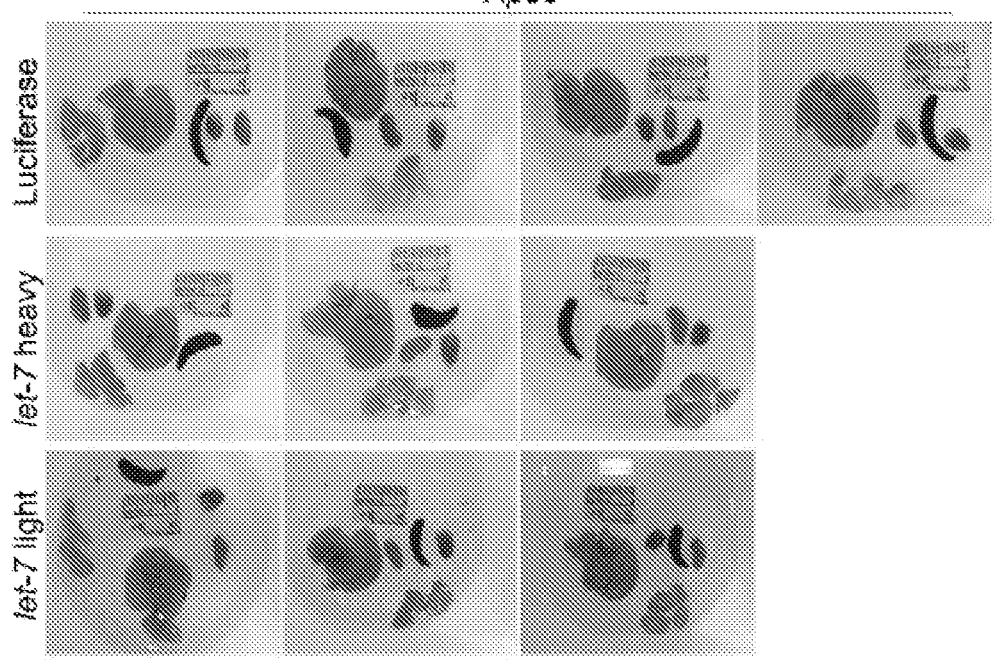
FIG. 26 is a set of images showing organs harvested from Apoe$^{-/-}$ and Frs2α$^{iECKO}$/Apoe$^{-/-}$ mice injected with let-7 miRNA (let-7 heavy, let-7 light) or a luciferase control.
Figure 26:
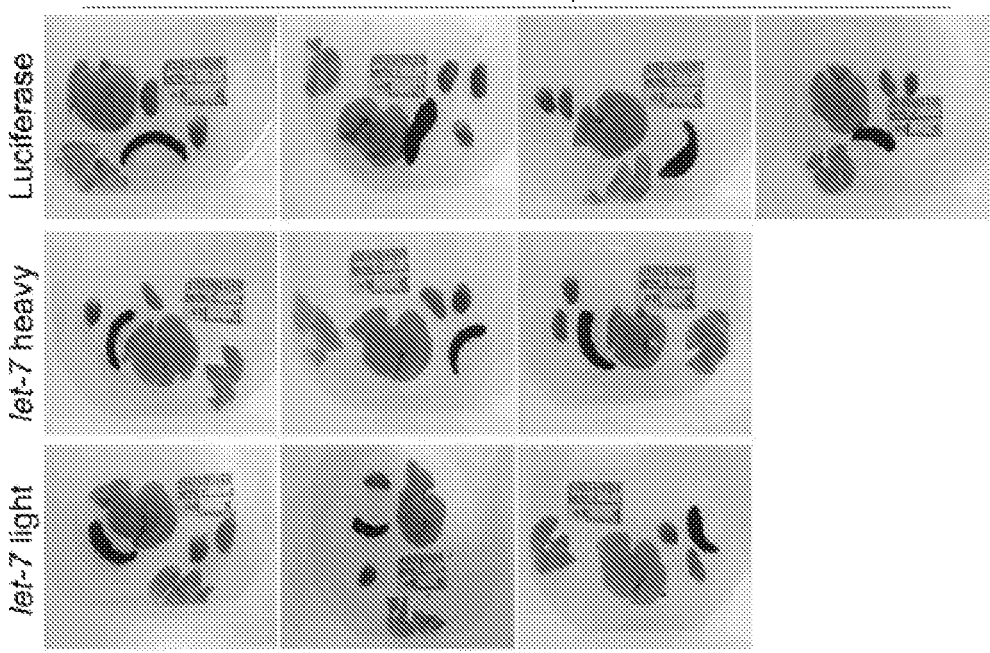
Figure 27:
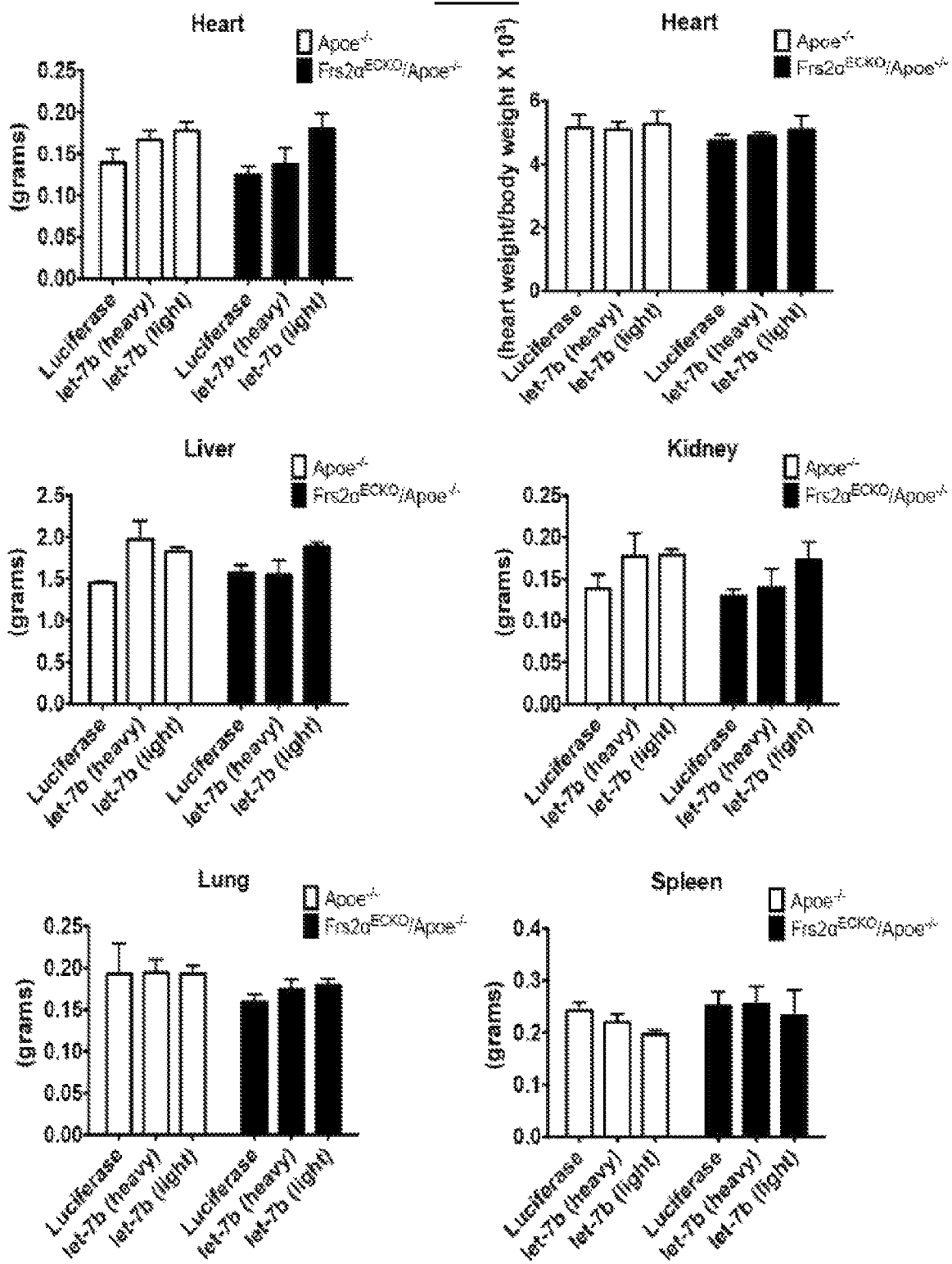
FIG. 27 is a set of plots showing weight of organs (heart, lung, liver, kidney, spleen) harvested from Apoe$^{-/-}$ and Frs2α$^{iECKO}$/Apoe$^{-/-}$ mice injected with let-7 miRNA (let-7 heavy, let-7 light) or a luciferase control.
Figure 28:
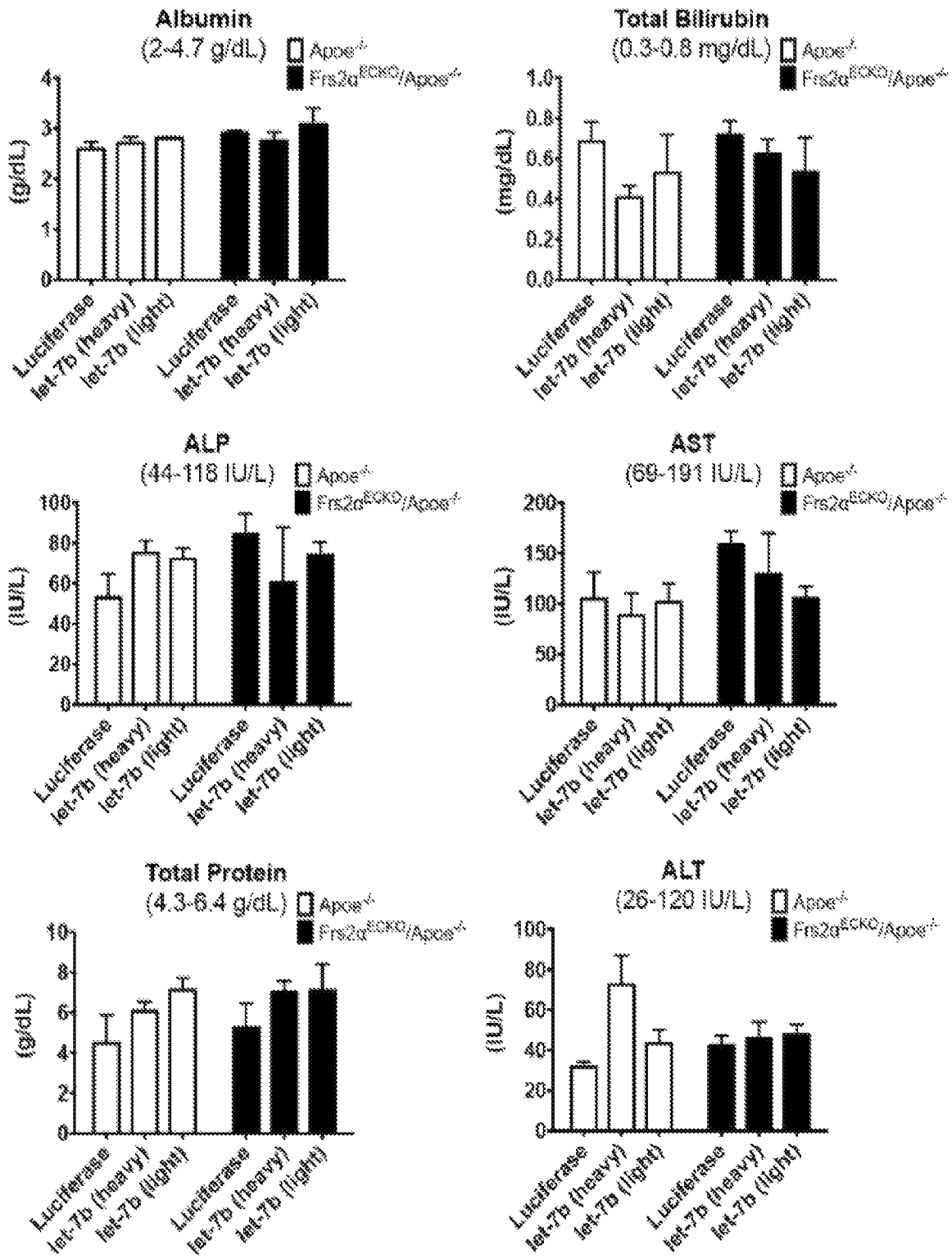
FIG. 28 is set of plots showing results of liver function test in Apoe$^{-/-}$ and Frs2α$^{iECKO}$/Apoe$^{-/-}$ mice injected with let-7 miRNA (let-7 heavy, let-7 light) or a luciferase control.
Figure 29:
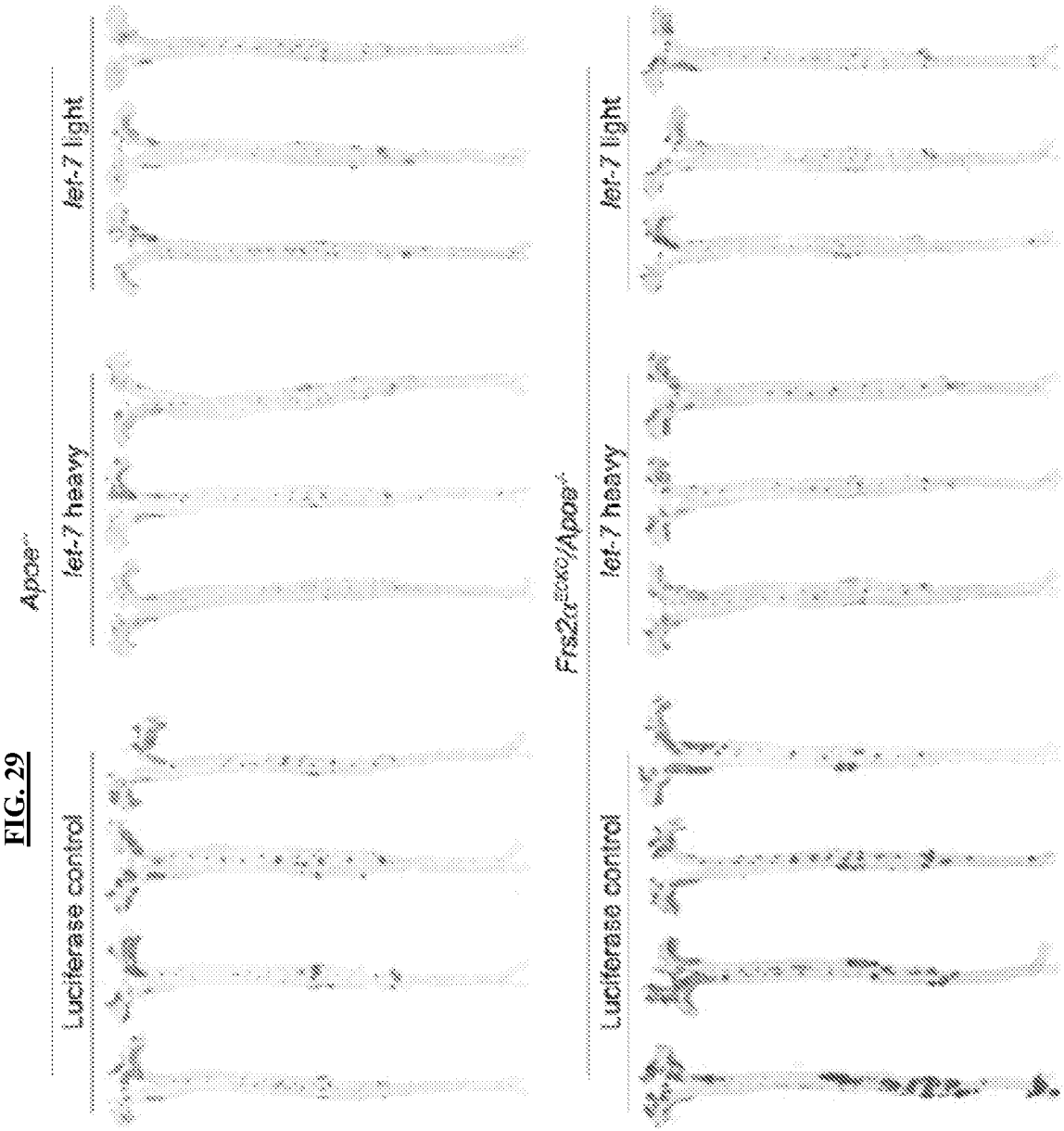
FIG. 29 is a set of images and plot showing Oil Red-O staining of whole aorta obtained from Apoe$^{-/-}$ and Frs2α$^{iECKO}$/Apoe$^{-/-}$ mice injected with let-7 miRNA (let-7 heavy, let-7 light) or a luciferase control.

Example 6: Delivery of Let-7 to Endothelial Cells Using 7C1 Nanoparticle Reduced Atherosclerotic Lesion Growth and Formation A decline in let-7 miRs expression has been previously linked to activation of TGFβ signaling (Chen et al., 2012, Cell reports 2: 1684-1696; Chen et al, 2014 Science signaling 7, ra90). In another study, the effect of delivery of let-7 miRNA to endothelial cells on reduction of atherosclerosis was investigated, thus it was tested if restoration of endothelial let-7 levels would reverse TGFβ activation and reduce atherosclerosis. Apoe null (Apoe$^{-/-}$) and Frs2α$^{iECKO}$/Apoe$^{-/-}$ mice were administered with a luciferase control, let-7 heavy (mi-let-7b$_H$), and let-7 light (mi-let-7b$_L$) using a nanoformulation (7C1 nanoparticle) for selective delivery to endothelial cells. A chemically modified let-7b miR was packaged into 7C1 nanoparticles (Dahlman et al., Nat Nanotechnol. 2014 August; 9(8): 648-655) and used for in vivo delivery in Apoe$^{-/-}$ and Frs2α$^{iECKO}$/Apoe$^{-/-}$ mice that demonstrate enhanced atherosclerosis. 7C1 intravenous injections were performed 12 times within 4 months. Measurements of the following were taken from mice in each group: body weight, complete blood counts, skin pictures, serum lipid profiles, organ weight, and whole aorta oil red-O staining and quantification (FIGS. 24C, 25, 23, 24B, 27, and 29). It was observed that let-7 injected mice did not scratch around their neck (FIG. 23), mice in all groups gained weight (FIG. 24C), their blood cell counts and serum lipid profile were all within normal range (FIGS. 25 and 24B) and all their organs appeared normal (FIGS. 26 and 27). Furthermore, a slight increase in total protein level and a reduction in lesion formation were observed in the let-7 injected group of mice (FIGS. 28 and 29).

Figure 30:
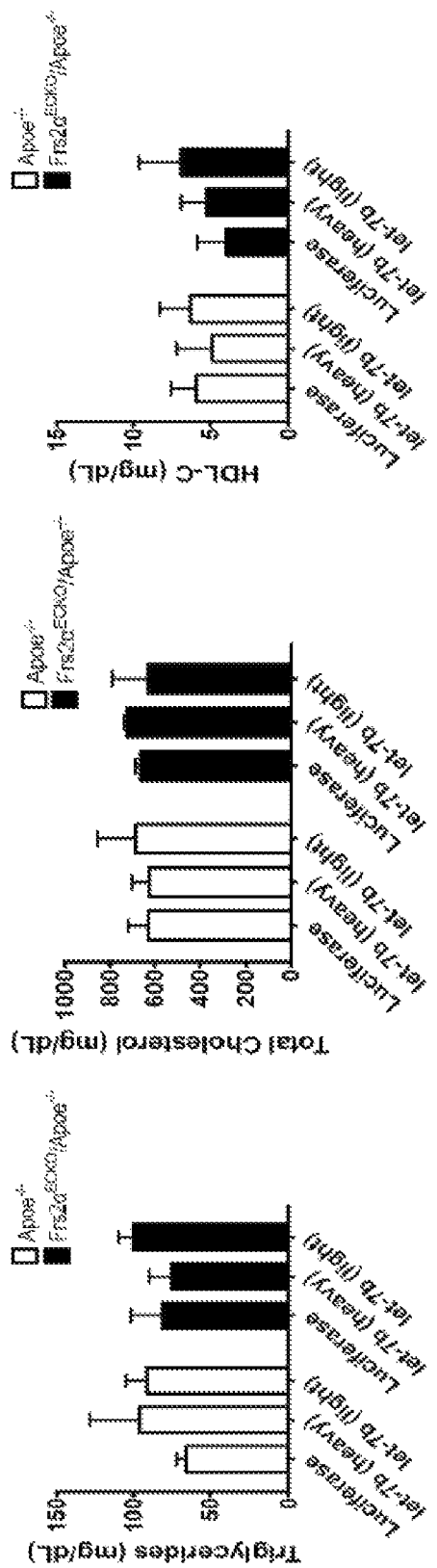
FIG. 30 is a set of plots showing triglyceride, cholesterol, and high density lipoprotein (HDL) levels in Apoe$^{-/-}$ and Frs2α$^{iECKO}$/Apoe$^{-/-}$ mice injected with let-7 miRNA (let-7 heavy, let-7 light) or a luciferase control.

FIG. 30 shows that triglyceride, cholesterol, and high density lipoprotein (HDL) levels in Apoe$^{-/-}$ and Frs2α$^{ECKO}$/Apoe$^{-/-}$ mice injected with let-7 miRNA (let-7 heavy, let-7 light) or a luciferase control were all similar. This finding is important because it shows the reduced plaque lesions in let-7 injected groups was not due to reduced triglyceride and/or reduced cholesterol in the blood.

Figure 24A:
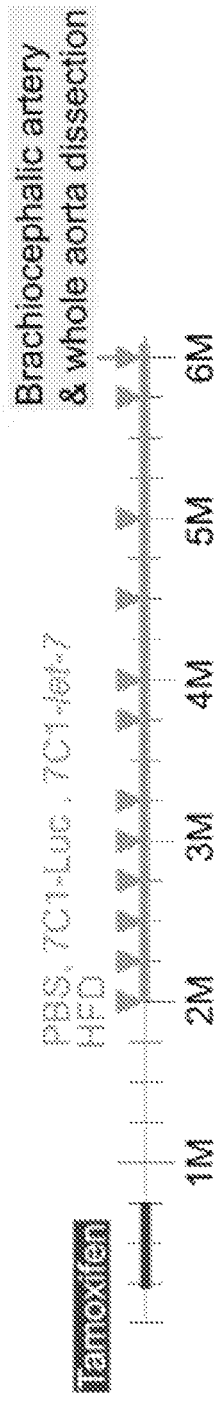
FIGS. 24A-24E are a series of graphs showing that 7C1-let-7 mimics treatment have no effect on mouse body weight and serum lipid profile.
Figure 24B:
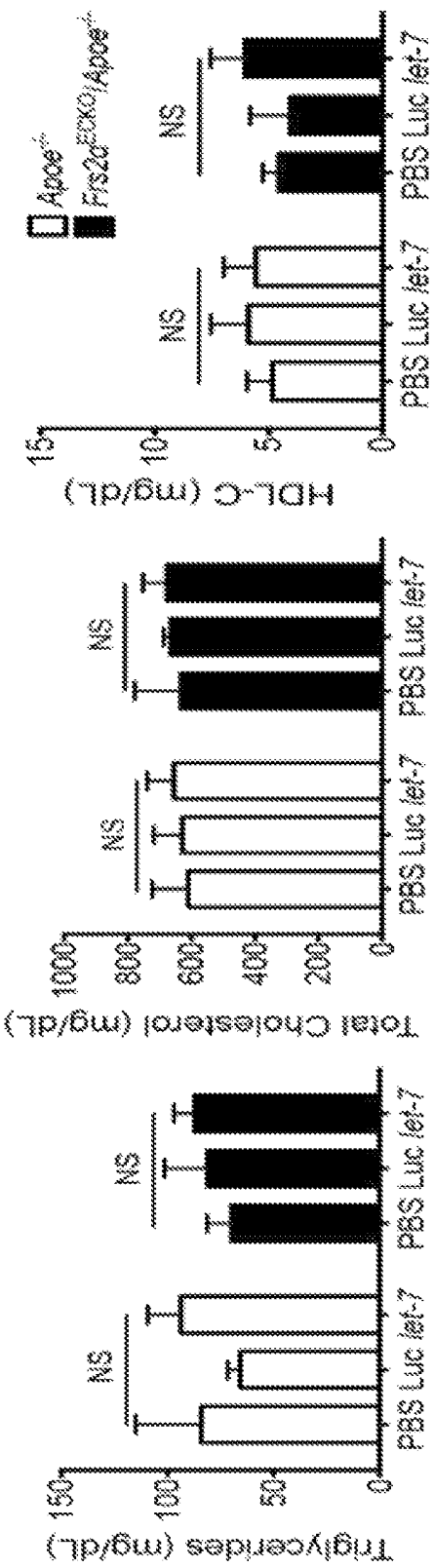
Figure 24C:
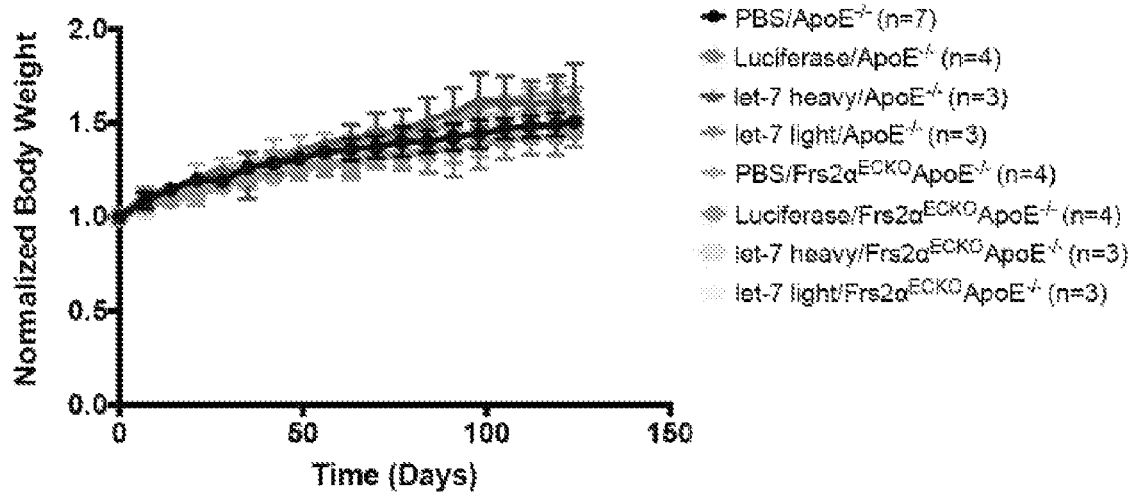
Figure 24D:
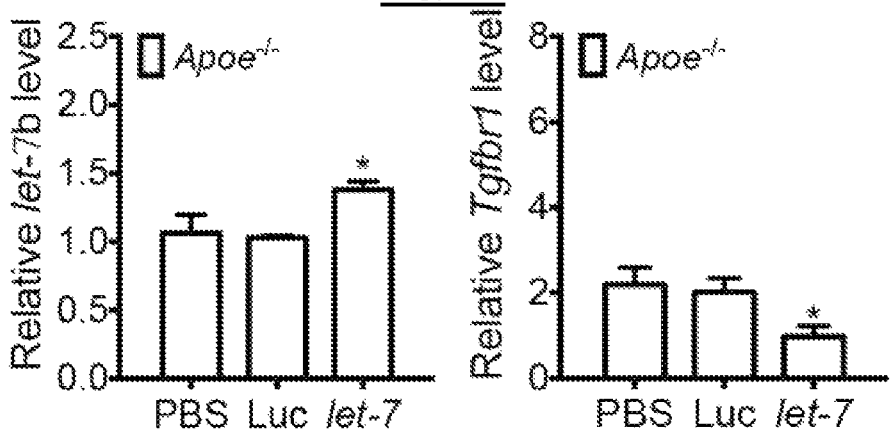
Figure 24E:
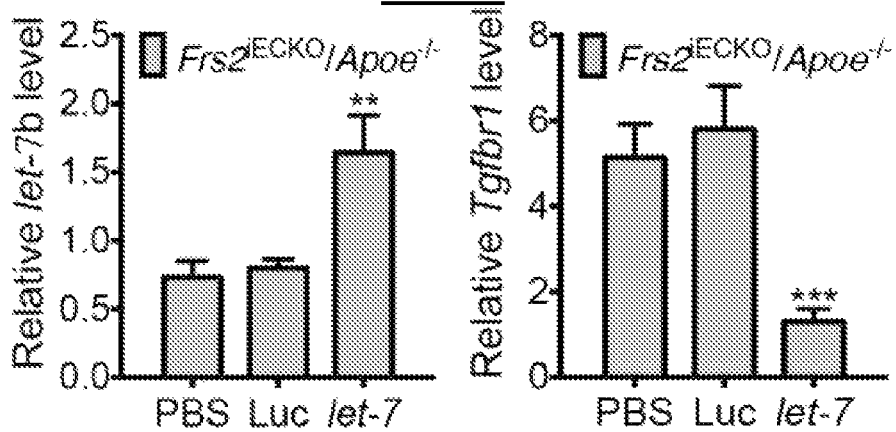
Figure 25:
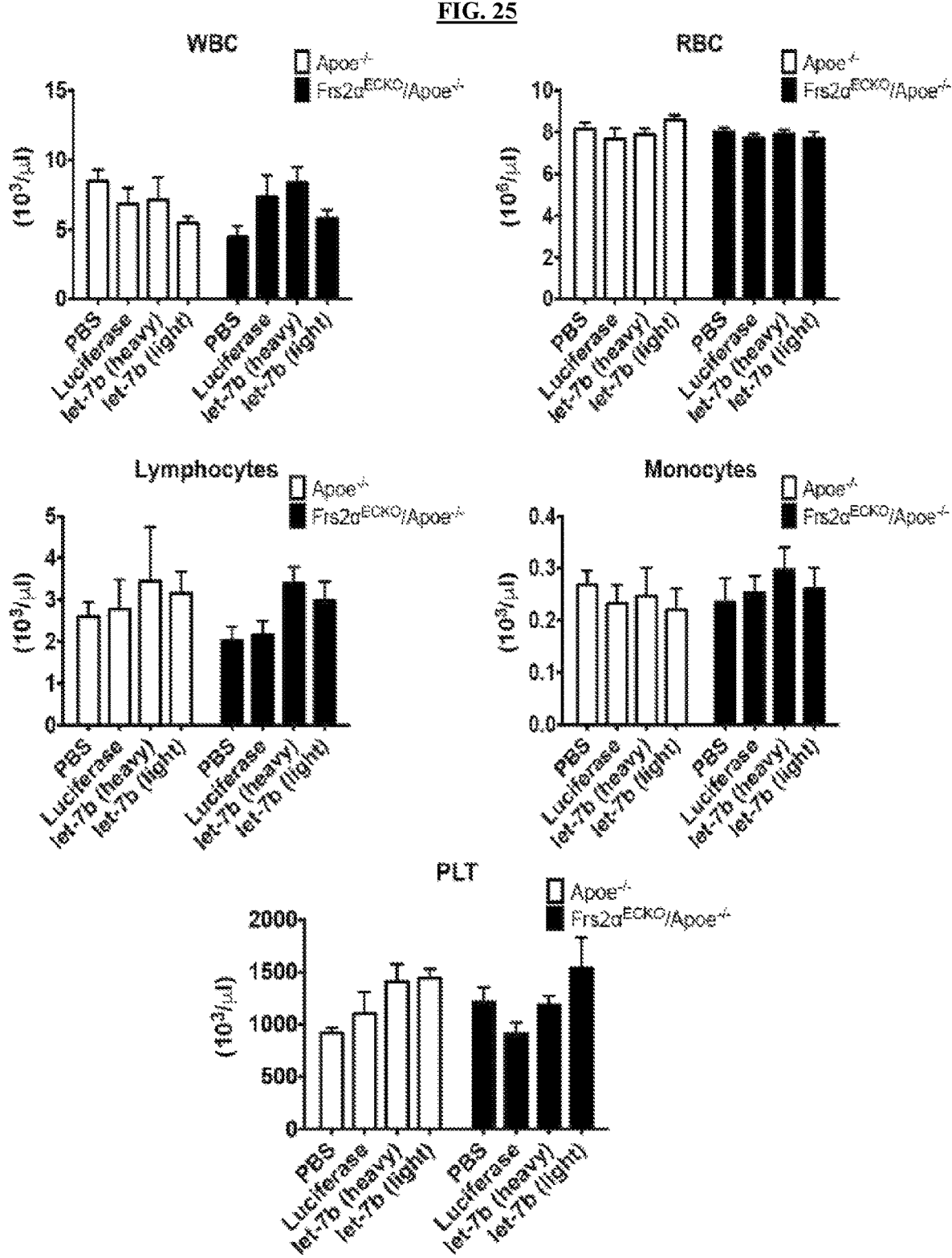
FIG. 25 is a set of plots showing blood cell counts (white blood cell (WBC), red blood cell (RBC), platelet (PLT), lymphocyte, and monocyte counts) in Apoe$^{-/-}$ and Frs2α$^{iECKO}$/Apoe$^{-/-}$ mice.
Figure 31:
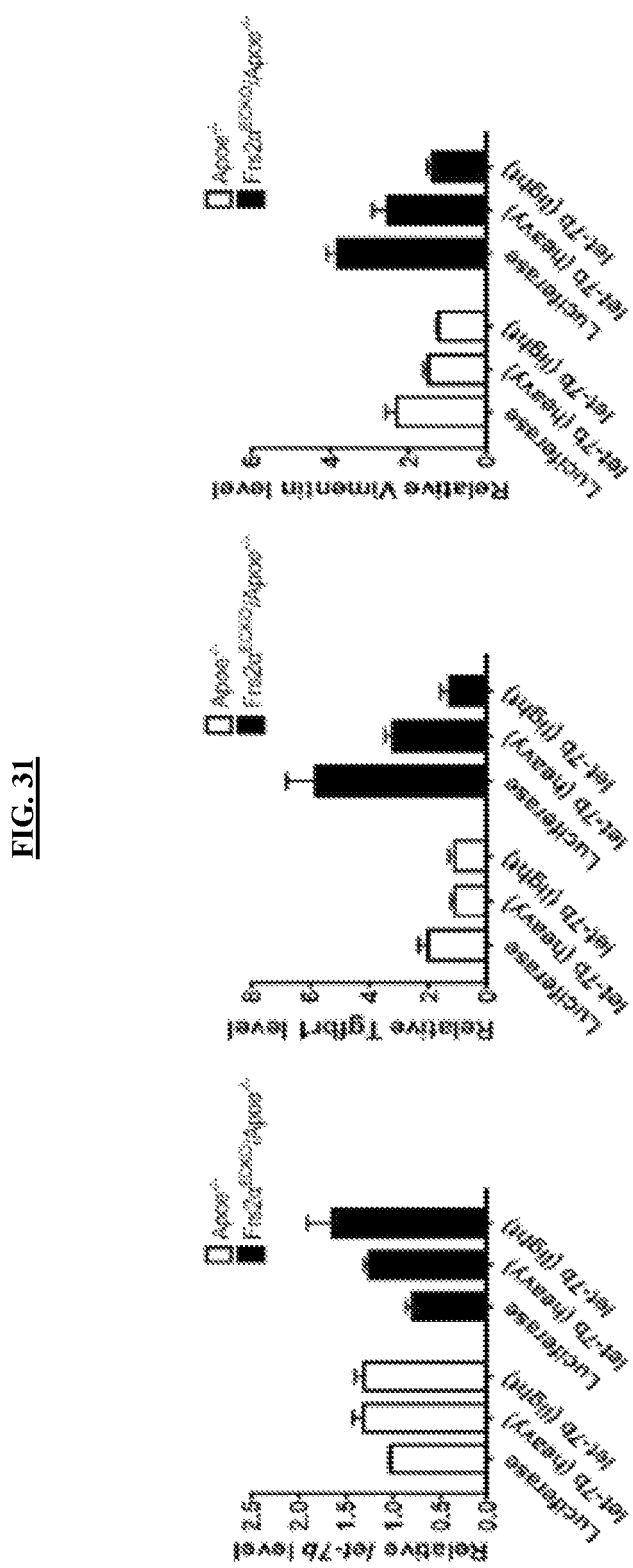
FIG. 31 is a set of plots showing let-7 and target gene expression in isolated lung endothelial cells in Apoe$^{-/-}$ and Frs2α$^{iECKO}$/Apoe$^{-/-}$ mice injected with let-7 miRNA (let-7 heavy, let-7 light) or a luciferase control.
Figure 31:
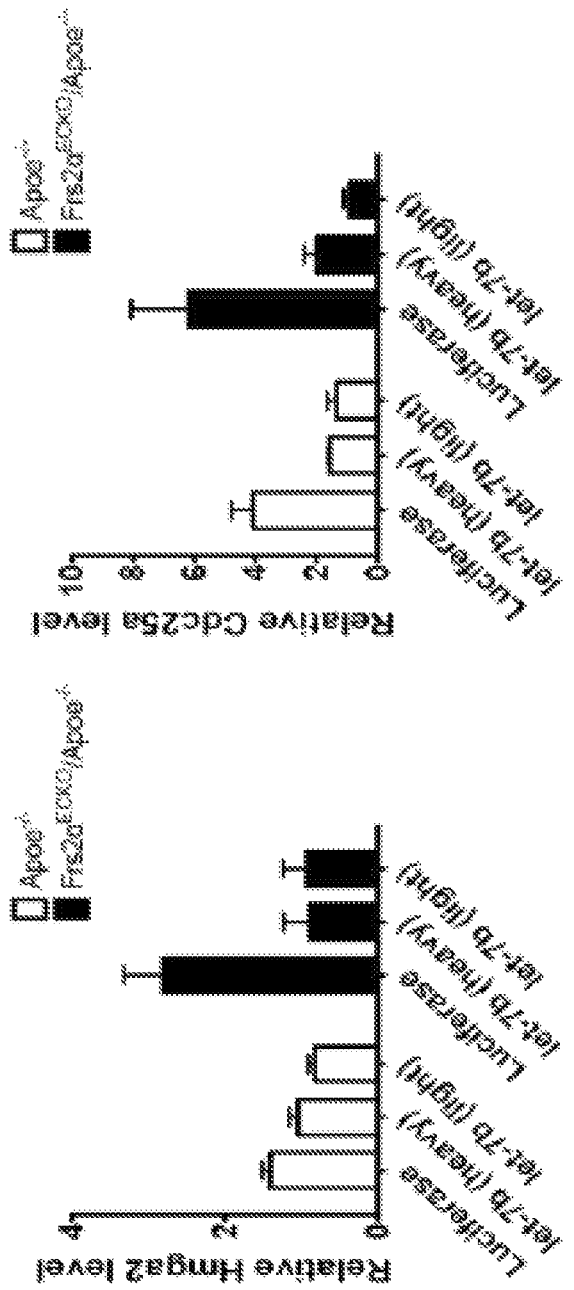
Figure 31:
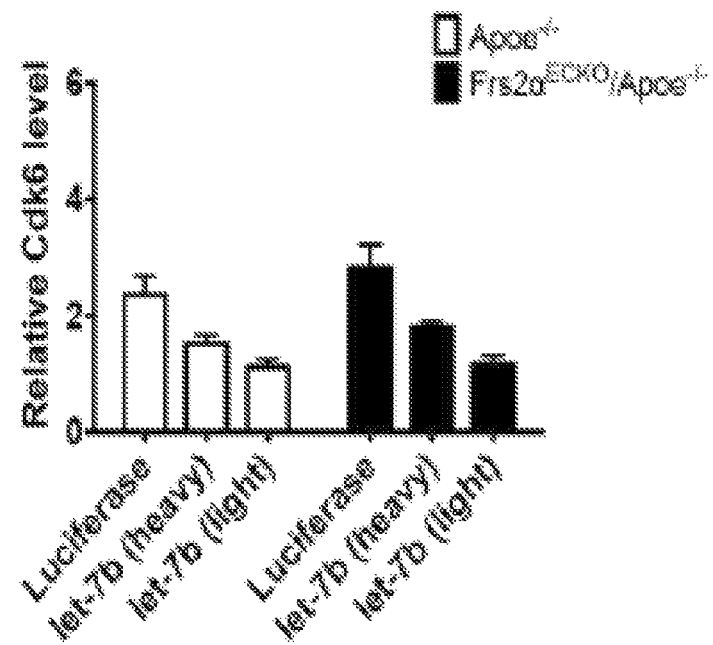
Figure 31:
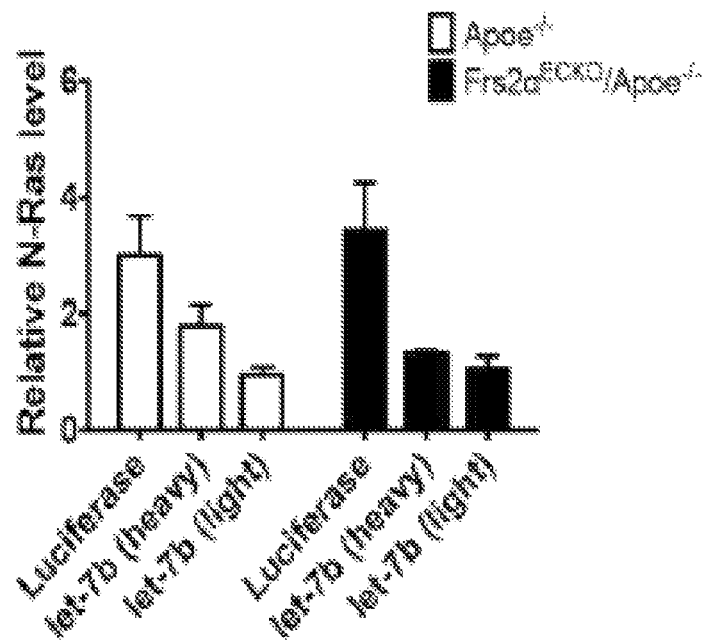

Intravenous therapy was initiated at the same time as the switch to the HFD and continued at intervals as shown in FIG. 24A. The let-7b miR administration had no effect on serum triglycerides, total cholesterol or HDL cholesterol levels (FIG. 24B). The normal weight gain seen in mice on the HFD was not affected (FIG. 24C), and there were no abnormalities in any of the biochemical parameters tested, including liver function tests (FIG. 28). Analysis of primary endothelial cells from the lungs of Apoe$^{-/-}$ and Frs2α$^{iECKO}$/Apoe$^{-/-}$ mice showed increased expression of let-7b miRNA, a consequent decrease in Tgfbr1, and let-7/TGFβdownstream gene expression (FIGS. 24D, 24E, and 31).

Figure 38A:
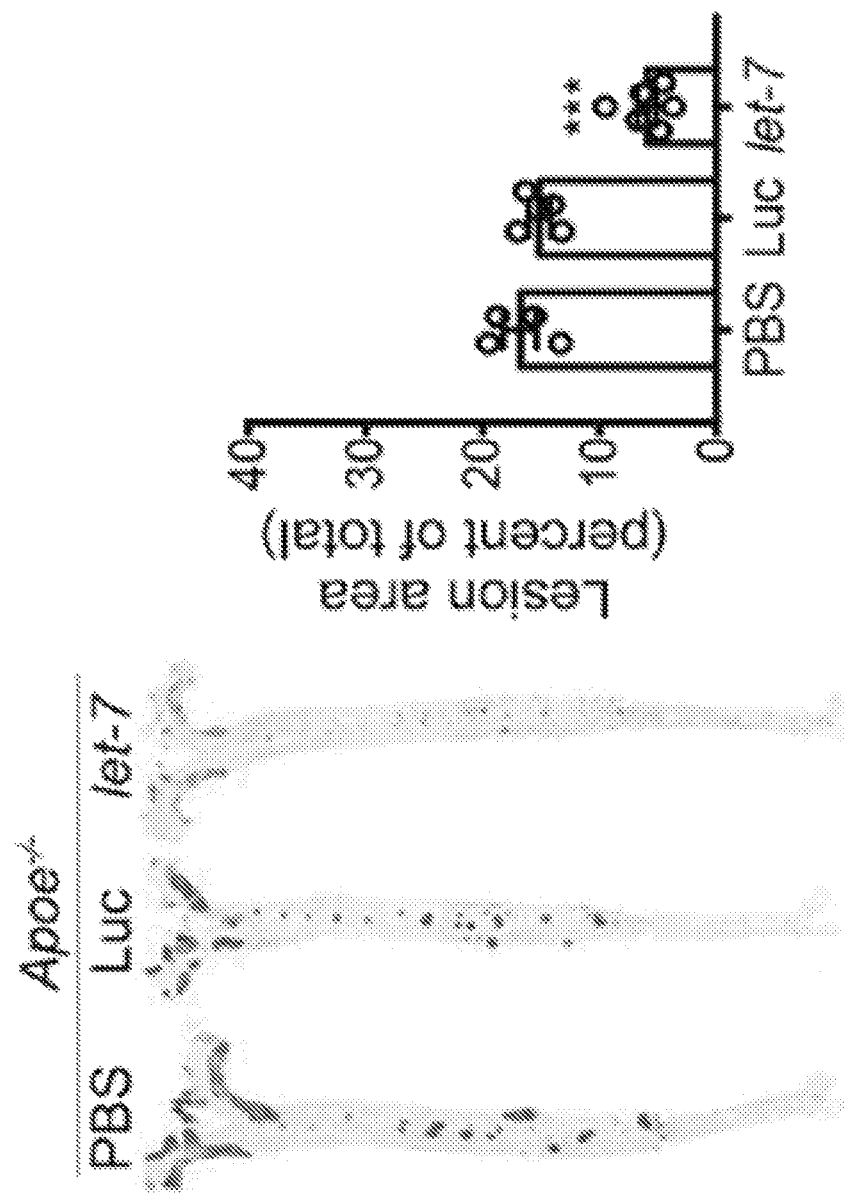
FIGS. 38A-38D are a series of images and histograms depicting that 7C1-let-7 mimics suppress atherosclerosis lesion development in both Apoe$^{-/-}$ and Frs2α$^{iECKO}$/Apoe$^{-/-}$ mice. Mice were injected intravenously with PBS, 7C1-Luciferase, and 7C1-let-7 mimics and concomitantly fed the high fat diet for 4 months (n=4 to 6 per group).
Figure 38B:
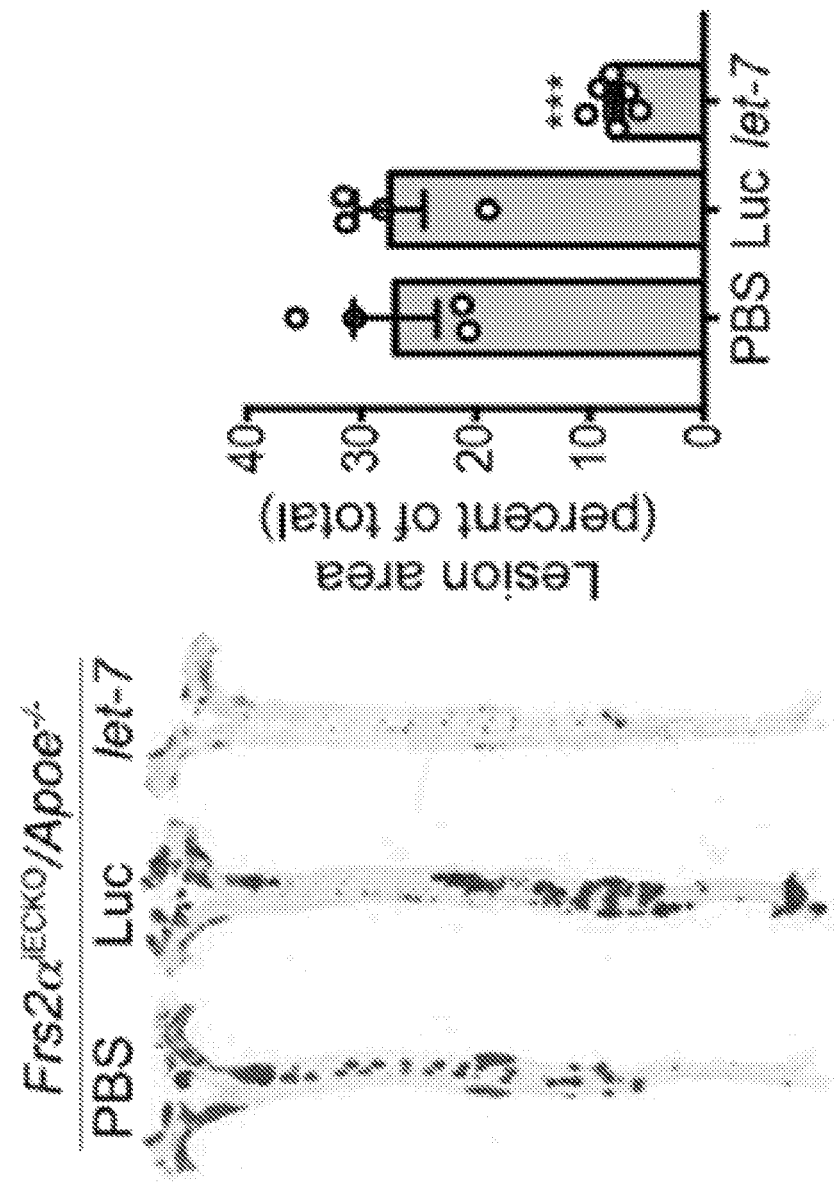
Figure 38C:
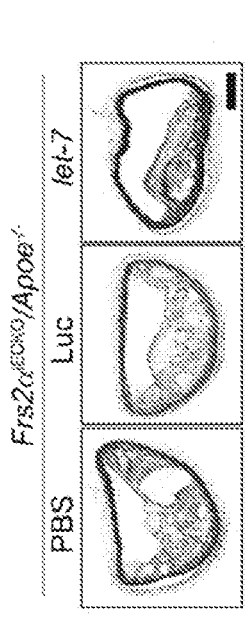
Figure 38C:
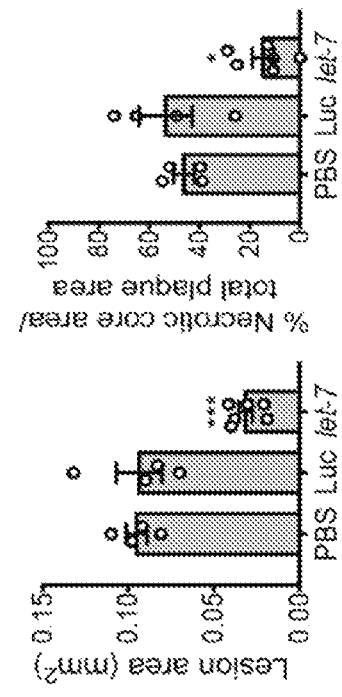
Figure 38D:
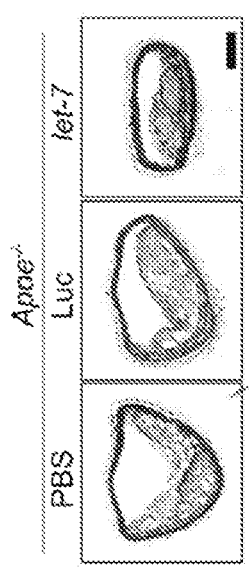
Figure 38D:
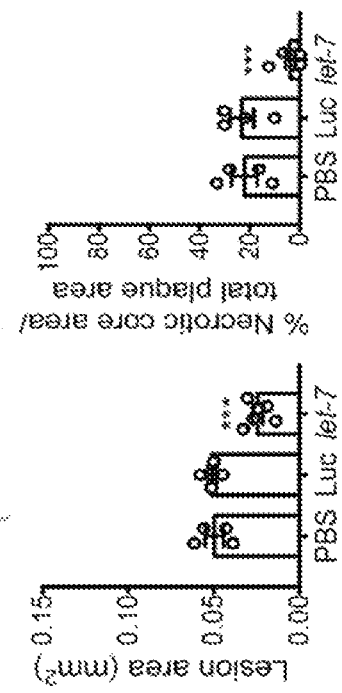

Examination of aortas of Apoe$^{-/-}$ and Frs2α$^{iECKO}$/Apoe$^{-/-}$ mice treated with let-7b miR 7C1 nanoparticles showed a 61% (Apoe$^{-/-}$) and 71% (Frs2α$^{iECKO}$/Apoe$^{-/-}$) reduction in Oil-red-O staining compared to control mice (FIGS. 38A-38B). Analysis of serial brachiocephalic artery sections (Movat staining) confirmed these finding: let-7 miR administration led to a significant reduction in the plaque area (50% in Apoe$^{-/-}$ and 66% in Frs2α$^{iECKO}$/Apoe$^{-/-}$ mice) and decrease in the necrotic core size (83% and 73%, respectively; FIGS. 38C-38D) that were similar to that seen in the Tgfbr$^{iECKO}$/Apoe$^{-/-}$ mice. Furthermore, let-7b therapy led to a decrease in the plaque cellularity and the number of neointimal αSMA$^+$ cells and F4/80$^+$ macrophages (FIGS. 42A-42D). Thus, endothelial-targeted nanoparticles loaded with let-7b miR achieved the same functional result as the deletion of endothelial TGFβR1 and TGFβR2 genes.

Figure 39A:
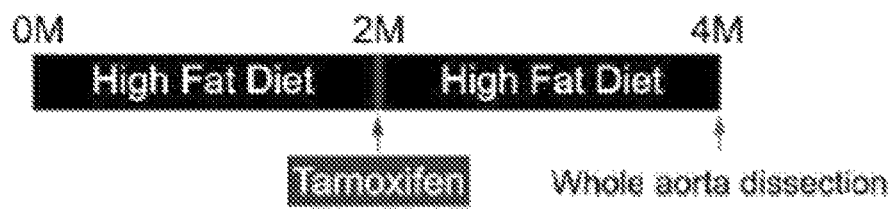
Figure 39B:
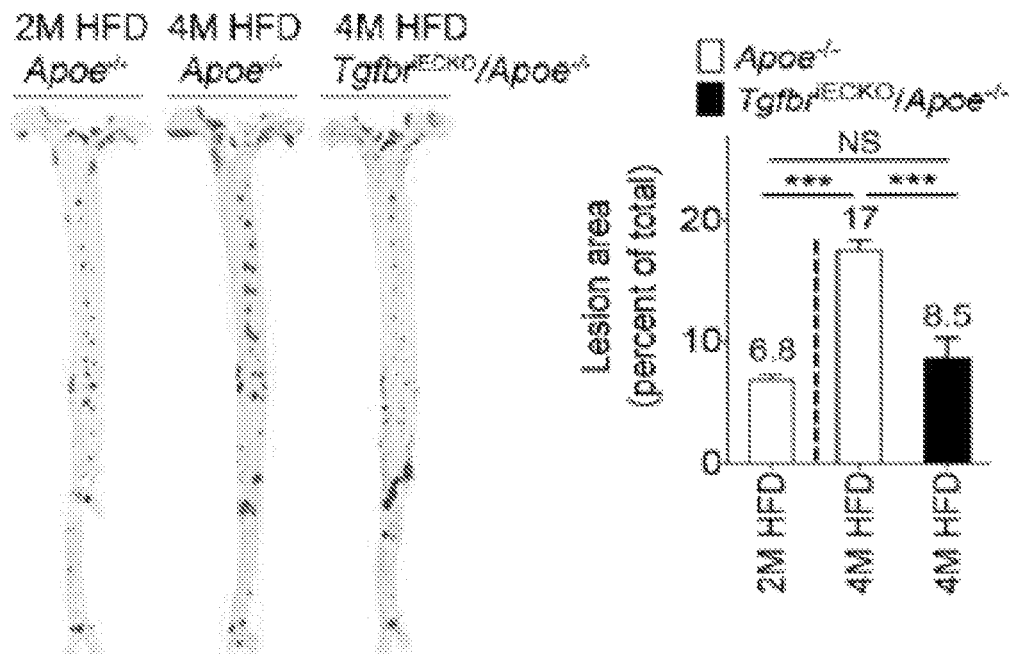

Given the profound effect of suppression of endothelial TGFβ activation on the development of atherosclerosis, a similar approach was taken to examine whether it would reduce progression and induce regression of established atherosclerotic lesions. To test this, 2 months after Cdh5CreER$^{T2}$; Tgfbr1$^{fl/fl}$; Tgfbr2$^{fl/fl}$; Apoe$^{-/-}$; mT/mG$^{fl/fl}$ mice were placed on the HFD, the animals were randomized to tamoxifen-driven Cre activation (generating Tgfbr$^{iECKO}$/Apoe$^{-/-}$ mice) or sham treatment and continued on the HFD diet (FIG. 39A). Two months later, both groups were sacrificed and the extent of atherosclerotic burden determined using whole aorta Oil-Red-O staining. As expected, the control mice demonstrated extensive progression of disease with the total aortic lesion area increasing from 6.8% to 17%. At the same time, mice with the induced endothelial TGFβR1/R2 deletion showed no significant disease progression (6.6% to 8.5%, p=NS) (FIG. 39B). Thus, endothelial deletion of TGFβR1 and R2 arrested atherosclerosis progression in the presence of strikingly elevated cholesterol levels.

Figure 39C:
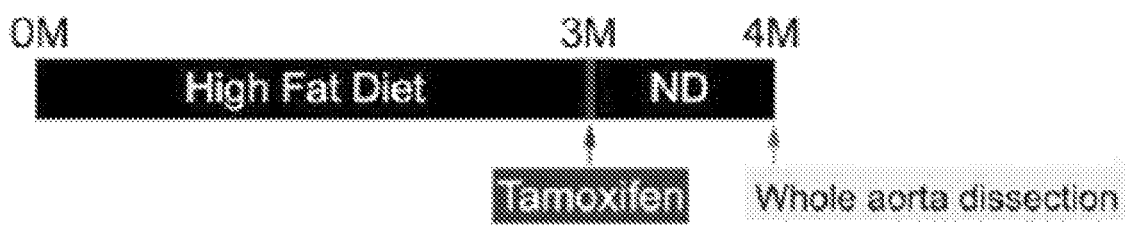
Figure 39D:
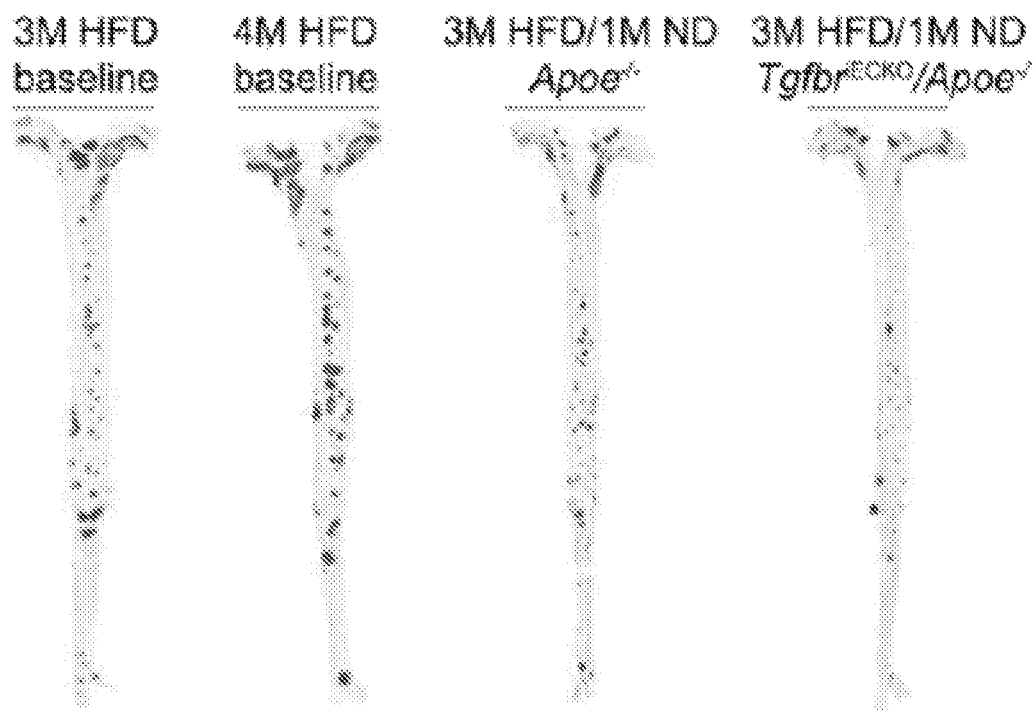
Figure 40A:
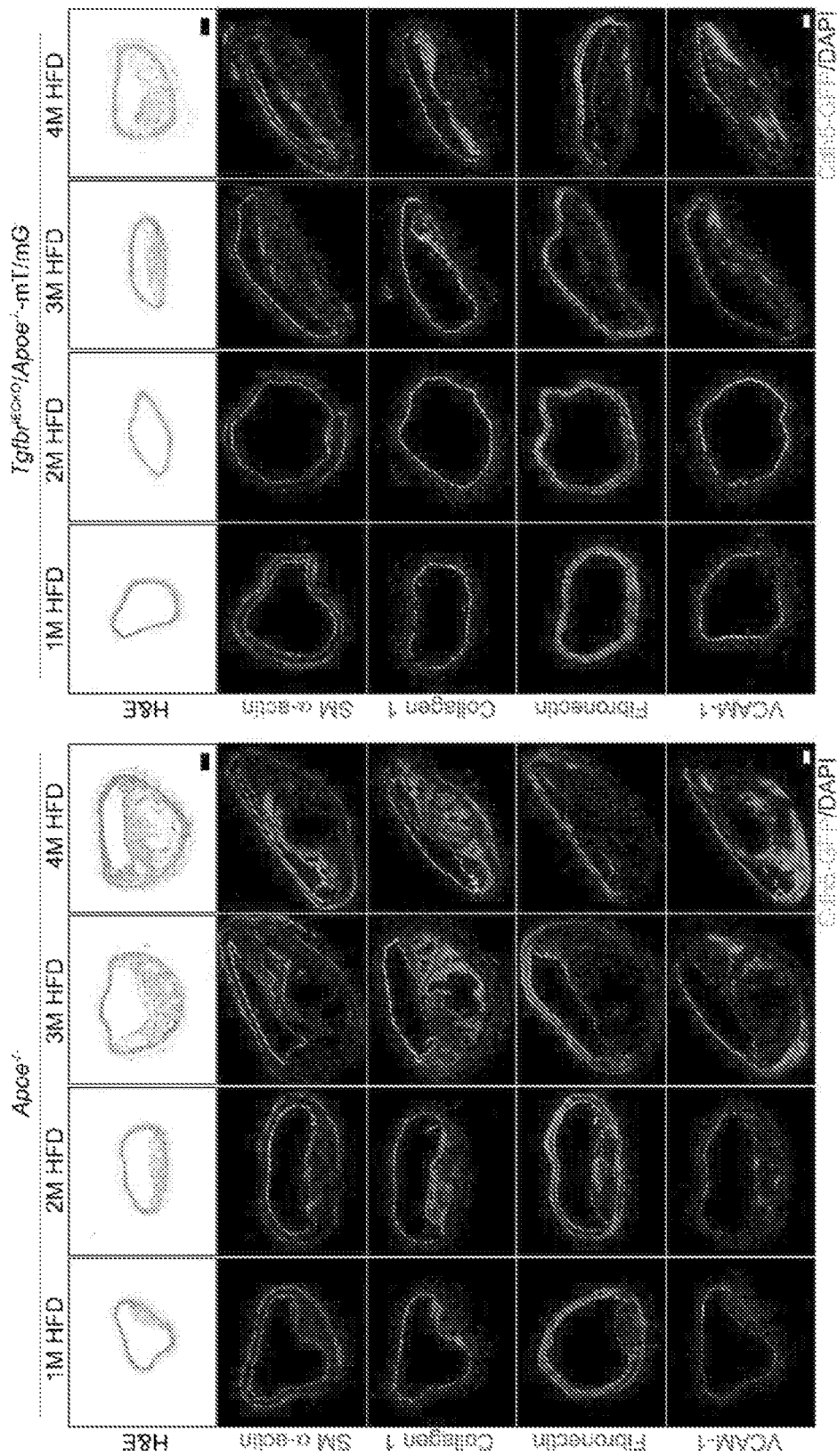
FIGS. 40A-40B are a series of images and histograms depicting that endothelial cell Tgfbr1/Tgfbr2 knockout reduce plaque cellularity and inhibit SM α-actin, collagen 1, fibronectin, and VCAM-1 expression in the plaques.
Figure 40B:
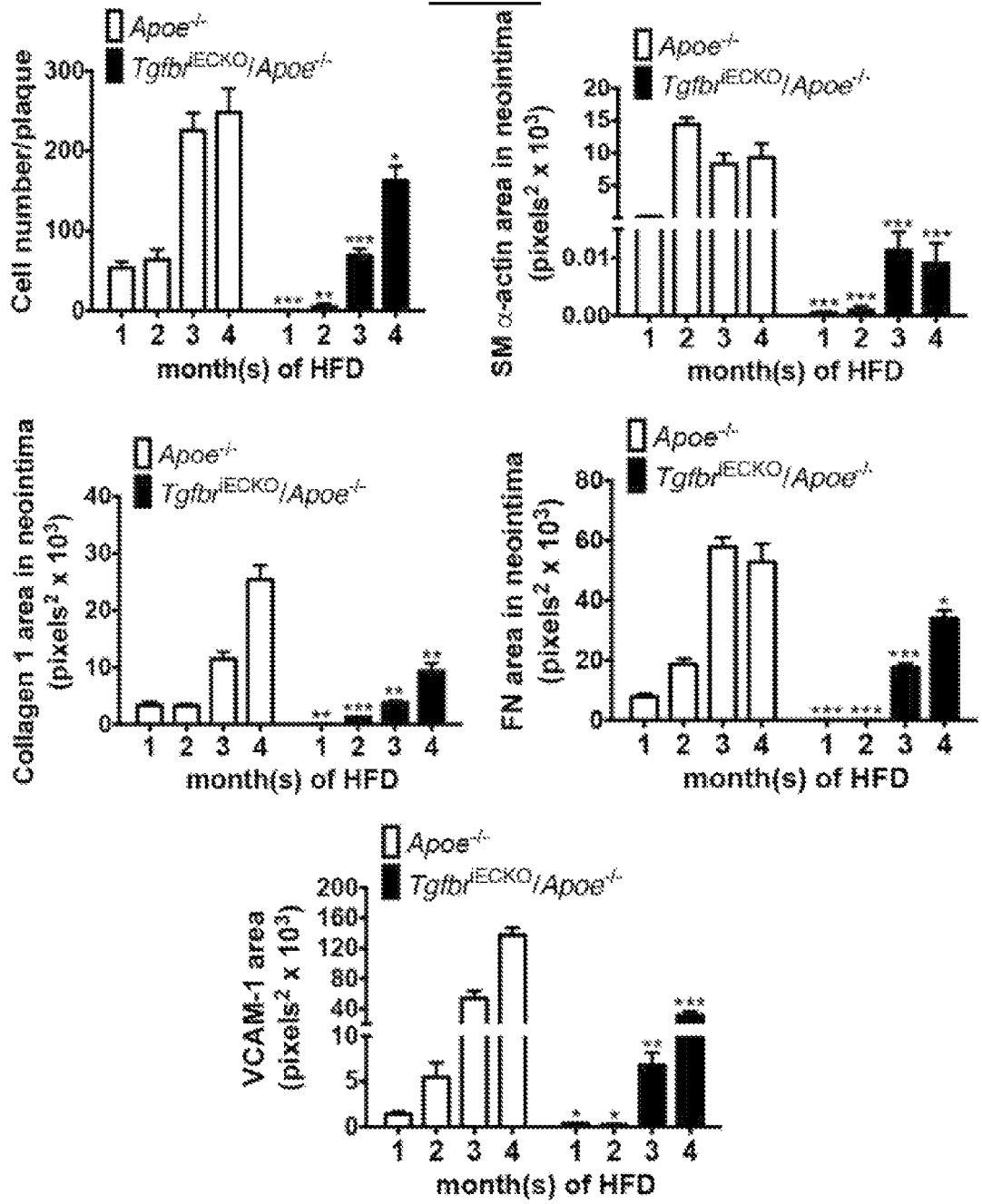

To test the effect of this intervention on lesion regression under normocholesterolemic conditions, Cdh5CreER$^{T2}$; Tgfbr$^{fl/fl}$; Tgfbr2$^{fl/fl}$; Apoe$^{-/-}$; mT/mG$^{fl/fl}$ mice were kept on the HFD for 3 months. At that time, they were switched to the normal chow diet and randomized to Cdh5CreER$^{T2}$ activation, inducing endothelial-specific Tgfβr1 and Tgfβr2 deletions (FIG. 39C). While both Apoe$^{-/-}$ and Tgfbr$^{iECKO}$/Apoe$^{-/-}$ mice showed an expected decrease in the lipid uptake, it was far more profound in the latter (FIGS. 39D&39G). Histological sections of the aortic root were used to analyze the extent of atherosclerotic plaques size and composition after one or two months of the normal chow diet (FIG. 39E). While there was no significant reduction in the aortic root plaque size in Apoe$^{-/-}$ mice either after 1 or 2 months of the normal chow diet, Tgfbr$^{iECKO}$/Apoe$^{-/-}$ mice showed a 47% decrease in lesion size after 1 month and a 71% decrease after 2 months (FIGS. 39F&39H). Morphological analysis of atherosclerotic palques showed expected plaque progression in Apoe$^{-/-}$ mice. At the same time, induction of Tgfβr1/Tgfβr2 deletions resulted in significant plaque regression.

In sum, the experiments demonstrate that the luciferase control or 7C1-let-7 injection had no effect on body weight, blood cell counts, organ appearance, organ weight, serum lipid profile, and liver function. 7C1-let-7 had an effect on plaque lesion size: reduced atherosclerotic lesion in both Apoe$^{-/-}$ and Frs2α$^{iECKO}$/Apoe$^{-/-}$ mice after 4 months on a high fat diet was observed.

Figure 32A:
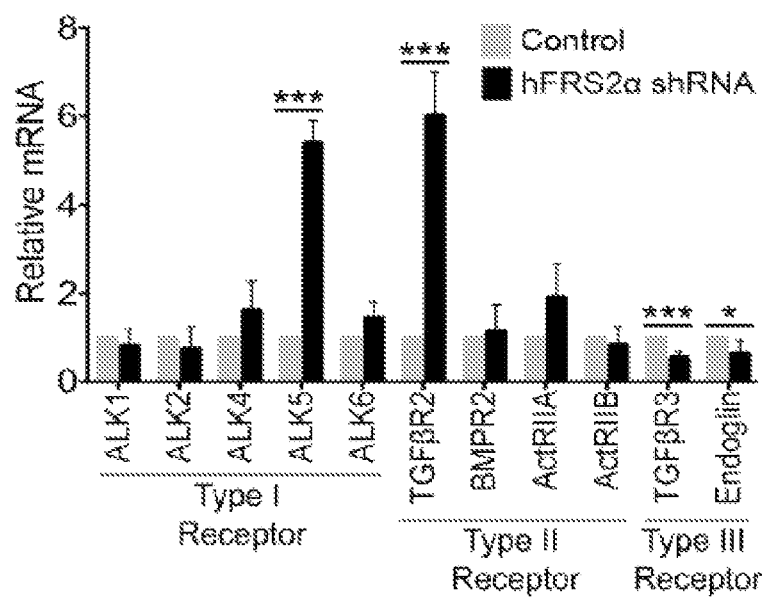
FIGS. 32A-32D are plots and blots showing TGFβ and BMP signaling in a FRS2α knockdown background.
Figure 32B:
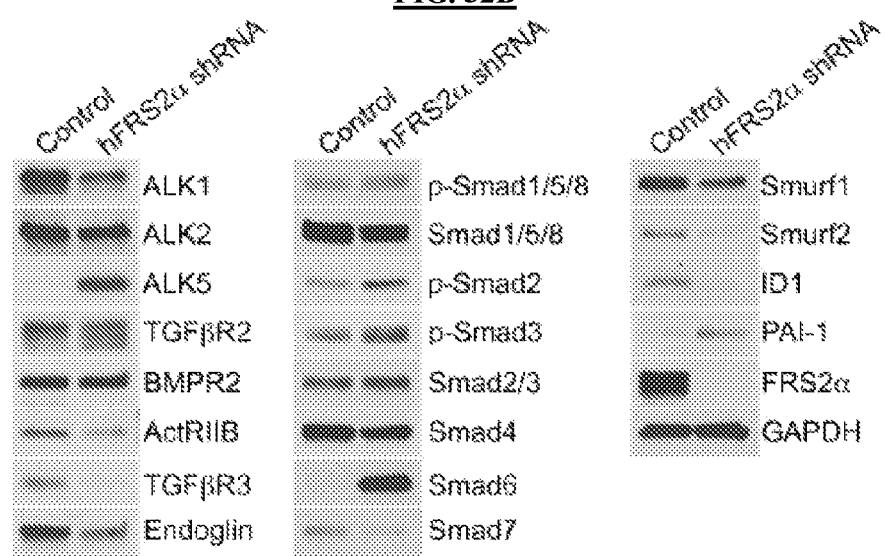
Figure 32D:
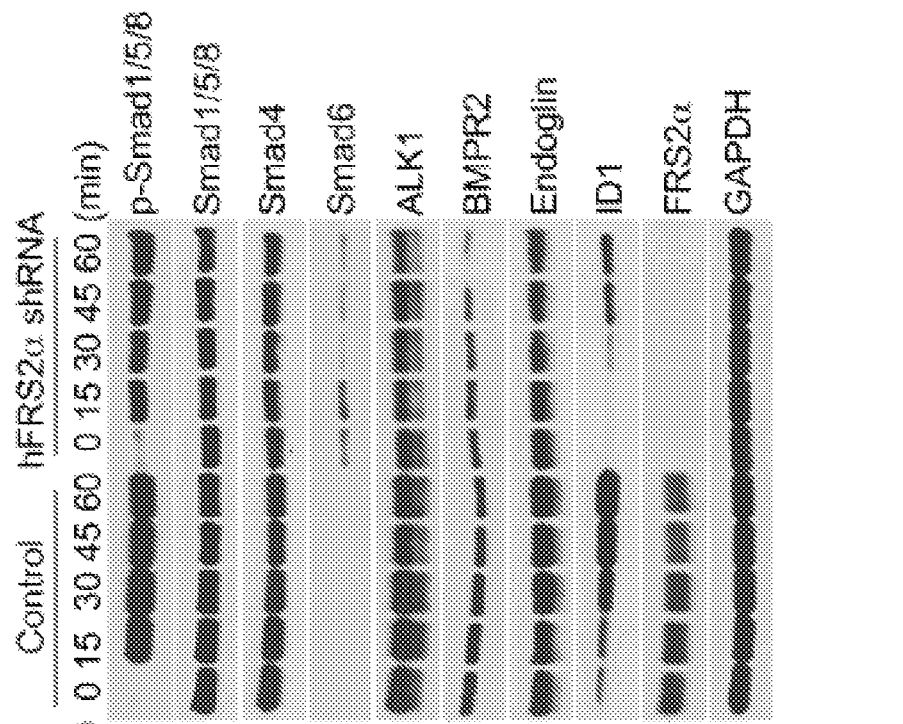
Figure 32C:
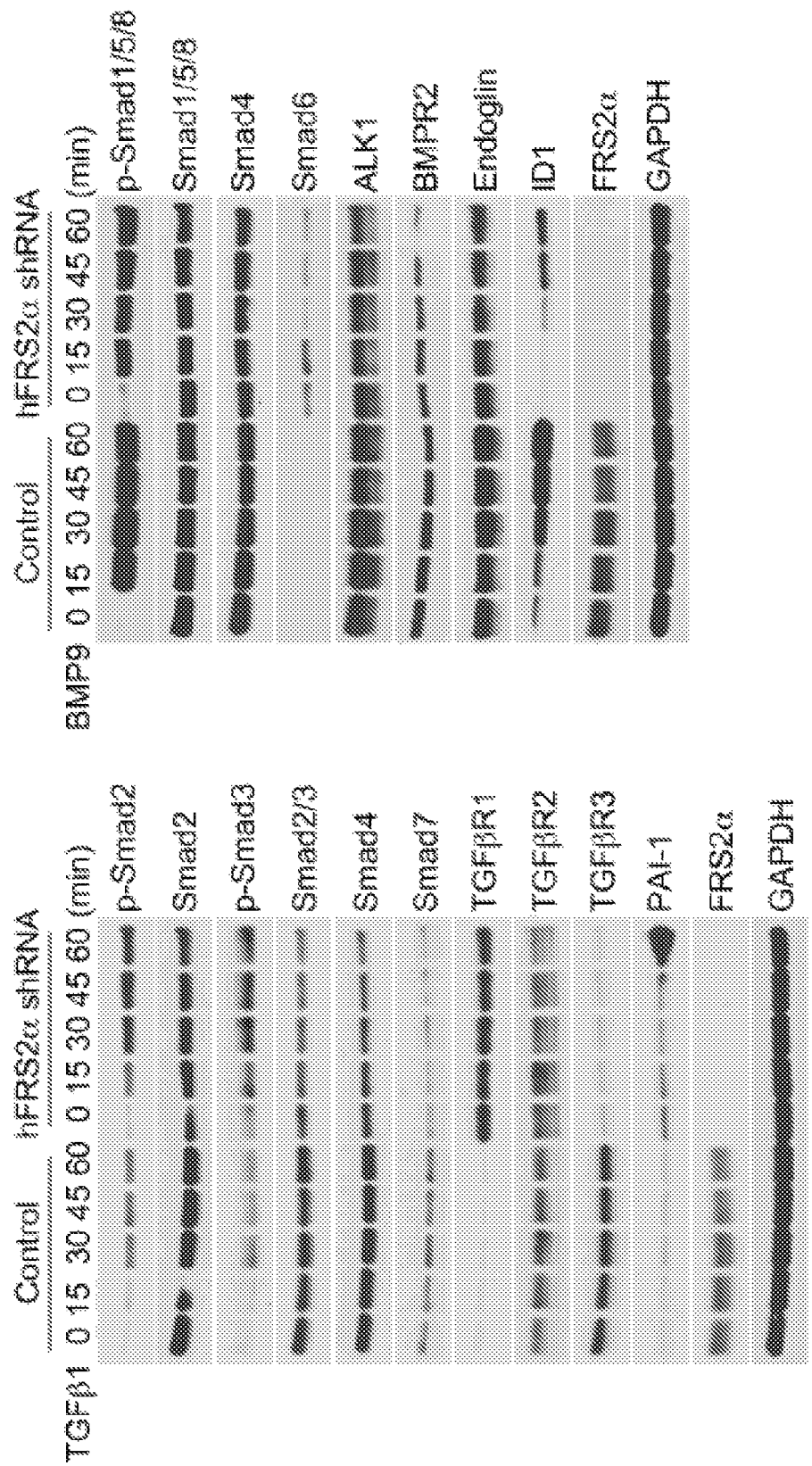

Example 7: Analysis of TGFβ Signaling in FRS2α Knockdown HUVEC and Endothelial Cells from Subjects Having No or Varying Degrees of Atherosclerosis/Coronary Artery Disease FIGS. 32A-32D are plots and blots showing TGFβ and BMP signaling in a FRS2α knockdown background. FIG. 32A shows levels of Type I, Type II, and Type III TGFβ receptors in a FRS2α knockdown background. FIG. 32B shows levels of TGFβ and BMP signaling components in a FRS2α knockdown background. FIG. 32C shows a time course of levels of TGFβ signaling components in a FRS2α knockdown background. FIG. 32D shows a time course of levels of BMP signaling components in a FRS2α knockdown background.

Figure 33A:
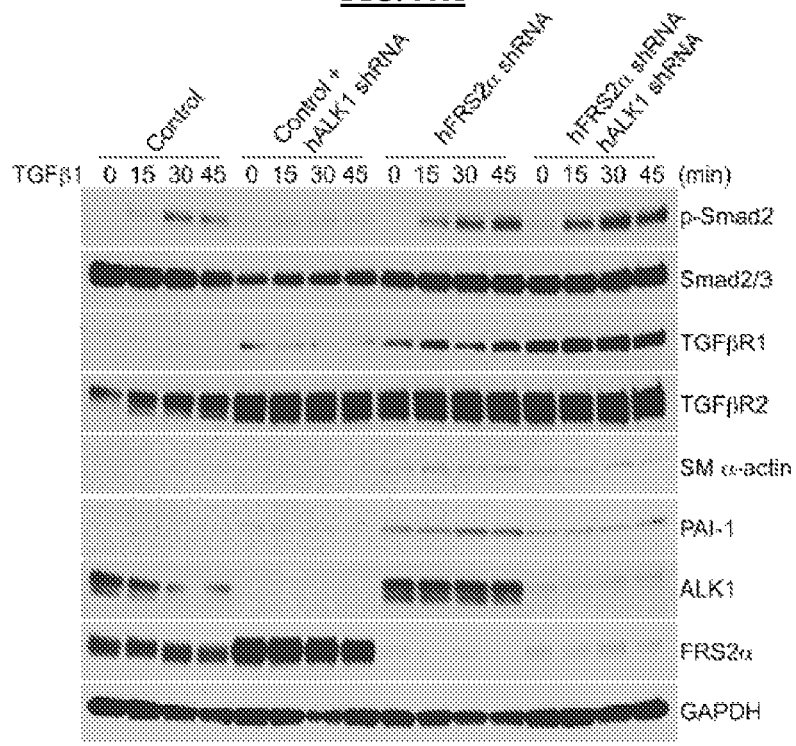
FIGS. 33A-33B are blots showing TGFβ and BMP signaling, respectively, in a ALK1 knockdown, TGFβR2 knockdown, FRS2α knockdown, ALK1/FRS2α knockdown, and TGFβR2/FRS2α knockdown background.
Figure 33B:
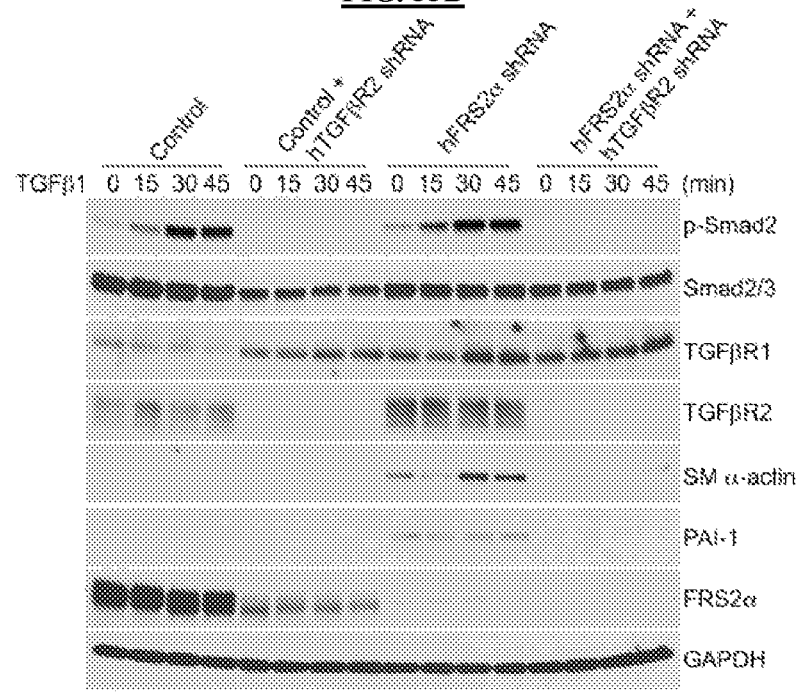

FIGS. 33A-33B are blots showing TGFβ and BMP signaling, respectively, in a ALK1 knockdown, TGFβR2 knockdown, FRS2α knockdown, ALK1/FRS2α knockdown, and TGFβR2/FRS2α knockdown background.

Figure 34A:
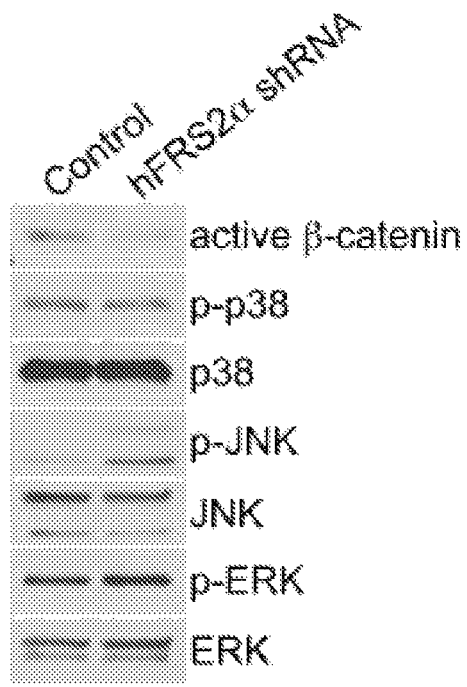
FIGS. 34A-34C are blots and an image showing MAPK signaling in a FRS2α knockdown background.
Figure 34B:
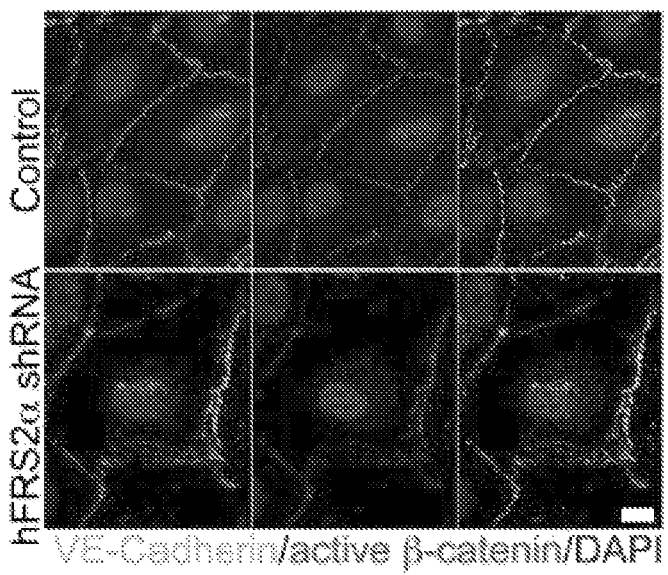
Figure 34C:
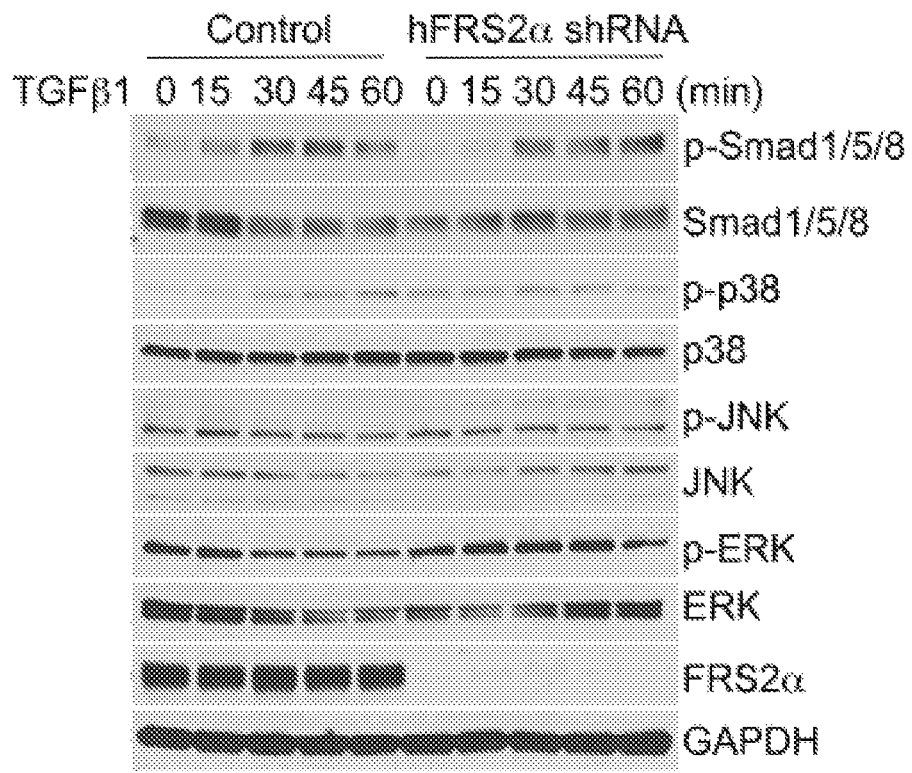

FIGS. 34A-34C are blots and an image showing MAPK signaling in a FRS2α knockdown background. FIGS. 34A and 34C show levels of MAPK signaling components in a FRS2α knockdown.

FIG. 34B shows an analysis using anti-VE cadherin and anti-active β-catenin. Nuclei were counterstained with DAPI.

FIGS. 35A-35C are images showing showing TGFβ signaling activity in endothelial cells from subjects having No/mild disease, moderate disease, and severe disease, using anti-CD31, anti-p-Smad3, and anti-p-Smad5 antibodies. FIG. 35A shows immunostaining for p-Smad3. FIG. 35B shows immunostaining for p-Smad5. FIG. 35C shows quantification of immunocytochemistry data from FIG. 35B. Nuclei were counterstained with DAPI.

Figure 36:
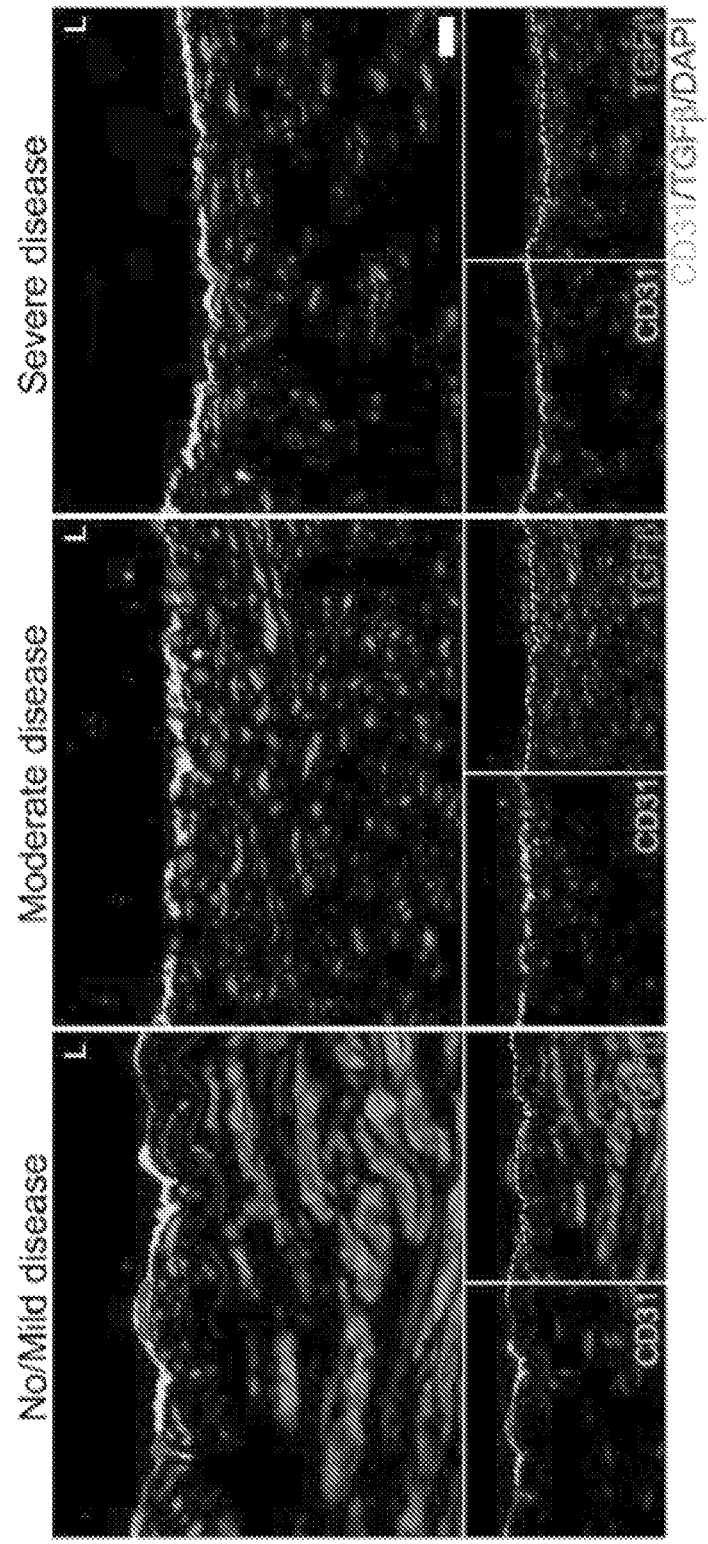
FIG. 36 are images showing TGFβ signaling activity in arteries from subjects having No/mild disease, moderate disease, and severe disease, using anti-CD31 and anti-TGFβ antibodies. Nuclei were counterstained with DAPI.

FIG. 36 are images showing TGFβ signaling activity in arteries from subjects having No/mild disease, moderate disease, and severe disease, using anti-CD31 and anti-TGFβ antibodies. Nuclei were counterstained with DAPI.

FIGS. 37A-37B are images and a plots showing NKX2.5 expression in endothelial cells from subjects having No/mild disease, moderate disease, and severe disease. Nuclei were counterstained with DAPI. FIG. 37A shows immunostaining for NKX2.5. FIG. 37B shows quantification of immunocytochemistry data from FIG. 37A.

Figure 43B:
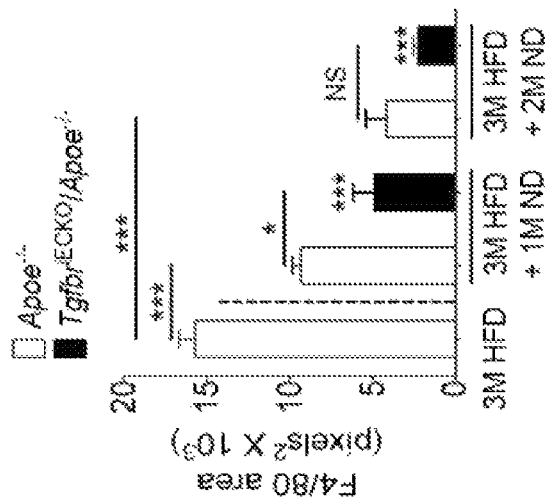
FIGS. 43A-43B are a series of images and histograms showing the effects of endothelial cell Tgfbr1/Tgfbr2 knockout on the regression of atherosclerosis macrophage content. Mice were fed the high-fat-diet for 3 months to induce advanced atherosclerotic lesions. Then the diet was changed to a normal diet for additional 1 or 2 months. Mice were simultaneously treated with tamoxifen or vehicle control.
Figure 43A:
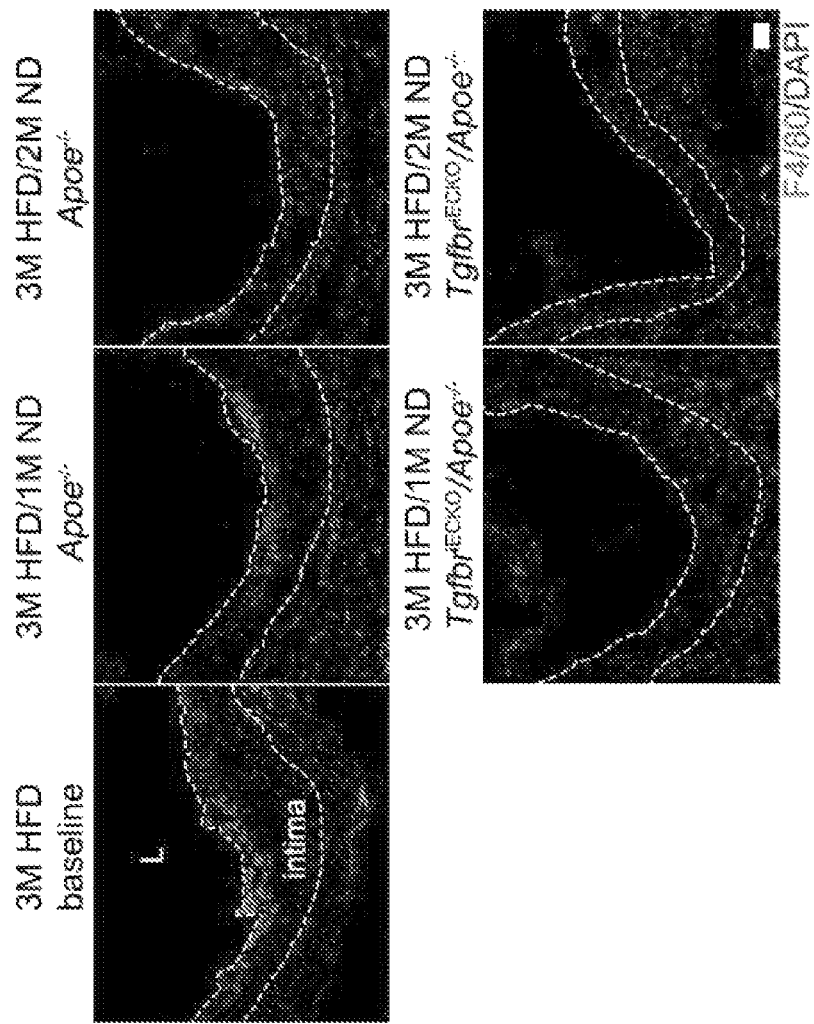

FIGS. 43A-43B are a series of images and histograms showing the effects of endothelial cell Tgfbr1/Tgfbr2 knockout on the regression of atherosclerosis macrophage content by measurement and histological analysis.

Figure 44A:
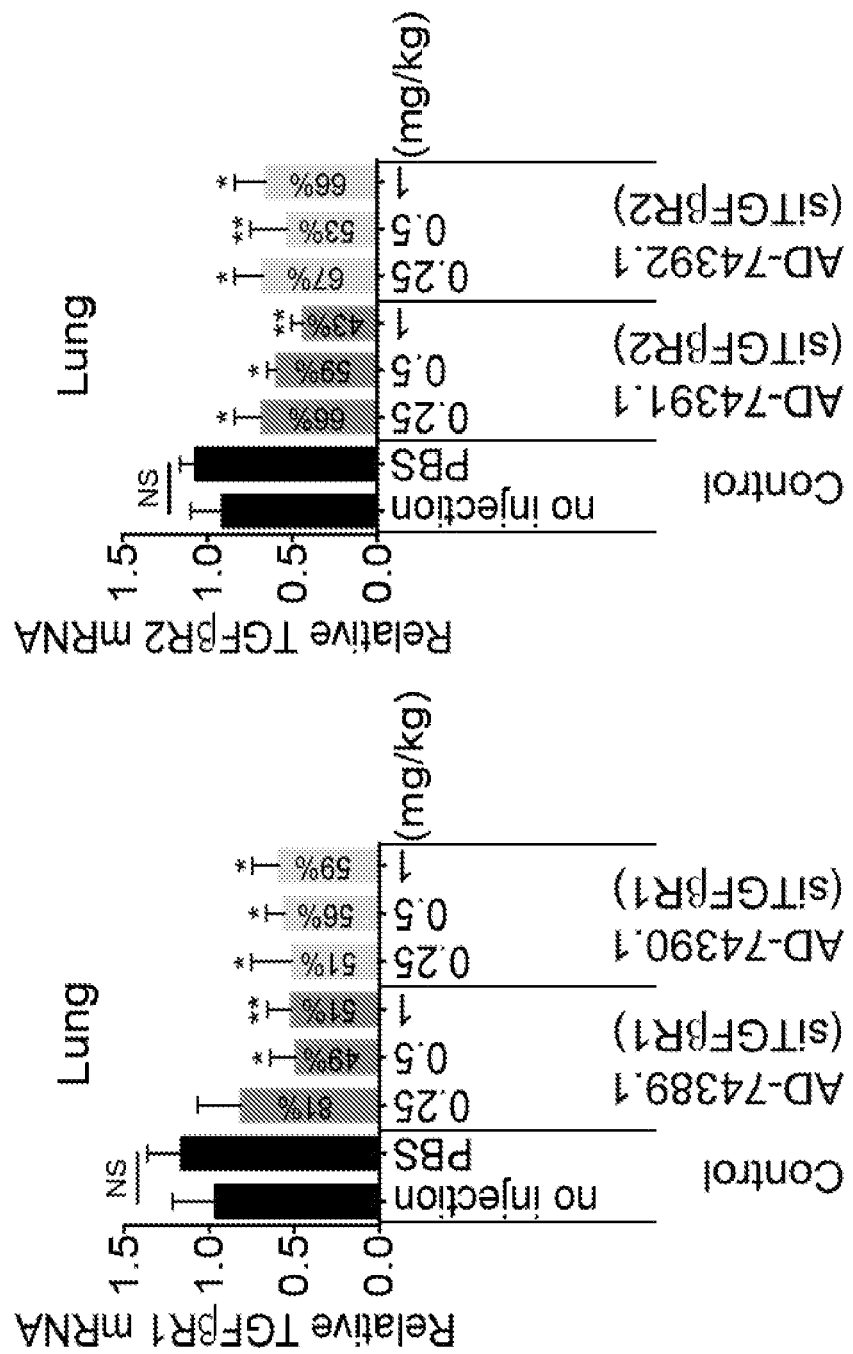
FIGS. 44A-44B are a series of histograms depicting the in vivo assessment of siTgfbr1 and siTgfbr2 in heart and lung endothelial cells (EC).
Figure 44B:
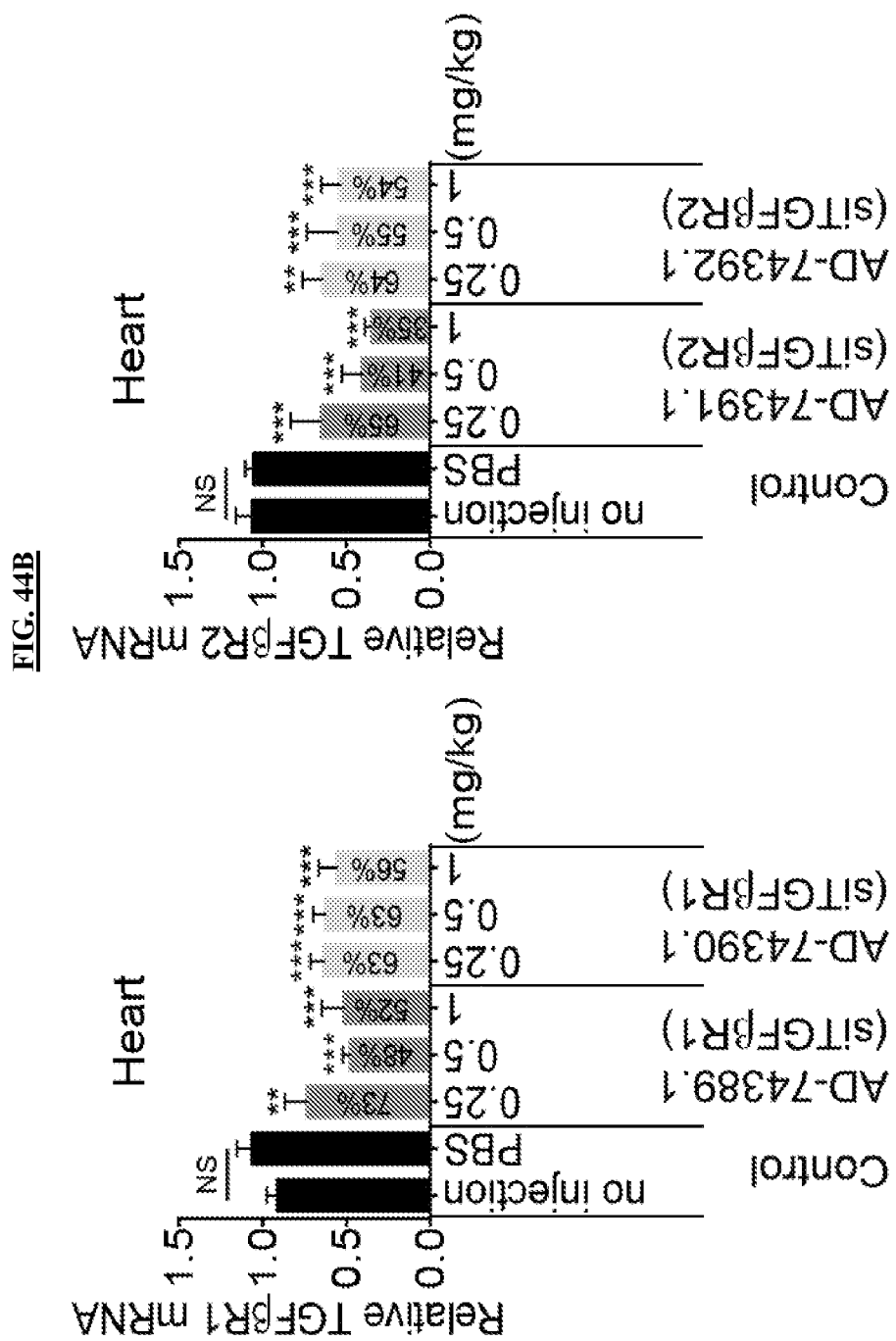

FIGS. 44A-44B are series of histograms depicting the in vivo assessment of siTgfbr1 and siTgfbr2 in heart and lung endothelial cells (EC). The Expression of Tgfbr1 and Tgfbr2 were analyzed by quantitative real-time PCR and showed that siTgfbr1 (AD-74389.1) and siTgfbr2 (AD-74391.1) have great knockdown efficiency in both lung and heart.

Figure 45A:
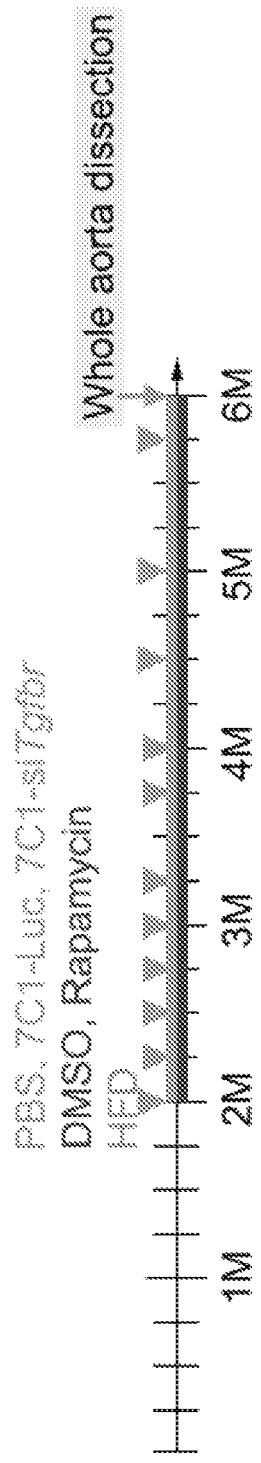
FIGS. 45A-45B are a graph and a series of images showing that 7C1-siTgfbr and rapamycin suppress atherosclerosis lesion development in Apoe$^{-/-}$ mice after 4 months of high fat diet.

Example 8: The Combination of 7C1-siTgfbr and Rapamycin Provides Optimal Reduction of Atherosclerotic Lesion FIGS. 45A-45B are a graph and series of images showing that 7C1-siTgfbr and rapamycin suppress atherosclerosis lesion development in Apoe$^1$ mice after 4 months of high fat diet.

Figure 45B:
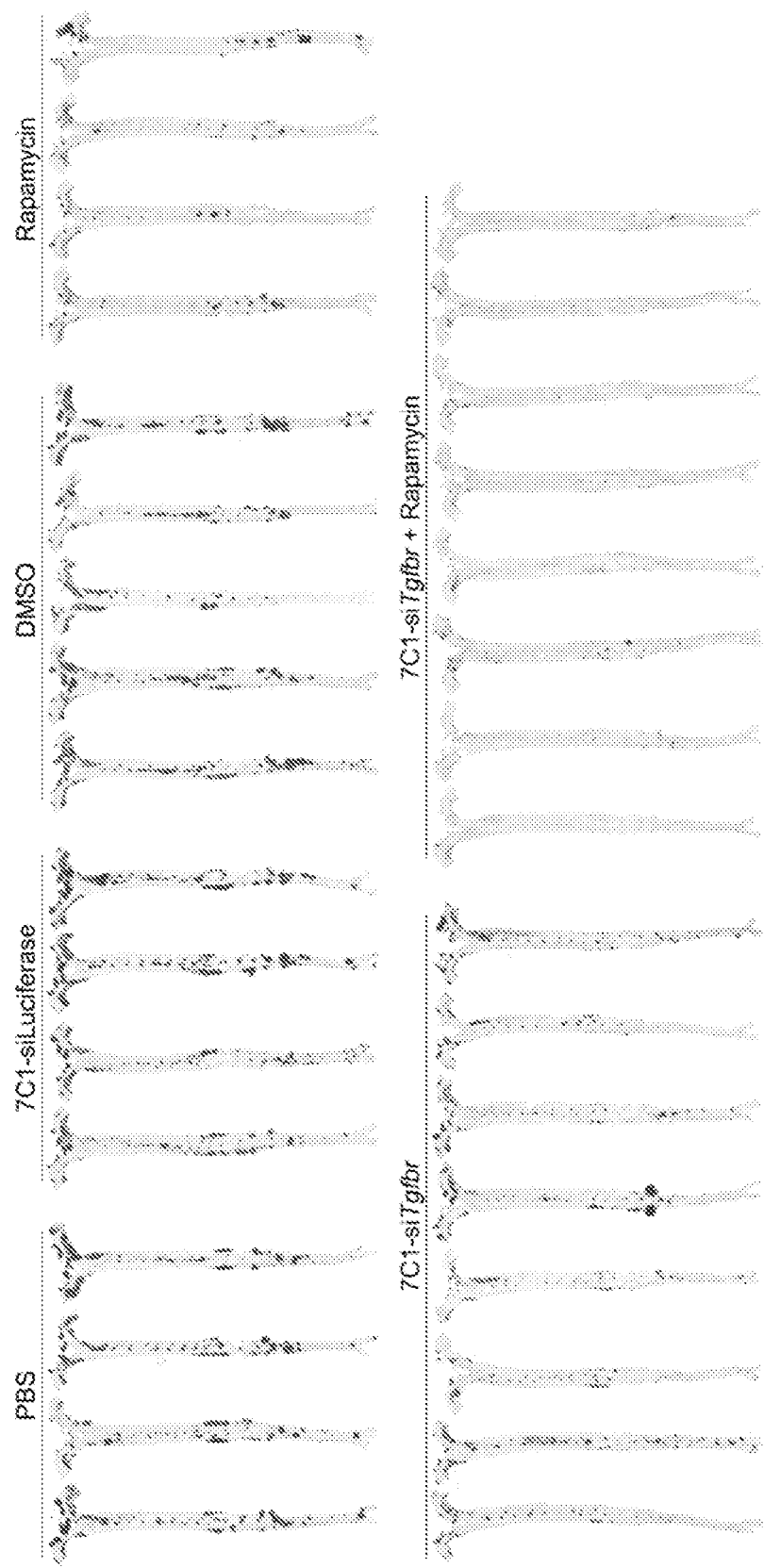

FIG. 46 is a histogram illustrating the quantification of atherosclerotic lesions from FIG. 45B. The quantification of the lesion area was performed by computing the percentage of lesion area over the total area of aorta. Mice treated with 7C1-siTgfbr exhibited 52% reduction in their atherosclerotic lesion, mice treated with rapamycin exhibited 58% reduction in their atherosclerotic lesion and mice treated with a combination of both 7C1-siTgfbr and rapamycin exhibited 92% reduction in their atherosclerotic lesion. These results highlight that the combination of when 7C1-siTgfbr and rapamycin allow reaching optimal results when used for atherosclerosis treatment.

Example 9

The results of this study show that activation of endothelial TGFβ signaling plays a key role in the development and progression of atherosclerosis. Selective inhibition of endothelial TGFβ signaling, using either Tgfβr1/Tgfβr2 deletions or nanoparticle-based let-7b miR delivery, delays the onset of the disease, reduces the rate of atherosclerosis progression in the settings of hypercholesterolemia and facilitates regression under normocholesterolemic conditions. Taken together, these data implicate endothelial TGFβ signaling as the key factor responsible for atherosclerotic plaque growth and maintenance.

TGFβ has long been recognized as an important regulator involved in a variety of biological roles including cell proliferation, differentiation, migration, adhesion, and extracellular matrix (ECM) production. Abnormal TGFβ signaling has been implicated in pathogenesis of a number diseases from systemic sclerosis and various fibrosis-associated illnesses to Marfan's syndrome, aortic aneurysms and related disorders, to inflammation-related syndromes and allergic disease among many others (Lafyatis et al, 2014 Nature reviews. Rheumatology 10, 706-719; Lan et al, 2013 Cardiovascular pathology: the official journal of the Society for Cardiovascular Pathology 22, 401-407; Pardali et al, 2012 International journal of biological sciences 8, 195-213; Frischmeyer-Guerrerio et al, 2013 Science translational medicine 5, 195ra194; Gallo et al, 2014 The Journal of clinical investigation 124, 448-460; Tedgui et al, 2006 Physiological reviews 86, 515-581).

Importantly, TGFβ signature has been detected in atherosclerosis (Schunkert et al., 2011 Nature genetics 43, 333-338) and expression of TGFβ ligands, receptors and various Smad proteins has been reported in atherosclerotic plaques (Pardali et al, 2012 International journal of biological sciences 8, 195-213; McCaffrey et al, 2009 Frontiers in bioscience 1, 236-245). However, the role of TGFβ in atherosclerosis has been controversial, with both pro- and anti-atherosclerotic effects reported (Toma et al, 2012 Cell and tissue research 347, 155-175; Tabas et al, 2015 J Cell Biol 209, 13-22). In particular, systemic inhibition of TGFβ signaling using a neutralizing anti-TGFβ1, -β2, and -β3 antibody was shown to accelerate the development of atherosclerosis in Apoe$^{-/-}$ mice (Mallat et al, 2001 Circulation research 89, 930-934) while treatment with anti-TGFβR2 antibody decreased plaque size of advanced lesions, but increased plaque vulnerability (Lutgens et al, 2002 Arterioscler Thromb Vasc Biol 22, 975-982). Mice with TGFβR2 knockout in CD11c$^+$ cells dendritic cells exhibited an increase in the plaque area (Lievens et al, 2013 European heart journal 34, 3717-3727) as did the Apoe$^{-/-}$ mice with disrupted TGFβ signaling in T cells (Gistera et al, 2013 Science translational medicine 5, 196ra100; Robertson et al, 2003 The Journal of clinical investigation 112, 1342-1350).

Among deleterious effects of activated endothelial TGFβ signaling is the induction of endothelial to mesenchymal transition (EndMT) (van Meeteren et al, 2012 Cell and tissue research 347, 177-186). EndMT is frequently observed in human atherosclerotic lesions (Chen et al, 2015 The Journal of clinical investigation 125, 4529-4543) and its extent strongly correlates with the severity of disease. It contributes directly to atherosclerotic plaque growth due to endothelial cells acquiring smooth muscle and mesenchymal (fibroblast) fate and extensive deposition of extracellular matrix. Indeed, induction of EndMT, and hence endothelial TGFβ signaling, in mice accelerates the development of atherosclerosis and increases plaque size. EndMT is also an important driver of inflammation due to increased endothelial expression of leukocyte adhesion molecules. For these reasons, in the present invention the endothelial TGFβ signaling cascade cells were specifically targeted using genetic and molecular approaches.

Both approaches were equally effective in reducing the total lesion burden and plaque size. In addition, plaque morphology was favorably affected with a decrease in the necrotic core size implying increased plaque stability. Importantly, favorable changes were seen in multiple vascular locations including the total aortic endothelium, aortic root and brachiocephalic artery. This was driven by a reduction in the extent of EndMT, as shown by decreased number of endothelial-derived αSMA-positive cells in the plaque, and a large decrease in plaque inflammation, as documented by decreased presence of Mac3$^+$ and F4/80$^+$ macrophages and T and B-cells, most likely due to decreased recruitment.

In summary, this study establishes endothelial TGFβ signaling as an important driver of atherosclerotic plaque growth and demonstrates a potential utility of a therapeutic intervention aimed at suppression of this process.

TABLE 1

Human subject characteristics*

| | Disease Severity by I/M Ratio | | | |
|---|---|---|---|---|
| | No/Mild I/M < 0.2 0.14 ± 0.03 n = 10 | Moderate I/M 0.2-1.0 0.4 ± 0.2 n = 15 | Severe I/M > 1.0 2.0 ± 1.4 n = 18 | P value |
| Explanted Hearts | | | | |
| Organ donors | 6 (60.0) | 8 (53.3) 1 | 0 (55.6) | 0.9470 |
| Transplant recipients | 4 (40.0) | 7 (46.7) | 8 (44.4) | 0.9470 |
| Demographics | | | | |
| Age (yr) | 42.3 ± 13.9 | 56.7 ± 8.3 | 61.6 ± 6.5 | <0.0001 |
| Male | 4 (40.0) | 10 (66.7) | 13 (72.2) | 0.2226 |
| Caucasian | 7 (70.0) | 10 (66.7) | 15 (83.3) | 0.5149 |
| Past Medical History | | | | |
| Coronary artery disease | 0 (0.0) | 0 (0.0) | 9 (50.0) | 0.0004 |
| Cerebrovascular disease | 1 (10.0) | 0 (0.0) | 4 (22.2) | 0.1377 |
| Peripheral vascular disease | 1 (10.0) | 1 (6.7) | 2 (11.1) | 0.9053 |
| Atherosclerosis Risk Factors | | | | |
| Diabetes mellitus | 2 (20.0) | 3 (20.0) | 6 (33.3) | 0.6135 |
| Hypertension | 4 (40.0) | 9 (60.0) | 11 (61.1) | 0.5155 |
| Hyperlipidemia | 2 (20.0) | 3 (20.0) | 7 (46.7) | 0.3954 |
| Tobacco use | 4 (40.0) | 7 (46.7) | 10 (55.6) | 0.7168 |
| Obesity | 4 (40.0) | 2 (13.3) | 5 (27.8) | 0.3135 |

*Left main coronary arteries were procured from the explanted hearts of 43 individuals within the operating room either at organ donation or cardiac transplantation. The degree of atherosclerotic disease was quantified as intima to media (I/M) ratio and deidentified clinical data was recorded. Data represent Number (%) or Mean ± SD. Comparisons between groups of categorical variables were by Chi-square test and of continuous variables were by one-way ANOVA.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing, inhibiting or reversing an endothelial-to-mesenchymal transition (EndMT) in an endothelial cell in a subject in need thereof, the method comprising administering to the subject a nanoparticle formulated for delivery to an endothelial cell, the nanoparticle comprising at least one siRNA that directly decreases in the endothelial cell of the subject the activity or level of at least one TGFβ receptor, thereby reducing, inhibiting or reversing the EndMT in the endothelial cell in the subject in need thereof, wherein the inhibitory RNA is an siRNA encoded by a nucleic acid selected from the group consisting of SEQ ID NOs: 35-38.

2. The method of claim 1, wherein the at least one TGFβ receptor comprises TGFβR1 or TGFβR2.

3. A method of reducing an atherosclerotic lesion in a subject, the method comprising administering to the subject a nanoparticle formulated for delivery to an endothelial cell, the nanoparticle comprising an inhibitory RNA that directly decreases in an endothelial cell in the subject the activity or level of a endothelial TGFβ signaling polypeptide selected from the group consisting of TGFβR1 and TGFβR2, thereby reducing or inhibiting the atherosclerotic lesion in the subject; wherein the inhibitory RNA is an siRNA encoded by a nucleic acid selected from the group consisting of SEQ ID NOs: 35-38.

4. A method of inhibiting progression of atherosclerosis in a subject, the method comprising administering to the subject a nanoparticle formulated for delivery to an endothelial cell, the nanoparticle comprising an inhibitory RNA that directly decreases in an endothelial cell in the subject the activity or level of a TGFβ signaling polypeptide selected from the group consisting of TGFβR1 and TGFβR2, thereby inhibiting progression of the atherosclerosis in the subject; wherein the inhibitory RNA is an siRNA encoded by a nucleic acid selected from the group consisting of SEQ ID NOs: 35-38.

5. A method of reversing atherosclerosis in a subject, the method comprising administering to the subject a nanoparticle formulated for delivery to an endothelial cell, the nanoparticle comprising an inhibitory RNA that directly decreases in an endothelial cell in the subject the activity or level of a TGFβ signaling polypeptide selected from the group consisting of TGFβR1 and TGFβR2, thereby reversing atherosclerosis in the subject; wherein the inhibitory RNA is an siRNA encoded by a nucleic acid selected from the group consisting of SEQ ID NOs: 35-38.

6. A method of treating atherosclerosis in a subject, the method comprising administering to the subject a nanoparticle formulated for delivery to an endothelial cell, the nanoparticle comprising an inhibitory RNA that directly decreases in an endothelial cell in the subject the activity or level of a TGFβ signaling polypeptide selected from the group consisting of TGFβR1 and TGFβR2, thereby treating atherosclerosis in the subject; wherein the inhibitory RNA is an siRNA encoded by a nucleic acid selected from the group consisting of SEQ ID NOs: 35-38.

* * * * *